(12) United States Patent
Geneste et al.

(10) Patent No.: US 9,657,034 B2
(45) Date of Patent: May 23, 2017

(54) SUBSTITUTED FURO[3,2-C]PYRIDINES, THIENO[3,2-C]PYRIDINES, THIENO[2,3-D]PYRIDAZINES AND PYRIDO[3,4-D]PYRIDAZINES AS PHOSPHODIESTERASE TYPE 10A INHIBITORS

(71) Applicants: AbbVie Deutschland GmbH & Co. KG, Wiesbaden (DE); AbbVie Inc., North Chicago, IL (US)

(72) Inventors: Hervé Geneste, Ludwigshafen (DE); Michael Ochse, Ludwigshafen (DE); Karla Drescher, Ludwigshafen (DE); Sean Turner, Ludwigshafen (DE); Berthold Behl, Ludwigshafen (DE); Loic Laplanche, Ludwigshafen (DE); Jürgen Dinges, North Chicago, IL (US); Clarissa Jakob, North Chicago, IL (US); Lawrence Black, North Chicago, IL (US); Katja Jantos, Ludwigshafen (DE)

(73) Assignees: AbbVie Deuschland GmbH & Co. KG, Wiesbaden (DE); AbbVie Inc., North Chicago, IL (US)

( * ) Notice: Subject to any disclaimer, the term of this patent is extended or adjusted under 35 U.S.C. 154(b) by 0 days.

(21) Appl. No.: 14/997,997

(22) Filed: Jan. 18, 2016

(65) Prior Publication Data
US 2016/0137668 A1 May 19, 2016

Related U.S. Application Data

(62) Division of application No. 13/663,008, filed on Oct. 29, 2012, now Pat. No. 9,273,068.
(Continued)

(51) Int. Cl.
*A61K 31/5025* (2006.01)
*A61K 31/4355* (2006.01)
(Continued)

(52) U.S. Cl.
CPC ......... *C07D 519/00* (2013.01); *C07D 401/06* (2013.01); *C07D 401/14* (2013.01);
(Continued)

(58) Field of Classification Search
CPC ............ A61K 31/4355; A61K 31/4365; A61K 31/5025; C07D 487/04; C07D 491/048; C07D 495/04
(Continued)

(56) References Cited

U.S. PATENT DOCUMENTS 5,624,922 A 4/1997 Johnson et al.
2013/0116241 A1 5/2013 Geneste et al.

FOREIGN PATENT DOCUMENTS

DE 69229874 12/1999
EP 0597540 5/1994
(Continued)

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*
(Continued)

*Primary Examiner* — Douglas M Willis
(74) *Attorney, Agent, or Firm* — Neal, Gerber & Eisenberg LLP

(57) ABSTRACT

The present invention relates to novel compounds of the formula I which are inhibitors of phosphodiesterase type 10A and to their use for the manufacture of a medicament and which thus are suitable for treating or controlling of medical disorders selected from neurological disorders and psychiatric disorders, for ameliorating the symptoms associated with such disorders and for reducing the risk of such disorders.

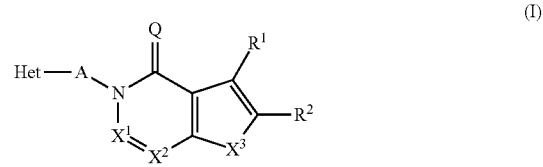

(I)

wherein

Q is O or S, $X^1$ is N or CH, $X^2$ is N or C—$R^7$; $X^3$ is O, S—$X^4$=C($R^8$)—, where C($R^8$) is bound to the carbon atom which carries $R^2$, or —$X^5$=C($R^9$)—, where $X^5$ is bound to the carbon atom which carries $R^2$; $X^4$ is N or C—$R^9$; $X^5$ is N;

Het is selected from optionally substituted phenyl, monocyclic hetaryl and fused bicyclic hetaryl;

$R^1$ is selected inter alia from hydrogen, halogen, OH, $C_1$-$C_4$-alkyl, trimethylsilyl, $C_1$-$C_4$-alkylsulfanyl, $C_1$-$C_4$-alkoxy-$C_1$-$C_4$-alkyl, $C_1$-$C_4$-alkoxy, $C_1$-$C_4$-alkoxy-$C_1$-$C_4$-alkoxy, the moiety $Y^1$-$Cyc^1$;

$R^2$ is selected inter alia from hydrogen, halogen, OH, $C_1$-$C_4$-alkyl, trimethylsilyl, $C_1$-$C_4$-alkoxy-$C_1$-$C_4$-alkyl, $C_1$-$C_4$-alkoxy, $C_1$-$C_4$-alkoxy-$C_1$-$C_4$-alkoxy, $C_2$-$C_4$-alkenyloxy, etc;

A represents one of the following groups $A^1$, $A^2$, $A^3$, $A^4$ or $A^5$:

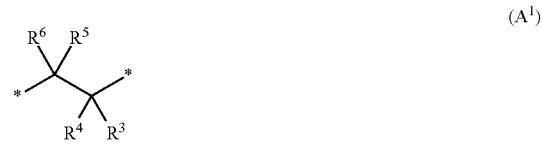

($A^1$)

(Continued)

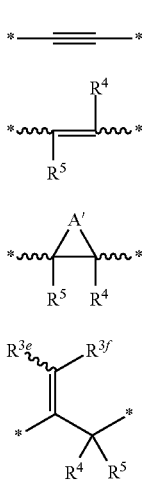

where * indicates the points of attachment to Het and to the nitrogen atom, respectively;
and where $R^3$ to $R^9$, $R^{3e}$, $R^{3f}$, A', $Y^1$ and $Cyc^1$ are defined in the claims.

61 Claims, No Drawings

Related U.S. Application Data

(60) Provisional application No. 61/557,874, filed on Nov. 9, 2011.

(51) Int. Cl.
| | |
|---|---|
| A61K 31/4365 | (2006.01) |
| C07D 487/04 | (2006.01) |
| C07D 491/048 | (2006.01) |
| C07D 495/04 | (2006.01) |
| C07D 519/00 | (2006.01) |
| C07D 401/14 | (2006.01) |
| C07D 401/06 | (2006.01) |
| C07D 471/04 | (2006.01) |
| C07D 417/14 | (2006.01) |
| C07D 413/14 | (2006.01) |
| C07D 405/14 | (2006.01) |

(52) U.S. Cl.
CPC ......... *C07D 405/14* (2013.01); *C07D 413/14* (2013.01); *C07D 417/14* (2013.01); *C07D 471/04* (2013.01); *C07D 491/048* (2013.01); *C07D 495/04* (2013.01)

(58) Field of Classification Search
USPC ......... 514/248, 301, 302; 544/235; 546/114, 546/115
See application file for complete search history.

(56) References Cited

FOREIGN PATENT DOCUMENTS

| JP | 3120857 | 12/2000 |
| WO | 2009029214 | 3/2009 |

OTHER PUBLICATIONS

Database Registry Accession No. 1050783-15-7 (2008).
Database Registry Accession No. 930535-75-4 (2007).
Database Registry Accession No. 1030804-14-8 (2008).
Database Registry Accession No. 1185320-37-9 (2009).
Database Registry Accession No. 1125421-79-5 (2009).
Database Registry Accession No. 1030169-89-1 (2008).
Database Registry Accession No. 1007801-38-8 (2008).
Database Registry Accession No. 931628-46-5 (2007).
Database Registry Accession No. 296792-07-9 (2007).
Database Registry Accession No. 692742-15-7 (2004).
Jordan, V.C. Nature Reviews: Drug Discovery (2003) 2:205.
Vippagunta et al. Advanced Drug Delivery Reviews (2001) 48:18.
Yamaguchi, M. et al., "Novel antiasthmatic agents with dual activities of thromboxane A2 synthetase inhibition and prochodilation. 2. 4-(3-pyridyl)-1(2H)-phthalazinones," J. Med. Chem. (1993) 36(25):4061-4068.
Yamaguchi, M. et al., "Novel antiasthmatic agents with dual activities of thromboxane A2 synthetase inhibition and prochodilation. 1. 2-[2-(1-imidazolyl)alkyl]-1(2H)-phthalazinones," J. Med. Chem. (1993) 36:4052-4060.
International Search Report and Written Opinion for Application No. PCT/EP2012/072150 dated Jan. 4, 2013 (17 pages).

* cited by examiner

SUBSTITUTED FURO[3,2-C]PYRIDINES, THIENO[3,2-C]PYRIDINES, THIENO[2,3-D]PYRIDAZINES AND PYRIDO[3,4-D]PYRIDAZINES AS PHOSPHODIESTERASE TYPE 10A INHIBITORS

CROSS-REFERENCE TO RELATED APPLICATION(S)

This is a divisional of U.S. patent application Ser. No. 13/663,008, filed on Oct. 29, 2012, which claims priority to U.S. Provisional Patent Application No. 61/557,874, filed on Nov. 9, 2011, the entire contents of all of which are fully incorporated herein by reference.

The present invention relates to novel compounds which are inhibitors of phosphodiesterase type 10A and to their use for the manufacture of a medicament and which thus are suitable for treating or controlling of medical disorders selected from neurological disorders and psychiatric disorders, for ameliorating the symptoms associated with such disorders and for reducing the risk of such disorders.

BACKGROUND OF THE INVENTION

Phosphodiesterase type 10A (hereinafter PDE10A) is a dual-substrate phosphodiesterase that can convert both cAMP to AMP and cGMP to GMP. PDE10A is highly prominent in the mammalian brain. In the rat, as well as in other mammalian species, PDE10A and the mRNA of PDE10A are highly enriched in the GABAergic medium spiny projection neurons (MSNs) of the striatal complex (caudate nucleus, nucleus accumbens, and olfactory tubercle) where the output is regulated by the effect of PDE10A on cAMP and cGMP signalling cascades (see e.g. C. J. Schmidt et al, The Journal of Pharmacology and Experimental Therapeutics 325 (2008) 681-690, A. Nishi, The Journal of Neuroscience 2008, 28, 10450-10471).

MSNs express two functional classes of neurons: the $D_1$ class expressing $D_1$ dopamine receptors and the $D_2$ class expressing $D_2$ dopamine receptors. The $D_1$ class of neurons is part of the 'direct' striatal output pathway, which broadly functions to facilitate behavioral responses. The $D_2$ class of neurons is part of the 'indirect' striatal output pathway, which functions to suppress behavioral responses that compete with those being facilitated by the 'direct' pathway. PDE10A regulation of cAMP and/or cGMP signaling in the dendritic compartment of these neurons may be involved in filtering the cortico/thalamic input into the MSN. Furthermore, PDE10A may be involved in the regulation of GABA release in the substantia nigra and globus pallidus (Seeger, T. F. et al. Brain Research, 2003, 985, 113-126). Inhibition of PDE10A results in striatal activation and behavioral suppression such as dampened locomotion, inhibition of conditioned avoidance response (CAR), and activity in the rat auditory gating model, suggesting that inhibitors of phosphodiesterase type 10A represent a novel class of antipsychotic agents.

The hypotheses around the physiological role of PDE10A and the therapeutic utility of PDE10A inhibitors derive in part from studies with papaverine (J. A. Siuciak et al. loc. cit.), the first extensively profiled pharmacological tool compound for this target. The PDE10A inhibitor papaverine was shown to be active in several antipsychotic models. Papaverine potentiated the cataleptic effect of the $D_2$ receptor antagonist haloperidol in rats, but did not cause catalepsy on its own (WO 03/093499). Papaverine reduced hyperactivity in rats induced by PCP, while reduction of amphetamine-induced hyperactivity was insignificant (WO 03/093499). These models suggest that PDE10A inhibition has the classic antipsychotic potential that would be expected from theoretical considerations. Papaverine, however has significant limitations in this regard with relatively poor potency and selectivity and a very short exposure half-life after systemic administration. It was found that inhibition of PDE10A reverses subchronic PCP-induced deficits in attentional set-shifting in rats suggesting that PDE10A inhibitors might alleviate cognitive deficits associated with schizophrenia. (Rodefer et al., Eur. J. Neurosci., 4 (2005) 1070-1076).

The discovery of a new class of PDE10A inhibitors with improved potency, selectivity, and pharmacokinetic properties, provided an opportunity to further explore the physiology of PDE10A and the potential therapeutic utility of inhibiting this enzyme. The new class of inhibitors are exemplified by MP-10 (PF-2545920: 2-{4-[1-methylpyridine-4-yl-1-H-pyrazol-3-3ly]phenoxymethyl}-quinoline) and TP-10, i.e. 2-{4-[pyridine-4-yl-1-(2,2,2-trifluoroethyl)-1-H-pyrazol-3-3ly]phenoxymethyl}-quinoline. The compounds offer a therapeutic approach to the treatment of schizophrenia (see C. J. Schmidt et al., loc cit.; S. M. Grauer et al., Journal of Pharmacology and Experimental Therapeutics, fast forward DOI 10.1124 JPET 109.155994). Positive signals in rodent models of schizophrenia include the: attenuation of conditioned avoidance response (CAR), inhibition of hyperactivity caused by amphetamine-induced dopamine release or phencyclidine (PCP) mediated NMDA receptor blockade, attenuation of pharmacologically impaired social or object recognition, and antagonism of apomorphine-induced climbing. Taken together, these data suggest a broad suppression of all 3 symptoms clusters (positive symptoms, negative symptoms & cognitive dysfunctions) linked to schizophrenia (see C. J. Schmidt et al., loc cit.; S. M. Grauer et al., loc. cit).

Beyond schizophrenia, selective PDE10 inhibitors may have the potential for the treatment of Huntington's disease (S. H. Francis et al., Physiol. Rev., 91 (2011) 651-690) and they may be a therapeutic option for substance abuse disorders (F. Sotty et al., J. Neurochem., 109 (2009) 766-775). Furthermore, it has been suggested that PDE10A inhibitors may be useful for treatment of obesity and non-insulin dependent diabetes (see e.g. WO 2005/120514, WO 2005/012485, Cantin et al, Bioorganic & Medicinal Chemistry Letters 17 (2007) 2869-2873).

In summary, inhibitors of PDE10A offer a promising therapeutic approach to the treatment or prevention of neurological and psychiatric disorders, in particular schizophrenia and related disorders, including symptoms linked to schizophrenia such as cognitive dysfunction.

Several classes of compounds which are inhibitors of PDE10A have been described in the art, the recent compound groups are:

Pyrido[3,2-e]pyridazines—see WO 2007/137819, WO 2007/137820, WO 2009/068246, WO 2009/068320, WO 2009/070583 and WO 2009/070584;

4-substituted phthalazines and quinazolines WO 2007/085954, WO 2007/022280, WO 2007/096743, WO 2007/103370, WO 2008/020302, WO 2008/006372 and WO 2009/036766;

4-substituted cinnazolines—see WO 2006/028957, WO 2007/098169, WO 2007/098214, WO 2007/103554, WO 2009/025823 and WO 2009/025839;

Isoquinolines and isoquinolinones—see WO 2007/100880 and WO 2009/029214

MP10 and MP10 like compounds: US 2007/0155779, WO 2008/001182 and WO 2008/004117; and Benzodiazepines—see WO 2007/082546.

For a further review see also T. Chappie et al. Current Opinion in Drug Discovery & Development 12(4), (2009) 458-467) and the literature cited therein.

Although some of the compounds of prior art are known to inhibit PDE10A effectively having $IC_{50}$ values of less than 50 nM, there is still an ongoing need for compounds which inhibit PDE10A. In particular, there is an ongoing need for compounds which have one of the following characteristics:

i. Selective inhibition of PDE10A, in particular vis-à-vis inhibition of the other ten phosphodiesterase families PDE1-9, 11 and their different gene variants; suitable selectivity with regard to molecular receptors, transporters channels, enzymes or other biomolecules whose interaction with the PDE10A ligand might cause undesired side effects;

ii. metabolic stability, in particular microsomal stability, e.g. measured in vitro, in liver microsomes from various species (e.g. rat or human) in human cells, such as hepatocytes;

iii. no or only low inhibition of cytochrome P450 (CYP) enzymes: cytochrome P450 (CYP) is the name for a superfamily of heme proteins having enzymatic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythromycin) are used at the same time as medicinal substances which are degraded by this enzyme system and thus compete for the same binding site on the enzyme, the degradation thereof may be slowed down and thus effects and side effects of the administered medicinal substance may be undesirably enhanced;

iv. a suitable solubility in water (in mg/ml);

v. suitable pharmacokinetics (time course of the concentration of the compound of the invention in plasma or in tissue, for example brain). The pharmacokinetics can be described by the following parameters: half-life, volume of distribution (in $l \cdot kg^{-1}$), plasma clearance (in $l \cdot h^{-1} \cdot kg^{-1}$), AUC (area under the curve, area under the concentration-time curve (in $ng \cdot h \cdot l^{-1}$), oral bioavailability, (the dose-normalized ratio of AUC after oral administration and AUC after intravenous administration), the so-called brain-plasma ratio (the ratio of AUC in brain tissue and AUC in plasma);

vi. no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radiolabelled dofetilide which is described in the literature (G. J. Diaz et al., Journal of Pharmacological and Toxicological Methods, 50 (2004), 187-199). A smaller IC50 in this dofetilide assay means a greater probability of potent hERG blockade. In addition, the blockade of the hERG channel can be measured by electrophysiological experiments on cells which have been transfected with the hERG channel, by so-called whole-cell patch clamping (G. J. Diaz et al., Journal of Pharmacological and Toxicological Methods, 50 (2004), 187-199).

vii. high free fraction in brain, i.e. the fraction of the compound bound to proteins should be low.

viii. low lipophilicity.

BRIEF DESCRIPTION OF THE INVENTION

The present invention is thus based on the object of providing compounds which inhibit PDE10A at low concentrations.

The compounds are further intended to display at least one of the properties i. to viii. mentioned above, in particular high selectivity with regard to inhibition of PDE10A, high selectivity vis-à-vis other phosphodiesterases such as, enhanced metabolic stability, in particular microsomal and/or cytosolic stability, low affinity to the HERG receptor, low inhibition of cytochrome P450 (CYP) enzymes, suitable solubility in water and suitable pharmacokinetics.

This object and further objects are achieved by the compounds of the general formula I described below, the N-oxides, the prodrugs, the hydrates and the tautomers thereof and the pharmaceutically suitable salts thereof:

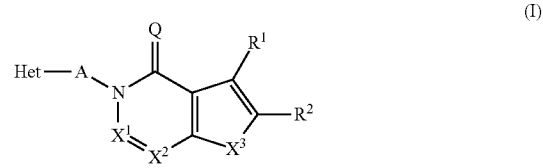

(I)

wherein

Q is O or S;

$X^1$ is N or CH;

$X^2$ is N or C—$R^7$;

$X^3$ is O, S, —$X^4$=C($R^8$)—, where C($R^8$) is bound to the carbon atom which carries $R^2$ or —$X^5$=C($R^9$)—, where $X^5$ is bound to the carbon atom which carries $R^2$;

$X^4$ is N or C—$R^9$;

$X^5$ is N;

Het is selected from i. monocyclic hetaryl having 1 or 2 nitrogen atoms and optionally a further heteroatom selected from O, S and N as ring members, which is unsubstituted or may carry 1, 2, 3 or 4 identical or different substituents $R^x$, ii. fused bicyclic hetaryl having 1 or 2 nitrogen atoms and optionally a further heteroatom selected from O, S and N as ring members, benzothienyl or benzofuryl, where bicyclic hetaryl, benzothienyl and benzofuryl are, independently of each other, unsubstituted or may carry 1, 2, 3 or 4 identical or different substituents $R^x$, and iii. phenyl, which carries a monocyclic hetaryl radical having 1 or 2 nitrogen atoms and optionally a further heteroatom selected from O, S and N as ring members, which in addition to monocyclic hetaryl, may carry 1, 2 or 3 identical or different substituents $R^x$, where $R^x$ is selected from the group consisting of H, halogen, $C_1$-$C_4$-alkyl, $C_1$-$C_4$-alkoxy, $C_1$-$C_4$-fluoroalkyl, $C_1$-$C_4$-fluoroalkoxy, $C_3$-$C_6$-cycloalkyl, $C_1$-$C_4$-alkoxy-$C_1$-$C_4$-alkoxy, $C_1$-$C_4$-alkoxy-$C_1$-$C_4$-alkyl, OH, hydroxy-$C_1$-$C_4$-alkyl, O—$C_3$-$C_6$-cycloalkyl, benzyloxy, C(O)O—($C_1$-$C_4$-alkyl), O—($C_1$-$C_4$- alkyl)-CO₂H, N(R^{x1})(R^{x2}), C(O)N(R^{x1})(R^{x2}), C₁-C₄-alkyl-N(R^{x1})(R^{x2}), —NR^{x3}—C(O)—N(R^{x1})(R^{x2}), NR^{x3}—C(O)O—(C₁-C₄-alkyl), —N(R^{x3})—SO₂—R^{x4}, phenyl, CN, —SF₅, —OSF₅, —SO₂R^{x4}, —SR^{x4} and trimethylsilyl, where R^{x1}, R^{x2}, R^{x3} and R^{x4}, independently of each other are selected from the group consisting of hydrogen, C₁-C₄-alkyl, C₁-C₄-fluoroalkyl and C₃-C₆-cycloalkyl or R^{x1} and R^{x2} form together with the N atom to which they are attached a 3- to 7-membered, nitrogen heterocycle which may have 1, 2 or 3 further different or identical heteroatoms or heteroatom containing groups selected from the group of O, N, S, SO and SO₂ as ring members and which may carry 1, 2, 3, 4, 5 or 6 substituents selected from C₁-C₄-alkyl, or two radicals R^x which are bound at adjacent carbon atoms may form a fused 5- or 6-membered saturated carbocyclic radical or a fused 5- or 6-membered heterocyclic radical having 1, 2 or 3 heteroatoms as ring members, which are selected from O, S and N;

is selected from the group consisting of hydrogen, halogen, OH, C₁-C₄-alkyl, trimethylsilyl, C₁-C₄-alkylsulfanyl, C₁-C₄-alkoxy-C₁-C₄-alkyl, C₁-C₄-alkoxy, C₁-C₄-alkoxy-C₁-C₄-alkoxy, C₁-C₄-alkylsulfanyl-C₁-C₄-alkoxy, C₂-C₄-alkenyloxy, C₁-C₄-fluoroalkyl, C₁-C₄-fluoroalkoxy, cyclopropyl, optionally substituted by 1, 2 or 3 methyl groups, fluorinated cyclopropyl, CN, NR^{x1}R^{x2}, NR^{x1}R^{x2}—C₁-C₄-alkoxy and the moiety Y¹-Cyc¹;

R² is selected from the group consisting of hydrogen, halogen, OH, C₁-C₄-alkyl, trimethylsilyl, C₁-C₄-alkoxy-C₁-C₄-alkyl, C₁-C₄-alkoxy, C₁-C₄-alkoxy-C₁-C₄-alkoxy, C₂-C₄-alkenyloxy, C₁-C₄-fluoroalkyl, C₁-C₄-fluoroalkoxy, cyclopropyl, optionally substituted by 1, 2 or 3 methyl groups, fluorinated cyclopropyl, CN and NR^{x1}R^{x2};

A represents one of the following groups A¹, A², A³; A⁴ or A⁵:

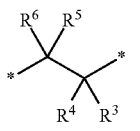
(A¹)

*≡* (A²)

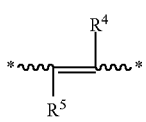
(A³)

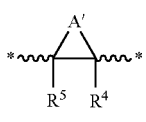
(A⁴)

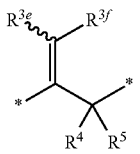
(A⁵)

where * indicates the points of attachment to Het and to the nitrogen atom, respectively;

R³, R⁴, R⁵, R⁶ independently of each other are selected from the group consisting of hydrogen, halogen, C₁-C₄-alkyl, trimethylsilyl, C₁-C₄-fluoroalkyl, C₁-C₄-fluoroalkoxy, C₃-C₆-cycloalkyl, or the radicals together with the carbon atoms to which they are bound form a saturated 3- to 6-membered carbocycle or a saturated 3- to 6-membered heterocycle having 1 or 2 non-adjacent heteroatoms as ring members, where the carbocycle and the heterocycle are unsubstituted or may carry 1, 2, 3 or 4 substituents selected from fluorine and methyl or either the radicals R³, R⁴ or the radicals R⁵, R⁶ together with the carbon atom to which they are bound form a saturated 3- to 6-membered carbocycle or a saturated 3- to 6-membered heterocycle having 1 or 2 non-adjacent heteroatoms as ring members, where the carbocycle and the heterocycle are unsubstituted or may carry 1, 2, 3 or 4 substituents selected from fluorine and methyl;

A' is a O, NR^{3a}, CR^{3b}R^{3c} or linear C₂-C₃-alkandiyl, where one of the CH₂-moieties of C₂-C₃-alkandiyl may be replaced by oxygen or NR^{3a}, and where 1, 2, 3, or 4 of the hydrogen atoms of C₂-C₃-alkandiyl may be replaced by a radical R^{3d}, where R^{3a} is hydrogen or C₁-C₄-alkyl, R^{3b}, R^{3c} independently of each other are selected from the group consisting of hydrogen, halogen, C₁-C₄-alkyl or R^{3b} and R^{3c} together form C₂-C₃-alkandiyl;

R^{3d} is selected from the group consisting of halogen and C₁-C₄-alkyl;

R^{3e}, R^{3f} independently of each other are selected from the group consisting of hydrogen and C₁-C₄-alkyl;

R⁷ is selected from the group consisting of hydrogen, halogen, OH, C₁-C₄-alkyl, trimethylsilyl, C₁-C₄-alkylsulfanyl, C₁-C₄-alkoxy-C₁-C₄-alkyl, C₁-C₄-alkoxy, C₁-C₄-alkoxy-C₁-C₄-alkoxy, C₁-C₄-alkylsulfanyl-C₁-C₄-alkoxy, C₂-C₄-alkenyloxy, C₁-C₄-fluoroalkyl, C₁-C₄-fluoroalkoxy, cyclopropyl, optionally substituted by 1, 2 or 3 methyl groups, fluorinated cyclopropyl, CN, NR^{x1}R^{x2}, NR^{x1}R^{x2}—C₁-C₄-alkoxy and the moiety Y²-Cyc²;

R⁸ is selected from the group consisting of hydrogen, halogen, OH, C₁-C₄-alkyl, trimethylsilyl, C₁-C₄-alkoxy-C₁-C₄-alkyl, C₁-C₄-alkoxy, C₁-C₄-alkoxy-C₁-C₄-alkoxy, C₂-C₄-alkenyloxy, C₁-C₄-fluoroalkyl, C₁-C₄-fluoroalkoxy, cyclopropyl, optionally substituted by 1, 2 or 3 methyl groups, fluorinated cyclopropyl, CN and NR^{x1}R^{x2};

R⁹ is selected from the group consisting of hydrogen, halogen, OH, C₁-C₄-alkyl, trimethylsilyl, C₁-C₄-alkylsulfanyl, C₁-C₄-alkoxy-C₁-C₄-alkyl, C₁-C₄-alkoxy, C₁-C₄-alkoxy-C₁-C₄-alkoxy, C₁-C₄-alkylsulfanyl-C₁-C₄-alkoxy, C₂-C₄-alkenyloxy, C₁-C₄-fluoroalkyl, C₁-C₄-fluoroalkoxy, cyclopropyl, optionally substituted by 1, 2 or 3 methyl groups, fluorinated cyclopropyl, CN, NR^{x1}R^{x2}, NR^{x1}R^{x2}—C₁-C₄-alkoxy and the moiety Y³-Cyc³;

Y¹, Y², Y³ independently of each other are selected from a chemical bond, CH₂, O, O—CH₂, NR^y, NR^y—CH₂, NR^y—S(O)₂, S, S(O), S(O)₂, 1,2-ethandiyl, 1,2-ethendiyl or 1,2-ethyndiyl, where R^y is selected from the group consisting of hydrogen, C₁-C₄-alkyl, C₁-C₄-alkylcarbonyl, C₁-C₄-alkylsulfonyl, C₁-C₄-fluoroalkylsulfonyl;

Cyc¹, Cyc², Cyc³ independently of each other are selected from the group consisting of phenyl, naphthyl, 4- to 8-membered saturated or partially unsaturated heteromonocyclic radicals, saturated or partially unsaturated 7- to 10 membered heterobicyclic radicals, 5- or 6-membered monocyclic hetaryl, and 8- to 10 membered bicyclic hetaryl, where the saturated or partially unsaturated heteromonocyclic and heterobicyclic radicals have 1, 2, 3 or 4 heteroatoms or heteroatom containing groups as ring members, which are selected from O, S, SO, $SO_2$ and N, and where the 5- or 6-membered monocyclic hetaryl and the 8- to 10-membered bicyclic hetaryl have 1, 2, 3 or 4 heteroatoms as ring members, which are selected from O, S and N, where phenyl, naphthyl, the saturated or partially unsaturated heteromonocyclic and heterobicyclic radicals and the mono and bicyclic heteroaromatic radicals are unsubstituted or carry 1, 2, 3, 4 or 5 radicals $R^{C1}$ or one radical $Y'$—$R^{C2}$ and 0, 1, 2, 3 or 4 radicals $R^{C1}$;

where $R^{C1}$ is selected from hydrogen, halogen, OH, CN, $NO_2$, $C_1$-$C_4$-alkyl, $C_1$-$C_4$-alkoxy, $C_1$-$C_4$-alkylsulfanyl, hydroxy-$C_1$-$C_4$-alkyl, $C_1$-$C_4$-alkoxy-$C_1$-$C_4$-alkyl, $C_1$-$C_4$-alkoxy-$C_1$-$C_4$-alkoxy, cyano-$C_1$-$C_4$-alkyl, $C_1$-$C_4$-fluoroalkyl, $C_1$-$C_4$-fluoroalkoxy, $C_1$-$C_4$-alkylsulfonyl, C(O)$R^a$, Z—C(O)$OR^b$, Z—C(O)$NR^cR^d$, S(O)$_2NR^cR^d$ and Z—$NR^eR^f$, where $R^a$ is selected from the group consisting of $C_1$-$C_4$-alkyl and $C_1$-$C_4$-fluoroalkyl, $R^b$ is selected from the group consisting of hydrogen, $C_1$-$C_4$-alkyl, $C_2$-$C_4$-alkenyl and $C_1$-$C_4$-fluoroalkyl, $R^c$, $R^d$ is selected from the group consisting of hydrogen, $C_1$-$C_4$-alkyl, $C_1$-$C_4$-fluoroalkyl, $C_1$-$C_4$-alkoxy and $C_1$-$C_4$-fluoroalkoxy, $R^e$, $R^f$ is selected from the group consisting of hydrogen, $C_1$-$C_4$-alkyl, $C_1$-$C_4$-fluoroalkyl, $C_1$-$C_4$-alkoxy and $C_1$-$C_4$-fluoroalkoxy, Z is a covalent bond or $C_1$-$C_4$-alkandiyl, or two radicals $R^{C1}$ which are bound at adjacent carbon atoms may form a fused 5- or 6-membered carbocyclic radical or a fused 5- or 6-membered heterocyclic radical having 1, 2 or 3 heteroatoms as ring members, which are selected from O, S and N;

or two radicals $R^{C1}$ which are bound at the same carbon atom may form a spiro 5- or 6-membered carbocyclic radical or a spiro 5- or 6-membered heterocyclic radical having 1 or 2 heteroatoms as ring members, which are selected from O, S and N, or two radicals $R^{C1}$ which are bound at the same carbon atom may form an oxygen atom, where the fused and the spiro radicals are unsubstituted or carry 1, 2, 3 or 4 radicals $R^{C3}$;

Y' is a chemical bond, $CH_2$, O, O—$CH_2$, S(O)$_2$, $NR^{3"}$, $NR^{3"}$—$CH_2$ or $NR^{3"}$—S(O)$_2$, where $R^{3"}$ is selected from the group consisting of hydrogen, $C_1$-$C_4$-alkyl, $C_1$-$C_4$-alkylcarbonyl, $C_1$-$C_4$-alkylsulfonyl, $C_1$-$C_4$-fluoroalkylsulfonyl;

$R^{C2}$ is a carbocyclic or heterocyclic radical selected from the group consisting of phenyl, 3- to 7-membered saturated or partially unsaturated monocarbocyclic radicals, 3- to 7-membered saturated or partially unsaturated heteromonocyclic radicals, having 1, 2 or 3 heteroatoms as ring members, which are selected from O, S and N, and 5- or 6-membered heteroaromatic radicals, having 1, 2 or 3 heteroatoms as ring members, which are selected from O, S and N, where the carbocyclic and the heterocyclic radical is unsubstituted or carries 1, 2, 3, 4 or 5 radicals $R^{C3}$;

$R^{C3}$ is selected from hydrogen, halogen, OH, CN, $C_1$-$C_4$-alkyl, $C_1$-$C_4$-alkoxy, hydroxy-$C_1$-$C_4$-alkyl, $C_1$-$C_4$-alkoxy-$C_1$-$C_4$-alkyl, cyano-$C_1$-$C_4$-alkyl, $C_1$-$C_4$-fluoroalkyl, $C_1$-$C_4$-fluoroalkoxy, $C_2$-$C_6$-alkenyl, C(O)$R^a$, benzyl, Z—C(O)$OR^b$, Z—C(O)$NR^cR^d$, S(O)$_2NR^cR^d$ and Z—$NR^eR^f$, where, Z, $R^a$, $R^b$, $R^c$, $R^d$, $R^e$ and $R^f$ are as defined above or two radicals $R^{C3}$ which are bound at the same atom may form an oxygen atom;

provided that for $X^3$ being O or S, at least one of the radicals $R^1$ and $R^7$ is a moiety $Y^1$-$Cyc^1$ or $Y^2$-$Cyc^2$, respectively;

further provided that for $X^3$ being $X^4$=C($R^8$), one or two of the radicals $R^1$, $R^7$ and $R^9$ are a moiety $Y^1$-$Cyc^1$, $Y^2$-$Cyc^2$ or $Y^3$-$Cyc^3$, respectively;

further provided that for $X^3$ being $X^5$=C($R^9$), one or two of the radicals $R^1$, $R^7$ and $R^9$ are a moiety $Y^1$-$Cyc^1$, $Y^2$-$Cyc^2$ or $Y^3$-$Cyc^3$, respectively;

and the N-oxides, the prodrugs, the tautomers and the hydrates thereof, and the pharmaceutically acceptable salts thereof.

The present invention therefore relates to the compounds of the general formula I, their tautomers, the hydrates thereof, the pharmaceutically suitable salts of the compounds of formula I, the prodrugs of the compounds of formula I and the pharmaceutically suitable salts of said prodrugs, tautomers or hydrates of the compounds of formula I.

The compounds of the formula I, their salts, their prodrugs, their hydrates and their tautomers effectively inhibit PDE10A even at low concentrations. They are additionally distinguished by a high selectivity in relation to the inhibition of the PDE10A vis-à-vis inhibition of other phosphodiesterase, such as PDE3 or PDE4. The compounds of the invention may additionally have one or more of the properties ii. to viii. mentioned above.

The compounds of the formula I, their salts, their prodrugs, their hydrates and their tautomers are therefore particularly suitable for treating disorders and conditions in creatures, especially human creatures, which can be treated or controlled by inhibition of phosphodiesterase type 10A.

The invention therefore also relates to the use of carboxamide compounds of the formula I, their tautomers, their hydrates and their pharmaceutically suitable salts for the manufacture of a medicament, in particular of a medicament which is suitable for the treatment of a disorder or a condition which can be treated by inhibition of phosphodiesterase type 10A.

The invention further relates to a medicament, in particular a medicament which is suitable for the treatment of a disorder or a condition which can be treated by inhibition of phosphodiesterase type 10A. The medicament comprises at least one compound of the formula I, as described herein, or a tautomer, or a hydrate or a prodrug of said compound I, or a pharmaceutically suitable salt of the compound of the formula I or a pharmaceutically suitable salt of the tautomer, the hydrate or the prodrug of compound of the formula I.

DETAILED DESCRIPTION OF THE INVENTION

The terms "compound of the formula I" and "compounds I" are used as synonyms.

The term "prodrugs" means compounds which are metabolized in vivo to the compounds I of the invention. Typical examples of prodrugs are described in C. G. Wermuth (editor): The Practice of Medicinal Chemistry, Academic Press, San Diego, 1996, pages 671-715. These include for example phosphates, carbamates, amino acids, esters, amides, peptides, ureas and the like. Suitable prodrugs in the present case may be for example derivatives of those compounds I carrying an OH or $NH_2$-group, where the OH or $NH_2$-group forms an ester/amide/peptide linkage, i.e. where one of the hydrogen atoms of the OH or $NH_2$-group is substituted by a $C_1$-$C_4$-alkylcarbonyl group, e.g. by acetyl, propionyl, n-propylcarbonyl, isopropylcarbonyl, n-butylcarbonyl or tert-butylcarbonyl (pivaloyl), by benzoyl, or by an acyl group derived from an amino acid, e.g. glycine, alanine, serine, phenylalanine and the like, which is linked to the oxygen or nitrogen of the OH or $NH_2$-group via the carbonyl group of the amino acid. Further suitable prodrugs are alkylcarbonyloxyalkyl carbonates or carbamates of compounds I carrying an OH- or $NH_2$-group in which one of the hydrogen atoms of the OH- or $NH_2$-group has been replaced by a group of the formula —C(=O)—O—CHR$^p$—O—C(=O)—R$^q$ in which R$^p$ and R$^q$ are independently of one another $C_1$-$C_4$-alkyl. Such carbonates and carbamates are described for example in J. Alexander, R. Cargill, S. R. Michelson, H. Schwam, J. Medicinal Chem. 1988, 31(2), 318-322. These groups can then be eliminated under metabolic conditions and result in compounds I. Therefore, said prodrugs and their pharmaceutically acceptable salts are also part of the invention.

The term "pharmaceutically acceptable salts" refers to cationic or anionic salts compounds, wherein the counter ion is derived from pharmaceutically acceptable non-toxic bases or acids including inorganic or organic bases and inorganic or organic acids.

When the compound of formula I or its prodrug or N-oxide is acidic, salts may be prepared from pharmaceutically acceptable non-toxic bases, including inorganic and organic bases. Salts derived from inorganic bases include salts, wherein the counter ion is aluminium, ammonium, calcium, copper, ferric, ferrous, lithium, magnesium, manganic, manganous, potassium, sodium, zinc ion and the like. Particularly preferred are the ammonium, calcium, magnesium, potassium, and sodium ions. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, dibenzylethylene-diamine, diethylamine, 2-diethylamino-ethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of formula I or its prodrug or N-oxide is basic, salts may be prepared from pharmaceutically acceptable non-toxic acids, including inorganic and organic acids. Such acids include acetic, trifluoroacetic acid, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of formula I are meant to also include the pharmaceutically acceptable salts.

The compounds of the invention may be in the form of a mixture of diastereomers, or of a mixture of diastereomers in which one of the two diastereomers is enriched, or of essentially diastereomerically pure compounds (diastereomeric excess de>90%). The compounds are preferably in the form of essentially diastereomerically pure compounds (diastereomeric excess de>90%). The compounds I of the invention may furthermore be in the form of a mixture of enantiomers (for example as racemate), of a mixture of enantiomers in which one of the two enantiomers is enriched, or essentially in enantiomerically pure compounds (enantiomeric excess ee>90%). It is preferred to employ the compounds enantiomerically pure or diastereomerically pure.

The present invention moreover relates to compounds as defined herein, wherein one or more of the atoms depicted in formula I have been replaced by its stable, preferably non-radioactive isotope (e.g., hydrogen by deuterium, $^{12}$C by $^{13}$C, $^{14}$N by $^{15}$N, $^{16}$O by $^{18}$O) and preferably wherein at least one hydrogen atom has been replaced by a deuterium atom. Of course, the compounds according to the invention contain more of the respective isotope than this naturally occurs and thus is anyway present in the compounds I.

The compounds of the formula I and their salts in the solid form may exist in more than one crystal structure (polymorphism), and may also be in the form of hydrates or other solvates. The present invention includes any polymorph of the compound I or its salt as well as any hydrate or other solvate.

In the context of the present description, unless stated otherwise, the terms "alkyl", "alkenyl", "alkoxy", "alkenyloxy", "fluoroalkyl", "fluoroalkoxy", "cycloalkyl", "fluorinated cycloalkyl", "alkylene", "alkandiyl", "hetaryl" and radicals derived therefrom, such as "alkylcarbonyl", "alkylsulfanyl", "alkylsulfonyl", "fluoroalkylsulfonyl", "hydroxyalkyl", "cyanoalkyl", "alkoxyalkyl", "alkoxyalkoxy", "alkylsulfanylalkyl", "alkylsulfanylalkoxy" and "hetarylmethyl" represent groups of individual radicals. The groups of noncyclic radicals "alkyl", "alkenyl", "alkoxy", "alkenyloxy", "fluoroalkyl", "fluoroalkoxy", "alkylene", "alkandiyl", and the groups of radicals derived therefrom always include both unbranched and branched "alkyl", "alkenyl", "alkoxy", "alkenyloxy", "fluoroalkyl", "fluoroalkoxy", "alkylene" and "alkandiyl", respectively.

The prefix $C_n$-$C_m$-indicates the respective number of carbons in the hydrocarbon unit. Unless indicated otherwise, fluorinated substituents preferably have one to five identical or different fluorine atoms.

The term "halogen" designates in each case, fluorine, bromine, chlorine or iodine, specifically fluorine, chlorine or bromine.

Examples of other meanings are:

Alkyl, and the alkyl moieties for example in alkylcarbonyl, alkylsulfanyl, alkylsulfonyl, alkylsulfanylalkyl and alkylsulfanylalkoxy: saturated, straight-chain or branched hydrocarbon radicals having one or more C atoms, e.g. 1 to 4 carbon atoms, e.g. $C_1$-$C_4$-alkyl such as methyl, ethyl, propyl, 1-methylethyl, n-butyl, 1-methylpropyl, 2-methylpropyl and 1,1-dimethylethyl.

Fluoroalkyl and the fluoroalkyl moieties for example in fluoroalkylsulfonyl: an alkyl radical having ordinarily 1 to 4 C atoms, in particular 1 or 2 C-atoms ($C_1$-$C_2$-fluoroalkyl) as mentioned above, whose hydrogen atoms are partly or completely replaced by fluorine atoms such as fluoromethyl, difluoromethyl, trifluoromethyl, 2-fluoroethyl, 2,2-difluoroethyl, 2,2,2-trifluoroethyl, pentafluoroethyl, 2-fluoro-1-methylethyl, 2,2-difluoro-1-methylethyl, 2,2-trifluoro-1-methylethyl, 2-fluoropropyl, 3-fluoropropyl, 2,2-difluoropropyl, 2,3-difluoropropyl, 3,3,3-trifluoropropyl, 2,3,3,3-pentafluoropropyl, heptafluoropropyl, 1-(fluoromethyl)-2-fluoroethyl, 4-fluorobutyl, and nonafluorobutyl.

Cycloalkyl, and the cycloalkyl moieties for example in cycloalkoxy or cycloalkyl-$C_1$-$C_4$-alkyl: monocyclic, saturated hydrocarbon groups having three or more C atoms, e.g. 3, 4, 5, 6 or 7 carbon ring members, such as cyclopropyl, cyclobutyl, cyclopentyl, cyclohexyl and cycloheptyl.

Fluorinated cycloalkyl: monocyclic, saturated hydrocarbon groups having three or more C atoms, e.g. 3, 4, 5, 6 or 7 carbon ring members, such as cyclopropyl, cyclobutyl, cyclopentyl, cyclohexyl and cycloheptyl, wherein at least one, e.g. 1, 2, 3, 4, 5 or 6 of the hydrogen atoms are replaced by fluorine atoms, examples including 1-fluorocyclopropyl, 2-fluorocyclopropyl, 2,2-difluorocyclopropyl, 1,2-difluorocyclopropyl, 2,3-difluorocyclopropyl, etc.

Cycloalkoxy: a cycloalkyl radical as defined above which is linked via an oxygen atom, e.g. cyclopropyloxy, cyclobutyloxy, cyclopentyloxy or cyclohexyloxy.

Cycloalkylalkyl: a cycloalkyl radical as defined above which is linked via an alkylene group, in particular via a methylene, 1,1-ethylene or 1,2-ethylene group, e.g. cyclopropylmethyl, cyclobutylmethyl, cyclopentylmethyl or cyclohexylmethyl.

Alkenyl, and alkenyl moieties for example in alkenyloxy: monounsaturated, straight-chain or branched hydrocarbon radicals having two or more C atoms, e.g. 2 to 4 carbon atoms and one C=C-double bond in any position, e.g. $C_2$-$C_4$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl.

Alkoxy or alkoxy moieties for example in alkoxyalkyl and alkoxyalkoxy:
an alkyl radical as defined above having preferably 1 to 4 C atoms, which is connected to the remainder of the molecule via an O atom: e.g. methoxy, ethoxy, n-propoxy, 1-methylethoxy, butoxy, 1-methylpropoxy, 2-methylpropoxy or 1,1-dimethylethoxy.

Fluoroalkoxy: alkoxy as described above, in which the hydrogen atoms of these groups are partly or completely replaced by fluorine atoms, i.e. for example $C_1$-$C_4$-fluoroalkoxy, in particular $C_1$-$C_2$-fluoroalkoxy, such as fluoromethoxy, difluoromethoxy, trifluoromethoxy, 2-fluoroethoxy, 2,2-difluoroethoxy, 2,2,2-trifluoroethoxy, pentafluoroethoxy, 2-fluoropropoxy, 3-fluoropropoxy, 2,2-difluoropropoxy, 2,3-difluoropropoxy, 3,3,3-trifluoropropoxy, 2,2,3,3,3-pentafluoropropoxy, heptafluoropropoxy, 1-(fluoromethyl)-2-fluoroethoxy, specifically fluoromethoxy, difluoromethoxy, trifluoromethoxy, 2-fluoroethoxy, or 2,2,2-trifluoroethoxy.

Hydroxyalkyl: an alkyl radical ordinarily having 1 to 4 C atoms, in which one hydrogen atom is replaced by an OH radical. Examples thereof are $CH_2$—OH, 1-hydroxyethyl, 2-hydroxyethyl, 1-hydroxypropyl, 2-hydroxypropyl, 1-methyl-1-hydroxyethyl, 1-methyl-2-hydroxyethyl, 3-hydroxypropyl, 2-hydroxybutyl, 3-hydroxybutyl, 4-hydroxybutyl, 1-methyl-2-hydroxypropyl, 1,1-dimethyl-2-hydroxyethyl, 1-methyl-1-hydroxypropyl etc.

Cyanoalkyl: an alkyl radical ordinarily having 1 to 4 C atoms, in which one hydrogen atom is replaced by a CN radical. Examples thereof are $CH_2$—CN, 1-cyanoethyl, 2-cyanoethyl, 1-cyanopropyl, 2-cyanopropyl, 1-methyl-1-cyanoethyl, 1-methyl-2-cyanoethyl, 3-cyanopropyl, 2-cyanobutyl, 3-cyanobutyl, 4-cyanobutyl, 1-methyl-2-cyanopropyl, 1,1-dimethyl-2-cyanoethyl, 1-methyl-1-cyanopropyl etc.

Alkoxyalkyl: an alkyl radical ordinarily having 1 to 4 C atoms, in which one hydrogen atom is replaced by an alkoxy radical ordinarily having 1 to 4 C atoms. Examples thereof are $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl, etc.

Alkoxyalkoxy: an alkoxyalkyl radical as defined above ordinarily having 1 to 4 C atoms both in the alkoxy and the alkyl moiety which is connected to the remainder of the molecule via an O atom: Examples thereof are $OCH_2$—$OCH_3$, $OCH_2$—$OC_2H_5$, n-propoxymethoxy, $OCH_2$—$OCH(CH_3)_2$, n-butoxymethoxy, (1-methylpropoxy)methoxy, (2-methylpropoxy)methoxy, $OCH_2$—$OC(CH_3)_3$, 2-(methoxy)ethoxy, 2-(ethoxy)ethoxy, 2-(n-propoxy)ethoxy, 2-(1-methylethoxy)ethoxy, 2-(n-butoxy)ethoxy, 2-(1-methylpropoxy)ethoxy, 2-(2-methylpropoxy)ethoxy, 2-(1,1-dimethyl-ethoxy)ethoxy, etc.

Alkylcarbonyl: alkyl as defined above preferably having 1 to 4 C atoms, which is connected via a carbonyl group to the remainder of the molecule, e.g. acetyl, propionyl, butyryl, isobutyryl, pentanoyl, pivaloyl and the like.

Alkylsulfanyl and the alkylsulfanyl radicals in alkylsulfanylalkyl and alkylsulfanylalkoxy: alkyl as defined above preferably having 1 to 4 C atoms, which is connected via an S atom to the remainder of the molecule, e.g. methylsulfanyl, ethylsulfanyl, n-propylsulfanyl and the like.

Alkylsulfonyl: alkyl as defined above preferably having 1 to 4 C atoms, which is connected via an $SO_2$ group to the remainder of the molecule, e.g. methylsulfonyl, ethylsulfonyl, n-propylsulfonyl and the like.

Fluoroalkylsulfanyl: fluoroalkyl as defined above preferably having 1 to 4 C atoms, which is connected via an S atom to the remainder of the molecule, e.g. fluoromethylsulfanyl, difluoromethylsulfanyl, trifluoromethylsulfanyl, 2-fluoroethylsulfanyl, 2,2-difluoroethylsulfanyl, 2,2,2-trifluoroethylsulfanyl, pentafluoroethylsulfanyl, 2-fluoropropylsulfanyl, 3-fluoropropylsulfanyl, 2,2-difluoropropylsulfanyl, 2,3-difluoropropylsulfanyl, and heptafluoropropylsulfanyl.

Fluoroalkylsulfonyl: fluoroalkyl as defined above preferably having 1 to 4 C atoms, which is connected via an $SO_2$ group to the remainder of the molecule, e.g. fluoromethylsulfonyl, difluoromethylsulfonyl, trifluoromethylsulfonyl, 2-fluoroethylsulfonyl, 2,2-difluoroethylsulfonyl, 2,2,2-trifluoroethylsulfonyl, pentafluoroethylsulfonyl, 2-fluoropropylsulfonyl, 3-fluoropropylsulfonyl, 2,2-difluoropropylsulfonyl, 2,3-difluoropropylsulfonyl, and heptafluoropropylsulfonyl.

Alkylsulfanylalkyl: an alkyl radical ordinarily having 1 to 4 C atoms, in which one hydrogen atom is replaced by an alkylsulfanyl radical ordinarily having 1 to 4 C atoms. Examples thereof are $CH_2$—$SCH_3$, $CH_2$—$SC_2H_5$, n-propylsulfanylmethyl, $CH_2$—$SCH(CH_3)_2$, n-butylsulfanylmethyl, (1-methylpropsulfanyl)methyl, (2-methylpropsulfanyl)methyl, $CH_2$—$OC(CH_3)_3$, 2-(methylsulfanyl)ethyl, 2-(ethylsulfanyl)ethyl, 2-(n-propylsulfanyl)ethyl, 2-(1-methylethylsulfanyl)ethyl, 2-(n-butylsulfanyl)ethyl, 2-(1-methylpropylsulfanyl)ethyl, 2-(2-methylpropylsulfanyl)ethyl, 2-(1,1-dimethylethylsulfanyl)ethyl, 2-(methylsulfanyl)propyl, 2-(ethylsulfanyl)propyl, 2-(n-propylsulfanyl)propyl, 2-(1-methylethylsulfanyl)propyl, 2-(n-butylsulfanyl)propyl, 2-(1-methylpropylsulfanyl)propyl, 2-(2-methylpropylsulfanyl)propyl, 2-(1,1-dimethylethylsulfanyl)propyl, 3-(methylsulfanyl)propyl, 3-(ethylsulfanyl)propyl, 3-(n-propylsulfanyl)propyl, 3-(1-methylethylsulfanyl)propyl, 3-(n-butylsulfanyl)propyl, 3-(1-methylpropylsulfanyl)propyl, 3-(2-methylpropylsulfanyl)propyl, 3-(1,1-dimethylpropylsulfanyl)propyl, 2-(methylsulfanyl)butyl, 2-(ethylsulfanyl)butyl, 2-(n-propylsulfanyl)butyl, 2-(1-methylethylsulfanyl)butyl, 2-(n-butylsulfanyl)butyl, 2-(1-methylpropylsulfanyl)butyl, 2-(2-methylpropylsulfanyl)butyl, 2-(1,1-dimethylethylsulfanyl)butyl, 3-(methylsulfanyl)butyl, 3-(ethylsulfanyl)butyl, 3-(n-propylsulfanyl)butyl, 3-(1-methylethylsulfanyl)butyl, 3-(n-butylsulfanyl)butyl, 3-(1-methylpropylsulfanyl)butyl, 3-(2-methylpropylsulfanyl)butyl, 3-(1,1-dimethyl-ethylsulfanyl)butyl, 4-(methylsulfanyl)butyl, 4-(ethylsulfanyl)butyl, 4-(n-propylsulfanyl)butyl, 4-(1-methylethylsulfanyl)butyl, 4-(n-butylsulfanyl)butyl, 4-(1-methylpropylsulfanyl)butyl, 4-(2-methylpropylsulfanyl)butyl, 4-(1,1-dimethylethylsulfanyl)butyl, etc.

"Alkylen" or "Alkandiyl": a saturated hydrocarbon chain having ordinarily from 1 to 4 carbon atoms, such as methylen (—$CH_2$—), 1,2-ethylen (—$CH_2CH_2$—), 1,1-ethandiyl (—$CH(CH_3)$—), 1,2-propandiyl, 1,3-propandiyl, 1,4-butandiyl, 1,2-butandiyl, 1,3-butandiyl, 1-methyl-1,2-propandiyl, 2-methyl-1,3-propandiyl, 1-methyl-1,1-ethandiyl, 1-methyl-1,2-propandiyl etc.

Saturated or partially unsaturated 4 to 7-membered monocarbocyclic radicals include cycloalkyl as defined above and cycloalkenyl having ordinarily from 4 to 7 carbon atoms as ring members, e.g. 1-cyclobuten-1-yl, 2-cyclobutenyl, 1-cyclopentenyl, 2-cyclopentenyl, 1-cyclohexenyl, 2-cyclohexenyl, 3-cyclohexenyl, 1-cycloheptenyl, 2-cycloheptenyl, 3-cycloheptenyl.

Saturated or partially unsaturated 7 to 10-membered bicarbocyclic radicals include bicyclic carbocyclic radicals which ordinarily have from 7 to 10 carbon atoms as ring members and which are saturated or which have one or more, e.g. one or two C=C double bonds, or which include a monounsaturated carbocycle where the double bond is part of a fused benzene ring, e.g. bicyclo[2,2,1]-1-heptyl, bicyclo[2,2,1]-2-heptyl, bicyclo[2,2,1]-7-heptyl, bicyclo[3,3,0]-1-octyl, bicyclo[3,3,0]-2-octyl, bicyclo[3,3,0]-3-octyl, bicyclo[2,2,2]-1-octyl, bicyclo[2,2,2]-2-octyl, bicyclo[3,2,1]-1-octyl, bicyclo[3,2,1]-2-octyl, bicyclo[3,2,1]-6-octyl, bicyclo[3,2,1]-8-octyl, bicyclo[4,3,0]-1-nonyl, bicyclo[4,3,0]-2-nonyl, bicyclo[4,3,0]-3-nonyl, bicyclo[4,3,0]-7-nonyl, bicyclo[4,3,0]-8-nonyl, bicyclo[4,4,0]-1-decyl, bicyclo[4,4,0]-2-decyl, bicyclo[4,4,0]-3-decyl, bicyclo[2,2,1]-hept-2-en-1-yl, bicyclo[2,2,1]-hept-2-en-2-yl, bicyclo[2,2,1]-hept-2-en-5-yl, bicyclo[2,2,1]-hept-2-en-7-yl, bicyclo[2,2,2]-oct-2-en-1-yl, bicyclo[2,2,2]-oct-2-en-2-yl, bicyclo[2,2,2]-oct-2-en-5-yl, bicyclo[2,2,2]-oct-2-en-7-yl, bicyclo[3,3,0]-2-octen-1-yl, bicyclo[3,3,0]-2-octen-2-yl, bicyclo[3,3,0]-2-octen-3-yl, bicyclo[3,3,0]-2-octen-4-yl, bicyclo[3,3,0]-2-octen-5-yl, bicyclo[3,3,0]-2-octen-6-yl, bicyclo[3,3,0]-2-octen-7-yl, bicyclo[3,3,0]-2-octen-8-yl, inden-1-yl, inden-2-yl, inden-4-yl, inden-6-yl, tetrahydro-1-naphthyl, tetrahydro-2-naphthyl, tetrahydro-5-naphthyl, tetrahydro-6-naphthyl, etc.

Heterocyclyl: a heterocyclic radical which may be saturated or partly unsaturated and which may be a monocyclic heterocyclic radical ordinarily having 3, 4, 5, 6, 7 or 8 ring atoms or a heterobicyclic radical ordinarily having 7, 8, 9 or 10 ring atoms, where ordinarily 1, 2, 3 or 4, in particular 1, 2 or 3, of the ring atoms are heteroatoms such as N, S or O, or heteroatom groups such as S(=O) or S(=O)$_2$ besides carbon atoms as ring members.

Examples of saturated heteromonocycles are in particular:

Saturated heteromonocyclic radical which ordinarily has 3, 4, 5, 6 or 7 ring atoms, where ordinarily 1, 2 or 3 of the ring atoms are heteroatoms such as N, S or O, besides carbon atoms as ring members. These include for example:

C-bonded, 3- or 4-membered saturated rings such as 2-oxiranyl, 2-oxetanyl, 3-oxetanyl, 2-aziridinyl, 3-thiethanyl, 1-azetidinyl, 2-azetidinyl.

C-bonded, 5-membered saturated rings such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl.

C-bonded, 6-membered saturated rings such as:
tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl.

N-bonded, 5-membered saturated rings such as:
tetrahydropyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl.

N-bonded, 6-membered saturated rings such as:
piperidin-1-yl, hexahydropyrimidin-1-yl, hexahydropyrazin-1-yl, hexahydro-pyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl.

Unsaturated heteromonocyclic radicals which ordinarily have 4, 5, 6 or 7 ring atoms, where ordinarily 1, 2 or 3 of the ring atoms are heteroatoms such as N, S or O, besides carbon atoms as ring members. These include for example:

C-bonded, 5-membered, partially unsaturated rings such as:
2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl.

C-bonded, 6-membered, partially unsaturated rings such as:
2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4- tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl.

N-bonded, 5-membered, partially unsaturated rings such as:
2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydroöxazol-3-yl, 2,3-dihydrothiazol-3-yl.

N-bonded, 6-membered, partially unsaturated rings such as:
1,2,3,4-tetrahydropyridin-1-yl, 1,2,5,6-tetrahydropyridin-1-yl, 1,4-dihydropyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl.

Examples of saturated or partially unsaturated heterobicycles are in particular radicals corresponding to saturated or partially unsaturated bicarbocyclic radicals, wherein 1, 2 or 3 CH or $CH_2$ moieties have been replaced by N, NH, O, S, S($=$O) or S($=$O)$_2$, such as 2-oxa-6-azaspiro-[3,4]octyl, 2-azabicyclo[2.2.1]heptyl, 5-azabicyclo[2.2.1]heptyl, 2,5-diazabicyclo[2.2.1]heptyl, 3-azabicyclo[3.2.1]octyl, 8-azabicyclo[3.2.1]octyl, 3,8-diazabicyclo[3.2.1]octyl, dihydroindolyl, dihydroindolizynyl, dihydroisoindolyl, dihydroquinolinyl, dihydroisoquinolinyl, chromenyl and chromanyl.

Hetaryl: a 5- or 6-membered aromatic heteromonocyclic radical (also termed 5- or 6-membered monocyclic hetaryl) which ordinarily has 1, 2, 3 or 4 heteroatoms as ring members, which are selected from O, S and N, and which has in particular 1, 2, 3 or 4 nitrogen atoms or a heteroatom selected from oxygen and sulfur and, if appropriate, 1 or 2 nitrogen atoms as ring members besides carbon atoms as ring members and a 8- to 10-membered aromatic heterobicyclic radical (also termed 8- to 10-membered bicyclic hetaryl) which ordinarily has 1, 2, 3 or 4 heteroatoms as ring members, which are selected from O, S and N, and which has in particular 1, 2, 3 or 4 nitrogen atoms or a heteroatom selected from oxygen and sulfur and, if appropriate, 1 or 2 nitrogen atoms as ring members besides carbon atoms as ring members: for example C-bonded, 5-membered monocyclic hetaryl having 1, 2 or 3 or 4 nitrogen atoms
or a heteroatom selected from oxygen and sulfur and, if appropriate, having 1, 2 or 3 nitrogen atoms as ring members, such as:
2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl.

C-bonded, 6-membered monocyclic hetaryl having 1, 2 or 3 nitrogen atoms as ring members, such as:
pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl.

N-bonded, 5-membered heteroaromatic radicals having 1, 2, 3 or 4 nitrogen atoms as ring members, such as:
pyrrol-1-yl, pyrazol-1-yl, imidazol-1-yl, 1,2,3-triazol-1-yl, 1,2,4-triazol-1-yl, tetrazol-1-yl.

bicyclic 8 to 10-membered hetaryl, hetaryl which has one of the aforementioned 5- or 6-membered heteroaromatic rings and a further aromatic carbocycle or 5- or 6-membered heterocycle fused thereto, for example a fused benzene, thiophene, furane, pyrrole, pyrazole, imidazole, pyridine or pyrimidine ring. These bicyclic hetaryl include for example quinolinyl, isoquinolinyl, cinnolinyl, indolyl, indolizynyl, isoindolyl, indazolyl, benzofuryl, benzothienyl, benzo[b]thiazolyl, benzoxazolyl, benzthiazolyl, benzimidazolyl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl.

Hetarylalkyl: a hetaryl radical as defined above which is linked via an alkylene group, in particular via a methylene, 1,1-ethylene or 1,2-ethylene group, to the remainder of the molecule.

The expression "optionally substituted" in the context of the present invention means that the respective moiety is unsubstituted or has 1, 2 or 3, in particular 1, substituents which are selected from halogen, $C_1$-$C_4$-alkyl, $C_1$-$C_4$-haloalkyl, OH, SH, CN, $CF_3$, O—$CF_3$, COOH, O—$CH_2$—COOH, $C_1$-$C_6$-alkoxy, $C_1$-$C_4$-haloalkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—($C_1$-$C_6$-alkyl)$_2$, $SO_2N$—$(C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2$NH-phenyl, CONH-hetaryl, $SO_2$NH-hetaryl, $SO_2$-phenyl, NH—$SO_2$-phenyl, NH—CO-phenyl, NH—$SO_2$-hetaryl and NH—CO-hetaryl, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

In relation to their use as inhibitors of PDE10A, the variables Het, A, A', Q, $X^1$, $X^2$, $X^3$, $Y^1$, $Y^2$, $Y^3$, $R^1$, $R^2$, $R^3$, $R^4$, $R^5$, $R^6$, $R^7$, $R^8$, $R^9$, $Cyc^1$, $Cyc^2$ and $Cyc^3$ preferably have the following meanings, where these represent, both considered on their own and in combination with at least one other or all, special configurations of the compounds of the formula I:

In a particular embodiment, Het is unsubstituted or may carry 1, 2, 3 or 4 identical or different substituents $R^x$. In this regard, $R^x$ is selected from the group consisting of H, halogen, $C_1$-$C_4$-alkyl, $C_1$-$C_4$-alkoxy, $C_1$-$C_4$-fluoroalkyl, $C_1$-$C_4$-fluoroalkoxy, $C_3$-$C_6$-cycloalkyl, $C_1$-$C_4$-alkoxy-$C_1$-$C_4$-alkoxy, $C_1$-$C_4$-alkoxy-$C_1$-$C_4$-alkyl, OH, hydroxy-$C_1$-$C_4$-alkyl, O—$C_3$-$C_6$-cycloalkyl, benzyloxy, C(O)O—($C_1$-$C_4$-alkyl), O—($C_1$-$C_4$-alkyl)-$CO_2$H, $N(R^{x1})(R^{x2})$, $C(O)N(R^{x1})(R^{x2})$, $C_1$-$C_4$-alkyl-$N(R^{x1})(R^{x2})$, —$NR^{x3}$—C(O)—$N(R^{x1})(R^{x2})$, $NR^{x3}$—C(O)O—($C_1$-$C_4$-alkyl), —$N(R^{x3})$—$SO_2$—$R^{x4}$, phenyl, CN, —$SF_5$, —$OSF_5$, —$SO_2R^{x4}$, —$SR^{x4}$ and trimethylsilyl, where $R^{x1}$, $R^{x2}$, $R^{x3}$ and $R^{x4}$, independently of each other are selected from the group consisting of hydrogen, $C_1$-$C_4$-alkyl, $C_1$-$C_4$-fluoroalkyl and $C_3$-$C_6$-cycloalkyl or $R^{x1}$ and $R^{x2}$ form together with the N atom to which they are attached a 3- to 7-membered, nitrogen heterocycle which may have 1, 2 or 3 further different or identical heteroatoms or heteroatom containing groups selected from the group of O, N, S, SO and $SO_2$ as ring members and which may carry 1, 2, 3, 4, 5 or 6 substituents selected from $C_1$-$C_4$-alkyl.

Het is preferably selected from the group consisting of C-bound 6-membered monocyclic hetaryl, which has 1 or 2 nitrogen atoms as ring members, and C-bound, fused bicyclic hetaryl, which has 1 or 2 nitrogen atoms as ring members and optionally a further heteroatom selected from O, S and N as ring member, where monocyclic hetaryl and bicyclic hetaryl may be unsubstituted or may carry 1, 2, 3 or 4 substituents $R^x$, in particular 0, 1 or 2 substituents $R^x$. In this regard, $R^x$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, phenyl, $C_3$-$C_6$-cycloalkyl, optionally substituted by 1, 2 or 3 methyl groups, and fluorinated $C_3$-$C_6$-cycloalkyl. In this regard, $R^x$ is in particular selected from fluorine, chlorine, methyl, fluoromethyl, difluoromethyl, trifluoromethyl, methoxy, fluoromethoxy, difluoromethoxy, trifluoromethoxy, phenyl, cyclopropyl, optionally substituted by 1, 2 or 3 methyl groups, and fluorinated cyclopropyl.

In a particular embodiment of the invention, Het is selected from fused bicyclic hetaryl, which has 1 or 2 nitrogen atoms as ring members and optionally a further heteroatom selected from O, S and N as ring member and which may be unsubstituted or may carry 1, 2, 3 or 4 substituents $R^x$, in particular 0, 1 or 2 substituents $R^x$. In this regard, $R^x$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl, optionally substituted by 1, 2 or 3 methyl groups, and fluorinated $C_3$-$C_6$-cycloalkyl. In this regard, $R^x$ is in particular selected from fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

In another particular embodiment of the invention, Het is selected from 6-membered monocyclic hetaryl, which may be unsubstituted or may carry 1, 2, 3 or 4 substituents $R^x$, in particular 0, 1 or 2 substituents $R^x$. In this regard, $R^x$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, phenyl, $C_3$-$C_6$-cycloalkyl, optionally substituted by 1, 2 or 3 methyl groups, and fluorinated $C_3$-$C_6$-cycloalkyl. In this regard, $R^x$ is in particular selected from fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl or one $R^x$ may also be phenyl.

Particular preference is given to those Het radicals, which have at least one imino-nitrogen as ring member, which is located in the position adjacent to the carbon atom which is bound to A. Particular preference is given to those Het radicals, which have at least one imino-nitrogen as ring member, which is located in the position adjacent to the carbon atom which is bound to tA and which are selected from the group consisting of C-bound 6-membered monocyclic hetaryl, which has 1 or 2 nitrogen atoms as ring members, benzofuryl and C-bound, fused bicyclic hetaryl, which has 1 or 2 nitrogen atoms as ring members and optionally a further heteroatom selected from O, S and N as ring member, where monocyclic hetaryl, benzofuryl and bicyclic hetaryl may be unsubstituted or may carry 1, 2, 3 or 4 substituents $R^x$, in particular 0, 1 or 2 substituents $R^x$. In this regard, $R^x$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, phenyl, $C_3$-$C_6$-cycloalkyl, optionally substituted by 1, 2 or 3 methyl groups, and fluorinated $C_3$-$C_6$-cycloalkyl. In this regard, $R^x$ is in particular selected from fluorine, chlorine, methyl, fluoromethyl, difluoromethyl, trifluoromethyl, methoxy, fluoromethoxy, difluoromethoxy, trifluoromethoxy, phenyl, cyclopropyl, optionally substituted by 1, 2 or 3 methyl groups, and fluorinated cyclopropyl.

Particular examples of Het are selected from the group consisting of 2-benzofuryl, 2-pyridyl, 2-pyrimidinyl, 4-pyrimidinyl, 2-pyrazinyl, 3-pyridazinyl, 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^x$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

In a particular embodiment of the invention, Het has at least one imino-nitrogen as ring member, which is located in the position adjacent to the carbon atom which is bound to A and Het is selected from the group consisting of fused bicyclic hetaryl, which has 1 or 2 nitrogen atoms as ring members and optionally a further heteroatom selected from O, S and N as ring member, where bicyclic hetaryl may be unsubstituted or may carry 1, 2, 3 or 4 substituents $R^x$, in particular 0, 1 or 2 substituents $R^x$. In this regard, $R^x$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl, optionally substituted by 1, 2 or 3 methyl groups, and fluorinated $C_3$-$C_6$-cycloalkyl. In this regard, $R^x$ is in particular selected from fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl. Particular examples of Het of this embodiment are 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^x$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

Particular preference is given to compounds, where Het is 2-quinolinyl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, thieno[3,2-b]pyridine-5-yl, and in particular 2-quinolinyl or imidazo[1,2-a]pyridine-2-yl, where these radicals are unsubstituted or may carry 1, 2 or 3 radicals $R^x$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

In particular embodiments of the invention, the variable $X^1$ is CH. In these particular embodiments, $X^2$ is preferably C—$R^7$, where $R^7$ is as defined above and in particular H or $Y^2$-$Cyc^2$. In these particular embodiments, $X^3$ is preferably S or $C(R^9)$=$C(R^8)$.

In further particular embodiments of the invention, the variable $X^1$ is N. In these particular embodiments, $X^2$ is preferably C—$R^7$, where $R^7$ is as defined above and in particular H or $Y^2$-$Cyc^2$. In these particular embodiments, $X^3$ is preferably S or $C(R^9)$=$C(R^8)$.

In particular embodiments of the invention, the variable $X^2$ is C—$R^7$. In these particular embodiments $R^7$ is as defined above and in particular H or $Y^2$-$Cyc^2$. In these embodiments, $X^1$ is CH or preferably N. In these particular embodiments, $X^3$ is preferably S or $C(R^9)$=$C(R^8)$.

In further particular embodiments of the invention, the variable $X^2$ is N. In this embodiment, $X^1$ is preferably CH. In these particular embodiments, $X^3$ is preferably $C(R^9)$=$C(R^8)$.

In particular embodiments of the invention $X^3$ is O, S, —$X^4$=$C(R^8)$—, where $C(R^8)$ is bound to the carbon atom which carries $R^2$.

In particular embodiments of the invention $X^3$ is S. In these embodiments, $X^1$ is CH or preferably N and $X^2$ is preferably C—$R^7$, where $R^7$ is as defined above and in particular H or $Y^2$-$Cyc^2$.

In particular embodiments of the invention $X^3$ is O. In these embodiments, $X^1$ is N or preferably CH, $X^2$ is preferably C—$R^7$, where $R^7$ is as defined above and in particular H or $Y^2$-$Cyc^2$ and $R^1$ is as defined above and in particular H or $Y^1$-$Cyc^1$.

In further particular embodiments of the invention, the variable $X^3$ is $C(R^9)$=$C(R^8)$. In these embodiments, $X^1$ is CH or preferably N and $X^2$ is preferably C—$R^7$, where $R^7$ is as defined above and in particular H or $Y^2$-$Cyc^2$.

In further particular embodiments of the invention, the variable $X^3$ is N=$C(R^9)$. In these embodiments, $X^1$ is CH or preferably N and $X^2$ is preferably C—$R^7$, where $R^7$ is as defined above and in particular H and $R^1$ is as defined above and in particular $Y^1$-$Cyc^1$.

In the embodiments of the invention, where $X^3$ is N=C($R^9$), $R^9$ is preferably H.

In further particular embodiments of the invention, the variable $X^3$ is N=$C(R^8)$. In these embodiments, $X^1$ is preferably CH and $X^2$ is preferably C—$R^7$, where $R^7$ is as defined above and in particular H or $Y^2$-$Cyc^2$.

In the embodiments of the invention, where $X^2$ is C—$R^7$, $R^7$ is preferably H or $Y^2$-$Cyc^2$.

In the embodiments of the invention, where $X^3$ is $C(R^9)$=$C(R^8)$, $R^9$ is preferably H or $Y^3$-$Cyc^3$, while $R^8$ is preferably hydrogen.

In the embodiments of the invention, where $X^3$ is N=C($R^8$), $R^8$ is preferably H.

In the embodiments of the invention, where $X^2$ is C—$R^7$, and where $X^3$ is $C(R^9)$=$C(R^8)$, $R^7$ is preferably H or $Y^2$-$Cyc^2$, $R^9$ is preferably H or $Y^3$-$Cyc^3$, while $R^8$ is preferably hydrogen, where preferably either $R^7$ is $Y^2$-$Cyc^2$ or $R^9$ is $Y^3$-$Cyc^3$ while one of $R^7$ and $R^9$ is different from $Y^2$-$Cyc^2$ or $Y^3$-$Cyc^3$, respectively, or both $R^7$ and $R^9$ are different from $Y^2$-$Cyc^2$ or $Y^3$-$Cyc^3$.

In this regard, those radicals $R^1$, $R^7$ and $R^9$, which are different from $Y^1$-$Cyc^1$, $Y^2$-$Cyc^2$, $Y^3$-$Cyc^3$, respectively, are in particular selected, independently of each other, from the group consisting of hydrogen, fluorine, $C_1$-$C_4$-alkyl, fluorinated $C_1$-$C_2$-alkyl, $C_1$-$C_4$-alkoxy, fluorinated $C_1$-$C_2$-alkoxy, cyclopropyl, optionally substituted by 1, 2 or 3 methyl groups, and fluorinated cyclopropyl. Those radicals $R^1$, $R^7$ and $R^9$, which are different from $Y^1$-$Cyc^1$, $Y^2$-$Cyc^2$, $Y^3$-$Cyc^3$, respectively, are most preferably hydrogen.

In particular preferred embodiments of the invention, $R^1$ is $Y^1$-$Cyc^1$. In these embodiments $X^1$ is CH or preferably N and $X^2$ is preferably C—$R^7$, where $R^7$ is as defined above and in particular H or $Y^2$-$Cyc^2$. In these embodiments, particular preference is given to compounds, where $X^3$ is S or $X^3$ is $C(R^9)$=$C(R^8)$, where $R^9$ is preferably H or $Y^3$-$Cyc^3$, while $R^8$ is preferably hydrogen.

$Y^3$-$Cyc^3$, while $R^8$ is preferably hydrogen.

In other particular preferred embodiments of the invention, $R^1$ is different from $Y^1$-$Cyc^1$ and in particular hydrogen. In these embodiments $X^1$ is CH or preferably N. In these embodiments $X^2$ is preferably C—$R^7$, where $R^7$ is as defined above and in particular $Y^2$-$Cyc^2$ and $X^3$ is S or $X^2$ is preferably C—$R^7$, where $R^7$ is as defined above and in particular H or $Y^2$-$Cyc^2$ and $X^3$ is $X^3$ is $C(R^9)$=$C(R^8)$, where $R^9$ is preferably H or $Y^3$-$Cyc^3$, while $R^8$ is preferably hydrogen.

In the moiety $Y^1$-$Cyc^1$, $Y^1$ is preferably selected from O, NH and a chemical bond.

In particular $Y^1$ is a chemical bond.

In the moiety $Y^2$-$Cyc^2$, $Y^2$ is preferably selected from O, NH and a chemical bond. In particular $Y^2$ is a chemical bond.

In the moiety $Y^3$-$Cyc^3$, $Y^3$ is preferably selected from O, NH and a chemical bond. In particular $Y^3$ is a chemical bond.

Preferably, $Cyc^1$ is selected from the groups of
(i) saturated 4-, 5-, 6-, 7- or 8-membered heteromonocycles or a saturated 7-, 8-, 9- or 10-membered heterobicycle, where the heteromonocycle and the heterobicycle have one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, 3, 4 or 5, in particular 1, 2, or 3 radicals R$^{C1}$ or one radical Y'—R$^{C2}$ and 0, 1, 2, 3 or 4, in particular 0, 1 or 2 radicals R$^{C1}$, where R$^{C1}$, R$^{C2}$ and Y' are as defined herein and where Y', if present, is preferably a chemical bond or O; and (ii) phenyl or a 5- or 6 membered monocyclic hetaryl, which has one heteroatom, selected from O, S and N as ring member and optionally one or two further heteroatoms as ring members, and which is in particular selected from the group consisting of pyridyl, pyrimidinyl, furyl, thienyl, pyrrolyl, imidazolyl, pyrazolyl, oxazolyl and thiazolyl, 9- or 10-membered bicyclic hetaryl which has one heteroatom, selected from O, S and N as ring member and optionally one or two further heteroatoms as ring members, and which is in particular selected from the group consisting of indolyl, quinolinyl, isoquinolinyl, quinazolinyl, benzimidazolyl, benzotriazolyl, benzopyrazolyl and benzofuryl, where phenyl and hetaryl are unsubstituted or carry 1, 2, 3, 4 or 5, in particular 1, 2, or 3 radicals R$^{C1}$ or one radical Y'—R$^{C2}$ and 0, 1, 2, 3 or 4, in particular 0, 1 or 2 radicals R$^{C1}$, where R$^{C1}$, R$^{C2}$ and Y' are as defined herein and where Y', if present, is preferably a chemical bond or O.

In this regard, R$^{C1}$ is preferably selected from the group consisting of fluorine, chlorine, CN, methyl, difluoromethyl, trifluoromethyl, methoxy and NH$_2$, or, if Cyc$^1$ is phenyl, two radicals R$^{C1}$ which are bound to adjacent carbon atoms, together with the phenyl ring to which they are bound, form a bicyclic heterocyclic radical, which is selected from 5- or 6-indolyl, 5- or 6-benzimidazolyl, 5- or 6-benzopyrazolyl, 5- or 6-benzotriazolyl, 5- or 6-benzofuranyl, 2,3-dihydrobenzofuran-5-yl, 2,3-dihydrobenzofuran-6-yl, 1,3-dihydroindol-2-on-5-yl, 1,3-dihydroindol-2-on-6-yl, 5- or 6-quinolinyl, 5- or 6-isoquinolinyl, 5- or 6-quinazolinyl, 2-amino-5-quinazolinyl, and 2-amino-6-quinazolinyl.

In this regard, R$^{C2}$ is preferably selected from the group consisting of phenyl, C$_3$-C$_6$-cycloalkyl, optionally substituted by 1, 2, or 3 methyl groups, fluorinated C$_3$-C$_6$-cycloalkyl, and 5- or 6-membered saturated heteromonocyclic radicals, having 1, 2 or 3 heteroatoms as ring members, which are selected from O, S and N, where phenyl the saturated heteromonocyclic radical is unsubstituted or carries 1, 2 or 3 radicals R$^{C3}$, which are preferably selected from fluorine, chlorine, CN, methyl, difluoromethyl, trifluoromethyl, methoxy and NH$_2$.

In particular, Cyc$^1$ is selected from the groups of (i) saturated 4-, 5-, 6- or 7-membered heteromonocycles, where the heteromonocycle has one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, or 3 radicals R$^{C1}$, where R$^{C1}$ is as defined herein; and (ii) phenyl or a 5- or 6 membered hetaryl, selected from pyridyl, pyrimidinyl, furyl, thienyl, pyrrolyl, imidazolyl, pyrazolyl, oxazolyl and thiazolyl, where phenyl and the 5- or 6 membered hetaryl are unsubstituted or carry 1, 2, 3, 4 or 5, in particular 1, 2, or 3 radicals R$^{C1}$ or one radical Y'—R$^{C2}$ and 0, 1, 2, 3 or 4, in particular 0, 1 or 2 radicals R$^{C1}$, where R$^{C1}$, R$^{C2}$ and Y' are as defined herein and where Y', if present, is preferably a chemical bond or O.

In particular embodiments of the invention, Cyc$^1$ is selected from the group consisting of saturated 4-, 5-, 6- or 7-membered heteromonocycles or a saturated 7-, 8-, 9- or 10-membered heterobicycle, where the heteromonocycle and the heterobicycle have one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, 3, 4 or 5, in particular 1, 2, or 3 radicals R$^{C1}$ or one radical Y'—R$^2$ and 0, 1, 2, 3 or 4, in particular 0, 1 or 2 radicals R$^{C1}$, where R$^{C1}$, R$^{C2}$ and Y' are as defined herein and where Y', if present, is preferably a chemical bond or O.

In special embodiments of the invention, Cyc$^1$ is selected from the group consisting of saturated 4-, 5-, 6- or 7-membered heteromonocycles, where the heteromonocycle has one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, or 3 radicals R$^{C1}$, where R$^{C1}$ is as defined herein.

In this particular and special embodiment, Y$^1$ is preferably selected from O, NH and a chemical bond, with particular preference given to Y$^1$ being a chemical bond.

In this particular and special embodiment Y$^1$-Cyc$^1$ is e.g. selected from the group consisting of 1-piperidinyl, 4,4-difluoro-1-piperidinyl, 4-piperidinyl, 1-methyl-4-piperidinyl, 1-piperazinyl, 4-methyl-1-piperazinyl, morpholin-4-yl, 2-oxa-6-azaspiro-[3,4]octyl, 2,5-diazabicyclo[2.2.1]heptan-2-yl, 3,8-diazabicyclo[3.2.1]octan-8-yl, thiomorpholin-4-yl, 1-oxothiomorpholin-4-yl, N-(oxetan-3-yl)amino, 1,1-dioxothiomorpholin-4-yl and oxetan-3-ylamino and especially from the group consisting of 1-piperidinyl, 4,4-difluoro-1-piperidinyl, 4-piperidinyl, 1-methyl-4-piperidinyl, 1-piperazinyl, 4-methyl-1-piperazinyl, morpholin-4-yl, thiomorpholin-4-yl, 1-oxothiomorpholin-4-yl, N-(oxetan-3-yl) amino, 1,1-dioxothiomorpholin-4-yl and oxetan-3-ylamino.

In other particular embodiments of the invention, Cyc$^1$ is phenyl or a 5- or 6 membered heteroaromatic radical, which has one heteroatom, selected from O, S and N as ring member and optionally one or two further heteroatoms as ring members, and which is in particular selected from the group consisting of pyridyl, pyrimidinyl, furyl, thienyl, pyrrolyl, imidazolyl, pyrazolyl, oxazolyl and thiazolyl, where phenyl and the 5- or 6 membered heteroaromatic radical are unsubstituted or either carry, independently of each other, carry 1, 2, 3, 4 or 5, in particular 1, 2, or 3 radicals R$^{C1}$ or one radical Y'—R$^{C2}$ and 0, 1, 2, 3 or 4, in particular 0, 1 or 2 radicals R$^{C1}$, where R$^{C1}$, R$^{C2}$ and Y' are as defined herein and where Y', if present, is preferably a chemical bond or O.

In special embodiments of the invention, Cyc$^1$ is selected from the group consisting of phenyl or a 5- or 6 membered hetaryl, selected from pyridyl, pyrimidinyl, furyl, thienyl, pyrrolyl, imidazolyl, pyrazolyl, oxazolyl and thiazolyl, where phenyl and the 5- or 6 membered hetaryl are unsubstituted or carry 1, 2, 3, 4 or 5, in particular 1, 2, or 3 radicals R$^{C1}$ or one radical Y'—R$^{C2}$ and 0, 1, 2, 3 or 4, in particular 0, 1 or 2 radicals R$^{C1}$, where R$^{C1}$, R$^{C2}$ and Y' are as defined herein and where Y', if present, is preferably a chemical bond or O.

In particular Cyc$^1$ is selected from the group consisting of phenyl and 5- or 6-membered hetaryl selected from the group consisting of pyridyl, pyrimidinyl, furyl, thienyl, pyrrolyl, imidazolyl, pyrazolyl, oxazolyl and thiazolyl, where phenyl and hetaryl are unsubstituted or carry 1, 2 or 3 radicals R$^{C1}$ which are selected from the group consisting of fluorine, chlorine, CN, methyl, difluoromethyl, trifluoromethyl, methoxy and NH$_2$, or, if Cyc$^1$ is phenyl, two radicals $R^{C1}$ which are bound to adjacent carbon atoms, together with the phenyl ring to which they are bound, form a bicyclic heterocyclic radical, which is selected from 5- or 6-indolyl, 5- or 6-benzimidazolyl, 5- or 6-benzopyrazolyl, 5- or 6-benzotriazolyl, 5- or 6-benzofuranyl, 2,3-dihydrobenzofuran-5-yl, 2,3-dihydrobenzofuran-6-yl, 1,3-dihydroindol-2-on-5-yl, 1,3-dihydroindol-2-on-6-yl, 5- or 6-quinolinyl, 5- or 6-isoquinolinyl, 5- or 6-quinazolinyl, 2-amino-5-quinazolinyl, and 2-amino-6-quinazolinyl. Amongst these, particular preference is given to compounds, where $Y^1$ is a chemical bond. Amongst these, particular preference is given to compounds, where $Cyc^1$ is selected from the group consisting of phenyl and 5- or 6-membered hetaryl selected from the group consisting of pyridyl, pyrimidinyl, furyl, thienyl, pyrrolyl, imidazolyl, pyrazolyl, oxazolyl and thiazolyl, where phenyl and hetaryl are unsubstituted or carry 1, 2 or 3 radicals $R^{C1}$ which are selected from the group consisting of fluorine, chlorine, CN, methyl, difluoromethyl, trifluoromethyl, methoxy and $NH_2$.

Preferably, $Cyc^2$ and $Cyc^3$ are, independently from each other, selected from the groups of
(i) saturated 4-, 5-, 6-, 7- or 8-membered heteromonocycles or a saturated 7-, 8-, 9- or 10-membered heterobicycle, where the heteromonocycle and the heterobicycle have one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O; and
(ii) phenyl or a 5- or 6 membered monocyclic hetaryl, which has one heteroatom, selected from O, S and N as ring member and optionally one or two further heteroatoms as ring members, and which is in particular selected from the group consisting of pyridyl, pyrimidinyl, furyl, thienyl, pyrrolyl, imidazolyl, pyrazolyl, oxazolyl and thiazolyl, 9- or 10-membered bicyclic hetaryl which has one heteroatom, selected from O, S and N as ring member and optionally one or two further heteroatoms as ring members, and which is in particular selected from the group consisting of indolyl, quinolinyl, isoquinolinyl, quinazolinyl, benzimidazolyl, benzotriazolyl, benzopyrazolyl and benzofuryl, where phenyl and hetaryl are unsubstituted or carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O.

In this regard, $R^{C1}$ is preferably selected from the group consisting of fluorine, chlorine, CN, methyl, difluoromethyl, trifluoromethyl, methoxy and $NH_2$, or, if $Cyc^2$ or $Cyc^3$ are phenyl, two radicals $R^{C1}$ which are bound to adjacent carbon atoms, together with the phenyl ring to which they are bound, form a bicyclic heterocyclic radical, which is selected from 5- or 6-indolyl, 5- or 6-benzimidazolyl, 5- or 6-benzopyrazolyl, 5- or 6-benzotriazolyl, 5- or 6-benzofuranyl, 2,3-dihydrobenzofuran-5-yl, 2,3-dihydrobenzofuran-6-yl, 1,3-dihydroindol-2-on-5-yl, 1,3-dihydroindol-2-on-6-yl, 5- or 6-quinolinyl, 5- or 6-isoquinolinyl, 5- or 6-quinazolinyl, 2-amino-5-quinazolinyl, and 2-amino-6-quinazolinyl.

In this regard, $R^{C2}$ is preferably selected from the group consisting of phenyl, $C_3$-$C_6$-cycloalkyl, optionally substituted by 1, 2, or 3 methyl groups, fluorinated $C_3$-$C_6$-cycloalkyl, and 5- or 6-membered saturated heteromonocyclic radicals, having 1, 2 or 3 heteroatoms as ring members, which are selected from O, S and N, where phenyl the saturated heteromonocyclic radical is unsubstituted or carries 1, 2 or 3 radicals $R^{C3}$, which are preferably selected from fluorine, chlorine, CN, methyl, difluoromethyl, trifluoromethyl, methoxy and $NH_2$.

In particular, $Cyc^2$ and $Cyc^3$ are, independently from each other, selected from the groups of
(i) saturated 4-, 5-, 6- or 7-membered heteromonocycles, where the heteromonocycle has one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, or 3 radicals $R^{C1}$, where $R^{C1}$ is as defined herein; and
(ii) phenyl or a 5- or 6 membered hetaryl, selected from pyridyl, pyrimidinyl, furyl, thienyl, pyrrolyl, imidazolyl, pyrazolyl, oxazolyl and thiazolyl, where phenyl and the 5- or 6 membered hetaryl are unsubstituted or carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O.

In particular embodiments of the invention, $Cyc^2$ and $Cyc^3$ are, independently from each other, selected from the group consisting of saturated 4-, 5-, 6- or 7-membered heteromonocycles or a saturated 7-, 8-, 9- or 10-membered heterobicycle, where the heteromonocycle and the heterobicycle have one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O.

In special embodiments of the invention, $Cyc^2$ and $Cyc^3$ are, independently from each other, selected from the group consisting of saturated 4-, 5-, 6- or 7-membered heteromonocycles, where the heteromonocycle has one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, or 3 radicals $R^{C1}$, where $R^{C1}$ is as defined herein.

In this particular and special embodiments $Y^2$ and $Y^3$ are, independently from each other preferably selected from O, NH and a chemical bond, with particular preference given to $Y^2$ and $Y^3$ being a chemical bond.

In this particular and special embodiments $Cyc^2$ and $Cyc^3$ are, independently from each other, e.g. selected from the group consisting of 1-piperidinyl, 4,4-difluoro-1-piperidinyl, 4-piperidinyl, 1-methyl-4-piperidinyl, 1-piperazinyl, 4-methyl-1-piperazinyl, morpholin-4-yl, 2-oxa-6-azaspiro[3,4]octyl, 2,5-diazabicyclo[2.2.1]heptan-2-yl, 3,8-diazabicyclo[3.2.1]octan-8-yl, thiomorpholin-4-yl, 1-oxothiomorpholin-4-yl, N-(oxetan-3-yl)amino, 1,1-dioxothiomorpholin-4-yl and oxetan-3-ylamino and especially from the group consisting of 1-piperidinyl, 4,4-difluoro-1-piperidinyl, 4-piperidinyl, 1-methyl-4-piperidinyl, 1-piperazinyl, 4-methyl-1-piperazinyl, morpholin-4-yl, thiomorpholin-4-yl, 1-oxothiomorpholin-4-yl, N-(oxetan-3-yl)amino, 1,1-dioxothiomorpholin-4-yl and oxetan-3-ylamino.

In other particular embodiments of the invention, $Y^2$-$Cyc^2$ and $Y^3$-$Cyc^3$ are, independently of each other, phenyl or a 5- or 6 membered heteroaromatic radical, which has one heteroatom, selected from O, S and N as ring member and optionally one or two further heteroatoms as ring members, and which is in particular selected from the group consisting of pyridyl, pyrimidinyl, furyl, thienyl, pyrrolyl, imidazolyl, pyrazolyl, oxazolyl and thiazolyl, where phenyl and the 5- or 6 membered heteroaromatic radical are unsubstituted or either carry, independently of each other, carry 1, 2, 3, 4 or 5, in particular 1, 2, or 3 radicals $R^{C1}$ or one radical $Y'$—$R^{C2}$ and 0, 1, 2, 3 or 4, in particular 0, 1 or 2 radicals $R^{C1}$, where $R^{C1}$, $R^{C2}$ and $Y'$ are as defined herein and where $Y'$, if present, is preferably a chemical bond or O.

In special embodiments of the invention, $Y^2$-$Cyc^2$ and $Y^3$-$Cyc^3$ are, independently from each other, selected from the group consisting of phenyl or a 5- or 6 membered hetaryl, selected from pyridyl, pyrimidinyl, furyl, thienyl, pyrrolyl, imidazolyl, pyrazolyl, oxazolyl and thiazolyl, where phenyl and the 5- or 6 membered hetaryl are unsubstituted or carry 1, 2, 3, 4 or 5, in particular 1, 2, or 3 radicals $R^{C1}$ or one radical $Y'$—$R^{C2}$ and 0, 1, 2, 3 or 4, in particular 0, 1 or 2 radicals $R^{C1}$, where $R^{C1}$, $R^{C2}$ and $Y'$ are as defined herein and where $Y'$, if present, is preferably a chemical bond or O.

In particular $Y^2$-$Cyc^2$ and $Y^3$-$Cyc^3$ are, independently from each other, selected from the group consisting of phenyl and 5- or 6-membered hetaryl selected from the group consisting of pyridyl, pyrimidinyl, furyl, thienyl, pyrrolyl, imidazolyl, pyrazolyl, oxazolyl and thiazolyl, where phenyl and hetaryl are unsubstituted or carry 1, 2 or 3 radicals $R^{C1}$ which are selected from the group consisting of fluorine, chlorine, CN, methyl, difluoromethyl, trifluoromethyl, methoxy and $NH_2$, or, if one or both of $Y^2$-$Cyc^2$ and $Y^3$-$Cyc^3$ are phenyl, two radicals $R^{C1}$ which are bound to adjacent carbon atoms, together with the phenyl ring to which they are bound, form a bicyclic heterocyclic radical, which is selected from 5- or 6-indolyl, 5- or 6-benzimidazolyl, 5- or 6-benzopyrazolyl, 5- or 6-benzotriazolyl, 5- or 6-benzofuranyl, 2,3-dihydrobenzofuran-5-yl, 2,3-dihydrobenzofuran-6-yl, 1,3-dihydroindol-2-on-5-yl, 1,3-dihydroindol-2-on-6-yl, 5- or 6-quinolinyl, 5- or 6-isoquinolinyl, 5- or 6-quinazolinyl, 2-amino-5-quinazolinyl, and 2-amino-6-quinazolinyl. Amongst these, particular preference is given to compounds, where $Y^2$-$Cyc^2$ and $Y^3$-$Cyc^3$ are, independently from each other, selected from the group consisting of phenyl and 5- or 6-membered hetaryl selected from the group consisting of pyridyl, pyrimidinyl, furyl, thienyl, pyrrolyl, imidazolyl, pyrazolyl, oxazolyl and thiazolyl, where phenyl and hetaryl are unsubstituted or carry 1, 2 or 3 radicals $R^{C1}$ which are selected from the group consisting of fluorine, chlorine, CN, methyl, difluoromethyl, trifluoromethyl, methoxy and $NH_2$.

With regard to $Cyc^1$, $Cyc^2$ and $Cyc^3$, and in particular with regard to the aforementioned particular or special embodiments of $Cyc^1$, $Cyc^2$ and $Cyc^3$, $R^{C1}$ is preferably selected from the group consisting of fluorine, chlorine, CN, methyl, difluoromethyl, trifluoromethyl, methoxy and $NH_2$.

With regard to $Cyc^1$, $Cyc^2$ and $Cyc^3$, and in particular with regard to the aforementioned particular or special embodiments of $Cyc^1$, $Cyc^2$ and $Cyc^3$, $R^{C2}$ is preferably selected from the group consisting of phenyl, $C_3$-$C_6$-cycloalkyl, optionally substituted by 1, 2, or 3 methyl groups, fluorinated $C_3$-$C_6$-cycloalkyl, and 5- or 6-membered saturated heteromonocyclic radicals, having 1, 2 or 3 heteroatoms as ring members, which are selected from O, S and N, where phenyl the saturated heteromonocyclic radical is unsubstituted or carries 1, 2 or 3 radicals $R^{C3}$, which are preferably selected from fluorine, chlorine, CN, methyl, difluoromethyl, trifluoromethyl, methoxy and $NH_2$.

Irrespectively from the aforementioned embodiments, $R^2$ is preferably selected from the group consisting of hydrogen, fluorine, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups, and fluorinated cyclopropyl.

Irrespectively from the aforementioned embodiments, $R^2$ is in particular hydrogen.

Irrespectively from the aforementioned embodiments, Q is in particular oxygen.

Particular embodiments of the invention relate to the compounds of the following formulae I-1 and I-2:

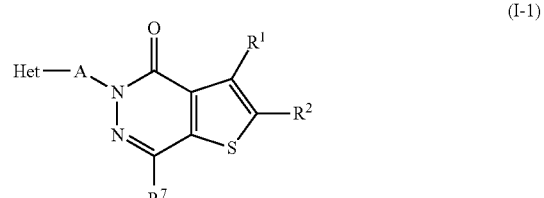

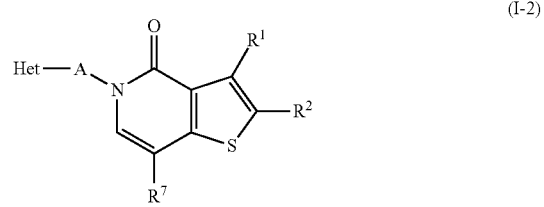

where Het, A, $R^1$, $R^2$ and $R^7$ are as defined here and in the claims.

Other particular embodiments of the invention relate to the compounds of the following formulae I-3 and I-4:

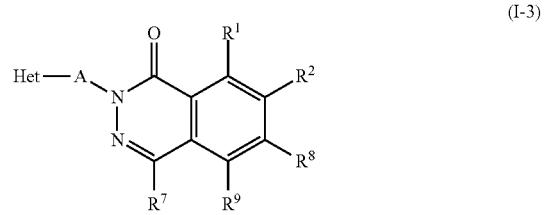

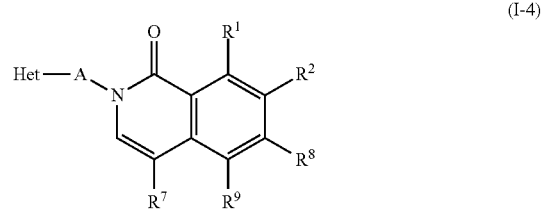

where Het, A, $R^1$, $R^2$, $R^7$, $R^8$ and $R^9$ are as defined here and in the claims.

Further particular embodiments of the invention relate to the compounds of the following formulae I-5 and I-6:

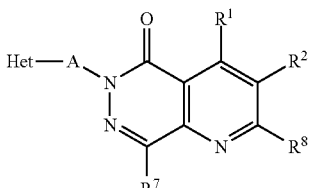

(I-5)

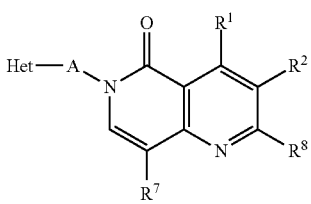

(I-6)

where Het, A, R$^1$, R$^2$, R$^7$ and R$^8$ are as defined here and in the claims.

Particular embodiments of the invention relate to the compounds of the following formulae I-7 and I-8:

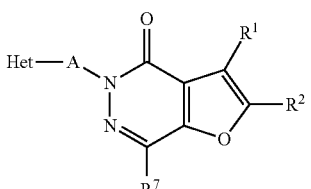

(I-7)

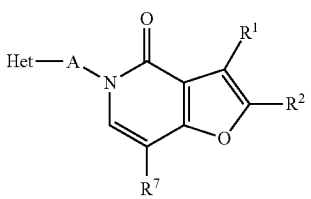

(I-8)

where Het, A, R$^1$, R$^2$ and R$^7$ are as defined here and in the claims.

Further particular embodiments of the invention relate to the compounds of the following formulae I-9 and I-10:

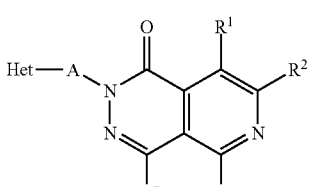

(I-9)

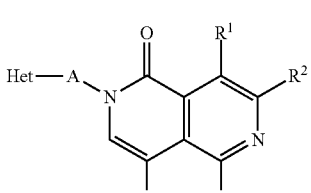

(I-10)

where Het, A, R$^1$, R$^2$, R$^7$ and R$^9$ are as defined here and in the claims.

In a particular embodiment of the invention, A in formula I is A$^1$, A$^2$, A$^3$ or A$^4$.

In a particular embodiment of the invention, A in formula I, and likewise in formulae I-1, I-2, I-3, I-4, I-5, I-6, I-7, I-8, I-9 and I-10 is a bivalent radical A$^1$. Preference is given to compounds of the formula I, and likewise to compounds of formulae I-1, I-2, I-3, I-4, I-5, I-6, I-7, I-8, I-9 and I-10, where R$^3$, R$^4$ are selected from hydrogen and fluorine and in particular to those compounds, where both R$^3$ and R$^4$ are hydrogen. Preference is given to compounds of the formula I, where R$^5$ and R$^6$ are, independently of each other, selected from the group consisting of hydrogen, fluorine and methyl, and in particular to those compounds, where both R$^5$ and R$^6$ are hydrogen.

In another particular embodiment of the invention, A in formula I, and likewise in formulae I-1, I-2, I-3, I-4, I-5, I-6, I-7, I-8, I-9 and I-10, is a bivalent radical A$^2$.

In another particular embodiment of the invention, A in formula I, and likewise in formulae I-1, I-2, I-3, I-4, I-5, I-6, I-7, I-8, I-9 and I-10, is a bivalent radical A$^3$. Preference is given to compounds of the formula I, and likewise to compounds of formulae I-1, I-2, I-3, I-4, I-5, I-6, I-7, I-8, I-9 and I-10, where R$^4$, R$^5$ are selected from hydrogen and fluorine. In particular, both R$^4$ and R$^5$ are hydrogen.

In another particular embodiment of the invention, A in formula I, and likewise in formulae I-1, I-2, I-3, I-4, I-5, I-6, I-7, I-8, I-9 and I-10, is a bivalent radical A$^4$. Preference is given to compounds of the formula I, and likewise to compounds of formulae I-1, I-2, I-3, I-4, I-5, I-6, I-7, I-8, I-9 and I-10, where R$^4$, R$^5$ are selected from hydrogen and fluorine and in particular to those compounds, where both R$^4$ and R$^5$ are hydrogen. In the bivalent radical A$^4$ the moiety A' is preferably CR$^{3b}$R$^{3c}$, where R$^{3b}$ and R$^{3c}$ are independently of each other selected from the group consisting of hydrogen, fluorine and methyl or together form CH$_2$CH$_2$ and where R$^{3b}$ and R$^{3b}$ are independently of each other in particular selected from the group consisting of hydrogen and fluorine. Particular preference is given to compounds of the formula I, and likewise to compounds of formulae I-1, I-2, I-3, I-4, I-5, I-6, I-7, I-8, I-9 and I-10, where A is a bivalent radical A$^4$, where the moiety A' is CR$^{3b}$R$^{3c}$, where R$^{3b}$ and R$^{3c}$ are as defined herein and where R$^{3b}$ and R$^{3c}$ are in particular, independently of each other, selected from the group consisting of hydrogen, fluorine and methyl or together form CH$_2$CH$_2$ and especially where both R$^{3b}$ and R$^{3c}$ are hydrogen or fluorine.

In another particular embodiment of the invention, A in formula I and likewise in formulae I-1, I-2, I-3, I-4, I-5, I-6, I-7, I-8, I-9 and I-10 is a bivalent radical A$^4$, where A' is O.

In another particular embodiment of the invention, A in formula I, and likewise in formulae I-1, I-2, I-3, I-4, I-5, I-6, I-7, I-8, I-9 and I-10, is a bivalent radical A$^4$, where A' is NR$^{3a}$ with R$^{3a}$ being as defined above in particular hydrogen or C$_1$-C$_4$-alkyl.

In another particular embodiment, A in formula I, and likewise in formulae I-1, I-2, I-3, I-4, I-5, I-6, I-7, I-8, I-9 and I-10, is a bivalent radical A$^4$, where A' is linear C$_2$-C$_3$-alkanediyl, where one of the CH$_2$-moieties of C$_2$-C$_3$-alkandiyl may be replaced by oxygen or NR$^{3a}$, and where 1, 2, 3, or 4 of the hydrogen atoms of C$_2$-C$_3$-alkandiyl may be replaced by a radical R$^{3d}$. R$^{3d}$ is preferably selected from halogen and C$_1$-C$_4$-alkyl.

In another particular embodiment of the invention, A in formula I, and likewise in formulae I-1, I-2, I-3, I-4, I-5, I-6, I-7, I-8, I-9 and I-10 is a bivalent radical A$^5$. Preference is given to compounds of the formula I, and likewise to compounds of formulae I-1, I-2, I-3, I-4, I-5, I-6, I-7, I-8, I-9 and I-10, where $R^4$, $R^5$ are selected from hydrogen and methyl and in particular to those compounds, where both $R^4$ and $R^5$ are hydrogen. Preference is given to compounds of the formula I, where $R^{3e}$ and $R^{3f}$ are, independently of each other, selected from the group consisting of hydrogen and methyl, and in particular to those compounds, where both $R^{3e}$ and $R^{3f}$ are hydrogen.

A particular preferred embodiment of the invention relates to the compounds of formula I-1.A, described below, to the N-oxides, the prodrugs, the hydrates and the tautomers thereof and to the pharmaceutically suitable salts thereof:

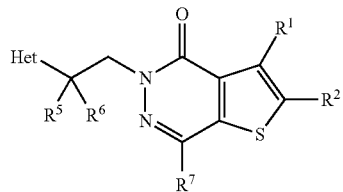

(I-1.A)

where Het, $R^1$, $R^2$, $R^5$, $R^6$ and $R^7$ are as defined here and in the claims.

Another particular preferred embodiment of the invention relates to the compounds of formula I-2.A, described below, to the N-oxides, the prodrugs, the hydrates and the tautomers thereof and to the pharmaceutically suitable salts thereof:

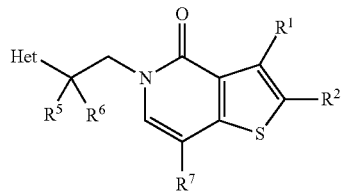

(I-2.A)

where Het, $R^1$, $R^2$, $R^5$, $R^6$ and $R^7$ are as defined here and in the claims.

Another particular preferred embodiment of the invention relates to the compounds of formula I-1.B, described below, to the N-oxides, the prodrugs, the hydrates and the tautomers thereof and to the pharmaceutically suitable salts thereof:

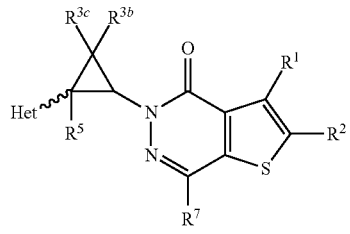

(I-1.B)

where Het, $R^1$, $R^2$, $R^{3b}$, $R^{3c}$, $R^5$ and $R^7$ are as defined here and in the claims and where $R^5$ is in particular hydrogen.

Another particular preferred embodiment of the invention relates to the compounds of formula I-2.B, described below,
to the N-oxides, the prodrugs, the hydrates and the tautomers thereof and to the pharmaceutically suitable salts thereof:

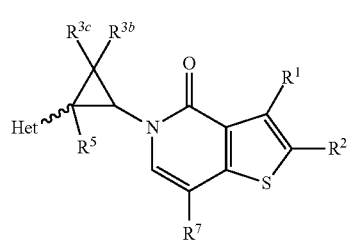

(I-2.B)

where Het, $R^1$, $R^2$, $R^{3b}$, $R^{3c}$, $R^5$ and $R^7$ are as defined here and in the claims and where $R^5$ is in particular hydrogen. In formulae I-1.B and I-2.B, the variables $R^{3b}$ and $R^{3c}$ are independently of each other in particular selected from the group consisting of hydrogen, fluorine and methyl or together form $CH_2CH_2$. Particular preference is given to compounds of the formulae I-1.B and I-2.B, where both $R^{3b}$ and $R^{3c}$ are hydrogen or fluorine.

Another particular preferred embodiment of the invention relates to the compounds of formula I-1.C, described below, to the N-oxides, the prodrugs, the hydrates and the tautomers thereof and to the pharmaceutically suitable salts thereof:

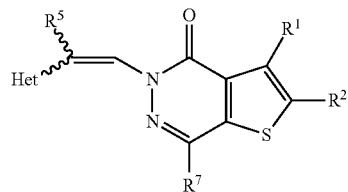

(I-1.C)

where Het, $R^1$, $R^2$, $R^5$ and $R^7$ are as defined here and in the claims and where $R^5$ is in particular hydrogen.

Another particular preferred embodiment of the invention relates to the compounds of formula I-2.C, described below, to the N-oxides, the prodrugs, the hydrates and the tautomers thereof and to the pharmaceutically suitable salts thereof:

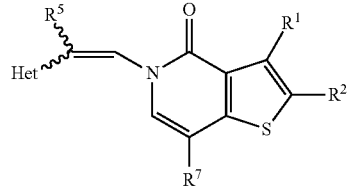

(I-2.C)

where Het, $R^1$, $R^2$, $R^5$ and $R^7$ are as defined here and in the claims and where $R^5$ is in particular hydrogen.

A particular preferred embodiment of the invention relates to the compounds of formula I-1.D, described below, to the N-oxides, the prodrugs, the hydrates and the tautomers thereof and to the pharmaceutically suitable salts thereof:

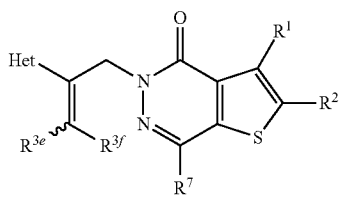

(I-1.D)

where Het, $R^1$, $R^2$, $R^{3e}$, $R^{3f}$ and $R^7$ are as defined here and in the claims and where $R^{3e}$ and $R^{3f}$ are in particular both hydrogen.

Another particular preferred embodiment of the invention relates to the compounds of formula I-2.D, described below, to the N-oxides, the prodrugs, the hydrates and the tautomers thereof and to the pharmaceutically suitable salts thereof:

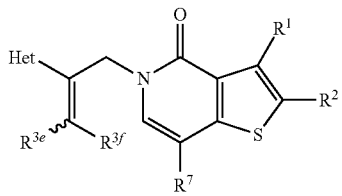

(I-2.D)

where Het, $R^1$, $R^2$, $R^{3e}$, $R^{3f}$ and $R^7$ are as defined here and in the claims and where $R^{3e}$ and $R^{3f}$ are in particular both hydrogen.

Particular embodiments of the invention relate to compounds of the formulae I-1, I-2, I-1.A, I-2.A, I-1.B, I-2.B, I-1.C, I-2.C, I-1.D, and I-2.D described above, to the N-oxides, the prodrugs, the hydrates and the tautomers thereof and to the pharmaceutically suitable salts thereof, where $R^1$ is a radical $Y^1$-$Cyc^1$ and $R^7$ is as defined above and in particular selected from the group consisting of hydrogen, fluorine, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups, fluorinated cyclopropyl and $Y^2$-$Cyc^2$, especially from the group consisting of hydrogen and $Y^2$-$Cyc^2$.

Further particular embodiments of the invention relate to compounds of the formulae I-1, I-2, I-1.A, I-2.A, I-1.B, I-2.B, I-1.C, I-2.C, I-1.D, and I-2.D, described above, to the N-oxides, the prodrugs, the hydrates and the tautomers thereof and to the pharmaceutically suitable salts thereof, where $R^1$ is selected from the group consisting of hydrogen, fluorine, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups and fluorinated cyclopropyl and $R^7$ is a moiety $Y^2$-$Cyc^2$. In these embodiments $R^1$ is in particular hydrogen.

A further particular preferred embodiment of the invention relates to the compounds of formula I-3.A, described below, to the N-oxides, the prodrugs, the hydrates and the tautomers thereof and to the pharmaceutically suitable salts thereof:

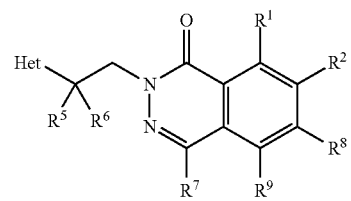

(I-3.A)

where Het, $R^1$, $R^2$, $R^5$, $R^6$, $R^7$, $R^8$ and $R^9$ are as defined here and in the claims.

Another particular preferred embodiment of the invention relates to the compounds of formula I-4.A, described below, to the N-oxides, the prodrugs, the hydrates and the tautomers thereof and to the pharmaceutically suitable salts thereof:

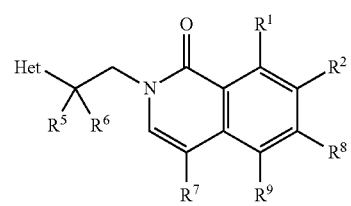

(I-4.A)

where Het, $R^1$, $R^2$, $R^5$, $R^6$, $R^7$, $R^8$ and $R^9$ are as defined here and in the claims.

Another particular preferred embodiment of the invention relates to the compounds of formula I-3.B, described below, to the N-oxides, the prodrugs, the hydrates and the tautomers thereof and to the pharmaceutically suitable salts thereof:

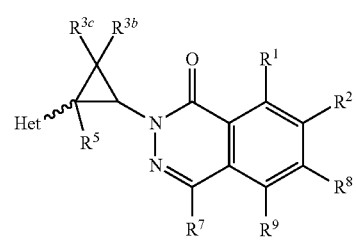

(I-3.B)

where Het, $R^1$, $R^2$, $R^{3b}$, $R^{3c}$, $R^7$, $R^8$ and $R^9$ are as defined here and in the claims and where $R^5$ is in particular hydrogen.

Another particular preferred embodiment of the invention relates to the compounds of formula I-4.B, described below, to the N-oxides, the prodrugs, the hydrates and the tautomers thereof and to the pharmaceutically suitable salts thereof:

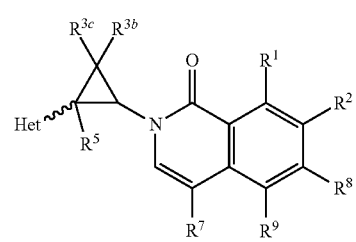

(I-4.B)

where Het, $R^1$, $R^2$, $R^{3b}$, $R^{3c}$, $R^7$, $R^8$ and $R^9$ are as defined here and in the claims and where $R^5$ is in particular hydrogen.

In formulae I-3.B and I-4.B, the variables $R^{3b}$ and $R^{3c}$ are independently of each other in particular selected from the group consisting of hydrogen, fluorine and methyl or together form $CH_2CH_2$. Particular preference is given to compounds of the formulae I-3.B and I-4.B, where both $R^{3b}$ and $R^{3c}$ are hydrogen or fluorine.

Another particular preferred embodiment of the invention relates to the compounds of formula I-3.C, described below, to the N-oxides, the prodrugs, the hydrates and the tautomers thereof and to the pharmaceutically suitable salts thereof:

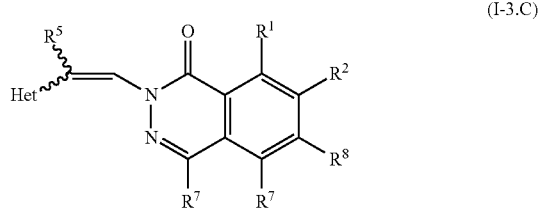

(I-3.C)

where Het, $R^1$, $R^2$, $R^5$, $R^7$, $R^8$ and $R^9$ are as defined here and in the claims and where $R^5$ is in particular hydrogen.

Another particular preferred embodiment of the invention relates to the compounds of formula I-4.C, described below, to the N-oxides, the prodrugs, the hydrates and the tautomers thereof and to the pharmaceutically suitable salts thereof:

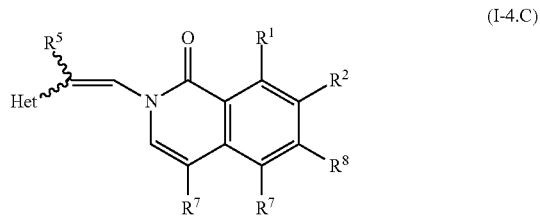

(I-4.C)

where Het, $R^1$, $R^2$, $R^5$, $R^7$, $R^8$ and $R^9$ are as defined here and in the claims and where $R^5$ is in particular hydrogen.

A further particular preferred embodiment of the invention relates to the compounds of formula I-3.D, described below, to the N-oxides, the prodrugs, the hydrates and the tautomers thereof and to the pharmaceutically suitable salts thereof:

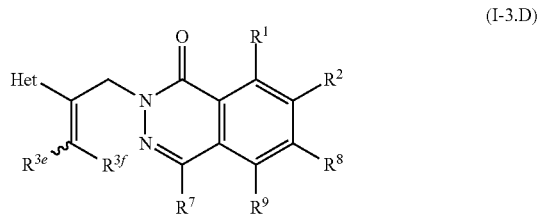

(I-3.D)

where Het, $R^1$, $R^2$, $R^{3e}$, $R^{3f}$, $R^7$, $R^8$ and $R^9$ are as defined here and in the claims and where $R^{3e}$ and $R^{3f}$ are in particular both hydrogen.

Another particular preferred embodiment of the invention relates to the compounds of formula I-4.D, described below, to the N-oxides, the prodrugs, the hydrates and the tautomers thereof and to the pharmaceutically suitable salts thereof:

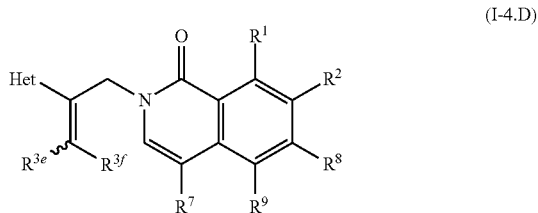

(I-4.D)

where Het, $R^1$, $R^2$, $R^{3e}$, $R^{3f}$, $R^7$, $R^8$ and $R^9$ are as defined here and in the claims and where $R^{3e}$ and $R^{3f}$ are in particular both hydrogen.

Particular embodiments of the invention relate to compounds of the formulae I-3, I-4, I-3.A, I-4.A, I-3.B, I-4.B, I-3.C, I-3.D, I-4.C, and I-4.D, described above, to the N-oxides, the prodrugs, the hydrates and the tautomers thereof and to the pharmaceutically suitable salts thereof, where $R^1$ is a radical $Y^1$-$Cyc^1$ and $R^7$, $R^8$ and $R^9$ are as defined above and where $R^7$ is in particular selected from the group consisting of hydrogen, fluorine, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups, fluorinated cyclopropyl and $Y^2$-$Cyc^2$, especially from the group consisting of hydrogen and $Y^2$-$Cyc^2$ and where $R^9$ is in particular selected from the group consisting of hydrogen, fluorine, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups, fluorinated cyclopropyl and $Y^3$-$Cyc^3$, especially from the group consisting of hydrogen and $Y^3$-$Cyc^3$, provided that none or only one of $R^7$ and $R^9$ is a moiety $Y^3$-$Cyc^3$, or $Y^3$-$Cyc^3$, respectively. $R^7$ and $R^9$ are in particular hydrogen.

Further particular embodiments of the invention relate to compounds of the formulae I-3, I-4, I-3.A, I-4.A, I-3.B, I-4.B, I-3.C, I-4.C, I-3.D and I-4.D, described above, to the N-oxides, the prodrugs, the hydrates and the tautomers thereof and to the pharmaceutically suitable salts thereof, where $R^1$ is selected from the group consisting of hydrogen, fluorine, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups and fluorinated cyclopropyl and where $R^7$ and $R^9$ are selected, independently of each other, from the group consisting of hydrogen, fluorine, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups, fluorinated cyclopropyl and $Y^2$-$Cyc^2$ or $Y^3$-$Cyc^3$, respectively, provided that either $R^7$ is $Y^2$-$Cyc^2$ or $R^9$ is $Y^3$-$Cyc^3$. In these embodiments $R^1$ is in particular hydrogen. In these embodiments the radical $R^7$ or $R^9$, which is different from $Y^2$-$Cyc^2$ or $Y^3$-$Cyc^3$, respectively, is in particular hydrogen.

A further particular preferred embodiment of the invention relates to the compounds of formula I-5.A, described below, to the N-oxides, the prodrugs, the hydrates and the tautomers thereof and to the pharmaceutically suitable salts thereof:

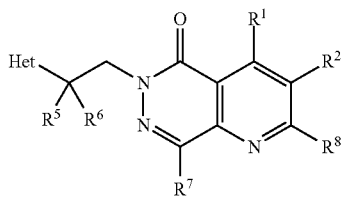

(I-5.A)

where Het, $R^1$, $R^2$, $R^5$, $R^6$, $R^7$ and $R^8$ are as defined here and in the claims.

Another particular preferred embodiment of the invention relates to the compounds of formula I-6.A, described below, to the N-oxides, the prodrugs, the hydrates and the tautomers thereof and to the pharmaceutically suitable salts thereof:

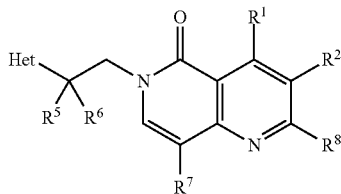

(I-6.A)

where Het, $R^1$, $R^2$, $R^5$, $R^6$, $R^7$ and $R^8$ are as defined here and in the claims.

A further particular preferred embodiment of the invention relates to the compounds of formula I-5.B, described below, to the N-oxides, the prodrugs, the hydrates and the tautomers thereof and to the pharmaceutically suitable salts thereof:

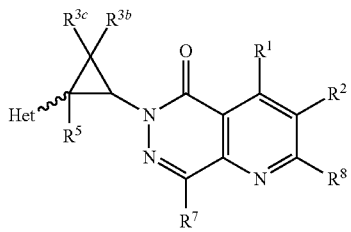

(I-5.B)

where Het, $R^1$, $R^2$, $R^{3b}$, $R^{3c}$, $R^5$, $R^7$ and $R^8$ are as defined here and in the claims and where $R^5$ is in particular hydrogen.

A further particular preferred embodiment of the invention relates to the compounds of formula I-6.B, described below, to the N-oxides, the prodrugs, the hydrates and the tautomers thereof and to the pharmaceutically suitable salts thereof:

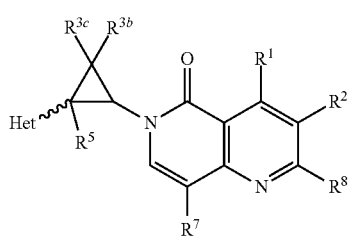

(I-6.B)

where Het, $R^1$, $R^2$, $R^{3a}$, $R^{3b}$, $R^5$, $R^7$ and $R^8$ are as defined here and in the claims and where $R^5$ is in particular hydrogen. In formulae I-5.B and I-6.B, the variables $R^{3b}$ and $R^{3c}$ are independently of each other in particular selected from the group consisting of hydrogen, fluorine and methyl or together form $CH_2CH_2$. Particular preference is given to compounds of the formulae I-5.B and I-6.B, where both $R^{3b}$ and $R^{3c}$ are hydrogen or fluorine.

A further particular preferred embodiment of the invention relates to the compounds of formula I-5.C, described below, to the N-oxides, the prodrugs, the hydrates and the tautomers thereof and to the pharmaceutically suitable salts thereof:

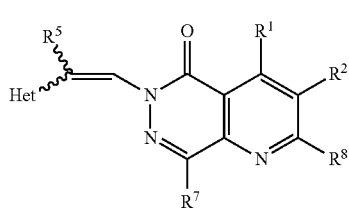

(I-5.C)

where Het, $R^1$, $R^2$, $R^5$, $R^7$ and $R^8$ are as defined here and in the claims and where $R^5$ is in particular hydrogen.

A further particular preferred embodiment of the invention relates to the compounds of formula I-6.C, described below, to the N-oxides, the prodrugs, the hydrates and the tautomers thereof and to the pharmaceutically suitable salts thereof:

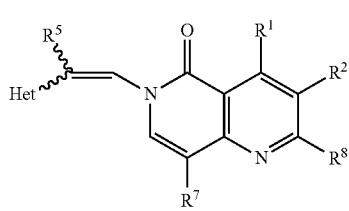

(I-6.C)

where Het, $R^1$, $R^2$, $R^5$, $R^7$ and $R^8$ are as defined here and in the claims and where $R^5$ is in particular hydrogen.

A further particular preferred embodiment of the invention relates to the compounds of formula I-5.D, described below, to the N-oxides, the prodrugs, the hydrates and the tautomers thereof and to the pharmaceutically suitable salts thereof:

(I-5.D)

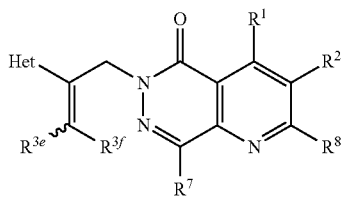

where Het, $R^1$, $R^2$, $R^{3e}$, $R^{3f}$, $R^7$, $R^8$ and $R^9$ are as defined here and in the claims and in particular, $R^{3e}$ and $R^{3f}$ are both hydrogen.

Another particular preferred embodiment of the invention relates to the compounds of formula I-6.D, described below, to the N-oxides, the prodrugs, the hydrates and the tautomers thereof and to the pharmaceutically suitable salts thereof:

(I-6.D)

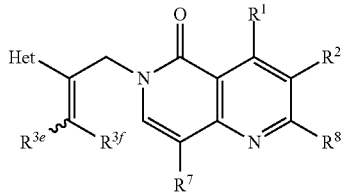

where Het, $R^1$, $R^2$, $R^{3e}$, $R^{3f}$, $R^7$, $R^8$ and $R^9$ are as defined here and in the claims and in particular, $R^{3e}$ and $R^{3f}$ are both hydrogen.

Particular embodiments of the invention relate to compounds of the formulae I-5, I-6, I-5.A, I-6.A, I-5.B, I-6.B, I-5.C, I-6.C, I-5.D and I-6.D, described above, to the N-oxides, the prodrugs, the hydrates and the tautomers thereof and to the pharmaceutically suitable salts thereof, where $R^1$ is a radical $Y^1$-$Cyc^1$ and $R^7$ is as defined above and in particular selected from the group consisting of hydrogen, fluorine, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups, fluorinated cyclopropyl and $Y^2$-$Cyc^2$, especially from the group consisting of hydrogen and $Y^2$-$Cyc^2$.

Further particular embodiments of the invention relate to compounds of the formulae I-5, I-6, I-5.A, I-6.A, I-5.B, I-6.B, I-5.C, I-6.C, I-5.D, and I-6.D, described above, to the N-oxides, the prodrugs, the hydrates and the tautomers thereof and to the pharmaceutically suitable salts thereof, where $R^1$ is selected from the group consisting of hydrogen, fluorine, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups and fluorinated cyclopropyl and $R^7$ is a moiety $Y^2$-$Cyc^2$. In these embodiments $R^1$ is in particular hydrogen.

A particular preferred embodiment of the invention relates to the compounds of formula I-7.A, described below, to the N-oxides, the prodrugs, the hydrates and the tautomers thereof and to the pharmaceutically suitable salts thereof:

(I-7.A)

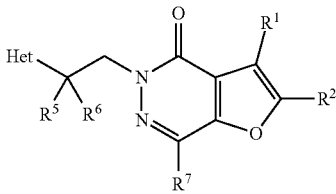

where Het, $R^1$, $R^2$, $R^5$, $R^6$ and $R^7$ are as defined here and in the claims.

Another particular preferred embodiment of the invention relates to the compounds of formula I-8.A, described below, to the N-oxides, the prodrugs, the hydrates and the tautomers thereof and to the pharmaceutically suitable salts thereof:

(I-8.A)

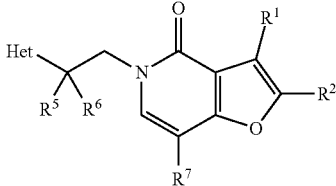

where Het, $R^1$, $R^2$, $R^5$, $R^6$ and $R^7$ are as defined here and in the claims.

Another particular preferred embodiment of the invention relates to the compounds of formula I-7.B, described below, to the N-oxides, the prodrugs, the hydrates and the tautomers thereof and to the pharmaceutically suitable salts thereof:

(I-7.B)

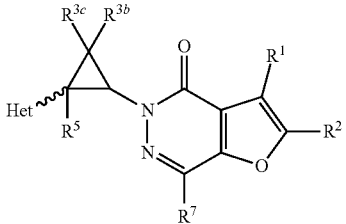

where Het, $R^1$, $R^2$, $R^{3b}$, $R^{3c}$, $R^5$ and $R^7$ are as defined here and in the claims and where $R^5$ is in particular hydrogen.

Another particular preferred embodiment of the invention relates to the compounds of formula I-8.B, described below, to the N-oxides, the prodrugs, the hydrates and the tautomers thereof and to the pharmaceutically suitable salts thereof:

(I-8.B)

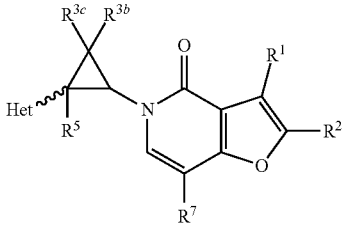

where Het, $R^1$, $R^2$, $R^{3b}$, $R^{3c}$, $R^5$ and $R^7$ are as defined here and in the claims and where $R^5$ is in particular hydrogen.

In formulae I-7.B and I-8.B, the variables $R^{3b}$ and $R^{3c}$ are independently of each other in particular selected from the group consisting of hydrogen, fluorine and methyl or together form $CH_2CH_2$. Particular preference is given to compounds of the formulae I-7.B and I-8.B, where both $R^{3b}$ and $R^{3c}$ are hydrogen or fluorine.

Another particular preferred embodiment of the invention relates to the compounds of formula I-7.C, described below, to the N-oxides, the prodrugs, the hydrates and the tautomers thereof and to the pharmaceutically suitable salts thereof:

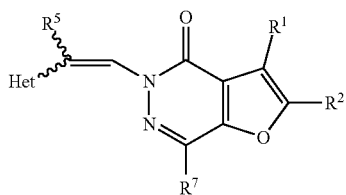

(I-7.C)

where Het, $R^1$, $R^2$, $R^5$ and $R^7$ are as defined here and in the claims and where $R^5$ is in particular hydrogen.

Another particular preferred embodiment of the invention relates to the compounds of formula I-8.C, described below, to the N-oxides, the prodrugs, the hydrates and the tautomers thereof and to the pharmaceutically suitable salts thereof:

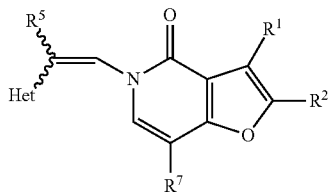

(I-8.C)

where Het, $R^1$, $R^2$, $R^5$ and $R^7$ are as defined here and in the claims and where $R^5$ is in particular hydrogen.

A particular preferred embodiment of the invention relates to the compounds of formula I-7.D, described below, to the N-oxides, the prodrugs, the hydrates and the tautomers thereof and to the pharmaceutically suitable salts thereof:

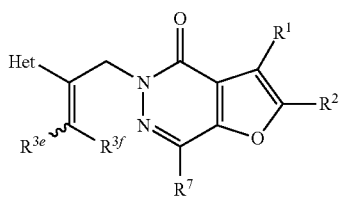

(I-7.D)

where Het, $R^1$, $R^2$, $R^{3f}$, $R^{3e}$ and $R^7$ are as defined here and in the claims where $R^{3e}$ and $R^{3f}$ are both in particular hydrogen.

Another particular preferred embodiment of the invention relates to the compounds of formula I-8.D, described below, to the N-oxides, the prodrugs, the hydrates and the tautomers thereof and to the pharmaceutically suitable salts thereof:

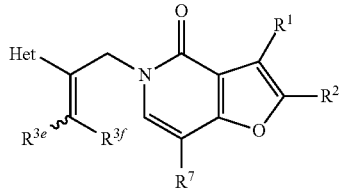

(I-8.D)

where Het, $R^1$, $R^2$, $R^{3f}$, $R^{3e}$ and $R^7$ are as defined here and in the claims where $R^{3e}$ and $R^{3f}$ are both in particular hydrogen.

Particular embodiments of the invention relate to compounds of the formulae I-7, I-8, I-7.A, I-8.A, I-7.B, I-8.B, I-7.C, I-8.C, I-7.D, and I-8.D described above, to the N-oxides, the prodrugs, the hydrates and the tautomers thereof and to the pharmaceutically suitable salts thereof, where $R^1$ is a radical $Y^1$-$Cyc^1$ and $R^7$ is as defined above and in particular selected from the group consisting of hydrogen, fluorine, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups, fluorinated cyclopropyl and $Y^2$-$Cyc^2$, especially from the group consisting of hydrogen and $Y^2$-$Cyc^2$.

Further particular embodiments of the invention relate to compounds of the formulae I-7, I-8, I-7.A, I-8.A, I-7.B, I-8.B, I-7.C, I-8.C, I-7.D and I-8.D, described above, to the N-oxides, the prodrugs, the hydrates and the tautomers thereof and to the pharmaceutically suitable salts thereof, where $R^1$ is selected from the group consisting of hydrogen, fluorine, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups and fluorinated cyclopropyl and $R^7$ is a moiety $Y^2$-$Cyc^2$. In these embodiments $R^1$ is in particular hydrogen.

A further particular preferred embodiment of the invention relates to the compounds of formula I-9.A, described below, to the N-oxides, the prodrugs, the hydrates and the tautomers thereof and to the pharmaceutically suitable salts thereof:

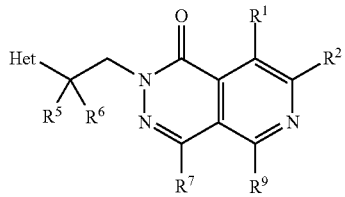

(I-9.A)

where Het, $R^1$, $R^2$, $R^5$, $R^6$, $R^7$ and $R^9$ are as defined here and in the claims.

Another particular preferred embodiment of the invention relates to the compounds of formula I-10.A, described below, to the N-oxides, the prodrugs, the hydrates and the tautomers thereof and to the pharmaceutically suitable salts thereof:

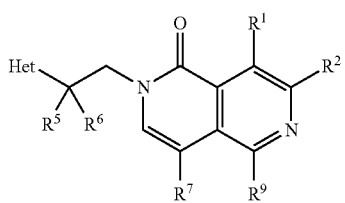
(I-10.A)

where Het, $R^1$, $R^2$, $R^5$, $R^6$, $R^7$, and $R^9$ are as defined here and in the claims.

Another particular preferred embodiment of the invention relates to the compounds of formula I-9.B, described below, to the N-oxides, the prodrugs, the hydrates and the tautomers thereof and to the pharmaceutically suitable salts thereof:

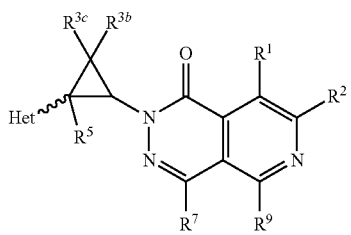
(I-9.B)

where Het, $R^1$, $R^2$, $R^{3b}$, $R^{3c}$, $R^7$, and $R^9$ are as defined here and in the claims and where $R^5$ is in particular hydrogen.

Another particular preferred embodiment of the invention relates to the compounds of formula I-10.B, described below, to the N-oxides, the prodrugs, the hydrates and the tautomers thereof and to the pharmaceutically suitable salts thereof:

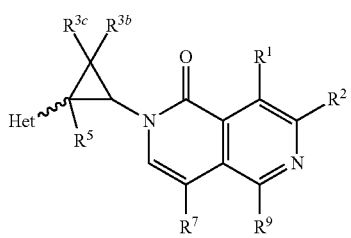
(I-10.B)

where Het, $R^1$, $R^2$, $R^{3b}$, $R^{3c}$, $R^7$, and $R^9$ are as defined here and in the claims and where $R^5$ is in particular hydrogen.

In formulae I-9.B and I-10.B, the variables $R^{3b}$ and $R^{3c}$ are independently of each other in particular selected from the group consisting of hydrogen, fluorine and methyl or together form $CH_2CH_2$. Particular preference is given to compounds of the formulae I-3.B and I-4.B, where both $R^{3b}$ and $R^{3c}$ are hydrogen or fluorine.

Another particular preferred embodiment of the invention relates to the compounds of formula I-9.C, described below, to the N-oxides, the prodrugs, the hydrates and the tautomers thereof and to the pharmaceutically suitable salts thereof:

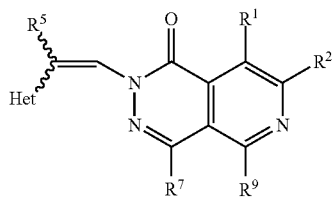
(I-9.C)

where Het, $R^1$, $R^2$, $R^5$, $R^7$, and $R^9$ are as defined here and in the claims and where $R^5$ is in particular hydrogen.

Another particular preferred embodiment of the invention relates to the compounds of formula I-10.C, described below, to the N-oxides, the prodrugs, the hydrates and the tautomers thereof and to the pharmaceutically suitable salts thereof:

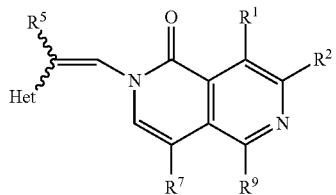
(I-10.C)

where Het, $R^1$, $R^2$, $R^5$, $R^7$, and $R^9$ are as defined here and in the claims and where $R^5$ is in particular hydrogen.

A further particular preferred embodiment of the invention relates to the compounds of formula I-9.D, described below, to the N-oxides, the prodrugs, the hydrates and the tautomers thereof and to the pharmaceutically suitable salts thereof:

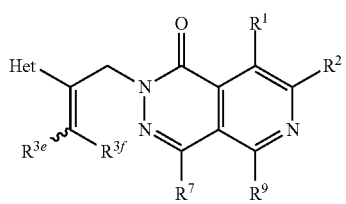
(I-9.D)

where Het, $R^1$, $R^2$, $R^{3e}$, $R^{3f}$, $R^7$, and $R^9$ are as defined here and in the claims and where $R^{3e}$ and $R^{3f}$ are in particular both hydrogen.

Another particular preferred embodiment of the invention relates to the compounds of formula I-10.D, described below, to the N-oxides, the prodrugs, the hydrates and the tautomers thereof and to the pharmaceutically suitable salts thereof:

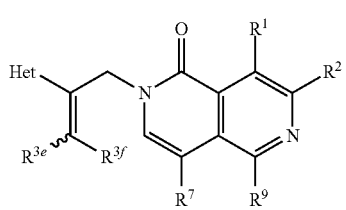
(I-10.D)

where Het, $R^1$, $R^2$, $R^{3e}$, $R^{3f}$, $R^7$, and $R^9$ are as defined here and in the claims and where $R^{3e}$ and $R^{3f}$ are in particular both hydrogen.

Particular embodiments of the invention relate to compounds of the formulae I-9, I-10, I-9.A, I-10.A, I-9.B, I-10.B, I-9.C, I-10.C, I-9.D and I-10.D, described above, to the N-oxides, the prodrugs, the hydrates and the tautomers thereof and to the pharmaceutically suitable salts thereof, where $R^1$ is a radical $Y^1$-$Cyc^1$ and $R^7$, and $R^9$ are as defined above and where $R^7$ is in particular selected from the group consisting of hydrogen, fluorine, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups, fluorinated cyclopropyl and $Y^2$-$Cyc^2$, especially from the group consisting of hydrogen and $Y^2$-$Cyc^2$ and where $R^9$ is in particular selected from the group consisting of hydrogen, fluorine, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups, fluorinated cyclopropyl and $Y^3$-$Cyc^3$, especially from the group consisting of hydrogen and $Y^3$-$Cyc^3$, provided that none or only one of $R^7$ and $R^9$ is a moiety $Y^3$-$Cyc^3$, or $Y^3$-$Cyc^3$, respectively. $R^7$ and $R^9$ are in particular hydrogen.

Further particular embodiments of the invention relate to compounds of the formulae I-9, I-10, I-9.A, I-10.A, I-9.B, I-10.B, I-9.C, I-10.C, I-9.D and I-10.D, described above, to the N-oxides, the prodrugs, the hydrates and the tautomers thereof and to the pharmaceutically suitable salts thereof, where $R^1$ is selected from the group consisting of hydrogen, fluorine, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups and fluorinated cyclopropyl and where $R^7$ and $R^9$ are selected, independently of each other, from the group consisting of hydrogen, fluorine, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups, fluorinated cyclopropyl and $Y^2$-$Cyc^2$ or $Y^3$-$Cyc^3$, respectively, provided that either $R^7$ is $Y^2$-$Cyc^2$ or $R^9$ is $Y^3$-$Cyc^3$. In these embodiments $R^1$ is in particular hydrogen. In these embodiments the radical $R^7$ or $R^9$, which is different from $Y^2$-$Cyc^2$ or $Y^3$-$Cyc^3$, respectively, is in particular hydrogen.

In formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D, $R^2$ is preferably selected from the group consisting of hydrogen, fluorine, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups, and fluorinated cyclopropyl. $R^2$ is in particular hydrogen.

Preference is given to compounds of the formulae I-1, I-2, I-3, I-4, I-5, I-6, I-7, I-8, I-9, I-10, I-1.A, I-1.B, I-2.A, I-2.B, I-1.C, I-2.C, I-3.A, I-4.A, I-3.B, I-4.B, I-3.C, I-4.C, I-5.A, I-6.A, I-5.B, I-6.B, I-5.C, I-6.C, I-7.A, I-8.A, I-7.B, I-8.B, I-7.C, I-8.C, I-9.A, I-10.A, I-9.B, I-10.B, I-9.C and I-10.C, where $R^{3b}$, $R^{3c}$, $R^5$ and $R^6$, if present, are, independently of each other, selected from the group consisting of hydrogen, fluorine and methyl, and in particular to those compounds, where both $R^5$ and $R^6$ are hydrogen.

In formulae I-3, I-4, I-5, I-6, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, $R^8$ is in particular hydrogen.

With regard to formulae I-1, I-2, I-3, I-5, I-4, I-6, I-7, I-8, I-9, I-10; I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D, the variable Het is as defined above and preferably selected from the group consisting of C-bound 6-membered monocyclic hetaryl, which has 1 or 2 nitrogen atoms as ring members, and C-bound, fused bicyclic hetaryl, which has 1 or 2 nitrogen atoms as ring members and optionally a further heteroatom selected from O, S and N as ring member, where monocyclic hetaryl and bicyclic hetaryl may be unsubstituted or may carry 1, 2, 3 or 4 substituents $R^x$, in particular 0, 1 or 2 substituents $R^x$. In this regard, $R^x$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, phenyl, $C_3$-$C_6$-cycloalkyl, optionally substituted by 1, 2 or 3 methyl groups, and fluorinated $C_3$-$C_6$-cycloalkyl. In this regard, $R^x$ is in particular selected from fluorine, chlorine, methyl, fluoromethyl, difluoromethyl, trifluoromethyl, methoxy, fluoromethoxy, difluoromethoxy, trifluoromethoxy, phenyl, cyclopropyl, optionally substituted by 1, 2 or 3 methyl groups, and fluorinated cyclopropyl.

In formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D, Het is in particular selected from the group consisting of fused bicyclic hetaryl, which has 1 or 2 nitrogen atoms as ring members and optionally a further heteroatom selected from O, S and N as ring member and which may be unsubstituted or may carry 1, 2, 3 or 4 substituents $R^x$, in particular 0, 1 or 2 substituents $R^x$. In this regard, $R^x$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl, optionally substituted by 1, 2 or 3 methyl groups, and fluorinated $C_3$-$C_6$-cycloalkyl. In this regard, $R^x$ is in particular selected from fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

In another particular embodiments of formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D Het is selected from 6-membered monocyclic hetaryl, which may be unsubstituted or may carry 1, 2, 3 or 4 substituents $R^x$, in particular 0, 1 or 2 substituents $R^x$. In this regard, $R^x$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, phenyl, $C_3$-$C_6$-cycloalkyl, optionally substituted by 1, 2 or 3 methyl groups, and fluorinated $C_3$-$C_6$-cycloalkyl. In this regard, $R^x$ is in particular selected from fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl or one $R^x$ may also be phenyl.

Particular preference is given to those compounds of I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D, to the N-oxides, the prodrugs, the hydrates and the tautomers thereof and to the pharmaceutically suitable salts thereof, where the Het radical has at least one imino-nitrogen as ring member, which is located in the position adjacent to the carbon atom which is bound to the group $CR^5$. Amongst these, particular preference is given to those, where the Het radical has at least one imino-nitrogen as ring member, which is located in the position adjacent to carbon atom bound to the group $CR^5$ and which is selected from the group consisting of C-bound 6-membered monocyclic hetaryl, which has 1 or 2 nitrogen atoms as ring members, and C-bound, fused bicyclic hetaryl, which has 1 or 2 nitrogen atoms as ring members and optionally a further heteroatom selected from O, S and N as ring member, where monocyclic hetaryl and bicyclic hetaryl may be unsubstituted or may carry 1, 2, 3 or 4 substituents $R^x$, in particular 0, 1 or 2 substituents $R^x$. In this regard, $R^x$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, phenyl, $C_3$-$C_6$-cycloalkyl, optionally substituted by 1, 2 or 3 methyl groups, and fluorinated $C_3$-$C_6$-cycloalkyl. In this regard, $R^x$ is in particular selected from fluorine, chlorine, methyl, fluoromethyl, difluoromethyl, trifluoromethyl, methoxy, fluoromethoxy, difluoromethoxy, trifluoromethoxy, phenyl, cyclopropyl, optionally substituted by 1, 2 or 3 methyl groups, and fluorinated cyclopropyl.

Particular examples of Het in formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D are selected from the group consisting of 2-benzofuryl, 2-pyridyl, 2-pyrimidinyl, 4-pyrimidinyl, 2-pyrazinyl, 3-pyridazinyl, 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^x$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

In a particular embodiment of the compounds of formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D Het has at least one imino-nitrogen as ring member, which is located in the position adjacent to carbon atom bound to the group $CR^5$ and Het is selected from the group consisting of fused bicyclic hetaryl, which has 1 or 2 nitrogen atoms as ring members and optionally a further heteroatom selected from O, S and N as ring member, where bicyclic hetaryl may be unsubstituted or may carry 1, 2, 3 or 4 substituents $R^x$, in particular 0, 1 or 2 substituents $R^x$. In this regard, $R^x$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl, optionally substituted by 1, 2 or 3 methyl groups, and fluorinated $C_3$-$C_6$-cycloalkyl. In this regard, $R^x$ is in particular selected from fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl. Particular examples of Het of this embodiment are 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^x$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

Particular preference is given to compounds, where Het in formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D is selected from the group consisting of 2-quinolinyl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, thieno[3,2-b]pyridine-5-yl, and in particular 2-quinolinyl or imidazo[1,2-a]pyridine-2-yl, where these radicals are unsubstituted or may carry 1, 2 or 3 radicals $R^x$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

With regard to formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D, the variables $Y^1$, $Y^2$, $Cyc^1$ and $Cyc^2$ are as defined above and in particular have the preferred meanings.

In particular, $Cyc^1$, if present in formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D is selected from the groups of (i) saturated 4-, 5-, 6- or 7-membered heteromonocycles, where the heteromonocycle has one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, or 3 radicals $R^{C1}$, where $R^{C1}$ is as defined herein; and (ii) phenyl or a 5- or 6 membered hetaryl, selected from pyridyl, pyrimidinyl, furyl, thienyl, pyrrolyl, imidazolyl, pyrazolyl, oxazolyl and thiazolyl, where phenyl and the 5- or 6 membered hetaryl are unsubstituted or carry 1, 2, 3, 4 or 5, in particular 1, 2, or 3 radicals $R^{C1}$ or one radical $Y'$—$R^{C2}$ and 0, 1, 2, 3 or 4, in particular 0 or 1 or 2 radicals $R^{C1}$, where $R^{C1}$, $R^{C2}$ and $Y'$ are as defined herein and where $Y'$, if present, is preferably a chemical bond or O.

In particular embodiments of the compounds of formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D, $Cyc^1$, if present, is selected from the group consisting of saturated 4-, 5-, 6- or 7-membered heteromonocycles or a saturated 7-, 8-, 9- or 10-membered heterobicycle, where the heteromonocycle and the heterobicycle have one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O.

In special embodiments of the compounds of formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D, $Cyc^1$, if present, is selected from the group consisting of saturated 4-, 5-, 6- or 7-membered heteromonocycles, where the heteromonocycle has one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, or 3 radicals $R^{C1}$, where $R^{C1}$ is as defined herein.

In these particular and special embodiments of the compounds of formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D, $Y^1$, if present, is preferably selected from O, NH and a chemical bond, with particular preference given to $Y^1$ being a chemical bond.

In these particular and special embodiments of the compounds of formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D, $Y^1$-$Cyc^1$. if present, is e.g. selected from the group consisting of 1-piperidinyl, 4,4-difluoro-1-piperidinyl, 4-piperidinyl, 1-methyl-4-piperidinyl, 1-piperazinyl, 4-methyl-1-piperazinyl, morpholin-4-yl, 2-oxa-6-azaspiro-[3,4]octyl, 2,5-diazabicyclo[2.2.1]heptan-2-yl, 3,8-diazabicyclo[3.2.1]octan-8-yl, thiomorpholin-4-yl, 1-oxothiomorpholin-4-yl, N-(oxetan-3-yl)amino, 1,1-dioxothiomorpholin-4-yl and oxetan-3-ylamino and especially from the group consisting of 1-piperidinyl, 4,4-difluoro-1-piperidinyl, 4-piperidinyl, 1-methyl-4-piperidinyl, 1-piperazinyl, 4-methyl-1-piperazinyl, morpholin-4-yl, thiomorpholin-4-yl, 1-oxothiomorpholin-4-yl, N-(oxetan-3-yl)amino, 1,1-dioxothiomorpholin-4-yl and oxetan-3-ylamino.

In other particular embodiments of the compounds of formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D, $Cyc^1$, if present, is phenyl or a 5- or 6 membered heteroaromatic radical, which has one heteroatom, selected from O, S and N as ring member and optionally one or two further heteroatoms as ring members, and which is in particular selected from the group consisting of pyridyl, pyrimidinyl, furyl, thienyl, pyrrolyl, imidazolyl, pyrazolyl, oxazolyl and thiazolyl, where phenyl and the 5- or 6 membered heteroaromatic radical are unsubstituted or either carry, independently of each other, carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O.

In other special embodiments of the compounds of formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D, $Cyc^1$, if present, is selected from the group consisting of phenyl or a 5- or 6 membered hetaryl, selected from pyridyl, pyrimidinyl, furyl, thienyl, pyrrolyl, imidazolyl, pyrazolyl, oxazolyl and thiazolyl, where phenyl and the 5- or 6 membered hetaryl are unsubstituted or carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^c$, where $R^{C1}$, $R^{C2}$ and Y' are as defined herein and where Y', if present, is preferably a chemical bond or O.

More particularly, $Cyc^1$, if present in formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D, is selected from the group consisting of phenyl and 5- or 6-membered hetaryl selected from the group consisting of pyridyl, pyrimidinyl, furyl, thienyl, pyrrolyl, imidazolyl, pyrazolyl, oxazolyl and thiazolyl, where phenyl and hetaryl are unsubstituted or carry 1, 2 or 3 radicals $R^{C1}$ which are selected from the group consisting of fluorine, chlorine, CN, methyl, difluoromethyl, trifluoromethyl, methoxy and NH$_2$, or, if $Cyc^1$ is phenyl, two radicals $R^{C1}$ which are bound to adjacent carbon atoms, together with the phenyl ring to which they are bound, form a bicyclic heterocyclic radical, which is selected from 5- or 6-indolyl, 5- or 6-benzimidazolyl, 5- or 6-benzopyrazolyl, 5- or 6-benzotriazolyl, 5- or 6-benzofuranyl, 2,3-dihydrobenzofuran-5-yl, 2,3-dihydrobenzofuran-6-yl, 1,3-dihydroindol-2-on-5-yl, 1,3-dihydroindol-2-on-6-yl, 5- or 6-quinolinyl, 5- or 6-isoquinolinyl, 5- or 6-quinazolinyl, 2-amino-5-quinazolinyl, and 2-amino-6-quinazolinyl. Amongst these, particular preference is given to compounds, where $Y^1$ is a chemical bond. Amongst these, particular preference is given to compounds, where $Cyc^1$ in formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-78.B, I-7.C, I-8.C, I-7.D, I-8.D, I-9.A, I-10.A, I-9.B, I-10.B, I-9.C, I-10.C, I-9.D and I-10.D, is selected from the group consisting of phenyl and 5- or 6-membered hetaryl selected from the group consisting of pyridyl, pyrimidinyl, furyl, thienyl, pyrrolyl, imidazolyl, pyrazolyl, oxazolyl and thiazolyl, where phenyl and hetaryl are unsubstituted or carry 1, 2 or 3 radicals $R^{C1}$ which are selected from the group consisting of fluorine, chlorine, CN, methyl, difluoromethyl, trifluoromethyl, methoxy and $NH_2$.

In particular, $Cyc^2$ and $Cyc^3$, if present in formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D, are, independently from each other, selected from the groups of (i) saturated 4-, 5-, 6- or 7-membered heteromonocycles, where the heteromonocycle has one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, or 3 radicals $R^{C1}$, where $R^{C1}$ is as defined herein; and (ii) phenyl or a 5- or 6 membered hetaryl, selected from pyridyl, pyrimidinyl, furyl, thienyl, pyrrolyl, imidazolyl, pyrazolyl, oxazolyl and thiazolyl, where phenyl and the 5- or 6 membered hetaryl are unsubstituted or carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O.

In particular embodiments of the compounds of formulae I-1, I-2, I-3, I-4, I-5, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D, Y2-Cyc2 and Y3-Cyc3, if present, are, independently from each other, selected from the group consisting of saturated 4-, 5-, 6- or 7-membered heteromonocycles or a saturated 7-, 8-, 9- or 10-membered heterobicycle, where the heteromonocycle and the heterobicycle have one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O.

In special embodiments of the compounds of formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D, $Y^2$-$Cyc^2$ and $Y^3$-$Cyc^3$, if present, are, independently from each other, selected from the group consisting of saturated 4-, 5-, 6- or 7-membered heteromonocycles, where the heteromonocycle has one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, or 3 radicals $R^{C1}$, where $R^{C1}$ is as defined herein.

In this particular and special embodiments of the compounds of formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D, $Y^2$-$Cyc^2$ and $Y^3$-$Cyc^3$, if present, are, independently from each other preferably selected from O, NH and a chemical bond, with particular preference given to $Y^2$ and $Y^3$ being a chemical bond.

In this particular and special embodiments of the compounds of formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D, $Y^2$-$Cyc^2$ and $Y^3$-$Cyc^3$, if present, are, independently from each other, e.g. selected from the group consisting of 1-piperidinyl, 4,4-difluoro-1-piperidinyl, 4-piperidinyl, 1-methyl-4-piperidinyl, 1-piperazinyl, 4-methyl-1-piperazinyl, morpholin-4-yl, 2-oxa-6-azaspiro-[3,4]octyl, 2,5-diazabicyclo[2.2.1]heptan-2-yl, 3,8-diazabicyclo[3.2.1]octan-8-yl, thiomorpholin-4-yl, 1-oxothiomorpholin-4-yl, N-(oxetan-3-yl)amino, 1,1-dioxothiomorpholin-4-yl and oxetan-3-ylamino and especially from the group consisting of 1-piperidinyl, 4,4-difluoro-1-piperidinyl, 4-piperidinyl, 1-methyl-4-piperidinyl, 1-piperazinyl, 4-methyl-1-piperazinyl, morpholin-4-yl, thiomorpholin-4-yl, 1-oxothiomorpholin-4-yl, N-(oxetan-3-yl) amino, 1,1-dioxothiomorpholin-4-yl and oxetan-3-ylamino.

In other particular embodiments of the compounds of formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-78.B, I-7.C, I-8.C, I-7.D, I-8.D, I-9.A, I-10.A, I-9.B, I-10.B, I-9.C, I-10.C, I-9.D and I-10.D, $Y^2$-$Cyc^2$ and $Y^3$-$Cyc^3$, if present, are, independently of each other, phenyl or a 5- or 6 membered heteroaromatic radical, which has one heteroatom, selected from O, S and N as ring member and optionally one or two further heteroatoms as ring members, and which is in particular selected from the group consisting of pyridyl, pyrimidinyl, furyl, thienyl, pyrrolyl, imidazolyl, pyrazolyl, oxazolyl and thiazolyl, where phenyl and the 5- or 6 membered heteroaromatic radical are unsubstituted or either carry, independently of each other, carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O.

In special embodiments of the compounds of formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D, $Y^2$-$Cyc^2$ and $Y^3$-$Cyc^3$, if present, are, independently from each other, selected from the group consisting of phenyl or a 5- or 6 membered hetaryl, selected from pyridyl, pyrimidinyl, furyl, thienyl, pyrrolyl, imidazolyl, pyrazolyl, oxazolyl and thiazolyl, where phenyl and the 5- or 6 membered hetaryl are unsubstituted or carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O.

In particular, $Y^2$-$Cyc^2$ and $Y^3$-$Cyc^3$, if present in formulae I-1, I-2, I-3, I-4, I-5, I-6, I-7, I-8, I-9, I-10, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D and I-10.D, $Y^2$-$Cyc^2$ and $Y^3$-$Cyc^3$, are, independently from each other, selected from the group consisting of phenyl and 5- or 6-membered hetaryl selected from the group consisting of pyridyl, pyrimidinyl, furyl, thienyl, pyrrolyl, imidazolyl, pyrazolyl, oxazolyl and thiazolyl, where phenyl and hetaryl are unsubstituted or carry 1, 2 or 3 radicals $R^{C1}$ which are selected from the group consisting of fluorine, chlorine, CN, methyl, difluoromethyl, trifluoromethyl, methoxy and $NH_2$, or, if one or both of $Y^2$-$Cyc^2$ and $Y^3$-$Cyc^3$ are phenyl, two radicals $R^{C1}$ which are bound to adjacent carbon atoms, together with the phenyl ring to which they are bound, form a bicyclic heterocyclic radical, which is selected from 5- or 6-indolyl, 5- or 6-benzimidazolyl, 5- or 6-benzopyrazolyl, 5- or 6-benzotriazolyl, 5- or 6-benzofuranyl, 2,3-dihydrobenzofuran-5-yl, 2,3-dihydrobenzofuran-6-yl, 1,3-dihydroindol-2-on-5-yl, 1,3-dihydroindol-2-on-6-yl, 5- or 6-quinolinyl, 5- or 6-isoquinolinyl, 5- or 6-quinazolinyl, 2-amino-5-quinazolinyl, and 2-amino-6-quinazolinyl. Amongst these, particular preference is given to compounds, where $Y^2$-$Cyc^2$ and $Y^3$-$Cyc^3$ are, independently from each other, selected from the group consisting of phenyl and 5- or 6-membered hetaryl selected from the group consisting of pyridyl, pyrimidinyl, furyl, thienyl, pyrrolyl, imidazolyl, pyrazolyl, oxazolyl and thiazolyl, where phenyl and hetaryl are unsubstituted or carry 1, 2 or 3 radicals $R^{C1}$ which are selected from the group consisting of fluorine, chlorine, CN, methyl, difluoromethyl, trifluoromethyl, methoxy and $NH_2$.

Particular embodiment of the invention relates to the compounds of formula I, to the N-oxides, the prodrugs, the hydrates and the tautomers thereof and to the pharmaceutically suitable salts thereof, where the compounds of the formula I are selected from the group consisting of:

3,7-di(pyridin-4-yl)-5-[2-(quinolin-2-yl)ethyl]thieno[2,3-d]pyridazin-4(5H)-one;
7-(pyridin-4-yl)-5-[2-(quinolin-2-yl)ethyl]thieno[2,3-d]pyridazin-4(5H)-one;
3-(pyridin-4-yl)-5-[2-(quinolin-2-yl)ethyl]thieno[2,3-d]pyridazin-4(5H)-one;
3-(pyridin-4-yl)-5-[2-(pyridin-2-yl)ethyl]thieno[2,3-d]pyridazin-4(5H)-one;
3,7-di(pyridin-4-yl)-5-[2-(pyridin-2-yl)ethyl]thieno[2,3-d]pyridazin-4(5H)-one;
5-[2-(quinolin-2-yl)ethyl]-3-[4-(trifluoromethyl)phenyl]thieno[2,3-d]pyridazin-4(5H)-one;
3-(4-methylphenyl)-5-[2-(quinolin-2-yl)ethyl]thieno[2,3-d]pyridazin-4(5H)-one;
3-[4-(propan-2-yl)phenyl]-5-[2-(quinolin-2-yl)ethyl]thieno[2,3-d]pyridazin-4(5H)-one;
3-(4-ethylphenyl)-5-[2-(quinolin-2-yl)ethyl]thieno[2,3-d]pyridazin-4(5H)-one;
4-{4-oxo-5-[2-(quinolin-2-yl)ethyl]-4,5-dihydrothieno[2,3-d]pyridazin-3-yl}benzonitrile;
3-(4-methoxyphenyl)-5-[2-(quinolin-2-yl)ethyl]thieno[2,3-d]pyridazin-4(5H)-one;
3-(4-fluorophenyl)-5-[2-(quinolin-2-yl)ethyl]thieno[2,3-d]pyridazin-4(5H)-one;
3-(4-ethoxyphenyl)-5-[2-(quinolin-2-yl)ethyl]thieno[2,3-d]pyridazin-4(5H)-one;
3-[4-(dimethylamino)phenyl]-5-[2-(quinolin-2-yl)ethyl]thieno[2,3-d]pyridazin-4(5H)-one;
(4-{4-oxo-5-[2-(quinolin-2-yl)ethyl]-4,5-dihydrothieno[2,3-d]pyridazin-3-yl}phenyl)acetonitrile;
3-(4-hydroxyphenyl)-5-[2-(quinolin-2-yl)ethyl]thieno[2,3-d]pyridazin-4(5H)-one;
3-(2-chlorophenyl)-5-[2-(quinolin-2-yl)ethyl]thieno[2,3-d]pyridazin-4(5H)-one;
3-(2-methylphenyl)-5-[2-(quinolin-2-yl)ethyl]thieno[2,3-d]pyridazin-4(5H)-one;
3-(2-ethylphenyl)-5-[2-(quinolin-2-yl)ethyl]thieno[2,3-d]pyridazin-4(5H)-one;
3-(2-fluorophenyl)-5-[2-(quinolin-2-yl)ethyl]thieno[2,3-d]pyridazin-4(5H)-one;
3-(2-methoxyphenyl)-5-[2-(quinolin-2-yl)ethyl]thieno[2,3-d]pyridazin-4(5H)-one;
3-(2-ethoxyphenyl)-5-[2-(quinolin-2-yl)ethyl]thieno[2,3-d]pyridazin-4(5H)-one;
3-(2-hydroxyphenyl)-5-[2-(quinolin-2-yl)ethyl]thieno[2,3-d]pyridazin-4(5H)-one;
5-[2-(quinolin-2-yl)ethyl]-3-[2-(trifluoromethyl)phenyl]thieno[2,3-d]pyridazin-4(5H)-one;
3-[3-(methoxymethyl)phenyl]-5-[2-(quinolin-2-yl)ethyl]thieno[2,3-d]pyridazin-4(5H)-one;
3-(3-methoxyphenyl)-5-[2-(quinolin-2-yl)ethyl]thieno[2,3-d]pyridazin-4(5H)-one;
3-(3-ethoxyphenyl)-5-[2-(quinolin-2-yl)ethyl]thieno[2,3-d]pyridazin-4(5H)-one;
3-[3-(dimethylamino)phenyl]-5-[2-(quinolin-2-yl)ethyl]thieno[2,3-d]pyridazin-4(5H)-one;
3-[4-Oxo-5-(2-quinolin-2-yl-ethyl)-4,5-dihydro-thieno[2,3-d]pyridazin-3-yl}-benzonitrile;
3-(3-fluorophenyl)-5-[2-(quinolin-2-yl)ethyl]thieno[2,3-d]pyridazin-4(5H)-one;
3-(3-hydroxyphenyl)-5-[2-(quinolin-2-yl)ethyl]thieno[2,3-d]pyridazin-4(5H)-one;
N,N-dimethyl-3-{4-oxo-5-[2-(quinolin-2-yl)ethyl]-4,5-dihydrothieno[2,3-d]pyridazin-3-yl}benzamide;
3-(3-methylphenyl)-5-[2-(quinolin-2-yl)ethyl]thieno[2,3-d]pyridazin-4(5H)-one;
5-[2-(quinolin-2-yl)ethyl]-3-(thiophen-2-yl)thieno[2,3-d]pyridazin-4(5H)-one;
3-(1-methyl-1H-indol-5-yl)-5-(2-quinolin-2-yl-ethyl)-5H-thieno[2,3-d]pyridazin-4-one;
3-(1H-indol-6-yl)-5-[2-(quinolin-2-yl)ethyl]thieno[2,3-d]pyridazin-4(5H)-one;
3-(pyrimidin-5-yl)-5-[2-(quinolin-2-yl)ethyl]thieno[2,3-d]pyridazin-4(5H)-one;
3-(2-methoxypyridin-3-yl)-5-[2-(quinolin-2-yl)ethyl]thieno[2,3-d]pyridazin-4(5H)-one;
3-(pyridin-3-yl)-5-[2-(quinolin-2-yl)ethyl]thieno[2,3-d]pyridazin-4(5H)-one;
3-(4-methoxypyridin-3-yl)-5-[2-(quinolin-2-yl)ethyl]thieno[2,3-d]pyridazin-4(5H)-one;
3-(furan-3-yl)-5-[2-(quinolin-2-yl)ethyl]thieno[2,3-d]pyridazin-4(5H)-one;
3-(quinolin-3-yl)-5-[2-(quinolin-2-yl)ethyl]thieno[2,3-d]pyridazin-4(5H)-one;
3-(isoquinolin-4-yl)-5-[2-(quinolin-2-yl)ethyl]thieno[2,3-d]pyridazin-4(5H)-one;
3-(isoquinolin-5-yl)-5-[2-(quinolin-2-yl)ethyl]thieno[2,3-d]pyridazin-4(5H)-one;
3-(1H-indol-4-yl)-5-(2-quinolin-2-yl-ethyl)-5H-thieno[2,3-d]pyridazin-4-one;
3-(2,3-dihydrobenzofuran-5-yl)-5-(2-quinolin-2-yl-ethyl)-5H-thieno[2,3-d]pyridazin-4-one;
3-(quinolin-5-yl)-5-[2-(quinolin-2-yl)ethyl]thieno[2,3-d]pyridazin-4(5H)-one;
3-(3,5-dimethyl-1,2-oxazol-4-yl)-5-[2-(quinolin-2-yl)ethyl]thieno[2,3-d]pyridazin-4(5H)-one;
3-(6-methoxypyridin-3-yl)-5-[2-(quinolin-2-yl)ethyl]thieno[2,3-d]pyridazin-4(5H)-one;

3-(2,3-dihydro-1,4-benzodioxin-6-yl)-5-[2-(quinolin-2-yl)ethyl]thieno[2,3-d]pyridazin-4(5H)-one;
3-(2-methylpyridin-4-yl)-5-[2-(quinolin-2-yl)ethyl]thieno[2,3-d]pyridazin-4(5H)-one;
3-(5-methoxypyridin-3-yl)-5-[2-(quinolin-2-yl)ethyl]thieno[2,3-d]pyridazin-4(5H)-one;
3-[6-(morpholin-4-yl)pyridin-3-yl]-5-[2-(quinolin-2-yl)ethyl]thieno[2,3-d]pyridazin-4(5H)-one;
3-(1,3-benzodioxol-5-yl)-5-[2-(quinolin-2-yl)ethyl]thieno[2,3-d]pyridazin-4(5H)-one;
3-(quinolin-6-yl)-5-[2-(quinolin-2-yl)ethyl]thieno[2,3-d]pyridazin-4(5H)-one;
3-(1-methyl-1H-pyrazol-4-yl)-5-[2-(quinolin-2-yl)ethyl]thieno[2,3-d]pyridazin-4(5H)-one;
3-[1-(2-methylpropyl)-1H-pyrazol-4-yl]-5-[2-(quinolin-2-yl)ethyl]thieno[2,3-d]pyridazin-4(5H)-one;
tert-butyl 2-{4-oxo-5-[2-(quinolin-2-yl)ethyl]-4,5-dihydrothieno[2,3-d]pyridazin-3-yl}-1H-pyrrole-1-carboxylate;
3-(2-methoxypyrimidin-5-yl)-5-[2-(quinolin-2-yl)ethyl]thieno[2,3-d]pyridazin-4(5H)-one;
5-[2-(quinolin-2-yl)ethyl]-3-(2,3,4-trifluorophenyl)thieno[2,3-d]pyridazin-4(5H)-one;
3-(4-fluoro-3-methylphenyl)-5-[2-(quinolin-2-yl)ethyl]thieno[2,3-d]pyridazin-4(5H)-one;
3-(4-fluoro-2-methylphenyl)-5-[2-(quinolin-2-yl)ethyl]thieno[2,3-d]pyridazin-4(5H)-one;
3-(3-chloro-4-fluorophenyl)-5-[2-(quinolin-2-yl)ethyl]thieno[2,3-d]pyridazin-4(5H)-one;
3-(2-chloro-4-fluorophenyl)-5-[2-(quinolin-2-yl)ethyl]thieno[2,3-d]pyridazin-4(5H)-one;
3-(3,4-dimethylphenyl)-5-[2-(quinolin-2-yl)ethyl]thieno[2,3-d]pyridazin-4(5H)-one;
3-(2,4-dimethylphenyl)-5-[2-(quinolin-2-yl)ethyl]thieno[2,3-d]pyridazin-4(5H)-one;
3-(2,4-difluorophenyl)-5-[2-(quinolin-2-yl)ethyl]thieno[2,3-d]pyridazin-4(5H)-one;
3-(2,4-dimethoxyphenyl)-5-[2-(quinolin-2-yl)ethyl]thieno[2,3-d]pyridazin-4(5H)-one;
3-(2,5-dimethoxyphenyl)-5-[2-(quinolin-2-yl)ethyl]thieno[2,3-d]pyridazin-4(5H)-one;
3-(2,3-difluorophenyl)-5-[2-(quinolin-2-yl)ethyl]thieno[2,3-d]pyridazin-4(5H)-one;
3-(3,4-dimethoxyphenyl)-5-[2-(quinolin-2-yl)ethyl]thieno[2,3-d]pyridazin-4(5H)-one;
3-(3,4-difluorophenyl)-5-[2-(quinolin-2-yl)ethyl]thieno[2,3-d]pyridazin-4(5H)-one;
3-(5-fluoro-2-methoxyphenyl)-5-[2-(quinolin-2-yl)ethyl]thieno[2,3-d]pyridazin-4(5H)-one;
3-(4-fluoro-2-methoxyphenyl)-5-[2-(quinolin-2-yl)ethyl]thieno[2,3-d]pyridazin-4(5H)-one;
3-(3,5-dimethoxyphenyl)-5-[2-(quinolin-2-yl)ethyl]thieno[2,3-d]pyridazin-4(5H)-one;
3-(2,5-difluorophenyl)-5-[2-(quinolin-2-yl)ethyl]thieno[2,3-d]pyridazin-4(5H)-one;
3-(2,3-dimethoxyphenyl)-5-[2-(quinolin-2-yl)ethyl]thieno[2,3-d]pyridazin-4(5H)-one;
3-(3-fluoro-4-methoxyphenyl)-5-[2-(quinolin-2-yl)ethyl]thieno[2,3-d]pyridazin-4(5H)-one;
3-(2-fluoro-3-methoxyphenyl)-5-[2-(quinolin-2-yl)ethyl]thieno[2,3-d]pyridazin-4(5H)-one;
3-(3,5-difluorophenyl)-5-[2-(quinolin-2-yl)ethyl]thieno[2,3-d]pyridazin-4(5H)-one;
3-(3-fluoro-5-methoxyphenyl)-5-[2-(quinolin-2-yl)ethyl]thieno[2,3-d]pyridazin-4(5H)-one;
3-(2-methoxy-5-methylphenyl)-5-[2-(quinolin-2-yl)ethyl]thieno[2,3-d]pyridazin-4(5H)-one;
3-(2,5-dichlorophenyl)-5-[2-(quinolin-2-yl)ethyl]thieno[2,3-d]pyridazin-4(5H)-one;
3-(naphthalen-2-yl)-5-[2-(quinolin-2-yl)ethyl]thieno[2,3-d]pyridazin-4(5H)-one;
3-phenyl-5-[2-(quinolin-2-yl)ethyl]thieno[2,3-d]pyridazin-4(5H)-one;
3-(1-benzofuran-2-yl)-5-[2-(quinolin-2-yl)ethyl]thieno[2,3-d]pyridazin-4(5H)-one;
3-(1H-indazol-5-yl)-5-[2-(quinolin-2-yl)ethyl]thieno[2,3-d]pyridazin-4(5H)-one;
3-(1-methyl-1H-pyrazol-5-yl)-5-[2-(quinolin-2-yl)ethyl]thieno[2,3-d]pyridazin-4(5H)-one;
3-(4,5-difluoro-2-methoxyphenyl)-5-[2-(quinolin-2-yl)ethyl]thieno[2,3-d]pyridazin-4(5H)-one;
3-(2-fluoro-4-methylphenyl)-5-[2-(quinolin-2-yl)ethyl]thieno[2,3-d]pyridazin-4(5H)-one;
3-(2-fluoro-5-methoxyphenyl)-5-[2-(quinolin-2-yl)ethyl]thieno[2,3-d]pyridazin-4(5H)-one;
3-methyl-4-{4-oxo-5-[2-(quinolin-2-yl)ethyl]-4,5-dihydrothieno[2,3-d]pyridazin-3-yl}benzonitrile;
5-[2-(6-fluoroquinolin-2-yl)ethyl]-3-(pyridin-4-yl)thieno[2,3-d]pyridazin-4(5H)-one;
5-[2,2-difluoro-2-(quinolin-2-yl)ethyl]-3-(pyridin-4-yl)thieno[2,3-d]pyridazin-4(5H)-one;
3-(pyridin-4-yl)-5-[2-(thieno[3,2-b]pyridin-5-yl)ethyl]thieno[2,3-d]pyridazin-4(5H)-one;
5-[2-(imidazo[1,2-a]pyridin-2-yl)ethyl]-3-(pyridin-4-yl)thieno[2,3-d]pyridazin-4(5H)-one;
5-[2-(7-fluoroimidazo[1,2-a]pyridin-2-yl)ethyl]-3-(pyridin-4-yl)thieno[2,3-d]pyridazin-4(5H)-one;
8-(pyridin-4-yl)-2-[2-(quinolin-2-yl)ethyl]phthalazin-1(2H)-one;
2-[2-(quinolin-2-yl)ethyl]-8-[4-(trifluoromethyl)phenyl]phthalazin-1(2H)-one;
8-(4-methylphenyl)-2-[2-(quinolin-2-yl)ethyl]phthalazin-1(2H)-one;
8-[4-(propan-2-yl)phenyl]-2-[2-(quinolin-2-yl)ethyl]phthalazin-1(2H)-one;
8-(4-ethylphenyl)-2-[2-(quinolin-2-yl)ethyl]phthalazin-1(2H)-one;
4-{4-oxo-3-[2-(quinolin-2-yl)ethyl]-3,4-dihydrophthalazin-5-yl}benzonitrile;
8-(4-methoxyphenyl)-2-[2-(quinolin-2-yl)ethyl]phthalazin-1(2H)-one;
8-(4-fluorophenyl)-2-[2-(quinolin-2-yl)ethyl]phthalazin-1(2H)-one;
(4-{4-oxo-3-[2-(quinolin-2-yl)ethyl]-3,4-dihydrophthalazin-5-yl}phenyl)acetonitrile;
8-(4-hydroxyphenyl)-2-[2-(quinolin-2-yl)ethyl]phthalazin-1(2H)-one;
8-(2-chlorophenyl)-2-[2-(quinolin-2-yl)ethyl]phthalazin-1(2H)-one;
8-(2-methylphenyl)-2-[2-(quinolin-2-yl)ethyl]phthalazin-1(2H)-one;
8-(2-ethylphenyl)-2-[2-(quinolin-2-yl)ethyl]phthalazin-1(2H)-one;
8-(2-fluorophenyl)-2-[2-(quinolin-2-yl)ethyl]phthalazin-1(2H)-one;
8-(2-methoxyphenyl)-2-[2-(quinolin-2-yl)ethyl]phthalazin-1(2H)-one;
8-(3-methoxyphenyl)-2-[2-(quinolin-2-yl)ethyl]phthalazin-1(2H)-one;
3-{4-oxo-3-[2-(quinolin-2-yl)ethyl]-3,4-dihydrophthalazin-5-yl}benzonitrile;
8-(3-fluorophenyl)-2-[2-(quinolin-2-yl)ethyl]phthalazin-1(2H)-one;

8-(3-hydroxyphenyl)-2-[2-(quinolin-2-yl)ethyl]phthalazin-1(2H)-one;
N,N-dimethyl-3-{4-oxo-3-[2-(quinolin-2-yl)ethyl]-3,4-dihydrophthalazin-5-yl}benzamide;
8-(3-methylphenyl)-2-[2-(quinolin-2-yl)ethyl]phthalazin-1(2H)-one;
2-[2-(quinolin-2-yl)ethyl]-8-(thiophen-2-yl)phthalazin-1(2H)-one;
8-(1-methyl-1H-indol-5-yl)-2-[2-(quinolin-2-yl)ethyl]phthalazin-1(2H)-one;
8-(3,5-dimethyl-1H-pyrazol-4-yl)-2-[2-(quinolin-2-yl)ethyl]phthalazin-1(2H)-one;
8-(1H-indol-5-yl)-2-[2-(quinolin-2-yl)ethyl]phthalazin-1(2H)-one;
8-(1H-indol-6-yl)-2-[2-(quinolin-2-yl)ethyl]phthalazin-1(2H)-one;
8-(pyrimidin-5-yl)-2-[2-(quinolin-2-yl)ethyl]phthalazin-1(2H)-one;
8-(2-methoxypyridin-3-yl)-2-[2-(quinolin-2-yl)ethyl]phthalazin-1(2H)-one;
8-(pyridin-3-yl)-2-[2-(quinolin-2-yl)ethyl]phthalazin-1(2H)-one;
8-(furan-3-yl)-2-[2-(quinolin-2-yl)ethyl]phthalazin-1(2H)-one;
8-(quinolin-3-yl)-2-[2-(quinolin-2-yl)ethyl]phthalazin-1(2H)-one;
8-(1H-indol-4-yl)-2-[2-(quinolin-2-yl)ethyl]phthalazin-1(2H)-one;
8-(2,3-dihydro-1-benzofuran-5-yl)-2-[2-(quinolin-2-yl)ethyl]phthalazin-1(2H)-one;
8-(3,4-dihydro-2H-1,5-benzodioxepin-7-yl)-2-[2-(quinolin-2-yl)ethyl]phthalazin-1(2H)-one;
8-(1-benzofuran-5-yl)-2-[2-(quinolin-2-yl)ethyl]phthalazin-1(2H)-one;
8-(6-methoxypyridin-3-yl)-2-[2-(quinolin-2-yl)ethyl]phthalazin-1(2H)-one;
8-(2,3-dihydro-1,4-benzodioxin-6-yl)-2-[2-(quinolin-2-yl)ethyl]phthalazin-1 (2H)-one;
8-(2-methylpyridin-4-yl)-2-[2-(quinolin-2-yl)ethyl]phthalazin-1(2H)-one;
8-(5-methoxypyridin-3-yl)-2-[2-(quinolin-2-yl)ethyl]phthalazin-1(2H)-one;
8-(5-fluoropyridin-3-yl)-2-[2-(quinolin-2-yl)ethyl]phthalazin-1(2H)-one;
8-(1,3-benzodioxol-5-yl)-2-[2-(quinolin-2-yl)ethyl]phthalazin-1(2H)-one;
8-(1-methyl-1H-pyrazol-4-yl)-2-[2-(quinolin-2-yl)ethyl]phthalazin-1(2H)-one;
8-[1-(2-methylpropyl)-1H-pyrazol-4-yl]-2-[2-(quinolin-2-yl)ethyl]phthalazin-1(2H)-one;
tert-butyl 2-{4-oxo-3-[2-(quinolin-2-yl)ethyl]-3,4-dihydrophthalazin-5-yl}-1H-pyrrole-1-carboxylate;
8-(3-chloro-4-fluorophenyl)-2-[2-(quinolin-2-yl)ethyl]phthalazin-1(2H)-one;
8-(2-chloro-4-fluorophenyl)-2-[2-(quinolin-2-yl)ethyl]phthalazin-1(2H)-one;
8-(3,4-dimethylphenyl)-2-[2-(quinolin-2-yl)ethyl]phthalazin-1(2H)-one;
8-(2,4-dimethoxyphenyl)-2-[2-(quinolin-2-yl)ethyl]phthalazin-1(2H)-one;
8-(2,5-dimethoxyphenyl)-2-[2-(quinolin-2-yl)ethyl]phthalazin-1(2H)-one;
8-(2,3-difluorophenyl)-2-[2-(quinolin-2-yl)ethyl]phthalazin-1(2H)-one;
8-(3,4-dimethoxyphenyl)-2-[2-(quinolin-2-yl)ethyl]phthalazin-1(2H)-one;
8-(3,4-difluorophenyl)-2-[2-(quinolin-2-yl)ethyl]phthalazin-1(2H)-one;
8-(5-fluoro-2-methoxyphenyl)-2-[2-(quinolin-2-yl)ethyl]phthalazin-1(2H)-one;
8-(4-fluoro-2-methoxyphenyl)-2-[2-(quinolin-2-yl)ethyl]phthalazin-1(2H)-one;
8-(3,5-dimethoxyphenyl)-2-[2-(quinolin-2-yl)ethyl]phthalazin-1(2H)-one;
8-(2,5-difluorophenyl)-2-[2-(quinolin-2-yl)ethyl]phthalazin-1(2H)-one;
8-(3-fluoro-4-methoxyphenyl)-2-[2-(quinolin-2-yl)ethyl]phthalazin-1(2H)-one;
8-(2-fluoro-3-methoxyphenyl)-2-[2-(quinolin-2-yl)ethyl]phthalazin-1(2H)-one;
8-(3,5-difluorophenyl)-2-[2-(quinolin-2-yl)ethyl]phthalazin-1(2H)-one;
8-(3-fluoro-5-methoxyphenyl)-2-[2-(quinolin-2-yl)ethyl]phthalazin-1(2H)-one;
8-(naphthalen-2-yl)-2-[2-(quinolin-2-yl)ethyl]phthalazin-1(2H)-one;
8-phenyl-2-[2-(quinolin-2-yl)ethyl]phthalazin-1(2H)-one;
8-(1-benzofuran-2-yl)-2-[2-(quinolin-2-yl)ethyl]phthalazin-1(2H)-one;
8-(1-methyl-1H-pyrazol-5-yl)-2-[2-(quinolin-2-yl)ethyl]phthalazin-1(2H)-one;
8-(4,5-difluoro-2-methoxyphenyl)-2-[2-(quinolin-2-yl)ethyl]phthalazin-1(2H)-one;
8-(2-fluoro-4-methylphenyl)-2-[2-(quinolin-2-yl)ethyl]phthalazin-1(2H)-one;
8-(2-fluoro-5-methoxyphenyl)-2-[2-(quinolin-2-yl)ethyl]phthalazin-1(2H)-one;
2-[2-(imidazo[1,2-a]pyridin-2-yl)ethyl]-8-(pyridin-3-yl)phthalazin-1(2H)-one;
2-[2-(imidazo[1,2-a]pyridin-2-yl)ethyl]-8-(pyridin-4-yl)phthalazin-1(2H)-one;
2-[2-(imidazo[1,2-a]pyridin-2-yl)ethyl]-8-(3-methoxypyridin-4-yl)phthalazin-1(2H)-one;
2-[2-(imidazo[1,2-a]pyridin-2-yl)ethyl]-8-(pyrimidin-5-yl)phthalazin-1(2H)-one;
2-[2-(imidazo[1,2-a]pyridin-2-yl)ethyl]-8-(1-methyl-1H-pyrazol-3-yl)phthalazin-1(2H)-one;
8-(furan-3-yl)-2-[2-(imidazo[1,2-a]pyridin-2-yl)ethyl]phthalazin-1(2H)-one;
2-[2-(imidazo[1,2-a]pyridin-2-yl)ethyl]-8-(2-oxo-2,3-dihydro-1H-indol-6-yl)phthalazin-1(2H)-one;
8-(3,4-dihydro-2H-chromen-6-yl)-2-[2-(imidazo[1,2-a]pyridin-2-yl)ethyl]phthalazin-1(2H)-one;
8-(1,1-dioxidothiomorpholin-4-yl)-2-[2-(quinolin-2-yl)ethyl]phthalazin-1(2H)-one;
2-[2-(imidazo[1,2-a]pyridin-2-yl)ethyl]-8-(morpholin-4-yl)phthalazin-1(2H)-one;
8-(1,1-dioxidothiomorpholin-4-yl)-2-[2-(imidazo[1,2-a]pyridin-2-yl)ethyl]phthalazin-1(2H)-one;
2-[2-(imidazo[1,2-a]pyridin-2-yl)ethyl]-8-(tetrahydro-1H-furo[3,4-c]pyrrol-5(3H)-yl)phthalazin-1(2H)-one;
8-(5,5-difluorohexahydrocyclopenta[c]pyrrol-2(1H)-yl)-2-[2-(imidazo[1,2-a]pyridin-2-yl)ethyl]phthalazin-1(2H)-one;
2-[2-(imidazo[1,2-a]pyridin-2-yl)ethyl]-8-(piperazin-1-yl)phthalazin-1 (2H)-one;
8-(4,4-difluoropiperidin-1-yl)-2-[2-(imidazo[1,2-a]pyridin-2-yl)ethyl]phthalazin-1(2H)-one;
8-[4-(chloromethyl)-4-(hydroxymethyl)piperidin-1-yl]-2-[2-(imidazo[1,2-a]pyridin-2-yl)ethyl]phthalazin-1(2H)-one;
2-[2-(imidazo[1,2-a]pyridin-2-yl)ethyl]-8-(piperidin-1-yl)phthalazin-1 (2H)-one;

8-(2,3-dihydro-4H-1,4-benzoxazin-4-yl)-2-[2-(imidazo[1,2-a]pyridin-2-yl)ethyl]phthalazin-1(2H)-one;

2-[2-(imidazo[1,2-a]pyridin-2-yl)ethyl]-8-[4-(trifluoromethyl)piperidin-1-yl]phthalazin-1(2H)-one;

2-[2-(imidazo[1,2-a]pyridin-2-yl)ethyl]-8-(4-methylpiperazin-1-yl)phthalazin-1(2H)-one;

8-(1,3-dihydro-2H-isoindol-2-yl)-2-[2-(imidazo[1,2-a]pyridin-2-yl)ethyl]phthalazin-1(2H)-one;

8-(7-benzyl-2,7-diazaspiro[4.4]non-2-yl)-2-[2-(imidazo[1,2-a]pyridin-2-yl)ethyl]phthalazin-1(2H)-one;

8-({[(3 aR,4S,6aS)-2-benzyloctahydrocyclopenta[c]pyrrol-4-yl]methyl}amino)-2-[2-(imidazo[1,2-a]pyridin-2-yl)ethyl]phthalazin-1(2H)-one;

tert-butyl (3R)-3-({3-[2-(imidazo[1,2-a]pyridin-2-yl)ethyl]-4-oxo-3,4-dihydrophthalazin-5-yl}amino)pyrrolidine-1-carboxylate;

8-(2,6-dimethylmorpholin-4-yl)-2-[2-(imidazo[1,2-a]pyridin-2-yl)ethyl]phthalazin-1(2H)-one;

2-[2-(imidazo[1,2-a]pyridin-2-yl)ethyl]-8-(1,4-oxazepan-4-yl)phthalazin-1(2H)-one;

tert-butyl 4-{3-[2-(imidazo[1,2-a]pyridin-2-yl)ethyl]-4-oxo-3,4-dihydrophthalazin-5-yl}-3,6-dihydropyridine-1(2H)-carboxylate;

5-(pyridin-4-yl)-2-[2-(quinolin-2-yl)ethyl]phthalazin-1(2H)-one;

5-(pyrimidin-5-yl)-2-[2-(quinolin-2-yl)ethyl]phthalazin-1(2H)-one;

5-(1-methyl-1H-pyrazol-5-yl)-2-[2-(quinolin-2-yl)ethyl]phthalazin-1(2H)-one;

5-(1,1-dioxidothiomorpholin-4-yl)-2-[2-(quinolin-2-yl)ethyl]phthalazin-1(2H)-one;

2-[2-(imidazo[1,2-a]pyridin-2-yl)ethyl]-5-(pyridin-3-yl)phthalazin-1(2H)-one;

2-[2-(imidazo[1,2-a]pyridin-2-yl)ethyl]-5-(pyrimidin-5-yl)phthalazin1(2H)-one;

2-[2-(imidazo[1,2-a]pyridin-2-yl)ethyl]-5-(morpholin-4-yl)phthalazin-1(2H)-one;

2-[2-(imidazo[1,2-a]pyridin-2-yl)ethyl]-5-(tetrahydro-1H-furo[3,4-c]pyrrol-5(3H)-yl)phthalazin-1(2H)-one;

2-[2-(imidazo[1,2-a]pyridin-2-yl)ethyl]-4-(pyrimidin-5-yl)phthalazin-1(2H)-one;

2-[2-(imidazo[1,2-a]pyridin-2-yl)ethyl]-4-(morpholin-4-yl)phthalazin-1(2H)-one;

3-(3-methoxypyridin-4-yl)-5-[2-(quinolin-2-yl)ethyl]thieno[3,2-c]pyridin-4(5H)-one;

3-(3-hydroxypyridin-4-yl)-5-[2-(quinolin-2-yl)ethyl]thieno[3,2-c]pyridin-4(5H)-one;

3-(1-methyl-1H-pyrazol-5-yl)-5-[2-(quinolin-2-yl)ethyl]thieno[3,2-c]pyridin-4(5)H-one;

3-(pyridin-4-yl)-5-[2-(quinolin-2-yl)ethyl]thieno[3,2-c]pyridin-4(5H)-one;

3-(pyrimidin-5-yl)-5-(2-quinolin-2-yl)ethyl)thieno[3,2-c]pyridin-4(5H)-one;

3-(2-oxoindolin-6-yl)-5-[2-(quinolin-2-yl)ethyl]thieno[3,2-c]pyridin-4(5H)-one;

3-(3-hydroxyphenyl)-5-[2-(quinolin-2-yl)ethyl]thieno[3,2-c]pyridin-4(5H)-one;

5-[2-(5-ethylpyridin-2-yl)ethyl]-3-(pyridin-4-yl)thieno[3,2-c]pyridin-4(5H)-one;

5-[2-(imidazo[1,2-a]pyridin-2-yl)ethyl]-3-(pyridin-4-yl)thieno[3,2-c]pyridin-4(5H)-one;

3-(morpholin-4-yl)-5-[2-(quinolin-2-yl)ethyl]thieno[3,2-c]pyridin-4(5H)-one;

tert-butyl-4-(4-oxo-5-(2-(quinolin-2-yl)ethyl)-4,5-dihydrothieno[3,2-c]pyridin-3-yl)-5,6-dihydropyridine-1(2H) carboxylate;

5-(2-(quinolin-2-yl)ethyl)-3-(1,2,3,6-tetrahydropyridin-4-yl)thieno[3,2-c]pyridin-4(5H)-one;

tert-butyl-4-(4-oxo-5-(2-(quinolin-2-yl)ethyl)-4,5-dihydrothieno[3,2-c]pyridin-3-yl)-piperidine-1 carboxylate;

3-(piperidin-4-yl)-5-[2-(quinolin-2-yl)ethyl]thieno[3,2-c]pyridin-4(5H)-one;

3-methyl-7-(pyridin-4-yl)-5-(2-(quinolin-2-yl)ethyl)thieno[3,2-c]pyridin-4(5H)-one;

3-(pyridin-4-yl)-5-[2-(5,6,7,8-tetrahydroquinolin-2-yl)ethyl]thieno[2,3-d]pyridazin-4(5H)-one;

(R)-tert-butyl 3-(3-(2-(imidazo[1,2-a]pyridin-2-yl)ethyl)-4-oxo-3,4-dihydrophthalazin-5-ylamino)pyrrolidine-1-carboxylate;

2-[2-(imidazo[1,2-a]pyridin-2-yl)ethyl]-8-[(3R)-pyrrolidin-3-ylamino]phthalazin-1(2H)-one;

5-(3-hydroxyphenyl)-2-[2-(quinolin-2-yl)ethyl]phthalazin-1(2H)-one;

(E)-8-(pyridin-4-yl)-2-(2-(quinolin-2-yl)vinyl)isoquinolin-1(2H)-one;

anti (rac) 8-(pyridin-4-yl)-2-(2-(quinolin-2-yl)cyclopropyl)isoquinolin-1(2H)-one;

anti (+)-8-(pyridin-4-yl)-2-(2-(quinolin-2-yl)cyclopropyl)isoquinolin-1(2H)-one;

anti (−)-8-(pyridin-4-yl)-2-(2-(quinolin-2-yl)cyclopropyl)isoquinolin-1(2H)-one;

8-(pyridin-4-yl)-2-(2-quinolin-2-yl-ethyl)isoquinolin-1(2H)-one;

anti (rac) 3-(pyridin-4-yl)-5-(2-(quinolin-2-yl)cyclopropyl)thieno[3,2-c]pyridin-4(5H)-one;

anti (+) 3-(pyridin-4-yl)-5-(2-(quinolin-2-yl)cyclopropyl)thieno[3,2-c]pyridin-4(5H)-one;

anti (−) 3-(pyridin-4-yl)-5-(2-(quinolin-2-yl)cyclopropyl)thieno[3,2-c]pyridin-4(5H)-one;

(E)-8-pyridin-4-yl-2-(2-quinolin-2-yl-vinyl)-2H-phthalazin-1-one;

anti (rac) 8-pyridin-4-yl-2-(2-quinolin-2-yl-cyclopropyl)-2H-phthalazin-1-one;

anti (+) 8-pyridin-4-yl-2-(2-quinolin-2-yl-cyclopropyl)-2H-phthalazin-1-one;

anti (−) 8-pyridin-4-yl-2-(2-quinolin-2-yl-cyclopropyl)-2H-phthalazin-1-one;

and the N-oxides, the prodrugs, the tautomers and the hydrates thereof, and the pharmaceutically acceptable salts thereof.

Further particular embodiments of the invention relate to the compounds of formula I, where the compounds of the formula I are selected from the group consisting of:

7-(pyridin-4-yl)-5-[2-(quinolin-2-yl)ethyl]furo[3,2-c]pyridin-4(5H)-one;

3-(pyridin-4-yl)-5-(2-(quinolin-2-yl)ethyl)furo[3,2-c]pyridin-4(5H)-one;

5-(2-(1H-benzo[d]imidazol-2-yl)ethyl)-3-(pyridin-4-yl)furo[3,2-c]pyridin-4(5H)-one;

5-(2-(imidazo[1,2-a]pyridin-2-yl)ethyl)-3-(pyridin-4-yl)furo[3,2-c]pyridin-4(5H)-one;

3-(pyrimidin-5-yl)-5-(2-(quinolin-2-yl)ethyl)furo[3,2-c]pyridin-4(5H)-one;

4-(pyridin-4-yl)-6-(2-(quinolin-2-yl)allyl)pyrido[2,3-d]pyridazin-5 (6H)-one;

syn 8-(pyridin-4-yl)-2-(2-(quinolin-2-yl)cyclopropyl)isoquinolin-1(2H)-one;

syn 3-(pyridin-4-yl)-5-(2-(quinolin-2-yl)cyclopropyl)thieno[3,2-c]pyridin-4(5H)-one;

anti 3-(pyridazin-4-yl)-5-(2-(quinolin-2-yl)cyclopropyl)furo[3,2-c]pyridin-4(5H)-one;

syn 3-(pyridazin-4-yl)-5-(2-(quinolin-2-yl)cyclopropyl)furo[3,2-c]pyridin-4(5H)-one;

anti 3-(pyridin-4-yl)-5-(2-(quinolin-2-yl)cyclopropyl)furo[3,2-c]pyridin-4(5H)-one;
syn 3-(pyridin-4-yl)-5-(2-(quinolin-2-yl)cyclopropyl)furo[3,2-c]pyridin-4(5H)-one;
anti 8-(oxetan-3-ylamino)-2-(2-(quinolin-2-yl)cyclopropyl)isoquinolin-1(2H)-one;
syn 8-(oxetan-3-ylamino)-2-(2-(quinolin-2-yl)cyclopropyl)isoquinolin-1(2H)-one;
anti 8-(pyridazin-4-yl)-2-(2-(quinolin-2-yl)cyclopropyl)isoquinolin-1(2H)-one;
syn 8-(pyridazin-4-yl)-2-(2-(quinolin-2-yl)cyclopropyl)isoquinolin-1(2H)-one;
anti 8-(6-fluoropyridin-3-yl)-2-(2-(quinolin-2-yl)cyclopropyl)isoquinolin-1(2H)-one;
syn 8-(6-fluoropyridin-3-yl)-2-(2-(quinolin-2-yl)cyclopropyl)isoquinolin-1(2H)-one;
anti 8-(2-fluoropyridin-4-yl)-2-(2-(quinolin-2-yl)cyclopropyl)isoquinolin-1(2H)-one;
syn 8-(2-fluoropyridin-4-yl)-2-(2-(quinolin-2-yl)cyclopropyl)isoquinolin-1(2H)-one;
anti 8-(pyridin-3-yl)-2-(2-(quinolin-2-yl)cyclopropyl)isoquinolin-1(2H)-one;
syn 8-(pyridin-3-yl)-2-(2-(quinolin-2-yl)cyclopropyl)isoquinolin-1(2H)-one;
anti 8-(pyrimidin-5-yl)-2-(2-(quinolin-2-yl)cyclopropyl)isoquinolin-1(2H)-one;
syn 8-(pyrimidin-5-yl)-2-(2-(quinolin-2-yl)cyclopropyl)isoquinolin-1(2H)-one;
anti 8-(1-methyl-1H-pyrazol-4-yl)-2-(2-(quinolin-2-yl)cyclopropyl)isoquinolin-1(2H)-one;
syn 8-(1-methyl-1H-pyrazol-4-yl)-2-(2-(quinolin-2-yl)cyclopropyl)isoquinolin-1(2H)-one;
anti 8-(3-fluoropyridin-4-yl)-2-(2-(quinolin-2-yl)cyclopropyl)isoquinolin-1(2H)-one;
syn 8-(3-fluoropyridin-4-yl)-2-(2-(quinolin-2-yl)cyclopropyl)isoquinolin-1(2H)-one;
anti 8-(2-fluoropyridin-4-yl)-2-(2-(quinolin-2-yl)cyclopropyl)isoquinolin-1(2H)-one;
syn 8-(2-fluoropyridin-4-yl)-2-(2-(quinolin-2-yl)cyclopropyl)isoquinolin-1(2H)-one;
anti 8-((3 S)-3-hydroxypiperidin-1-yl)-2-(2-(quinolin-2-yl)cyclopropyl)isoquinolin-1(2H)-one;
syn 8-((3 S)-3-hydroxypiperidin-1-yl)-2-(2-(quinolin-2-yl)cyclopropyl)isoquinolin-1(2H)-one;
anti 8-(3-methoxypiperidin-1-yl)-2-(2-(quinolin-2-yl)cyclopropyl)isoquinolin-1(2H)-one;
syn 8-(3-methoxypiperidin-1-yl)-2-(2-(quinolin-2-yl)cyclopropyl)isoquinolin-1(2H)-one;
anti 8-morpholino-2-(2-(quinolin-2-yl)cyclopropyl)isoquinolin-1(2H)-one;
syn 8-morpholino-2-(2-(quinolin-2-yl)cyclopropyl)isoquinolin-1(2H)-one;
anti 1-(1-oxo-2-(2-(quinolin-2-yl)cyclopropyl)-1,2-dihydroisoquinolin-8-yl)piperidine-4-carbonitrile;
syn 1-(1-oxo-2-(2-(quinolin-2-yl)cyclopropyl)-1,2-dihydroisoquinolin-8-yl)piperidine-4-carbonitrile;
anti 8-((3R,4R)-4-fluoro-3-hydroxypiperidin-1-yl)-2-(2-(quinolin-2-yl)cyclopropyl)isoquinolin-1(2H)-one;
syn 8-((3R,4R)-4-fluoro-3-hydroxypiperidin-1-yl)-2-(2-(quinolin-2-yl)cyclopropyl)isoquinolin-1(2H)-one;
anti 8-((3 S)-3-hydroxypyrrolidin-1-yl)-2-(2-(quinolin-2-yl)cyclopropyl)isoquinolin-1(2H)-one;
syn 8-((3 S)-3-hydroxypyrrolidin-1-yl)-2-(2-(quinolin-2-yl)cyclopropyl)isoquinolin-1(2H)-one;
anti 8-((3R)-3-hydroxypyrrolidin-1-yl)-2-(2-(quinolin-2-yl)cyclopropyl)isoquinolin-1(2H)-one;
syn 8-((3R)-3-hydroxypyrrolidin-1-yl)-2-(2-(quinolin-2-yl)cyclopropyl)isoquinolin-1(2H)-one;
anti 8-(methyl(oxetan-3-yl)amino)-2-(2-(quinolin-2-yl)cyclopropyl)isoquinolin-1(2H)-one;
syn 8-(methyl(oxetan-3-yl)amino)-2-(2-(quinolin-2-yl)cyclopropyl)isoquinolin-1(2H)-one;
anti 8-(4-methoxypiperidin-1-yl)-2-(2-(quinolin-2-yl)cyclopropyl)isoquinolin-1(2H)-one;
syn 8-(4-methoxypiperidin-1-yl)-2-(2-(quinolin-2-yl)cyclopropyl)isoquinolin-1(2H)-one;
anti 8-(4-hydroxypiperidin-1-yl)-2-(2-(quinolin-2-yl)cyclopropyl)isoquinolin-1(2H)-one;
syn 8-(4-hydroxypiperidin-1-yl)-2-(2-(quinolin-2-yl)cyclopropyl)isoquinolin-1(2H)-one;
anti 8-(1-acetylpiperidin-4-ylamino)-2-(2-quinolin-2-cyclopropyl)isoquinolin-1(2H)-one;
syn 8-(1-acetylpiperidin-4-ylamino)-2-(2-quinolin-2-cyclopropyl)isoquinolin-1(2H)-one;
anti 8-(piperidin-4-ylamino)-2-(2-(quinolin-2-yl)cyclopropyl)isoquinolin-1(2H)-one;
syn 8-(piperidin-4-ylamino)-2-(2-(quinolin-2-yl)cyclopropyl)isoquinolin-1(2H)-one;
anti 2-(2-(quinolin-2-yl)cyclopropyl)-8-(tetrahydro-2H-pyran-4-yl)isoquinolin-1(2H)-one;
syn 2-(2-(quinolin-2-yl)cyclopropyl)-8-(tetrahydro-2H-pyran-4-yl)isoquinolin-1(2H)-one;
anti 2-(2-(quinolin-2-yl)cyclopropyl)-8-(2-oxa-6-azaspiro[3.4]octan-6-yl)isoquinolin-1 (2H)-one;
syn 2-(2-(quinolin-2-yl)cyclopropyl)-8-(2-oxa-6-azaspiro[3.4]octan-6-yl)isoquinolin-1 (2H)-one;
anti 8-(dihydro-1H-furo[3,4-c]pyrrol-5(3H,6H,6aH)-yl)-2-(2-(quinolin-2-yl)cyclopropyl)isoquinolin-1(2H)-one;
syn 8-(dihydro-1H-furo[3,4-c]pyrrol-5(3H,6H,6aH)-yl)-2-(2-(quinolin-2-yl)cyclopropyl)isoquinolin-1(2H)-one;
anti 8-(4,4-difluoropiperidin-1-yl)-2-(2-(quinolin-2-yl)cyclopropyl)isoquinolin-1(2H)-one;
syn 8-(4,4-difluoropiperidin-1-yl)-2-(2-(quinolin-2-yl)cyclopropyl)isoquinolin-1(2H)-one;
anti 8-morpholino-2-(2-(quinolin-2-yl)cyclopropyl)isoquinolin-1(2H)-one;
syn 8-morpholino-2-(2-(quinolin-2-yl)cyclopropyl)isoquinolin-1(2H)-one;
anti 8-(3-(difluoromethyl)pyrrolidin-1-yl)-2-(2-(quinolin-2-yl)cyclopropyl)isoquinolin-1(2H)-one;
syn 8-(3-(difluoromethyl)pyrrolidin-1-yl)-2-(2-(quinolin-2-yl)cyclopropyl)isoquinolin-1(2H)-one;
anti 8-((1R,5S)-3-oxa-8-azabicyclo[3.2.1]octan-8-yl)-2-(2-(quinolin-2-yl)cyclo-propyl)isoquinolin-1(2H)-one;
syn 8-((1R,5S)-3-oxa-8-azabicyclo[3.2.1]octan-8-yl)-2-(2-(quinolin-2-yl)cyclo-propyl)isoquinolin-1(2H)-one;
anti 8-(4-methylpiperazin-1-yl)-2-(2-(quinolin-2-yl)cyclopropyl)isoquinolin-1(2H)-one;
syn 8-(4-methylpiperazin-1-yl)-2-(2-(quinolin-2-yl)cyclopropyl)isoquinolin-1(2H)-one;
anti 8-(3-(fluoromethyl)pyrrolidin-1-yl)-2-(2-(quinolin-2-yl)cyclopropyl)isoquinolin-1(2H)-one;
syn 8-(3-(fluoromethyl)pyrrolidin-1-yl)-2-(2-(quinolin-2-yl)cyclopropyl)isoquinolin-1(2H)-one;
anti 8-((1R,5S)-8-oxa-3-azabicyclo[3.2.1]octan-3-yl)-2-(2-(quinolin-2-yl)cyclopropyl)isoquinolin-1(2H)-one;
syn 8-((1R,5S)-8-oxa-3-azabicyclo[3.2.1]octan-3-yl)-2-(2-(quinolin-2-yl)cyclopropyl)isoquinolin-1(2H)-one;
anti 8-(4-fluorophenyl)-2-(2-(quinolin-2-yl)cyclopropyl)isoquinolin-1(2H)-one;
syn 8-(4-fluorophenyl)-2-(2-(quinolin-2-yl)cyclopropyl)isoquinolin-1(2H)-one;

syn 8-((3R)-3-hydroxypyrrolidin-1-yl)-2-(2-(quinolin-2-yl)cyclopropyl)isoquinolin-1(2H)-one;

anti 8-(furan-3-yl)-2-(2-(quinolin-2-yl)cyclopropyl)isoquinolin-1(2H)-one;
syn 8-(furan-3-yl)-2-(2-(quinolin-2-yl)cyclopropyl)isoquinolin-1(2H)-one;
anti 8-(4,5-dihydrofuran-3-yl)-2-(2-(quinolin-2-yl)cyclopropyl)isoquinolin-1(2H)-one;
syn 8-(4,5-dihydrofuran-3-yl)-2-(2-(quinolin-2-yl)cyclopropyl)isoquinolin-1(2H)-one;
anti 8-(4-methoxyphenyl)-2-(2-(quinolin-2-yl)cyclopropyl)isoquinolin-1(2H)-one;
syn 8-(4-methoxyphenyl)-2-(2-(quinolin-2-yl)cyclopropyl)isoquinolin-1(2H)-one;
anti 2-(2-(6-fluoroquinolin-2-yl)cyclopropyl)-8-morpholinoisoquinolin-1(2H)-one;
syn 2-(2-(6-fluoroquinolin-2-yl)cyclopropyl)-8-morpholinoisoquinolin-1(2H)-one;
anti 2-(2-(6-fluoroquinolin-2-yl)cyclopropyl)-8-(pyridin-3-yl)isoquinolin-1 (2H)-one;
syn 2-(2-(6-fluoroquinolin-2-yl)cyclopropyl)-8-(pyridin-3-yl)isoquinolin-1 (2H)-one;
anti 2-(2-(6-fluoroquinolin-2-yl)cyclopropyl)-8-(pyrimidin-5-yl)isoquinolin-1(2H)-one;
syn 2-(2-(6-fluoroquinolin-2-yl)cyclopropyl)-8-(pyrimidin-5-yl)isoquinolin-1(2H)-one;
anti 2-(2-(6-fluoroquinolin-2-yl)cyclopropyl)-8-(pyridin-4-yl)isoquinolin-1(2H)-one;
syn 2-(2-(6-fluoroquinolin-2-yl)cyclopropyl)-8-(pyridin-4-yl)isoquinolin-1(2H)-one;
anti 4-fluoro-8-(pyridin-4-yl)-2-(2-(quinolin-2-yl)cyclopropyl)isoquinolin-1(2H)-one;
syn 4-fluoro-8-(pyridin-4-yl)-2-(2-(quinolin-2-yl)cyclopropyl)isoquinolin-1(2H)-one;
anti 4-chloro-8-(pyrimidin-5-yl)-2-(2-(quinolin-2-yl)cyclopropyl)isoquinolin-1(2H)-one;
syn 4-chloro-8-(pyrimidin-5-yl)-2-(2-(quinolin-2-yl)cyclopropyl)isoquinolin-1(2H)-one;
anti 4-(pyridin-4-yl)-6-(2-(quinolin-2-yl)cyclopropyl)pyrido[2,3-d]pyridazin-5(6H)-one;
syn 4-(pyridin-4-yl)-6-(2-(quinolin-2-yl)cyclopropyl)pyrido[2,3-d]pyridazin-5(6H)-one;
anti 2-(2-(6-fluoroquinolin-2-yl)cyclopropyl)-8-(pyridin-4-yl)phthalazin-1(2H)-one;
syn 2-(2-(6-fluoroquinolin-2-yl)cyclopropyl)-8-(pyridin-4-yl)phthalazin-1(2H)-one;
anti 7-fluoro-3-(pyridin-4-yl)-5-(2-(quinolin-2-yl)cyclopropyl)thieno[3,2-c]pyridin-4(5H)-one;
syn 7-fluoro-3-(pyridin-4-yl)-5-(2-(quinolin-2-yl)cyclopropyl)thieno[3,2-c]pyridin-4(5H)-one;
anti 3-(2-fluoropyridin-4-yl)-5-(2-(6-fluoroquinolin-2-yl)cyclopropyl)thieno[3,2-c]pyridin-4(5H)-one;
syn 3-(2-fluoropyridin-4-yl)-5-(2-(6-fluoroquinolin-2-yl)cyclopropyl)thieno[3,2-c]pyridin-4(5H)-one;
anti 5-(2-(6-fluoroquinolin-2-yl)cyclopropyl)-3-(pyridin-4-yl)thieno[3,2-c]pyridin-4(5H)-one;
syn 5-(2-(6-fluoroquinolin-2-yl)cyclopropyl)-3-(pyridin-4-yl)thieno[3,2-c]pyridin-4(5H)-one;
anti 3-(pyrimidin-5-yl)-5-(2-(quinolin-2-yl)cyclopropyl)thieno[3,2-c]pyridin-4(5H)-one;
syn 3-(pyrimidin-5-yl)-5-(2-(quinolin-2-yl)cyclopropyl)thieno[3,2-c]pyridin-4(5H)-one;
anti 3-(pyrimidin-5-yl)-5-(2-(quinolin-2-yl)cyclopropyl)thieno[3,2-c]pyridin-4(5H)-one;
syn 3-(pyrimidin-5-yl)-5-(2-(quinolin-2-yl)cyclopropyl)thieno[3,2-c]pyridin-4(5H)-one;
anti 3-(pyrimidin-5-yl)-5-(2-(quinolin-2-yl)cyclopropyl)thieno[3,2-c]pyridin-4(5H)-one;
syn 3-(pyrimidin-5-yl)-5-(2-(quinolin-2-yl)cyclopropyl)thieno[3,2-c]pyridin-4(5H)-one;
anti 3-(6-fluoropyridin-3-yl)-5-(2-(quinolin-2-yl)cyclopropyl)thieno[3,2-c]pyridin-4(5H)-one;
syn 3-(6-fluoropyridin-3-yl)-5-(2-(quinolin-2-yl)cyclopropyl)thieno[3,2-c]pyridin-4(5H)-one;
anti 3-(2-methylpyrimidin-5-yl)-5-(2-(quinolin-2-yl)cyclopropyl)thieno[3,2-c]pyridin-4(5H)-one;
syn 3-(2-methylpyrimidin-5-yl)-5-(2-(quinolin-2-yl)cyclopropyl)thieno[3,2-c]pyridin-4(5H)-one;
anti 3-(pyridazin-4-yl)-5-(2-(quinolin-2-yl)cyclopropyl)thieno[3,2-c]pyridin-4(5H)-one;
syn 3-(pyridazin-4-yl)-5-(2-(quinolin-2-yl)cyclopropyl)thieno[3,2-c]pyridin-4(5H)-one;
anti 3-(2-fluoropyridin-4-yl)-5-(2-(quinolin-2-yl)cyclopropyl]thieno[3,2-c]pyridin-4(5H)-one;
syn 3-(2-fluoropyridin-4-yl)-5-(2-(quinolin-2-yl)cyclopropyl)thieno[3,2-c]pyridin-4(5H)-one;
anti 3-(morpholin-4-yl)-5[2-(quinolin-2-yl)cyclopropyl]thieno[3,2-c]pyridin-4(5H)-one;
syn 3-(morpholin-4-yl)-5[2-(quinolin-2-yl)cyclopropyl]thieno[3,2-c]pyridin-4(5H)-one;
anti 3-(pyridin-3-yl)-5-[2-(thieno[3,2-b]pyridin-5-yl)cyclopropyl]thieno[3,2-c]pyridin-4(5H)-one;
syn 3-(pyridin-3-yl)-5-[2-(thieno[3,2-b]pyridin-5-yl)cyclopropyl]thieno[3,2-c]pyridin-4(5H)-one;
anti 3-(pyridin-3-yl)-5-[2-(quinolin-2-yl)cyclopropyl]thieno[3,2-c]pyridin-4(5H)-one;
syn 3-(pyridin-3-yl)-5-[2-(quinolin-2-yl)cyclopropyl]thieno[3,2-c]pyridin-4(5H)-one;
anti 3-(pyrimidin-5-yl)-5-[2-(quinolin-2-yl)cyclopropyl]thieno[2,3-d]pyridazin-4(5H)-one;
syn 3-(pyrimidin-5-yl)-5-[2-(quinolin-2-yl)cyclopropyl]thieno[2,3-d]pyridazin-4(5H)-one;
anti 3-(pyridin-4-yl)-5-[2-(thieno[3,2-b]pyridin-5-yl)cyclopropyl]thieno[2,3-d]pyridazin-4(5H)-one;
syn 3-(pyridin-4-yl)-5-[2-(thieno[3,2-b]pyridin-5-yl)cyclopropyl]thieno[2,3-d]pyridazin-4(5H)-one;
anti 3-(pyridin-4-yl)-5-[2-(thieno[3,2-b]pyridin-5-yl)cyclopropyl]thieno[3,2-c]pyridin-4(5H)-one;
syn 3-(pyridin-4-yl)-5-[2-(thieno[3,2-b]pyridin-5-yl)cyclopropyl]thieno[3,2-c]pyridin-4(5H)-one;
anti 3-(pyridin-4-yl)-5-[2-(quinolin-2-yl)cyclopropyl]thieno[3,2-c]pyridin-4(5H)-one;
syn 3-(pyridin-4-yl)-5-[2-(quinolin-2-yl)cyclopropyl]thieno[3,2-c]pyridin-4(5H)-one;
anti 3-(pyridin-4-yl)-5-[2-(quinolin-2-yl)cyclopropyl]thieno[2,3-d]pyridazin-4(5H)-one;
syn 3-(pyridin-4-yl)-5-[2-(quinolin-2-yl)cyclopropyl]thieno[2,3-d]pyridazin-4(5H)-one;
anti 5-(pyrimidin-5-yl)-2-[2-(quinolin-2-yl)cyclopropyl]isoquinolin-1(2H)-one;
syn 5-(pyrimidin-5-yl)-2-[2-(quinolin-2-yl)cyclopropyl]isoquinolin-1(2H)-one;
anti 5-(pyridin-4-yl)-2-[2-(quinolin-2-yl)cyclopropyl]isoquinolin-1(2H)-one;
syn 5-(pyridin-4-yl)-2-[2-(quinolin-2-yl)cyclopropyl]isoquinolin-1(2H)-one;
anti 5-(pyridin-3-yl)-2-[2-(quinolin-2-yl)cyclopropyl]isoquinolin-1(2H)-one;
syn 5-(pyridin-3-yl)-2-[2-(quinolin-2-yl)cyclopropyl]isoquinolin-1(2H)-one;
anti 5-(morpholin-4-yl)-2-(2-(quinolin-2-yl)cyclopropyl]isoquinolin-1(2H)-one;
syn 5-(morpholin-4-yl)-2-(2-(quinolin-2-yl)cyclopropyl]isoquinolin-1(2H)-one;

anti 4-fluoro-8-(pyrimidin-5-yl)-2-(2-(quinolin-2-yl)cyclopropyl)isoquinolin-1(2H)-one;
syn 4-fluoro-8-(pyrimidin-5-yl)-2-(2-(quinolin-2-yl)cyclopropyl)isoquinolin-1(2H)-one;
8-(pyridin-4-yl)-2-[2-(quinolin-2-yl)ethyl]pyrido[3,4-d]pyridazin-1(2H)-one;
5-[2-(imidazo[1,2-a]pyridin-2-yl)ethyl]-7-(1-methyl-1H-imidazol-4-yl)-3-(pyridin-4-yl)thieno[2,3-d]pyridazin-4(5H)-one;
5-[2-(imidazo[1,2-a]pyridin-2-yl)ethyl]-7-(1-methyl-1H-pyrazol-4-yl)-3-(pyridin-4-yl)thieno[2,3-d]pyridazin-4(5H)-one;
5-[2-(imidazo[1,2-a]pyridin-2-yl)ethyl]-7-(pyridin-3-yl)-3-(pyridin-4-yl)thieno[2,3-d]pyridazin-4(5H)-one;
5-[2-(6-chloroquinolin-2-yl)ethyl]-3-(pyridin-4-yl)thieno[3,2-c]pyridin-4(5H)-one;
5-[2-(3-methylquinolin-2-yl)ethyl]-3-(pyridin-4-yl)thieno[3,2-c]pyridin-4(5H)-one;
5-[2-(8-fluoroquinolin-2-yl)ethyl]-3-(pyridin-4-yl)thieno[3,2-c]pyridin-4(5H)-one;
5-[2-(6-fluoroquinolin-2-yl)ethyl]-3-(pyridin-3-yl)thieno[3,2-c]pyridin-4(5H)-one;
5-[2-(6-fluoroquinolin-2-yl)ethyl]-3-(pyridin-4-yl)thieno[3,2-c]pyridin-4(5H)-one;
5-[2-(imidazo[1,2-a]pyridin-2-yl)ethyl]-3-(pyridin-3-yl)thieno[3,2-c]pyridin-4(5H)-one;
3-(pyridin-4-yl)-5-[2-(quinoxalin-2-yl)ethyl]thieno[2,3-d]pyridazin-4(5H)-one;
5-[2-(1,5-naphthyridin-2-yl)ethyl]-3-(pyridin-4-yl)thieno[2,3-d]pyridazin-4(5H)-one;
5-[2-(1H-indazol-1-yl)ethyl]-3-(pyridin-4-yl)thieno[2,3-d]pyridazin-4(5H)-one;
3-(1-methyl-1H-pyrazol-3-yl)-5-[2-(quinolin-2-yl)ethyl]thieno[2,3-d]pyridazin-4(5H)-one;
3-(1H-pyrazol-3-yl)-5-[2-(quinolin-2-yl)ethyl]thieno[2,3-d]pyridazin-4(5H)-one;
5-[2-(1H-benzimidazol-1-yl)ethyl]-3-(pyridin-4-yl)thieno[2,3-d]pyridazin-4(5H)-one;
5-[2-(1H-benzimidazol-2-yl)ethyl]-3-(pyridin-4-yl)thieno[2,3-d]pyridazin-4(5H)-one;
5-[2-(6-chloroquinolin-2-yl)ethyl]-3-(pyridin-4-yl)thieno[2,3-d]pyridazin-4(5H)-one;
3-(pyridin-3-ylethynyl)-5-[2-(quinolin-2-yl)ethyl]thieno[2,3-d]pyridazin-4(5H)-one;
3-(pyridin-4-ylethynyl)-5-[2-(quinolin-2-yl)ethyl]thieno[2,3-d]pyridazin-4(5H)-one;
5-[2-(3,5-dimethylpyridin-2-yl)ethyl]-3-(pyridin-4-yl)thieno[2,3-d]pyridazin-4(5H)-one;
5-[2-(7-fluoroquinolin-2-yl)ethyl]-3-(pyridin-4-yl)thieno[2,3-d]pyridazin-4(5H)-one;
5-[2-(pyrazin-2-yl)ethyl]-3-(pyridin-4-yl)thieno[2,3-d]pyridazin-4(5H)-one;
2-[2-(1,6-naphthyridin-2-yl)ethyl]-8-(pyridin-4-yl)isoquinolin-1(2H)-one;
2-[2-(8-fluoroquinolin-2-yl)ethyl]-8-(pyridin-4-yl)isoquinolin-1(2H)-one;
8-(pyridin-4-yl)-2-[1-(quinolin-2-yl)propan-2-yl]isoquinolin-1(2H)-one;
2-[2-(3-methylquinolin-2-yl)ethyl]-8-(pyridin-4-yl)isoquinolin-1(2H)-one;
2-[2-(imidazo[1,2-a]pyridin-2-yl)ethyl]-8-(1H-pyrazol-3-yl)phthalazin-1(2H)-one;
8-(morpholin-4-yl)-2-[2-(quinolin-2-yl)ethyl]phthalazin-1(2H)-one;
2-[2-(imidazo[1,2-a]pyridin-2-yl)ethyl]-8-(1-oxa-4,9-diazaspiro[5.6]dodec-9-yl)phthalazin-1 (2H)-one;
2-[2-(imidazo[1,2-a]pyridin-2-yl)ethyl]-8-(2-oxa-7-azaspiro[3.5]non-7-yl)phthalazin-1 (2H)-one;
8-[(3R)-3-hydroxypiperidin-1-yl]-2-[2-(imidazo[1,2-a]pyridin-2-yl)ethyl]phthalazin-1(2H)-one;
8-[(3 S)-3-hydroxypiperidin-1-yl]-2-[2-(imidazo[1,2-a]pyridin-2-yl)ethyl]phthalazin-1(2H)-one;
2-[2-(imidazo[1,2-a]pyridin-2-yl)ethyl]-8-(2-oxa-6-azaspiro[3.3]hept-6-yl)phthalazin-1(2H)-one;
2-[2-(imidazo[1,2-a]pyridin-2-yl)ethyl]-8-(1,2-oxazolidin-2-yl)phthalazin-1(2H)-one;
8-(hexahydrocyclopenta[b][1,4]oxazin-4(4aH)-yl)-2-[2-(imidazo[1,2-a]pyridin-2-yl)ethyl]phthalazin-1(2H)-one;
2-[2-(imidazo[1,2-a]pyridin-2-yl)ethyl]-8-(tetrahydrofuran-3-yl)phthalazin-1(2H)-one;
2-[2-(imidazo[1,2-a]pyridin-2-yl)ethyl]-8-(3-oxa-8-azabicyclo[3.2.1]oct-8-yl)phthalazin-1 (2H)-one;
2-[2-(imidazo[1,2-a]pyridin-2-yl)ethyl]-8-(2-oxa-6-azaspiro[3.4]oct-6-yl)phthalazin-1(2H)-one;
2-[2-(imidazo[1,2-a]pyridin-2-yl)ethyl]-8-(2,2,6,6-tetrafluoromorpholin-4-yl)phthalazin-1 (2H)-one;
8-(4-hydroxypiperidin-1-yl)-2-[2-(imidazo[1,2-a]pyridin-2-yl)ethyl]phthalazin-1(2H)-one;
2-[2-(imidazo[1,2-a]pyridin-2-yl)ethyl]-8-(2-methylpyrimidin-5-yl)phthalazin-1(2H)-one;
8-(2-cyclopropylpyrimidin-5-yl)-2-[2-(imidazo[1,2-a]pyridin-2-yl)ethyl]phthalazin-1(2H)-one;
2-[2-(imidazo[1,2-a]pyridin-2-yl)ethyl]-8-(pyridazin-4-yl)phthalazin-1(2H)-one;
8-(5-fluoropyridin-3-yl)-2-[2-(imidazo[1,2-a]pyridin-2-yl)ethyl]phthalazin-1(2H)-one;
8-[2-(3-fluorophenyl)morpholin-4-yl]-2-[2-(imidazo[1,2-a]pyridin-2-yl)ethyl]phthalazin-1(2H)-one;
2-[2-(imidazo[1,2-a]pyridin-2-yl)ethyl]-8-(2-methoxypyrimidin-5-yl)phthalazin-1(2H)-one;
2-[2-(imidazo[1,2-a]pyridin-2-yl)ethyl]-8-[2-(trifluoromethyl)pyridin-4-yl]phthalazin-1(2H)-one;
2-[2-(imidazo[1,2-a]pyridin-2-yl)ethyl]-8-(8-oxa-3-azabicyclo[3.2.1]oct-3-yl)phthalazin-1 (2H)-one;
2-[2-(imidazo[1,2-a]pyridin-2-yl)ethyl]-8-[2-(trifluoromethyl)morpholin-4-yl]phthalazin-1(2H)-one;
8-(2,2-dimethylmorpholin-4-yl)-2-[2-(imidazo[1,2-a]pyridin-2-yl)ethyl]phthalazin-1(2H)-one;
8-[2-(4-chlorophenyl)morpholin-4-yl]-2-[2-(imidazo[1,2-a]pyridin-2-yl)ethyl]phthalazin-1(2H)-one;
8-[2-(3,4-difluorophenyl)morpholin-4-yl]-2-[2-(imidazo[1,2-a]pyridin-2-yl)ethyl]phthalazin-1(2H)-one;
2-[2-(imidazo[1,2-a]pyridin-2-yl)ethyl]-8-(piperidin-4-yl)phthalazin-1(2H)-one;
2-[2-(imidazo[1,2-a]pyridin-2-yl)ethyl]-8-(tetrahydro-2H-pyran-4-yl)phthalazin-1(2H)-one;
8-(2,6-diazabicyclo[3.2.1]oct-6-yl)-2-[2-(imidazo[1,2-a]pyridin-2-yl)ethyl]phthalazin-1(2H)-one;
8-[(1 S,5S)-3,6-diazabicyclo[3.2.0]hept-3-yl]-2-[2-(imidazo[1,2-a]pyridin-2-yl)ethyl]phthalazin-1(2H)-one;
8-(furan-2-yl)-2-[2-(imidazo[1,2-a]pyridin-2-yl)ethyl]phthalazin-1(2H)-one;
2-[2-(imidazo[1,2-a]pyridin-2-yl)ethyl]-8-(1-methyl-1H-pyrazol-4-yl)phthalazin-1(2H)-one;
8-(hexahydropyrrolo[3,4-c]pyrrol-2(1H)-yl)-2-[2-(imidazo[1,2-a]pyridin-2-yl)ethyl]phthalazin-1(2H)-one;
8-(2,7-diazaspiro[4.4]non-2-yl)-2-[2-(imidazo[1,2-a]pyridin-2-yl)ethyl]phthalazin-1(2H)-one;
8-[(1 S,4S)-2,5-diazabicyclo[2.2.1]hept-2-yl]-2-[2-(imidazo[1,2-a]pyridin-2-yl)ethyl]phthalazin-1(2H)-one;
8-(2,7-diazaspiro[3.5]non-7-yl)-2-[2-(imidazo[1,2-a]pyridin-2-yl)ethyl]phthalazin-1(2H)-one;

8-(2,6-diazaspiro[3.5]non-6-yl)-2-[2-(imidazo[1,2-a]pyridin-2-yl)ethyl]phthalazin-1(2H)-one;

8-(piperidin-4-yl)-2-[2-(5,6,7,8-tetrahydroimidazo[1,2-a]pyridin-2-yl)ethyl]phthalazin-1(2H)-one;

8-[2-(aminomethyl)-4-chloropyrrolidin-1-yl]-2-[2-(imidazo[1,2-a]pyridin-2-yl)ethyl]phthalazin-1(2H)-one;

2-[2-(imidazo[1,2-a]pyridin-2-yl)ethyl]-4,8-di(pyridin-4-yl)phthalazin-1(2H)-one;

2-[2-(imidazo[1,2-a]pyridin-2-yl)ethyl]-8-[(3 aR,4S,7R,7aS)-octahydro-1H-4,7-epiminoisoindol-8-yl]phthalazin-1(2H)-one;

8-[5-(4-chlorophenyl)-2,5-diazabicyclo[2.2.1]hept-2-yl]-2-[2-(imidazo[1,2-a]pyridin-2-yl)ethyl]phthalazin-1(2H)-one;

4-bromo-2-[2-(imidazo[1,2-a]pyridin-2-yl)ethyl]-8-(pyridin-4-yl)phthalazin-1(2H)-one;

2-[2-(imidazo[1,2-a]pyridin-2-yl)ethyl]-8-[(3 aS,8aS)-octahydropyrrolo[3,4-c]azepin-2(1H)-yl]phthalazin-1 (2H)-one;

2-[2-(imidazo[1,2-a]pyridin-2-yl)ethyl]-8-[(3 aS,8aR)-octahydropyrrolo[3,4-c]azepin-2(1H)-yl]phthalazin-1 (2H)-one;

tert-butyl (3aR,4S,7R,7aS)-8-{3-[2-(imidazo[1,2-a]pyridin-2-yl)ethyl]-4-oxo-3,4-dihydrophthalazin-5-yl}octahydro-2H-4,7-epiminoisoindole-2-carboxylate;

8-(hexahydro-5H-furo[2,3-c]pyrrol-5-yl)-2-[2-(imidazo[1,2-a]pyridin-2-yl)ethyl]phthalazin-1(2H)-one;

2-[2-(imidazo[1,2-a]pyridin-2-yl)ethyl]-8-(1,2,3,6-tetrahydropyridin-4-yl)phthalazin-1 (2H)-one;

2-[2-(imidazo[1,2-a]pyridin-2-yl)ethyl]-8-[(3 S)-tetrahydrofuran-3-ylamino]phthalazin-1(2H)-one;

2-[2-(imidazo[1,2-a]pyridin-2-yl)ethyl]-8-[(3R)-tetrahydrofuran-3-ylamino]phthalazin-1(2H)-one;

8-{[5-(hydroxymethyl)-1,4-dioxan-2-yl]methoxy}-2-[2-(imidazo[1,2-a]pyridin-2-yl)ethyl]phthalazin-1(2H)-one;

2-[2-(imidazo[1,2-a]pyridin-2-yl)ethyl]-8-(oxetan-3-yloxy)phthalazin-1(2H)-one;

2-[2-(imidazo[1,2-a]pyridin-2-yl)ethyl]-8-(pyridin-4-ylmethoxy)phthalazin-1(2H)-one;

2-[2-(imidazo[1,2-a]pyridin-2-yl)ethyl]-8-(morpholin-4-ylmethyl)phthalazin-1(2H)-one;

2-[2-(imidazo[1,2-a]pyridin-2-yl)ethyl]-8-(pyridin-3-yloxy)phthalazin-1(2H)-one;

2-[2-(imidazo[1,2-a]pyridin-2-yl)ethyl]-8-[(oxetan-3-ylmethyl)amino]phthalazin-1(2H)-one;

2-[2-(imidazo[1,2-a]pyridin-2-yl)ethyl]-8-(tetrahydro-2H-pyran-4-ylamino)phthalazin-1(2H)-one;

2-[2-(imidazo[1,2-a]pyridin-2-yl)ethyl]-8-[(1-methylazetidin-3-yl)amino]phthalazin-1(2H)-one;

2-[2-(imidazo[1,2-a]pyridin-2-yl)ethyl]-8-(1,3-oxazol-2-ylamino)phthalazin-1(2H)-one;

2-[2-(imidazo[1,2-a]pyridin-2-yl)ethyl]-8-[methyl(oxetan-3-yl)amino]phthalazin-1(2H)-one;

2-[2-(imidazo[1,2-a]pyridin-2-yl)ethyl]-8-(piperidin-4-ylamino)phthalazin-1(2H)-one;

8-[(1-acetylpiperidin-3-yl)amino]-2-[2-(imidazo[1,2-a]pyridin-2-yl)ethyl]phthalazin-1(2H)-one;

8-[(1-acetylpiperidin-4-yl)amino]-2-[2-(imidazo[1,2-a]pyridin-2-yl)ethyl]phthalazin-1(2H)-one;

2-[2-(imidazo[1,2-a]pyridin-2-yl)ethyl]-8-(tetrahydrofuran-3-ylamino)phthalazin-1(2H)-one;

2-[2-(imidazo[1,2-a]pyridin-2-yl)ethyl]-8-(tetrahydro-2H-pyran-3-ylamino)phthalazin-1(2H)-one;

2-[2-(imidazo[1,2-a]pyridin-2-yl)ethyl]-8-(piperidin-3-ylamino)phthalazin-1 (2H)-one;

2-[2-(imidazo[1,2-a]pyridin-2-yl)ethyl]-8-{methyl[(3-methyloxetan-3-yl)methyl]amino}phthalazin-1(2H)-one;

2-[2-(imidazo[1,2-a]pyridin-2-yl)ethyl]-8-(oxetan-3-ylamino)phthalazin-1(2H)-one;

8-{[(3 aS,4S,6aS)-octahydrocyclopenta[c]pyrrol-4-ylmethyl]amino}-2-[2-(5,6,7,8-tetrahydroimidazo[1,2-a]pyridin-2-yl)ethyl]phthalazin-1(2H)-one;

5-(morpholin-4-yl)-2-[2-(quinolin-2-yl)ethyl]phthalazin-1(2H)-one;

2-[2-(1H-benzimidazol-2-yl)ethyl]-5-(pyridin-4-yl)phthalazin-1 (2H)-one;

4-(pyridin-3-yl)-2-[2-(quinolin-2-yl)ethyl]phthalazin-1 (2H)-one;

5-(1,4-dihydropyrimidin-5-yl)-2-[2-(5,6,7,8-tetrahydroimidazo[1,2-a]pyridin-2-yl)ethyl]phthalazin-1 (2H)-one;

2-[2-(imidazo[1,2-a]pyridin-2-yl)ethyl]-5-(pyridin-4-yl)phthalazin-1(2H)-one;

5-(pyridin-3-yl)-2-[2-(quinolin-2-yl)ethyl]phthalazin-1 (2H)-one;

2-[2-(imidazo[1,2-a]pyridin-2-yl)ethyl]-8-{[(3-methyloxetan-3-yl)methyl]amino}-phthalazin-1 (2H)-one;

4-(pyridin-4-yl)-6-[2-(quinolin-2-yl)ethyl]pyrido[2,3-d]pyridazin-5(6H)-one;

4-(morpholin-4-yl)-6-[2-(quinolin-2-yl)ethyl]pyrido[2,3-d]pyridazin-5(6H)-one;

4-(oxetan-3-ylamino)-6-[2-(quinolin-2-yl)ethyl]pyrido[2,3-d]pyridazin-5(6H)-one;

2-[2-(6-methoxypyridin-2-yl)ethyl]-8-(pyridin-4-yl)isoquinolin-1(2H)-one;

2-[2-(1,3-benzothiazol-2-yl)ethyl]-8-(pyridin-4-yl)isoquinolin-1(2H)-one;

2-[2-(5-methylpyridin-2-yl)ethyl]-8-(pyridin-4-yl)isoquinolin-1(2H)-one;

5-[(E)-2-(6-methoxyquinolin-2-yl)ethenyl]-3-(pyridin-4-yl)thieno[3,2-c]pyridin-4(5H)-one;

8-(pyridin-4-yl)-2-[(E)-2-(quinazolin-2-yl)ethenyl]isoquinolin-1(2H)-one;

5-[(E)-2-(6-chloroquinolin-2-yl)ethenyl]-3-(pyridin-4-yl)thieno[3,2-c]pyridin-4(5H)-one;

5-[(E)-2-(3-methylquinolin-2-yl)ethenyl]-3-(pyridin-4-yl)thieno[3,2-c]pyridin-4(5H)-one;

8-(pyridin-4-yl)-2-[(E)-2-(quinolin-2-yl)ethenyl]isoquinolin-1(2H)-one;

5-[(E)-2-(1,3-benzothiazol-2-yl)ethenyl]-3-(pyridin-4-yl)thieno[3,2-c]pyridin-4(5H)-one;

3-(pyridin-4-yl)-5-[(E)-2-(quinolin-2-yl)ethenyl]thieno[3,2-c]pyridin-4(5H)-one;

and the enantiomers, the N-oxides, the prodrugs, the tautomers and the hydrates thereof, and the pharmaceutically acceptable salts thereof.

The compounds of the invention of the general formula I and the starting materials used to prepare them can be prepared in analogy to known processes of organic chemistry as are described in standard works of organic chemistry, e.g. Houben-Weyl, "Methoden der Organischen Chemie", Thieme-Verlag, Stuttgart, Jerry March "Advanced Organic Chemistry", 5$^{th}$ edition, Wiley & Sons and the literature cited therein, and R. Larock, "Comprehensive Organic Transformations", 2$^{nd}$ edition, Weinheim, 1999 and the literature cited therein. The compounds of the invention of the general formula I are advantageously prepared by the methods described below and/or in the experimental section.

Compounds of the formula I, wherein Q is oxygen, can be prepared e.g. by reacting a compound of the formula II

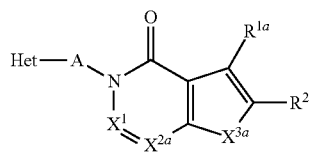

(II)

wherein
$X^{2a}$ is N or C—$R^{7a}$;
$X^{3a}$ is S, O, N=C($R^8$), C($R^{9a}$)=C($R^8$) or N=C($R^9$);
Het, A, $X^1$, $R^2$, $R^6$ and $R^8$ are as defined for formulae I, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D or I-10.D;
$R^{1a}$, $R^{7a}$, $R^{9a}$ independently of each other, are selected from the group consisting of hydrogen, halogen, $C_1$-$C_4$-alkyl, trimethylsilyl, $C_1$-$C_4$-alkylsulfanyl, $C_1$-$C_4$-alkoxy-$C_1$-$C_4$-alkyl, $C_1$-$C_4$-alkoxy, $C_1$-$C_4$-alkoxy-$C_1$-$C_4$-alkoxy, $C_1$-$C_4$-alkylsulfanyl-$C_1$-$C_4$-alkoxy, $C_2$-$C_4$-alkenyloxy, $C_1$-$C_4$-fluoroalkyl, $C_1$-$C_4$-fluoroalkoxy, CN, $NR^{x1}R^{x2}$, $NR^{x1}R^{x2}$—$C_1$-$C_4$-alkoxy;
provided that 1 or 2 of the radicals $R^{1a}$, $R^{7a}$ and $R^{9a}$, in particular exactly one of these radicals is bromine or iodine, while the others are different from bromine or iodine;
with a compound of formula III, M-Y-Cyc (III)

where Y has one of the meanings given for $Y^1$, $Y^2$, and $Y^3$ and Cyc has one of the meanings given herein for $Cyc^1$, $Cyc^2$, and $Cyc^3$ and wherein
M is a Li, B(OR$^{B1}$)(OR$^{B2}$) radical or an Sn(R$^{Sn}$)$_3$ radical, where $R^{B1}$ and $R^{B2}$ are, independently of each other, hydrogen or $C_1$-$C_4$-alkyl or $R^{B1}$ and $R^{B2}$ together form a $C_2$-$C_6$-alkandiyl moiety, e.g. ethan-1,2-diyl, propan-1,3-diyl or 1,1,2,2-tetramethylethan-1,2-diyl, and wherein $R^{Sn}$ is $C_1$-$C_6$-alkyl or $C_3$-$C_6$-cycloalkyl or phenyl.

Amongst the compounds of formula III, where Y is a chemical bond, particular preference is given to the compounds of formula IIIa and, if $R^{B1}$ and $R^{B2}$ are hydrogen, the trimers thereof.

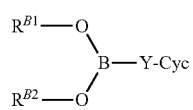

(IIIa)

The reaction of the compound II with the compound III can be performed by analogy to known coupling reactions in the presence of suitable transition metal catalysts, in particular palladium catalysts.

Typical reactions conditions are those of Stille coupling (see e.g. Stille et al. Angew. Chem. Int. Ed. Engl. 1986, 25, 508; J. Eluguero et al.; Synthesis 1997, 5, 563-566) or Suzuki coupling (see e.g. A. Suzuki et al, Chem. Rev. 1995, 95, 2457-2483, N. Zhe et al.; J. Med. Chem. 2005, 48 (5), 1569-1609; Young et al.; J. Med. Chem. 2004, 47 (6), 1547-1552; C. Slee et al.; Bioorg. Med. Chem. Lett. 2001, 9, 3243-3253).

In a similar manner, compounds of the formula I, where $Y^1$, $Y^2$ or $Y^3$ is NH or were $Cyc^1$-$Y^1$, $Cyc^2$-$Y^2$ or $Cyc^3$-$Y^3$ ($Y^1$, $Y^2$ or $Y^3$ are single bonds) an N-bound heterocycle ($Y^1$, $Y^2$ or $Y^3$ are single bonds) can be prepared by reacting a compound of the formula II, as defined above, with a compound of the formula III'

H—Y-Cyc (III')

where Y and Cyc are as defined for formula III. The reaction of II with III' is preferably carried out in an aprotic solvent, such as dimethylsulfoxide, acetonitrile, N-methylpyrrolidone, dimethylformamide, dimethylacetamide, tetramethyl urea, or mixtures thereof or mixtures thereof with halogenated hydrocarbons such as dichloromethane. The reaction is preferably carried out in the presence of a suitable base, e.g. an alkalimetal carbonate such as lithium carbonate, sodium carbonate, potassium carbonate or caesium carbonate or an alkalimetal alkoxide.

Compounds of the formula I, where Q is O, can also be prepared e.g. by reacting a compound of the formula IIa

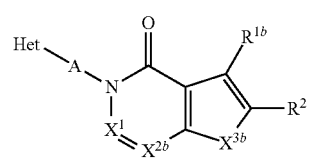

(IIa)

wherein
$X^{2b}$ is N or C—$R^{7b}$;
$X^{3b}$ is S, O, N=C($R^8$), C($R^{9b}$)=C($R^8$) or N=C($R^9$);
Het, A, $X^1$, $R^2$ and $R^8$ are as defined for formulae I, I-1.A, I-1.B, I-2.A, I-2.B, I-1.C, I-2.C, I-1.D, I-2.D, I-3.A, I-4.A, I-3.B, I-4.B, I-3.C, I-4.C, I-3.D, I-4.D, I-5.A, I-6.A, I-5.B, I-6.B, I-5.C, I-6.C, I-5.D, I-6.D, I-7.A, I-8.A, I-7.B, I-8.B, I-7.C, I-8.C, I-7.D, I-8.D, I-9.A, I-10.A, I-9.B, I-10.B, I-9.C, I-10.C, I-9.D or I-10.D;
$R^{1b}$, $R^{7b}$, $R^{9b}$ independently of each other, are selected from the group consisting of hydrogen, $C_1$-$C_4$-alkyl, trimethylsilyl, $C_1$-$C_4$-alkylsulfanyl, $C_1$-$C_4$-alkoxy-$C_1$-$C_4$-alkyl, $C_1$-$C_4$-alkoxy, $C_1$-$C_4$-alkoxy-$C_1$-$C_4$-alkoxy, $C_1$-$C_4$-alkylsulfanyl-$C_1$-$C_4$-alkoxy, $C_2$-$C_4$-alkenyloxy, $C_1$-$C_4$-fluoroalkyl, $C_1$-$C_4$-fluoroalkoxy, CN, $NR^{x1}R^{x2}$, $NR^{x1}R^{x2}$—$C_1$-$C_4$-alkoxy or a moiety M;
provided that 1 or 2 of the radicals $R^{1b}$, $R^{7b}$ and $R^{9b}$, in particular exactly one of these radicals is moiety M, while the others are different from M, where M is as defined for formula III and in particular a B(OR$^{B1}$)(OR$^{B2}$) radical;
with a compound of formula IIIb, Hal-Y-Cyc (IIIb)

where Y and Cyc are as defined herein and wherein Hal is bromine or iodine.

The reaction of the compound IIa with the compound IIIb can be performed by analogy tot the reaction of compound II with compound III.

The compounds II, IIa, III, III', IIIa and IIIb are known or can be prepared by standard methods of organic chemistry.

Compounds of the formula I, where $Y^1$-$Cyc^1$, $Y^2$-$Cyc^2$ or $Y^3$-$Cyc^3$ is a N-bound radical can be obtained by a coupling reaction between the compound II and the corresponding amine in the presence of a palladium catalyst in terms of a Buchwald-Hartwig reaction. Suitable palladium catalyst are for example tris-(dibenzylidene-acetone)dipalladium(0)

($Pd_2(dba)_3$), [1,1-bis(diphenylphosphino)ferrocene]dichloro-palladium(II) ($PdCl_2(dppf)$) or palladium acetate ($Pd(OAc)_2$). The reaction is usually carried out in the presence of a tri(substituted)phosphine, e.g. a triarylphosphine such as triphenylphosphine, tritolylphosphine or 2,2'-bis(diphenylphosphino)-1,1'-binaphthalene (BINAP), tri(cyclo)alkylphosphine such as tris-n-butylphosphine, tris(tert-butyl)phosphine or tris(cyclohexylphosphine), or dicyclohexyl-(2',4',6'-tri-iso-propyl-biphenyl-2-yl)-phosphane (X-Phos). Usually, the reaction is performed in the presence of a base such as an alkaline alkoxide, earth alkine alkoxide, alkaline carbonate or earth alkaline carbonate such as or sodium tert-butoxide or cesium carbonate.

Compounds of the formula I (or likewise the compounds II), where Q is O and A is a radical $A^1$ can be prepared according to the following reaction schemes 1 and 2 by successively reacting compounds of the formulae V or Va, respectively with a suitable hydroxy compound IV, in terms of a Mitsunobu reaction.

Scheme 1:

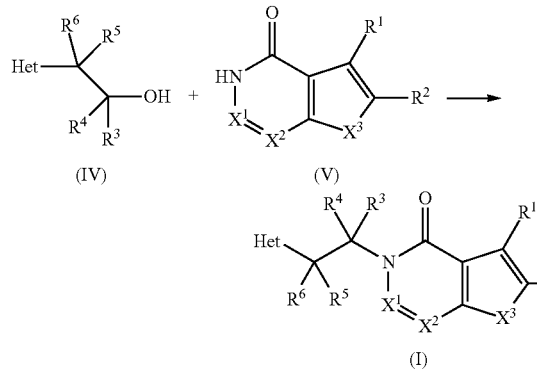

Scheme 2:

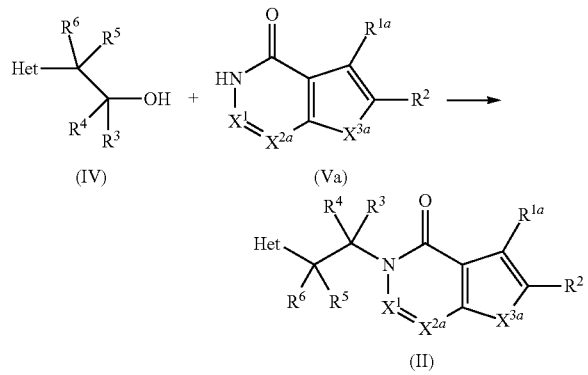

In schemes 1 and 2, $X^1$, $X^2$, $X^3$, $X^{2a}$, $X^{3a}$, $R^1$, $R^{1a}$, $R^2$, $R^3$, $R^4$, $R^5$, $R^6$ and Het are as defined above. Compounds of the formulae V and Va, respectively, can be prepared in analogy to known methods, e.g. as described in Natl. Symposium Vacuum Technol., Chicago, (Trans.), 161-3; 1956, Journal of Organic Chemistry, 74(10), 3849-3855; 2009, or Journal of Heterocyclic Chemistry, 8(1), 57-60; 1971.

Alternatively, compounds of the formula I (or likewise the compounds II), where Q is O and A is a radical $A^1$ can be prepared by hydrogenation of compounds of the formula I (or likewise the compounds II), where A is $A^3$.

Compounds of the formula I (or likewise the compounds II), where Q is O and A is a radical $A^3$ can be prepared according to the following reaction schemes 3 and 4 by successively reacting compounds of the formulae V or Va, respectively with a suitable halocompound VI.

Scheme 3:

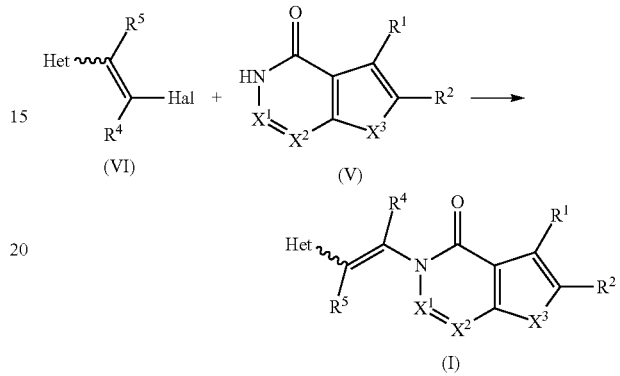

Scheme 4:

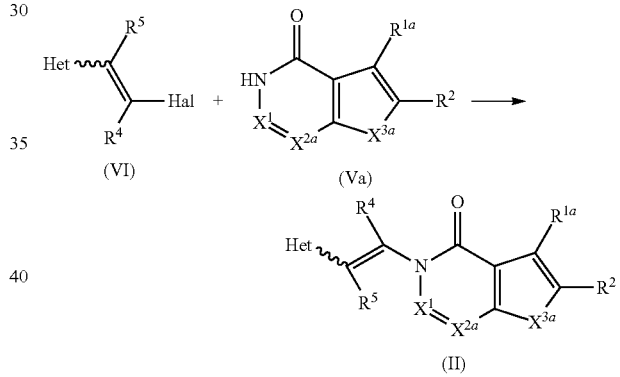

In schemes 3 and 4, $X^1$, $X^2$, $X^3$, $X^{2a}$, $X^{3a}$, $R^1$, $R^{1a}$, $R^2$, $R^4$, $R^5$ and Het are as defined above. Hal is halogen, preferably bromine or iodine. The reaction is usually performed in the presence of a base. Suitable bases are alkali metal carbonates and hydrogen carbonates or earth metal carbonates and hydrogencarbonates such as cesium carbonate.

Compounds of the formula I (or likewise the compounds II), where Q is O and A is a radical $A^4$ can be prepared according to the following reaction schemes 5 and 6 by successively reacting compounds of the formulae V or Va, respectively with a suitable halocompound VII.

Scheme 5:

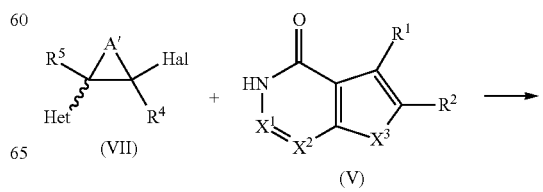

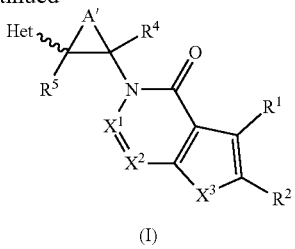

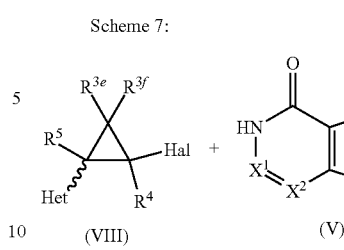

Scheme 6:

(VII) (Va) → (II)

In schemes 5 and 6, $X^1$, $X^2$, $X^3$, $X^{2a}$, $X^{3a}$, $R^1$, $R^{1a}$, $R^2$, $R^4$, $R^5$, A' and Het are as defined above. Hal is halogen, preferably bromine or iodine. The reaction is usually performed in the presence of a base. Suitable bases are alkali metal carbonates and hydrogen carbonates or earth metal carbonates and hydrogencarbonates such as cesium carbonate.

Alternatively, compounds of the formula I (or likewise the compounds II), where Q is O and A is a radical $A^4$ with A' being a $CR^{3b}R^{3c}$ ($R^{3b}$ and $R^{3c}$ are as defined above) can be prepared by cyclopropanation of compounds of the formula I (or likewise the compounds II), where A is $A^3$, in terms of a Simmon-Smith reaction. Compounds of the formula I (or likewise the compounds II), where Q is O and A is a radical $A^4$ with A' being a O can be prepared by epoxidation of compounds of the formula I (or likewise the compounds II), where A is $A^3$, using hydrogen peroxide.

Compounds of the formula I (or likewise the compounds II), where A is a radical $A^4$ can be obtained in the form of enantiomers, for example as racemate, in the form of a mixture of enanantiomers, as pure enantiomers or in the form of diastereomers.

Compounds of the formula I (or likewise the compounds II), where Q is O and A is a radical $A^5$ can be prepared according to the following reaction schemes 7 and 8 by reacting compounds of the formulae V or Va, respectively with a suitable halocompound VIII under basic conditions for a longer period.

Scheme 7:

(VIII) + (V) →

(I) A = $A^4$ (I) A = $A^5$

Scheme 8:

+ →

(II) A = $A^4$

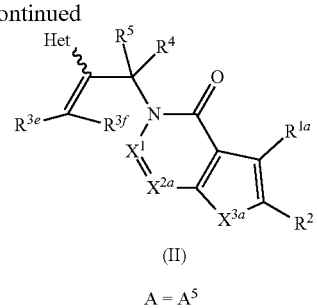

(II)

A = A⁵

In schemes 7 and 8, $X^1$, $X^2$, $X^3$, $X^{2a}$, $X^{3a}$, $R^1$, $R^{1a}$, $R^2$, $R^{3e}$, $R^{3f}$, $R^4$, $R^5$, and Het are as defined above. Hal is halogen, preferably bromine or iodine. The reaction is usually performed in the presence of a base. Suitable bases are alkali metal carbonates and hydrogen carbonates or earth metal carbonates and hydrogencarbonates such as cesium carbonate Apart from that, compounds of the formula I and likewise compounds of the formula II, where Q is S can be prepared by successively reacting compounds of the formulae I and II, where Q is O with a suitable sulfurizing agent, such as Lawenson's reagent or $P_2S_5$.

The N-oxides of compound I may be prepared from the compounds of formula I according to conventional oxidation methods, for example by treating said compounds with an organic peracid; such as metachloroperbenzoic acid or 3-chloroperbenzoic acid [Journal of Medicinal Chemistry 38(11), 1892-1903 (1995), WO 03/64572]; or with inorganic oxidizing agents; such as hydrogen peroxide [cf. Journal of Heterocyclic Chemistry 18 (7), 1305-1308 (1981)] or oxone [cf. Journal of the American Chemical Society 123(25), 5962-5973 (2001)]. The oxidation may lead to pure mono-N-oxides or to a mixture of different N-oxides, which can be separated by conventional methods; such as chromatography.

Compounds of the formula IIa can be prepared from compounds of the formula II by suitable metal-halogen exchange reactions.

The compounds of the formulae III, IIIa, IV, V and Va are well known in the art or can be prepared by anology to well established reactions of organic synthetic chemistry or by analogy to the methods as described in standard works of organic chemistry, e.g. Houben-Weyl, "Methoden der Organischen Chemie", Thieme-Verlag, Stuttgart, Jerry March "Advanced Organic Chemistry", 5$^{th}$ edition, Wiley & Sons and the literature cited therein, and R. Larock, "Comprehensive Organic Transformations", 2$^{nd}$ edition, Weinheim, 1999 and the literature cited therein. Compounds of the formula VI can be prepared in analogy to known methods, e.g in terms of a Wittig reaction. Compounds of the formula VII can be prepared in analogy to known methods. E.g., compounds of the formula VII, where A' is $CR^{3b}R^{3c}$ can be prepared by cyclopropanation of compounds VI in terms of a Simmon-Smith reaction.

The reactions are usually performed in an organic solvent, including aprotic organic solvent, e.g. substituted amides, lactames and ureas; such as dimethylformamide, dimethylacetamide, N-methylpyrrolidone, tetramethyl urea, cyclic ethers; such as dioxane, tetrahydrofurane, halogenated hydrocarbons; such as dichloromethane, and mixtures thereof as well as mixtures thereof with $C_1$-$C_6$-alkanols and/or water.

The reactions described above will be usually performed at temperatures ranging from −10° C. to 100° C., depending on the reactivity of the used compounds.

The reaction mixtures are worked up in a conventional way, e.g. by mixing with water, separating the phases and, where appropriate, purifying the crude products by chromatography. The intermediates and final products in some cases result in the form of colorless or pale brownish, viscous oils which are freed of volatiles or purified under reduced pressure and at moderately elevated temperature. If the intermediates and final products are obtained as solids, the purification can also take place by recrystallization or digestion.

Due to their capability of inhibiting PDE10A at low concentrations, the compounds of the formula I, their N-oxides, their hydrates, their tautomers and their prodrugs and the pharmaceutically acceptable salts thereof, are particularly suitable for treating disorders or conditions, which can be treated by inhibition of phosphodiesterase type 10A. The terms "treating" and "treatment" in terms of the present invention have to be understood to include both curative treatment of the cause of a disease or disorder, the treatment of the symptoms associated with a disease or disorder, i.e. controlling the disease or disorder or ameliorating the conditions or symptoms associated with a disease or disorder, and prophylactic treatment, i.e. a treatment for reducing the risk of a disease or disorder.

Neurological and psychiatric disorders or conditions which can be treated by inhibition of PDE10A, including curative treatment, control or amelioration and prophylaxis, include CNS disorders, in particular schizophrenia, depression, bipolar disorders, cognitive dysfunctions associated with schizophrenia, cognitive dysfunctions associated with Alzheimer's disease, Huntington's disease (Huntington chorea), anxiety and substance-related disorders, especially substance use disorder, substance tolerance conditions associated with substance withdrawal. Disorders or conditions which can be treated by inhibition of PDE10A, including curative treatment, control or amelioration and prophylaxis, also include treatment of diet induced obesity.

Thus, the invention relates to the use of compounds of formula I, their N-oxides, their hydrates, their tautomers and their prodrugs and the pharmaceutically acceptable salts thereof, for treatment of disorders or conditions, which can be treated by inhibition of phosphodiesterase type 10A, i.e. the invention relates to the use of such compounds for curative treatment of such a disease or disorder, controlling such a disease or disorder, ameliorating the symptoms associated with such a disease or disorder and reducing the risk for such a disease or disorder.

The present invention also relates to a method for the treatment of a medical disorder, selected from neurological and psychiatric disorders which can be treated by inhibition of phosphodiesterase type 10A, said method comprising administering an effective amount of at least one compound, selected from the group of compounds of formula I, their N-oxides, their hydrates, their tautomers, their prodrugs and the pharmaceutically acceptable salts thereof, to a mammal in need thereof.

The present invention in particular relates to:
 a method for treating, controlling, ameliorating or reducing the risk of schizophrenia in a mammalian;
 a method for treating, controlling, ameliorating or reducing the risk of cognitive disturbances associated with schizophrenia in a mammalian;
 a method for treating, controlling, ameliorating or reducing the risk of depression in a mammalian;

a method for treating, controlling, ameliorating or reducing the risk of bipolar disorders in a mammalian;

a method for treating or ameliorating the symptoms associated with substance use disorders in a mammalian;

a method for treating or ameliorating the symptoms associated with diet-induced obesity in a mammalian;

a method for treating, controlling, ameliorating or reducing the risk of cognitive disturbances associated with Alzheimer's disease in a mammalian;

a method for treating, controlling, ameliorating or reducing the risk of behavioral symptoms in Alzheimer's disease;

a method for treating, controlling, ameliorating or reducing the risk of anxiety in a mammalian;

a method for treating, controlling, ameliorating or reducing the risk of Huntington's disease in a mammalian;

which methods comprising administering an effective amount of at least one compound, selected from the group of compounds of formula I, their N-oxides, their hydrates, their tautomers, their prodrugs and the pharmaceutically acceptable salts thereof, to a mammal in need thereof.

The subject treated in the present methods is generally a mammal, preferably a human being, male or female, in whom inhibition of PDE10A is desired. The terms "effective amount" and "therapeutically effective amount" mean the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes, wherein there may be a slowing, interrupting, arresting, controlling, or stopping of the progression of the disorders described herein, but does not necessarily indicate a total elimination of all disorder symptoms, as well as the prophylactic therapy of the mentioned conditions, particularly in a patient who is predisposed to such disease or disorder. The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of and or "administering a" compound should be understood to mean providing a compound of the invention or a prodrug of a compound of the invention to the individual in need of treatment.

A preferred embodiment of the present invention provides a method for treating schizophrenia, comprising: administering to a patient in need thereof an effective amount of at least one compound, selected from the group of compounds of formula I, their N-oxides, their hydrates, their tautomers, their prodrugs and the pharmaceutically acceptable salts thereof.

In another preferred embodiment, the present invention provides a method for treating cognitive disturbances associated with schizophrenia, comprising: administering to a patient in need thereof an effective amount of at least one compound, selected from the group of compounds of formula I, their N-oxides, their hydrates, their tautomers, their prodrugs and the pharmaceutically acceptable salts thereof.

At present, the fourth edition of the Diagnostic and Statistical Manual of Mental Disorders (DSM-IV) (1994, American Psychiatric Association, Washington, D.C.), provides a diagnostic tool including schizophrenia and other psychotic disorders. These include: disorders having psychotic symptoms as the defining feature. The term psychotic refers to delusions, prominent hallucinations, disorganized speech, disorganized or catatonic behavior. The disorder includes: paranoid, disorganized, catatonic, undifferentiated, and residual schizophrenia, schizophreniform disorder, schizoaffective disorder, delusional disorder, brief psychotic disorder, shared psychotic disorder, psychotic disorder due to a general medical condition, substance-induced psychotic disorder, and psychotic disorder not otherwise specified. The skilled artisan will recognize that there are alternative nomenclatures, nosologies, and classification systems for neurological and psychiatric disorders, and particular schizophrenia, and that these systems evolve with medical scientific progress. Thus, the term "schizophrenia" is intended to include like disorders that are described in other diagnostic sources.

In another preferred embodiment, the present invention provides a method for treating substance-related disorders, comprising: administering to a patient in need thereof an effective amount of at least one compound, selected from the group of compounds of formula I, their N-oxides, their hydrates, their tautomers, their prodrugs and the pharmaceutically acceptable salts thereof.

In another preferred embodiment, the present invention provides a method for treating anxiety, comprising: administering to a patient in need thereof an effective amount of at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

In another preferred embodiment, the present invention provides a method for treating depression, comprising:

administering to a patient in need thereof an effective amount of at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including depression and related disorders. Depressive disorders include, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder. As used herein the term "depression" includes treatment of those depression disorders and related disorder as described in the DSM-1V.

In another preferred embodiment, the present invention provides a method for treating substance-related disorders, especially substance dependence, substance abuse, substance tolerance, and substance withdrawal, comprising: administering to a patient in need thereof an effective amount at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including disorders related to taking a drug of abuse (including alcohol), to the side effects of a medication, and to toxin exposure. Substances include alcohol, amphetamine and similarly acting sympathomimetics, caffeine, cannabis, cocaine, hallucinogens, inhalants, nicotine, opioids, phencyclidine (PCP) or similarly acting arylcyclohexylamines, and sedatives, hypnotics, or anxiolytics. Also, polysubstance dependence and other unknown substance-related disorders are included. The skilled artisan will recognize that there are alternative nomenclatures, nosologies, and classification systems for neurological and psychiatric disorders, and particular substance-related disorders, and that these systems evolve with medical scientific progress. Thus, the term "substance-related disorder" is intended to include like disorders that are described in other diagnostic sources.

In the treatment, prevention, control, amelioration, or reduction of risk of conditions which require inhibition of PDE10A an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. When treating, preventing, controlling, ameliorating, or reducing the risk of neurological and psychiatric disorders or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams, in the case of a 70 kg adult human, the total daily dose will generally be from about 7 milligrams to about 350 milligrams. This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention may be administered by conventional routes of administration, including parenteral (e.g., intramuscular, intrapentoneal, intravenous, ICV, intracisternal injection or infusion, subcutaneous injection, or implant), oral, by inhalation spray, nasal, vaginal, rectal, sublingual, or topical routes of administration.

The compounds according to the present invention are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of formula I is used contemporaneously with one or more other drugs, a pharmaceutical composition in unit dosage form containing such other drugs and the compound of formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formula I. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The present invention also relates to pharmaceutical compositions (i.e. medicaments) which comprise at least one compound of the present invention and, where appropriate, one or more suitable excipients.

These excipients/drug carriers are chosen according to the pharmaceutical form and the desired mode of administration.

The compounds of the present invention can be used to manufacture pharmaceutical compositions for parenteral (e.g., intramuscular, intraperitoneal, intravenous, ICV, intracisternal injection or infusion, subcutaneous injection, or implant), oral, sublingual, intratracheal, intranasal, topical, transdermal, vaginal or rectal administration, and be administered to animals or humans in unit dose forms, mixed with conventional pharmaceutical carriers, for the prophylaxis or treatment of the above impairments or diseases.

In the pharmaceutical compositions, the at least one compound of the present invention may be formulated alone or together with further active compounds, in suitable dosage unit formulations containing conventional excipients, which generally are non-toxic and/or pharmaceutically acceptable. Carriers or excipients can be solid, semisolid or liquid materials which serve as vehicles, carriers or medium for the active compound. Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik und angrenzende Gebiete [Encyclopedia of auxiliary substances for pharmacy, cosmetics and related fields], $4^{th}$ edition, Aulendorf: ECV-Editio-Kantor-Verlag, 1996.

Suitable unit dose forms include forms for oral administration, such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

If a solid composition is prepared in the form of tablets, the main ingredient is mixed with a pharmaceutical carrier such as gelatin, starch, lactose, magnesium stearate, talc, silicon dioxide or the like.

The tablets may be coated with sucrose, a cellulose derivative or another suitable substance or be treated otherwise in order to display a prolonged or delayed activity and in order to release a predetermined amount of the active basic ingredient continuously.

A preparation in the form of gelatin capsules is obtained by mixing the active ingredient with an extender and taking up the resulting mixture in soft or hard gelatin capsules.

A preparation in the form of a syrup or elixir or for administration in the form of drops may comprise active ingredients together with a sweetener, which is preferably calorie-free, methylparaben or propylparaben as antiseptics, a flavoring and a suitable coloring.

The water-dispersible powders or granules may comprise the active ingredients mixed with dispersants, wetting agents or suspending agents such as polyvinylpyrrolidones, and sweeteners or taste improvers.

Rectal administration is achieved by the use of suppositories which are prepared with binders which melt at the rectal temperature, for example cocobutter or polyethylene glycols. Parenteral administration is effected by using aqueous suspensions, isotonic salt solutions or sterile and injectable solutions which comprise pharmacologically suitable dispersants and/or wetting agents, for example propylene glycol or polyethylene glycol.

The active basic ingredient may also be formulated as microcapsules or liposomes/centrosomes, if suitable with one or more carriers or additives.

In addition to the compounds of the general formula I, their prodrugs, their N-oxides, their tautomers, their hydrates or their pharmaceutically suitable salts, the compositions of the invention may comprise further active basic ingredients which may be beneficial for the treatment of the impairments or diseases indicated above.

The present invention thus further relates to pharmaceutical compositions in which a plurality of active basic ingredients are present together, where at least one thereof is a compound of the invention.

When producing the pharmaceutical compositions, the compounds according to the invention are optionally mixed or diluted with one or more carriers.

The compounds of the invention also include those compounds in which one or more atoms have been replaced by their stable, non-radioactive isotopes, for example, a hydrogen atom by deuterium.

Stable isotopes (e.g., deuterium, $^{13}$C, $^{15}$N, $^{18}$O) are non-radioactive isotopes which contain one additional neutron than the normally abundant isotope of the respective atom. Deuterated compounds have been used in pharmaceutical research to investigate the in vivo metabolic fate of the compounds by evaluation of the mechanism of action and metabolic pathway of the non deuterated parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36(10): 927-932 (1995); Kushner et al., *Can. J. Physiol. Pharmacol.*, 77, 79-88 (1999).

Incorporation of a heavy atom particularly substitution of deuterium for hydrogen, can give rise to an isotope effect that could alter the pharmacokinetics of the drug. This effect is usually insignificant if the label is placed at a metabolically inert position of the molecule.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., *Drugs Fut,* 21(11), 1116 (1996); Brickner, S J et al., *J Med Chem,* 39(3), 673 (1996); Mallesham, B et al., *Org Lett,* 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

The following examples are intended for further illustration of the present invention.

Abbreviations which have been used in the descriptions of the schemes and the Examples that follow are: BINAP for 2,2'-bis(diphenylphosphino)-1,1'-binaphthyl; DCM for dichloromethane; DEAD for diethyl azodicarboxylate; DIAD for diisopropyl azodicarboxylate; DMF for dimethylformamide; EA for ethyl acetate; EDCI 1-ethyl-3-(3-dimethylaminopropyl)carbodiimide; Et for ethyl; EX. for EXAMPLE; HMPA for hexamethylphosphoramide; HOBT for hydroxybenzotriazole; i-Pr for isopropyl; LDA for lithium diisopropylamide; MeOH for methanol; PE for petroleum ether; $Pd_2(dba)_3$ for tris (dibenzylideneacetone) dipalladium(0); $PdCl_2(dppf)$ for 1,1'-bis (diphenylphosphino)ferrocene-palladium (II)-dichloride; $R_t$ for retention time; TEA for triethylamine; THF for tetrahydrofuran; TMEDA for N,N,N',N'-tetramethyl 1,2-ethanediamine; TMSCl for trimethylsilyl chloride.

LC-MS measurements were run on Agilent 1200 HPLC/6100 SQ System.

The compounds I of the invention were purified in some cases by preparative HPLC. The compounds I then result as the salts.

PREPARATION EXAMPLES

I. Preparation of Intermediates

The starting materials used in the examples are either commercially available or can be synthesized by the average skilled person trained in organic chemistry following routine laboratory practice as outlined, for example in the examples below.

a) Preparation of Compounds of the General Formula Het-A$^1$-OH a1) 2-Quinolin-2-yl-ethanol

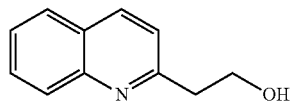

a1.1) Quinolin-2-yl-acetic acid ethyl ester

To a suspension of vacuum dried Zn dust (6.0 g, 93.8 mmol) in dry THF (100 mL) was added TMSCl (0.5 mL) dropwise over 5 min under $N_2$ atmosphere and under stirring. The mixture was stirred for 30 min and warmed to 45° C. Ethyl bromoacetate (5.2 mL, 46.9 mmol) was added dropwise via a syringe. After addition, the mixture was stirred at the same temperature for 1 h. After sedation at room temperature for 2 h, a clear orange solution was formed. The orange solution (50 mL) was carefully sucked into a syringe through a long needle and added to a mixture of 2-bromoquinoline (2.0 g, 9.6 mmol) and $PdCl_2(dppf)$ (200 mg, 0.27 mmol) in a three-neck flask. The mixture was refluxed under $N_2$ for 3 h. The reaction was monitored with LC-MS. Ethyl acetate (200 mL) was added to dilute the mixture and water (50 mL) was added to quench the reaction. The mixture was filtered through a celite pad. The filtration was partitioned between brine and ethyl acetate. The organic layer was separated, washed with brine (100 mL), dried over sodium sulfate and concentrated. The residue was purified with silica column (PE/EA=3:1) to give the title compound as orange oil (1.0 g, 48%). LC-MS (ESI+): m/e 216 (M+H)$^+$, $R_t$: 0.62 min.

a1.2) 2-Quinolin-2-yl-ethanol

To a cold (0° C.) solution of the compound from Example a1.1a (10 g, 45 mmol) in THF (200 mL) was added LiAlH$_4$ (2.65 mg, 70 mmol) in small portions over a period of 5 min. The resulting mixture was stirred for 1 h. Water was added dropwise very slowly. Then more water and EA were added. The organic phase was collected, dried and concentrated. The residue was purified by silica gel chromatography (PE/EA=2:1) to give the title compound as a yellow solid (2.5 g, 30%). LC-MS (ESI+): m/e 174 (M+H)$^+$, $R_t$: 0.75 min.

a2) 2-(6-Fluoroquinolin-2-yl)-ethanol

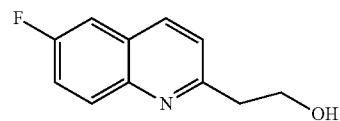 [SMILES: OCCc1ccc2cc(F)ccc2n1]

6-Fluoro-2-methylquinoline (1.00 g, 6.20 mmol) and sodium hydroxide were each added sequentially to the mixture of HCHO in water. Then 2 mL of EtOH were added to the mixture. The resulting solution was stirred at about 85° C. overnight. The organic layer was extracted with EA (3×10 mL), collected and dried with anhydrous Na$_2$SO$_4$, filtered and concentrated to afford a pink oil. The crude material was purified by chromatography on silica-gel (eluent: PE/EA=6/1) and then further purified by combi-flash chromatography (NH$_4$HCO$_3$/H$_2$O, MeOH/H$_2$O=40%~60%) to give 360 mg of the title product (yield: 30.3%).

LC-MS: m/e (M+H): 192.7, $R_t$: 1.63 min.

a3) 2-Thieno[3,2-b]pyridin-5-yl-ethanol

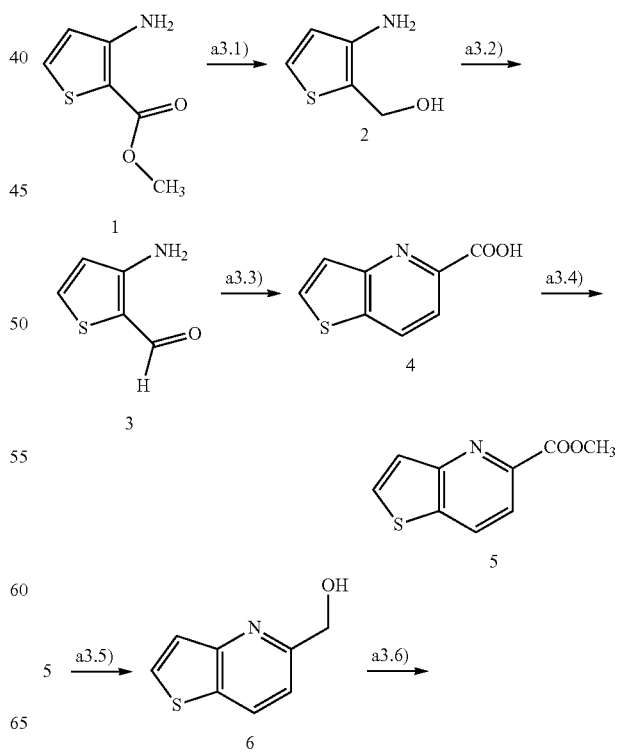

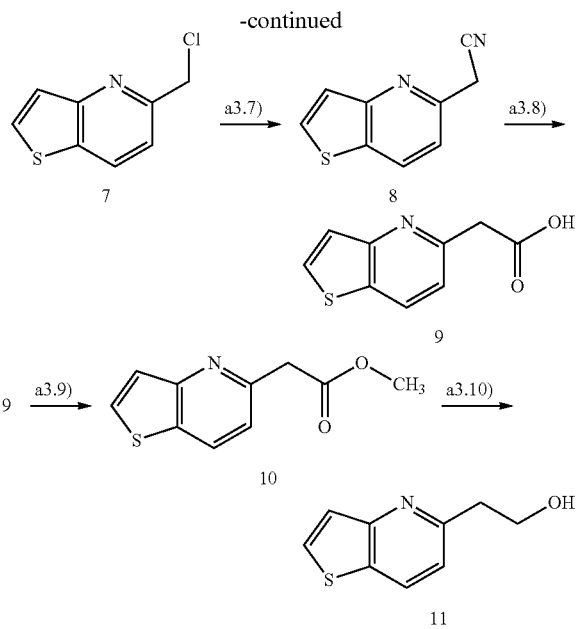

a3.1) Compound (2)

To a suspension of LiAlH$_4$ (1.39 g, 36.58 mmol) in anhydrous THF (30 mL) was added a solution of methyl 3-aminothiophene 2-carboxylate (compound 1, 5.00 g, 31.81 mmol) dropwise at 0° C. The reaction mixture was stirred at room temperature overnight. Water (4 mL) was added dropwise to quench the reaction. The mixture was stirred for 30 min. and then more water was added (10 mL). The solid was filtered off and then washed with NaOH solution (50 mL, 5 N). The filtrate was concentrated in vacuo and the residue was dissolved in EtOAc (200 mL). The solution was dried over Na$_2$SO$_4$, filtered and concentrated in vacuo. The crude solid was used in the next step without further purification (2.71 g, yield 66%). LC-MS (ESI+): m/e 130 (M+H)$^+$, R$_t$: 1.57 min.

a3.2) Compound (3)

A mixture of compound 2 (8.14 g, 63.00 mmol) and MnO$_2$ (32.8 g, 0.378 mol) in EtOAc (100 mL) was stirred at 30° C. for 48 h. The mixture was filtered and the filtrate was concentrated in vacuo. The residue was used in the next step without further purification (6.82 g, yield 85%). LC-MS (ESI+): m/e 128 (M+H)$^+$, R$_t$: 1.55 min.

a1.3) Compound (4)

To a solution of compound 3 (6.82 g, 53.62 mmol) in EtOH (70 mL) was added a mixture of pyruvic acid (9.44 g, 0.107 mol) and NaOH (10.7 g, 0.268 mol) in H$_2$O (70 mL) in one portion. The mixture was heated at 60° C. for 2 h, then cooled and extracted with Et$_2$O/EtOAc (1:1, 30 mL). The aqueous layer was acidified with HCl (2 N) to pH=3 at 0° C. and the water was removed under reduced pressure. The residue was co-evaporated with toluene (50 mL×3) and then used in the next step without further purification. LC-MS (ESI+): m/e 180 (M+H)$^+$, R$_t$: 1.50 min.

a3.4) Compound (5)

To a mixture of crude compound 4 (7 g, 39 mmol) in methanol (60 mL) was added thionyl chloride (10 mL) dropwise at 0° C. The reaction mixture was then heated at 65° C. for 3 h. The excess of solvent was removed under reduced pressure. The residue was diluted with EtOAc (100 mL) and washed with saturated NaHCO$_3$ aqueous solution (30 mL×4) and brine (30 mL). The organic layer was dried over Na$_2$SO$_4$, filtered and concentrated in vacuo. The residue was purified on a silica column (PE/EtOAc=5:1, v/v) to afford the title product as an off-white solid (715 mg, total yield 9.5%). LC-MS (ESI+): m/e 194 (M+H)$^+$, R$_t$: 1.78 min.

a3.5) Compound (6)

To a solution of compound 5 (100 mg, 0.52 mmol) in THF (2 mL) was added LiBH$_4$ (11 mg) in one portion. The mixture was allowed to stir at room temperature overnight. The reaction was quenched with saturated NH$_4$Cl solution, and then extracted with EtOAc (20 mL). The organic layer was washed with brine (10 mL), dried over Na$_2$SO$_4$, filtered and concentrated in vacuo. The yellow residue was used in the next step without further purification. LC-MS (ESI+): m/e 166 (M+H)$^+$, R$_t$: 1.44 min.

a3.6) Compound (7)

A mixture of compound 6 (100 mg, crude) and thionyl chloride (1 mL) in DCM (3 mL) was stirred at room temperature for 3 h. The mixture was concentrated in vacuo. The residue was diluted with EtOAc (20 mL) and washed with saturated NaHCO$_3$ solution (6 mL×4) and brine (6 mL). The organic layer was dried over Na$_2$SO$_4$, filtered and concentrated in vacuo. The red residue was used in the next step without further purification. LC-MS (ESI+): m/e 184 (M+H)$^+$, R$_t$: 1.88 min.

a3.7) Compound (8)

A mixture of compound 7 (580 mg, 3.157 mmol) and NaCN (170 mg, 3.473 mmol) in EtOH (12 mL) and H$_2$O (4 mL) was stirred at 50° C. for 60 h. The mixture was diluted with EtOAc (50 mL) and washed with brine (15 mL×4). The organic layer was dried over Na$_2$SO$_4$, filtered and concentrated in vacuo. The residue was purified on a silica column (PE/EtOAc=10:1, v/v) to afford the title product as an off-white solid (280 mg, yield 51%). LC-MS (ESI+): m/e 175 (M+H)$^+$, R$_t$: 1.89 min.

a3.8) Compound (9)

A mixture of compound 8 (200 mg, 1.148 mmol), sodium hydroxide (459 mg, 11.48 mmol) in EtOH (4 mL) and water (0.5 mL) was stirred at 70° C. overnight. The solvent was concentrated, the residue was adjusted to pH=3. The solution was concentrated. The product was used in the next step without further purification
LC-MS (ESI+): m/e 194 (M+H)$^+$, R$_t$: 1.16 min a3.9) Compound (10)

To a mixture of 2-(thieno[3,2-b]pyridin-5-yl)acetic acid from Example a3.8 (77 mg, 0.399 mmol) in MeOH (5 mL) was added SOCl$_2$ (0.5 mL, 6.85 mmol) dropwise at 0° C. The reaction mixture was stirred at room temperature for 5 h. The excess of solvent was removed under reduced pressure. The residue was diluted with EtOAc (100 mL) and washed with saturated NaHCO$_3$ aqueous solution (5 mL×2) and brine (30 mL). The organic layer was dried over Na$_2$SO$_4$, filtered and concentrated in vacuo. The residue was purified by Pre-TLC (PE/EtOAc=2:1, v/v) to afford the title product as an oil (55 mg, yield 65%).

LC-MS (ESI+): m/e 208 (M+H)$^+$, R$_t$: 1.69 min.

a3.10) 2-Thieno[3,2-b]pyridin-5-yl-ethanol

To a solution of methyl 2-(thieno[3,2-b]pyridin-5-yl)acetate (70 mg, 0.338 mmol) from Example a3.9) in THF (4 mL) was added LiBH$_4$ (8.09 mg, 0.372 mmol) in one portion. The mixture was allowed to stir at room temperature overnight. The reaction was quenched with saturated NH$_4$Cl solution, and then extracted with EtOAc (3×10 mL). The organic layer was washed with brine (10 mL), dried over Na$_2$SO$_4$, filtered and concentrated in vacuo. The yellow residue was used in the next step without further purification.

LC-MS (ESI+): m/e 180 (M+H)$^+$, R$_t$: 1.57 min a4) 2-(Imidazo[1,2-a]pyridin-2-yl)ethanol

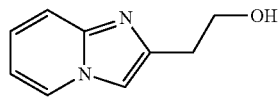 [SMILES: OCCc1cn2ccccc2n1]

a4.1) Ethyl 2-(imidazo[1,2-a]pyridin-2-yl)acetate

A mixture of ethyl 4-chloro-3-oxobutanoate (15 g, 91 mmol) and pyridin-2-amine (8.58 g, 91 mmol) in THF (80 mL) was refluxed overnight. Then, the reaction mixture was concentrated and the residue purified by silica gel chromatography (PE:EA=1:1) to afford ethyl 2-(imidazo[1,2-a]pyridine-2-yl)acetate (5 g, yield 26.9%).

LC-MS (ESI+): m/e 205 (M+H)$^+$, R$_t$: 0.54 min.

a4.2) 2-(Imidazo[1,2-a]pyridin-2-yl)ethanol

To a solution of ethyl 2-(imidazo[1,2-a]pyridin-2-yl)acetate (3.1 g, 15.18 mmol) in THF (30 mL), LiBH$_4$ (0.661 g, 30.4 mmol) was added and the mixture was stirred at room temperature overnight. Saturated NH$_4$Cl was added dropwise to quench the reaction. The solution was extracted with EA (3×100 mL). The organic phase was collected, dried over Na$_2$SO$_4$, filtered and concentrated. The title compound was used without further purification in the next step.

LC-MS (ESI+): m/e 163 (M+H)$^+$, R$_t$: 1.35 min a5) 2-(7-Fluoroimidazo[1,2-a]pyridin-2-yl)ethanol

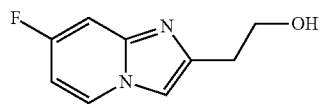

a5.1) 4-Fluoropyridin-2-amine

A mixture of N-(diphenylmethylene)-4-fluoropyridin-2-amine (2.0 g, 7.24 mmol) in THF (50 mL) and 1N HCl (aq) (50 mL) was stirred at about room temperature overnight. The aqueous layer was adjusted to pH>10 with 5N NaOH. The aqueous layer was extracted with ethyl acetate (3×50 mL), concentrated. The mixture was purified by column chromatography (PE/EA=4/1) to give the title compound (300 mg, yield: 37%).

LC-MS: m/e 113 (M+H); R$_t$:1.36 min. $^1$H NMR (CDCl$_3$): 4.62 (s, 2H), 6.16 (dd, J=10.8 Hz, 2.4, 1H) 6.38-6.42 (m, 1H), 8.00 (dd, J=9.2 Hz, 6 Hz, 1H).

a5.2) Ethyl 2-(7-fluoroimidazo[1,2-a]pyridin-2-yl)acetate

A mixture of 4-fluoropyridin-2-amine (1.0 g, 8.92 mmol) and ethyl 4-chloro-3-oxobutanoate (1.46 mL, 10.7 mmol) in THF (20 mL) was stirred at about reflux overnight. The residue was concentrated and was chromatographed on the C18 ISCO Combiflash system using the following gradient: A: Water (0.1% NH$_4$HCO$_3$); B: Methanol; 10% B to 60% B over 20 min to give 350 mg product as brown oil (350 mg, yield: 17.6%).

LC-MS: m/e 223 (M+H); R$_t$:1.62 min; $^1$H NMR (CDCl$_3$): 1.29 (t, 3H), 3.84 (s, 2H), 4.21 (q, 2H), 7.66-7.69 (m, 1H), 7.19 (dd, J=8.2, 2.4 Hz, 1H), 7.56 (s, 1H), 8.01-8.04 (m, 1H).

a5.3) 2-(7-Fluoroimidazo[1,2-a]pyridin-2-yl)ethanol

LiAlH$_4$ (0.171 g, 4.50 mmol) was added to the solution of ethyl 2-(7-fluoroimidazo[1,2-a]pyridin-2-yl)acetate (0.5 g, 2.25 mmol) in THF (15 mL) and the reaction was stirred for about 2 h. The reaction was quenched with H$_2$O and concentrated. The residue was diluted with methanol (3 mL) and filtered. The filtrate was purified by C18 ISCO Combiflash system using the following gradient: A: Water (0.1% NH$_4$HCO$_3$); B: Methanol; 10% B to 50% B over 20 min (100 mg, yield: 24.6%).

a6) 2-(5,6,7,8-Tetrahydroquinolin-2-yl)ethanol

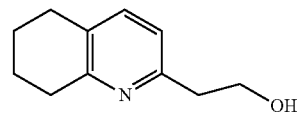 [SMILES: OCCc1ccc2c(n1)CCCC2]

a6.1) Ethyl 2-(5,6,7,8-tetrahydroquinolin-2-yl)acetate

A solution of 7.56 g (74.7 mmol) of diisopropylamine in 100 mL of water-free THF was cooled to −30° C. and n-BuLi (31.9 g, 15% solution in n-hexane, 74.7 mmol mmol) was added via a syringe. The mixture was allowed to stir for 30 min. After cooling to −70° C., 8.68 g (74.7 mmol) tetramethylethylenediamine in 20 mL of THF were added and the mixture was allowed at −70° C. for 1 h. Then, 5 g (34.00 mmol) of 2-methyl-5,6,7,8-tetrahydroquinoline and 3.87 g (35.7 mmol) of ethyl carbonochloridate were added. The mixture was allowed to warm to room temperature within 2 h while being stirring. The reaction mixture was poured onto conc. cold aqueous ammonium chloride solution and extracted with EA (3 times). The combined organic phase was once extracted with a saturated ammonium chloride solution, washed with a saturated sodium bicarbonate solution and dried (magnesium sulfate). After removal of the solvent, the crude product was purified by flash column chromatography (eluent: heptane/EA 1/2) to provide 2.16 g (29%) of the title compound.

a6.2) 2-(5,6,7,8-Tetrahydroquinolin-2-yl)ethanol

Under N$_2$, 4.56 mL (4.56 mmol) of lithium aluminium hydride (1M in THF) was cooled to 0° C. and ethyl 2-(5,6,7,8-tetrahydroquinolin-2-yl)acetate (1 g, 4.56 mmol) dissolved in a small quantity of THF was slowly added. The mixture was allowed to stir for 1.5 h. To the reaction mixture 173 mg of H$_2$O in THF, 173 mg of 10% ige NaOH and 3×173 mg of H$_2$O were added. The mixture was then stirred for 30 min. Magnesium sulfate was added. After removal of the solvent, the crude product (0.78 g, 96%) was purified by chromatography (eluent: EA/heptane 3/1) to give the title compound.

a7) 2-(1H-benzo[d]imidazol-2-yl)ethanol

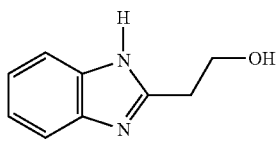 [SMILES: OCCc1nc2ccccc2[nH]1]

Commercially available from Sigma-Aldrich.

a8) 1-(quinolin-2-yl)propan-2-ol

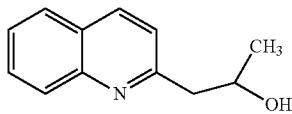

CAS-No.: 156538-90-8, commercially available from Enamine (Ukraine, Kiew, order number EN300-95420.

a9) 2-(8-fluoroquinolin-2-yl)ethanol

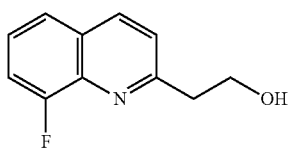 [SMILES: OCCc1ccc2cccc(F)c2n1]

To a solution of formaldehyde and paraformaldehyde (0.187 g, 6.20 mmol) in 2 mL of water was added -fluoro-2-methylquinoline (1 g, 6.20 mmol) and then sodium hydroxide (0.37 g, 9.31 mmol) dissolved in 2 mL of water. Then 2-3 mL of ethanol were added. The mixture was stirred at 85° C. for 48 hours. After cooling to room temperature, the reaction mixture was poured onto ice-water. The reaction mixture was mixed with DCM and water. The organic phase was washed with water, dried and concentrated. The residue was purified by chromatography (eluent: DCM/methanol) to give 0.316 g (26.6%) of the title compound as bright yellow oily compound.

a10) 2-(7-fluoroquinolin-2-yl)ethanol

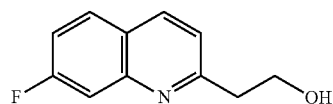 [SMILES: OCCc1ccc2ccc(F)cc2n1]

a10.1) tert-butyl 2-(7-fluoroquinolin-2-yl) acetate

To a solution of diisopropylamine (0.753 g, 7.45 mmol) in THF was added at −78° C. n-butyl lithium (0.437 g, 6.82 mmol, 2.5 molar) over a period of 15 min. Then the mixture was stirred for further 30 min at −78° C. A solution of 7-fluoro-2-methylquinoline (1 g, 6.20 mmol) in 2 mL of THF was added at −78° C. After stirring for a further hour solution of di-tert-butyl dicarbonate (1.49 g, 6.82 mmol) in 1 mL of THF was added. The reaction mixture was allowed to warm up to room temperature over a period of 2 h. The reaction mixture was mixed with water and EA. The aqueous phase was extracted with EA. The combined organic phases were dried and concentrated to give the title compound (790 mg, 48.7%) as red oil.

a10.2) 2-(7-fluoroquinolin-2-yl)ethanol

To 3.03 mL of lithiumaluminiumhydride in THF (1 molar, 115 mg, 3.03 mmol) was added the compound of example a10.1 at 0° C. Then the mixture was stirred for 2 h at 0° C. and then stirred at room temperature for 20 h. The reaction mixture was mixed with water and 10% by weight aq. NaOH solution. The mixture was stirred for 30 min, dried and concentrated to give 250 mg of the title compound (43.2%).

a11) 2-(1,6-naphthyridin-2-yl)ethanol

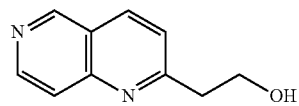 [SMILES: OCCc1ccc2cnccc2n1]

The title compound was prepared in analogy to the method described in example a9).

a12) 2-(1,5-naphthyridin-2-yl)ethanol

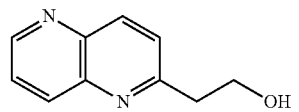 [SMILES: OCCc1ccc2ncccc2n1]

The title compound was prepared in analogy to the method described in example a9).

a13) 2-(1H-benzo[d]imidazole-2-yl)ethanol

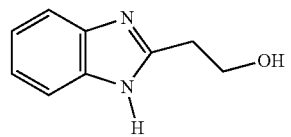 [SMILES: OCCc1nc2ccccc2[nH]1]

Commercially available from Matrix Scientific, catalogue number 27653 a14) 2-(1H-benzo[d]imidazol-1-yl)ethanol

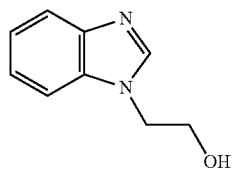 [SMILES: OCCn1cnc2ccccc21]

Commercially available from Matrix Scientific, catalogue number 054768.

b) Preparation of Compounds of the General Formula Het-A$^1$-OS(O)$_2$CF$_3$ b1) Trifluoromethanesulfonic acid 2,2-difluoro-2-quinolin-2-yl ethyl ester

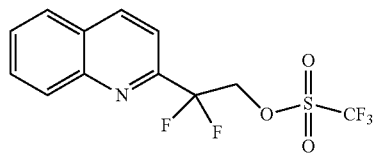

b1.1) Difluoroquinolin-2-yl acetic acid ethyl ester

2-Bromoquinoline (5.0 g, 24.0 mmol), ethyl 2-bromodifluoroacetate (5.8 g, 28.8 mmol) and copper powder (3.5 g, 55.2 mmol) in DMSO (20 mL) were stirred at 55° C. for 5 hours. The solid was filtered off, water (100 mL) and EA (150 mL) were added. The organic layer was separated, dried over sodium sulfate and concentrated to give the title compound as a yellow oil (4.2 g, 70%), which was used in the next step without further purification. LC-MS (ESI+): m/e 252 (M+H)$^+$, R$_t$: 0.93 min.

b1.2) 2,2-Difluoro-2-quinolin-2-ylethanol

To a solution of difluoroquinolin-2-yl acetic acid ethyl ester (2 g, 7.9 mmol) in ethanol (20 mL) was added NaBH$_4$ (317 mg, 1.0 mmol) at 0° C. under N$_2$. The mixture was stirred for 1 hour and then at room temperature for 1.5 hours. The solution was quenched with dilute HCl (0.1 N, 20 mL). The mixture was neutralized with saturated NaHCO$_3$ solution and extracted with EtOAc (3*100 mL). The combined organic layer was dried over sodium sulfate. The solvent was evaporated and the residue was purified by column chromatography on silica gel (PE: EA=10:1) to give the title compound as a yellow solid (0.7 g, 44%). LC-MS (ESI+): m/e 210 (M+H)$^+$, R$_t$: 0.75 min.

b1.3) Trifluoromethanesulfonic acid 2,2-difluoro-2-quinolin-2-yl ethyl ester

To a solution of 2,2-difluoro-2-quinolin-2-ylethanol (300 mg, 1.4 mmol) and triethylamine (217 mg, 2.1 mmol) in anhydrous DCM (5 mL) was added dropwise trifluoromethanesulphonic anhydride (606 mg, 2.1 mmol) at −70° C. The reaction mixture was stirred for 1 hour. The resulting solution was warmed slowly to room temperature and stirred for 1 hour. The solid was removed by filtration. Water (5 mL) and DCM (30 mL) were added, the organic layer was separated, dried over sodium sulfate and evaporated to give the crude title compound as an orange oil (450 mg, 92%), which was used in the next step without further purification. LC-MS (ESI+): m/e 342 (M+H)$^+$, R$_t$: 1.01 min.

c) Preparation of Compounds of the General Formula Het-A$^4$-Br c1) syn-2-(2-Bromocyclopropyl)quinoline

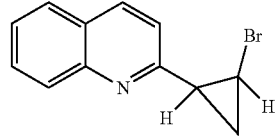

c1.1) (Z)-2-(2-Bromovinyl)quinoline

A suspension of 24.97 g (57.3 mmol) of (bromomethyl)triphenylphosphonium bromide in 160 mL of THF was chilled to −70° C. under argon. Then, 6.43 g (57.3 mmol) of potassium tert-butoxide were added portionwise and the suspension was allowed to stir at this temperature for 1 h. A solution of 7.5 g of (47.7 mmol) quinoline-2-carbaldehyde in 40 mL of THF was slowly added dropwise. The mixture was allowed to stir at −75° C. for further 5 hours and then warmed to room temperature overnight. 160 mL of PE were added. The precipitate formed was sucked off. The mother liquid was evaporated and the residue was stirred with diisopropyl ether. The residue formed was sucked off. Purification by chromatography (heptane/EA 3/1) yielded 6.6 g (59.1%) of the title compound.

c1.2) syn 2-(2-Bromocyclopropyl)quinoline

A solution of diethylzinc in hexane (5.54 g, 44.9 mL, 44.9 mmol) was chilled to 0° C. under argon. Trifluoroacetic acid (5.11 g, 3.46 mL, 44.9 mmol) was added dropwise over 20 minutes. The mixture was stirred for further 20 minutes at 0° C. Then, a solution of diiodomethane (12.01 g, 3.62 mL, 44.9 mmol) in dichloromethane was added at 0° C. over a period of 20 minutes. A solution of (Z)-2-(2-bromovinyl)quinoline (2.1 g, 8.97 mmol) in DCM was added dropwise and the mixture was stirred over night at room temperature. The total amount of DCM was 350 mL. The reaction mixture was quenched by addition of saturated aqueous ammonium chloride and then extracted with DCM. The organic phase was washed with water. The combined organic phases were evaporated. The residue was stirred with EA. Active charcoal was added and the mixture was stirred for some further minutes. The solids were filtered off and the filtrate was concentrated. Purification by chromatography (CombiFlash Rf, normal phase chromatography, gradient elution using cyclohexane in EA up to a concentration of 15%) yielded 0.78 g (34.8%) of the title compound.

c2) syn 2-(2-bromocyclopropyl)-6-fluoroquinoline

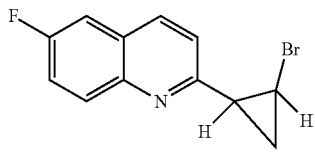 [SMILES: Fc1ccc2nc(C3CC3Br)ccc2c1]

c2.1) (Z)-2-(2-bromovinyl)-6-fluoroquinoline

To as suspension of (bromomethyl)triphenylphosphonium bromide (14.94 g, 34.3 mmol) in 100 mL of THF was added potassium tert-butoxide (3.84 g, 34.3 mmol) portionwise under Ar. Then the reaction mixture was stirred for 1 h at this temperature. 6-Fluoroquinoline-2-carbaldehyde (5 g, 28.5 mmol) in 40 mL of THF was added. The resulting reaction mixture was stirred for 5 h at −75° C. and allowed to warm up overnight. The reaction mixture was diluted with petrol ether and the solid was sucked off. The mother liquid was concentrated, diisopropyl ether was added and the formed precipitate was sucked off. The mother liquid was purified by column chromatography (cyclohexane/EA) to give 4.7 g (65.3%) of the title compound as brown solid. LC-MS: m/e 254.0.

c2.2) syn 2-(2-bromocyclopropyl)-6-fluoroquinoline

The title compound was prepared in analogy to the method described for example c1.2. LC-MS: 268.0 c3) syn 5-(2-bromocyclopropyl)thieno[3,2-b]pyridine

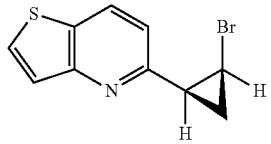 [SMILES: Br[C@H]1C[C@H]1c1ccc2sccc2n1]

The title compound was prepared in analogy to the method described in example c1.2 starting from (Z)-5-(2-bromovinyl)thieno[3,2-b]pyridine. LC-MSM m/e 255.9 (M+H)+ d) Preparation of Compounds of the General Formula Het-A³-Br d1) (Z)-2-(2-bromovinyl)-3-methylquinoline

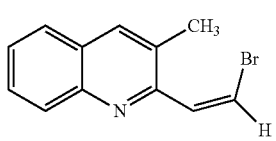

To a suspension of (bromomethyl)triphenylphosphonium bromide (3.06 g, 7.01 mmol) in 30 mL of THF, potassium tert-butoxide (0.78 g, 7.01 mmol) was added portionwise at −75° C. under argon. After completion of the addition, the mixture was stirred for 1 h a −75° C. Then, a solution of 3-methylquinoline-2-carbaldehyde (1 g, 5.84 mmol) in 20 mL of THF was added. The reaction mixture was stirred for 5 h at −75° C. and then allowed to warm up to room temperature overnight. For work-up, the reaction mixture was diluted with diisopropyl ether (1:1) and the precipitate formed was sucked off. The filtrate was concentrated and triturated in diisopropyl ether. The precipitate was sucked off. The filtrate was purified by column chromatography (normal phase, eluent: cyclohexane/EA) to give 492.5 mg (34%) of the title compound as yellow solid. LC-MS: m/e 248.0 (M+H)+; $R_t$ 1.561 min.

d2) (Z)-2-(2-bromovinyl)-6-methoxyquinoline

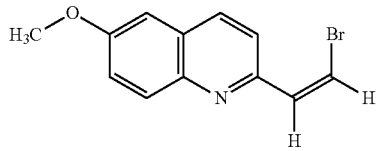

The title compound was prepared in analogy to the method described in example d1 but using 6-methoxyquinoline-2-carbaldehyde instead of 3-methylquinoline-2-carbaldehyde. LC-MS: m/e 265.1 (M+H)+; $R_t$ 1.78 min d3) (Z)-2-(2-bromovinyl)-6-chloroquinoline

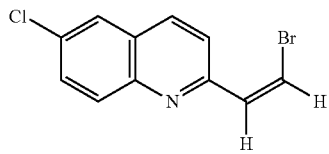 [SMILES: Clc1ccc2nc(/C=C\Br)ccc2c1]

The title compound was prepared in analogy to the method described in example d1 but using 6-chloroquinoline-2-carbaldehyde instead of 3-methylquinoline-2-carbaldehyde. LC-MS: m/e 268.1 $R_t$ 4.609 min.

d4) (Z)-5-(2-bromovinyl)thieno[3,2-b]pyridine

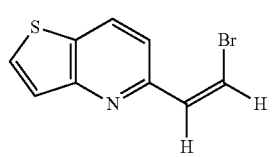 [SMILES: Br/C=C\c1ccc2sccc2n1]

The title compound was prepared in analogy to the method described in example d1 but using thieno[3,2-b]pyridine-5-carbaldehyde. LC-MS: m/e 239.9.

II. Preparation of Compounds of the Formula I

II.1 Preparation of Compounds of the Formula I in which A is A¹, X¹ is N, and X³ is S

Example 1: 3,7-di(pyridin-4-yl)-5-[2-(quinolin-2-yl)ethyl]thieno[2,3-d]pyridazin-4(5H)-one

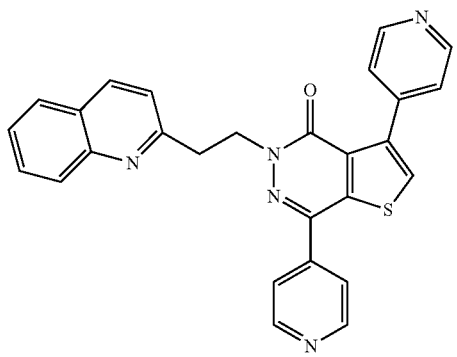 [SMILES: O=c1c2c(-c3ccncc3)csc2c(-c2ccncc2)nn1CCc1ccc2ccccc2n1]

1.1 4-Bromothiophene-3-carboxylic acid

To a mixture of Mg (1.4 g, 60 mmol) and $I_2$ (0.1 g) in anhydrous THF (2 mL) was added dropwise a solution of 2-bromo-propane (7.4 g, 60 mmol) in anhydrous THF (60 mL) at room temperature under nitrogen during a period of 30 min. After the addition, the mixture was refluxed until the most of magnesium was consumed. The resulting Grignard reagent was added dropwise to a solution of 3,4-dibromothiophene (12.1 g, 50 mmol) in anhydrous THF (60 mL) at 0° C. under nitrogen within about 30 min. The mixture was allowed to stir at 0° C. for 1.5 h. Excessive $CO_2$ was purged into the mixture at −30° C. and the reaction mixture was stirred until the temperature rose to room temperature. Then the reaction was quenched with water (30 mL) and basified with 8% aq. NaOH solution to pH 11 and was washed with ethyl acetate (3×60 mL). The aqueous layer was acidified with 5% aq. HCl to pH 1~2, the precipitate was filtered and was dried to give the title compound as off-white solid (5.8 g, yield 56%).

LC-MS (ESI+): m/e 209 (M+H)⁺, $R_t$: 0.69 min.

1.2 4-Bromo-2-isonicotinoylthiophene-3-carboxylic acid

To a solution of diisoproplyamine (5.3 g, 53 mmol) in anhydrous THF (40 mL) at −30° C. was added n-BuLi (23.2 mL, 58 mmol, 2.5M in hexanes) dropwise. The mixture was stirred at the same temperature for 0.5 h, then cooled to −78° C. and HMPA (0.86 g, 4.8 mmol) was added slowly. Then the solution of 4-bromothiophene-3-carboxylic acid (5.0 g, 24 mmol) in anhydrous THF (50 mL) was added slowly. The mixture was stirred at the same temperature for 1 h, N-methoxy-N-methyl-4-pyridinecarboxamide (8.0 g, 48 mmol) was added dropwise into the stirring mixture at −78° C. The reaction mixture was stirred for another 1 h at room temperature and was then quenched with $H_2O$ (10 mL). The aqueous layer was acidified with 5% aq. HCl to pH 1~2, the precipitate was collected by filtration. The filter cake was washed with DCM (10*50 mL). The title compound was dissolved in DCM; the solid insoluble in DCM was the side product. The filtrate was extracted with DCM (3×200 mL). The organic layers were dried over $Na_2SO_4$ and concentrated under reduced pressure. The crude product was washed with DCM to give the title compound (0.8 g, yield 10.7%) as a yellow solid.

LC-MS (ESI+): m/e 312 (M+H)⁺, $R_t$: 1.45 min.

1.3 Ethyl 4-bromo-2-isonicotinoylthiophene-3-carboxylate

To a solution of the compound from example 1.2 (2.5 g, 8 mmol) and $Cs_2CO_3$ (5.2 g, 16 mmol) in $CH_3CN$ (500 mL) was added $CH_3CH_2I$ (3.0 g, 19.2 mmol) dropwise. The mixture stirred at 30° C. for 48 h. The mixture was filtered and concentrated to give the title compound as yellow oil (2 g, 73.5% yield).

LC-MS (ESI+): m/e 340 (M+H)⁺, $R_t$: 0.81 min

1.4 Ethyl 2-isonicotinoyl-4-(pyridin-4-yl)thiophene-3-carboxylate

A mixture of the compound from example 1.3 (500 mg, 1.47 mmol), 4-pyridineboronic acid (271 mg, 2.21 mmol), $Na_2CO_3$ (390 mg, 3.68 mmol) and Pd(dppf)$Cl_2$ (122 mg, 0.15 mmol) in dioxane/$H_2O$ (3:1) (12 mL) was stirred at 100° C. under argon for 2 h. The mixture was concentrated and the residue was purified by Prep-HPLC to give the title product as white solid (318 mg, 64% yield).

LC-MS (ESI+): m/e 339 (M+H)⁺, $R_t$: 0.61 min

1.5 3,7-Di(pyridin-4-yl)thieno[2,3-d]pyridazin-4(5H)-one

A mixture of the compound from example 1.4 (200 mg, 0.59 mmol) in $NH_2NH_2 \cdot H_2O$ (2 mL) and EtOH (10 mL) was stirred at room temperature for 30 min. The mixture was filtered and the solid was dried to obtain the title compound as a white solid (150 mg, 83.1%). LC-MS (ESI+): m/e 307 (M+H)⁺, $R_t$: 1.56 min.

1.6 3,7-Di(pyridin-4-yl)-5-[2-(quinolin-2-yl)ethyl]thieno[2,3-d]pyridazin-4(5H)-one To a solution of 3,7-di(pyridin-4-yl)thieno[2,3-d]pyridazin-4(5H)-one from example 1.5 (100 mg, 0.32 mmol), 2-quinolin-2-yl-ethanol from example a1 (58 mg, 0.33 mmol) and PPh₃ (256 mg, 0.98 mmol) in DCM (10 mL), DIAD (198 mg, 0.98 mmol) was added dropwise. The mixture was stirred at room temperature for 3 h, concentrated and the residue was purified by Prep-HPLC to give the title compound as white solid (26 mg, 17.6% yield).

LC-MS (ESI+): m/e 462 (M+H)⁺, $R_t$: 2.00 min; ¹H-NMR (DMSO-d, 400 MHz): δ 3.46 (t, J=7.2 Hz, 2H), 4.71 (t, J=7.2 Hz, 2H), 7.49-7.51 (m, 3H), 7.54-7.57 (m, 1H), 7.62 (dd, J=4.4, 1.6 Hz, 2H), 7.68-7.72 (m, 1H), 7.84 (d, J=8.4 Hz, 1H), 7.94 (d, J=7.2 Hz, 1H), 8.28-8.30 (m, 2H), 8.60 (dd, J=4.6, 1.6 Hz, 2H), 8.70 (dd, J=4.6, 1.6 Hz, 2H).

Example 2: 7-(Pyridin-4-yl)-5-[2-(quinolin-2-yl)ethyl]thieno[2,3-d]pyridazin-4(5H)-one

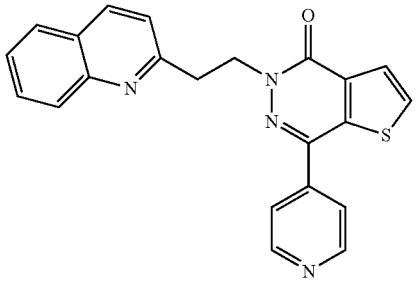 [SMILES: O=c1c2ccsc2c(-c2ccncc2)nn1CCc1ccc2ccccc2n1]

2.1 2-Isonicotinoylthiophene-3-carboxylic acid

To a solution of diisopropylamine (5.2 g, 51.5 mmol) in anhydrous THF (40 mL) at −30° C. was added n-BuLi (23.2 mL, 56.2 mmol, 2.5M in THF) dropwise. The mixture was stirred at the same temperature for 0.5 h, then cooled to −78° C. and HMPA (0.8 g, 4.7 mmol) was added slowly. Then a solution of thiophene-3-carboxylic acid (3.0 g, 23.4 mmol) in anhydrous THF (50 mL) was added slowly. The mixture was stirred at the same temperature for 1 h, N-methoxy-N-methyl-4-pyridinecarboxamide (5.0 g, 46.9 mmol) was added drop wise into the stirring mixture at −78° C. The reaction mixture was stirred for another 1 h at room temperature and was then quenched with $H_2O$ (10 mL). The aqueous layer was acidified with 5% aq. HCl to pH 1~2, the precipitate was collected by filtration. The filter cake wash with DCM and the filtrate was extracted with DCM (3×200 mL). The organic layers were dried over $Na_2SO_4$ and concentrated under reduced pressure. The crude product was washed with DCM to give the title product (2.2 g, yield 40%) as a white solid.

LC-MS (ESI+): m/e 234 (M+H)+, $R_t$: 0.57 min.

2.2 Ethyl 2-isonicotinoylthiophene-3-carboxylate

To a solution of 2-isonicotinoylthiophene-3-carboxylic acid (2.2 g, 9.4 mmol) from example 2.1 and $Cs_2CO_3$ (6.2 g, 18.9 mmol) in $CH_3CN$ (500 mL) was added $CH_3CH_2I$ (2.9 g, 18.9 mmol) dropwise. The mixture was stirred at 30° C. for 48 h. The mixture was filtered and concentrated to give the title compound as yellow oil (2.1 g, 85.5% yield).

LC-MS (ESI+): m/e 340 (M+H)+, $R_t$: 0.81 min

2.3 7-(Pyridin-4-yl)thieno[3,2-d]pyridazin-4(5H)-one

The mixture of ethyl 2-isonicotinoylthiophene-3-carboxylate (200 mg, 0.77 mmol) from example 2.2 in $NH_2NH_2.H_2O$ (2 mL) and EtOH (10 mL) was stirred at room temperature for 30 min. The mixture was filtered and the solid dried to obtain the title compound (150 mg, 85.1% yield).

LC-MS (ESI+): m/e 230 (M+H)+, $R_t$: 1.52 min.

2.4 7-(Pyridin-4-yl)-5-[2-(quinolin-2-yl)ethyl]thieno[2,3-d]pyridazin-4(5H)-one To a solution of 7-(pyridin-4-yl)thieno[3,2-d]pyridazin-4(5H)-one (100 mg, 0.44 mmol) from example 2.3, 2-quinolin-2-yl-ethanol from example a1 (83 mg, 0.48 mmol) and $PPh_3$ (343 mg, 1.31 mmol) in DCM (10 mL), DEAD (228 mg, 1.31 mmol) was added dropwise. The mixture stirred at room temperature for 3 h, concentrated and the purified by Prep-HPLC to give the title compound as a white solid (20 mg, 11.8% yield).

LC-MS (ESI+): m/e 385 (M+H)+, $R_t$: 1.87 min; $^1$H-NMR (DMSO-d6, 400 MHz): δ 3.49 (t, J=7.2 Hz, 2H), 4.76 (t, J=7.2 Hz, 2H), 7.49-7.57 (m, 2H), 7.58 (dd, J=4.4, 1.6 Hz, 2H), 7.67-7.72 (m, 1H), 7.78 (d, J=5.2 Hz, 1H), 7.85 (d, J=8.0 Hz, 1H), 7.93 (d, J=7.6 Hz, 1H), 8.21 (d, J=5.2 Hz, 1H), 7.93 (d, J=8.8 Hz, 1H), 8.66 (dd, J=4.2, 1.6 Hz, 2H).

Example 3: 3-(Pyridin-4-yl)-5-[2-(quinolin-2-yl)ethyl]thieno[2,3-d]pyridazin-4(5H)-one

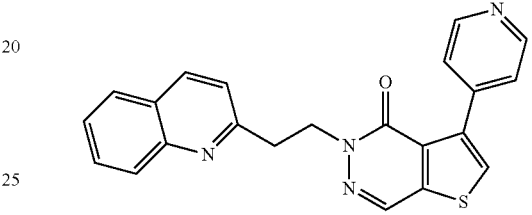

3.1 4-Bromo-2-formyl-thiophene-3-carboxylic acid

To a solution of (i-Pr)$_2$NH (1.09 g, 10.8 mmol) in anhydrous THF (15 mL) was added dropwise n-BuLi (5.0 mL, 12.5 mmol, 2.5M in hexane) at −30° C. The mixture was stirred at the same temperature for 0.5 h. Then, the mixture was cooled to −78° C. and the solution of 4-bromothiophene-3-carboxylic acid from example 1.1 (1.0 g, 4.85 mmol) and HMPA (0.17 g, 0.95 mmol) in anhydrous THF (20 mL) was added slowly. The mixture was stirred at the same temperature for 1 h, anhydrous DMF (0.6 g, 8.22 mmol) was added dropwise into the stirring mixture at −78° C. The reaction mixture was stirred for another 45 min at room temperature and then quenched with water. The aqueous layer was acidified with 5% aq. HCl to pH 1~2, the precipitate was collected by filtration, the filtrate was extracted with DCM (3×50 mL). The organic layers were dried over $Na_2SO_4$ and concentrated under reduced pressure. The crude product was washed with $CH_2Cl_2$ to give the title product (0.68 g, 60.2%) as a solid.

LC-MS: m/e (M+H)+: 235.7; $R_t$: 0.64 min.

3.2 4-Bromo-2-formyl-thiophene-3-carboxylic acid ethyl ester

4-Bromo-2-formyl-thiophene-3-carboxylic acid (0.16 g, 0.68 mmol), $K_2CO_3$ (0.188 g, 1.36 mmol), and 4 mL of anhydrous DMF were stirred at room temperature for 10 min, then iodoethane was added (0.128 g, 0.8 mmol) dropwise. The reaction solution was stirred at 50° C. for 3 h. The reaction mixture was cooled, extracted with EA (3×50 mL), concentrated and the residue was purified by TLC (PE/EA=8/1) to give 0.4 g of the title compound (yield: 63.5%).

LC-MS: m/e (M+H)+: 263.7, $R_t$: 0.88 min.

3.3 3-Bromo-5H-thieno[2,3-d]pyridazin-4-one

4-Bromo-2-formyl-thiophene-3-carboxylic acid ethyl ester (1.0 g, 3.8 mmol), $NH_2NH_2.H_2O$ (0.27 g, 4.58 mmol)

and 20 mL of EtOH were refluxed under nitrogen for 5 h. The reaction mixture was cooled and precipitate formed, then filtered to give the title compound (0.2 g, yield: 23%).

LC-MS: m/e (M+H)⁺: 231.7, $R_t$: 1.29 min

3.4 3-Bromo-5-[2-(quinolin-2-yl)ethyl]thieno[2,3-d]pyridazin-4(5H)-one

To a stirred solution of PPh₃ (977 mg, 3.73 mmol) and DEAD (1.13 mL) in 15 mL of anhydrous THF was added a solution of 3-bromo-5H-thieno[2,3-d]pyridazin-4-one (429 mg, 1.86 mmol) and 2-quinolin-2-yl-ethanol from example a1 (355 mg, 2.05 mmol) in 15 mL of anhydrous THF while being cooled with an ice-bath. Then the resulting mixture was stirred in nitrogen atmosphere at 45° C. overnight. The reaction mixture was concentrated and the product was recrystallized from EA to give the title compound (370 mg, 53.6%).

LC-MS: m/e (M+H)⁺: 386.7, $R_t$: 2.02 min

3.5 3-(Pyridin-4-yl)-5-[2-(quinolin-2-yl)ethyl]thieno[2,3-d]pyridazin-4(5H)-one 3-Bromo-5-[2-(quinolin-2-yl)ethyl]thieno[2,3-d]pyridazin-4(5H)-one (130 mg, 0.33 mmol), pyridine-4-yl-boronic acid (45.7 mg, 0.37 mmol), Pd(dppf)Cl₂ (15 mg) and K₂CO₃ (93 mg, 0.67 mmol) were dissolved in dioxane/H₂O (3/1, 2.8 mL). The mixture was stirred in nitrogen atmosphere at 120° C. for 1 h in a microwave tube. The solution was concentrated and purified by TLC (DCM/MeOH=10/1) and recrystallized from MeOH to give the title product (90 mg, 69.4%).

LC-MS: m/e (M+H)⁺: 385.7, $R_t$: 1.90 min. ¹H NMR (DMSO, 400 MHz) δ: 8.48-8.45 (m, 3H), 8.25 (d, J=8.4 Hz, 1H), 8.02 (s, 1H), 7.93-7.88 (m, 2H), 7.72 (t, J=8.4 Hz, 1H), 7.58 (t, J=7.2 Hz, 1H), 7.48-7.42 (m, 3H), 4.72 (t, J=7.0 Hz, 2H), 3.49 (t, J=7.0 Hz, 2H)

Example 4: 3-(Pyridin-4-yl)-5-[2-(pyridin-2-yl)ethyl]thieno[2,3-d]pyridazin-4(5H)-one

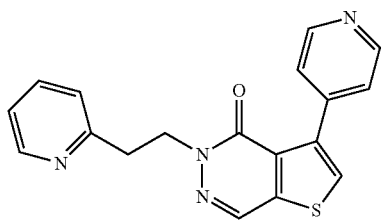 [SMILES: O=c1c2c(-c3ccncc3)csc2cnn1CCc1ccccn1]

4.1 3-Bromo-5-(2-pyridin-2-yl-ethyl)-5H-thieno[2,3-d]pyridazin-4-one

The title compound was prepared in analogy to the process described in Example 3.4 starting from 3-bromo-5H-thieno[2,3-d]-pyridazin-4-one and 2-pyridin-2-yl-ethanol. Yield: 76.3%.

LC-MS: m/e (M+H)⁺: 336.7, $R_t$: 1.51 min

4.2 3-(Pyridin-4-yl)-5-[2-(pyridin-2-yl)ethyl]thieno[2,3-d]pyridazin-4(5H)-one The title compound was prepared in analogy to the process described in Example 3.5 starting from 3-bromo-5-(2-pyridin-2-yl-ethyl)-5H-thieno[2,3-d]pyridazin-4-one and pyridine-4-ylboronic acid. Yield: 33.1%.

LC-MS: m/e (M+H): 335.7, $R_t$: 1.69 min. ¹H NMR (DMSO, 400 MHz) δ: 8.60 (d, J=5.2 Hz, 2H), 8.47 (d, J=4.4 Hz, 1H), 8.16 (s, 1H), 7.53-7.48 (m, 2H), 7.43 (d, J=5.2 Hz, 2H), 7.11-7.04 (m, 2H), 4.57 (t, J=7.6 Hz, 2H), 3.24 (t, J=7.4 Hz, 2H).

Example 5: 3,7-Di(pyridin-4-yl)-5-[2-(pyridin-2-yl)ethyl]thieno[2,3-d]pyridazin-4(5H)-one

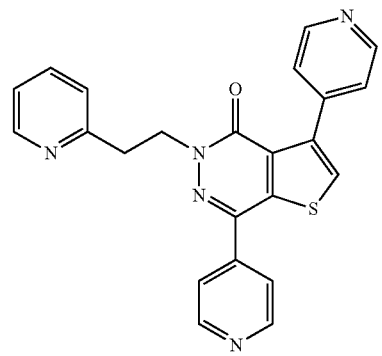 [SMILES: O=c1c2c(-c3ccncc3)csc2c(-c2ccncc2)nn1CCc1ccccn1]

5.1 3-Bromo-7-pyridin-4-yl-5H-thieno[2,3-d]pyridazin-4-one

The title compound was prepared in analogy to the process described in Example 3.3 starting from ethyl 4-bromo-2-isonicotinoyl-thiophene-3-carboxylic acid from Example 1.3. Yield: 56.8%.

LC-MS: m/e (M+H)⁺:308.7, $R_t$: 1.59 min.

5.2 3-Bromo-7-pyridin-4-yl-5-[2-(pyridin-2-yl)ethyl]thieno[2,3-d]pyridazin-4(5H)-one The title compound was prepared in analogy to the process described in Example 3.4 starting from 3-bromo-7-pyridin-4-yl-5H-thieno[2,3-d]pyridazin-4-one and 2-pyridin-2-yl-ethanol. Yield: 70%.

LC-MS: m/e (M+H)⁺: 413.7; $R_t$: 1.84 min.

5.3 3,7-Di(pyridin-4-yl)-5-[2-(pyridin-2-yl)ethyl]thieno[2,3-d]pyridazin-4(5H)-one The title compound was prepared in analogy to the process described in Example 3.5 starting from 3-bromo-7-pyridin-4-yl-5-[2-(pyridin-2-yl)ethyl]thieno[2,3-d]pyridazin-4(5H)-one and pyridine-4-ylboronic acid. Yield: 75.2%.

LC-MS: m/e (M+H)⁺: 412.7, $R_t$: 1.71 min; ¹H NMR (DMSO, 400 MHz) δ: 8.78 (d, J=5.2 Hz, 2H), 8.71 (d, J=4.4 Hz, 2H), 8.56 (d, J=4.8 Hz, 1H), 7.70-7.67 (m, 3H), 7.60 (t, J=7.6 Hz, 1H), 7.51 (d, J=5.2 Hz, 2H), 7.21 (d, J=7.6 Hz, 1H), 7.17-7.14 (m, 1H), 4.75 (t, J=7.6 Hz, 2H), 3.37 (t, J=7.4 Hz, 2H).

Example 6: 5-[2-(Quinolin-2-yl)ethyl]-3-[4-(trifluoromethyl)phenyl]thieno[2,3-d]pyridazin-4(5H)-one

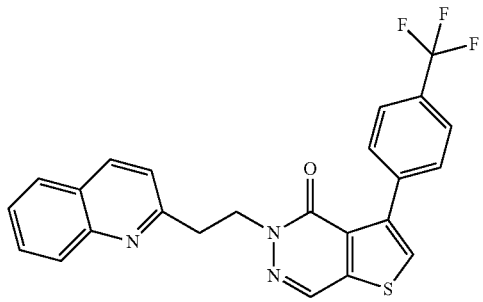 [SMILES: O=c1c2c(-c3ccc(C(F)(F)F)cc3)csc2cnn1CCc1ccc2ccccc2n1]

3-Bromo-5-[2-(quinolin-2-yl)ethyl]thieno[2,3-d]pyridazin-4(5H)-one Example 3.4 (100 mg, 0.26 mmol), 4-(trifluoromethyl)phenylboronic acid (0.26 mmol), Pd(dppf)Cl$_2$ (12.7 mg) and K$_2$CO$_3$ (72 mg, 0.527 mmol) were dissolved in dioxane/H$_2$O (3/1, 2.8 mL). The mixture was stirred at 110° C. for 0.5 h in a microwave tube. The solution was concentrated and purified by prep-TLC to give the title product.

LC-MS: m/e (M+H)$^+$: 452, R$_t$: 2.36, $^1$H NMR (CDCl$_3$, 400 MHz) δ: 3.50 (t, 2H, J=7.6 Hz), 4.75 (t, 2H, J=7.6 Hz), 7.33 (d, 1H, J=4.4 Hz), 7.48-7.53 (m, 2H), 7.59-7.69 (m, 5H), 7.78 (d, 1H, J=7.6 Hz), 8.00 (d, 1H, J=8.0), 8.06 (d, 1H, J=8.0 Hz), 8.23 (s, 1H)

Examples 7 to 92 were prepared analogously to the method described for Example 6.

| EX. | Name | LC-MS: m/e (M + H)$^+$/ R$_t$ [min] | $^1$H NMR (CDCl$_3$) δ: |
|---|---|---|---|
| 7 | 3-(4-methylphenyl)-5-[2-(quinolin-2-yl)ethyl]thieno[2,3-d]pyridazin-4(5H)-one | 398/2.32 | 2.40 (s, 3H), 3.50 (t, 2H, J = 7.6 Hz), 4.73 (t, 2H, J = 7.6 Hz), 7.22 (d, 2H, J = 8.0 Hz), 7.32 (d, 1H, J = 7.6 Hz), 7.40 (d, 2H, J = 7.6 Hz), 7.45 (s, 1H), 7.49 (t, 1H, J = 7.2 Hz), 7.67 (t, 1H, J = 7.2 Hz), 7.77 (d, 1H, J = 7.6 Hz), 8.01-8.06 (m, 2H), 8.19 (s, 1H) |
| 8 | 3-[4-(propan-2-yl)phenyl]-5-[2-(quinolin-2-yl)ethyl]thieno[2,3-d]pyridazin-4(5H)-one | 426/2.46 | 1.29 (d, 6H, J = 6.8 Hz), 2.95 (m, 1H), 3.49 (t, 2H, J = 7.6 Hz), 4.75 (t, 2H, J = 8 Hz), 7.27~7.31 (m, 3H), 7.44~7.49 (m, 4H), 7.66 (t, 1H, J = 8.4 Hz), 7.75 (d, 1H, J = 8 Hz), 8.01~8.04 (m, 2H), 8.18 (s, 1H) |
| 9 | 3-(4-ethylphenyl)-5-[2-(quinolin-2-yl)ethyl]thieno[2,3-d]pyridazin-4(5H)-one | 412/2.34 | 1.28 (t, 3H, J = 7.6 Hz), 2.70 (q, 2H, J = 7.6 Hz), 3.49 (t, 2H, J = 7.6 Hz), 4.74 (t, 2H, J = 7.6 Hz), 7.25 (d, 2H, J = 8.0 Hz), 7.31 (d, 1H, J = 8.4 Hz), 7.44-7.50 (m, 4H), 7.65-7.69 (m, 1H), 7.77 (d, 1H, J = 8.4 Hz), 8.00-8.05 (m, 2H), 8.19 (s, 1H) |
| 10 | 4-{4-oxo-5-[2-(quinolin-2-yl)ethyl]-4,5-dihydrothieno[2,3-d]pyridazin-3-yl}benzonitrile | 409/2.11 | 3.49 (t, 2H, J = 7.6 Hz), 4.74 (t, 2H, J = 7.6 Hz), 7.33 (d, 1H, J = 8.0 Hz), 7.50-7.58 (m, 4H), 7.66-7.68 (m, 3H), 7.79 (d, 1H, J = 7.6 Hz), 7.98 (d, 1H, J = 8.0 Hz), 8.07 (d, 1H, J = 8.0 Hz), 8.25 (s, 1H) |
| 11 | 3-(4-methoxyphenyl)-5-[2-(quinolin-2-yl)ethyl]thieno[2,3-d]pyridazin-4(5H)-one | 414/2.18 | 3.50 (t, 2H, J = 7.6 Hz), 3.85 (s, 3H), 4.74 (t, 2H, J = 7.6 Hz), 6.94 (d, 2H, J = 8.4 Hz), 7.31 (d, 1H, J = 8.4 Hz), 7.42-7.51 (m, 4H), 7.65-7.69 (m, 1H), 7.77 (d, 1H, J = 8.4 Hz), 8.00-8.06 (m, 2H), 8.19 (s, 1H) |
| 12 | 3-(4-fluorophenyl)-5-[2-(quinolin-2-yl)ethyl]thieno[2,3-d]pyridazin-4(5H)-one | 402/2.21 | 3.50 (t, 2H, J = 7.6 Hz), 4.74 (t, 2H, J = 7.6 Hz), 7.06-7.11 (m, 2H), 7.32 (d, 1H, J = 8.4 Hz), 7.45-7.52 (m, 4H), 7.65-7.69 (m, 1H), 7.78 (d, 1H, J = 8.4 Hz), 8.01 (d, 1H, J = 8.4 Hz), 8.06 (d, 1H, J = 8.4 Hz), 8.21 (s, 1H) |
| 13 | 3-(4-ethoxyphenyl)-5-[2-(quinolin-2-yl)ethyl]thieno[2,3-d]pyridazin-4(5H)-one | 428/2.26 | 1.44 (t, 3H, J = 6.8 Hz), 3.49 (t, 2H, J = 7.6 Hz), 4.05~4.11 (m, 2H), 4.74 (t, 2H, J = 7.6 Hz), 6.93 (d, 2H, J = 8.4 Hz), 7.32 (d, 1H, J = 8.4 Hz), 7.42~7.51 (m, 4H), 7.67 (t, 1H, J = 7.6 Hz), 7.77 (d, 1H, J = 8 Hz), 8.00~8.06 (m, 2H), 8.19 (s, 1H) |
| 14 | 3-[4-(dimethylamino)phenyl]-5-[2-(quinolin-2-yl)ethyl]thieno[2,3-d]pyridazin-4(5H)-one | 427/2.26 | 2.99 (s, 6H), 3.50 (t, 2H, J = 7.6 Hz), 4.75 (t, 2H, J = 7.6 Hz), 6.77 (d, 2H, J = 8.8 Hz), 7.31 (d, 1H, J = 8.8 Hz), 7.38 (s, 1H), 7.43-7.51 (m, 3H), 7.65-7.69 (m, 1H), 7.77 (d, 1H, J = 8.0 Hz), 8.01-8.05 (m, 2H), 8.16 (s, 1H). |
| 15 | (4-{4-oxo-5-[2-(quinolin-2-yl)ethyl]-4,5-dihydrothieno[2,3-d]pyridazin-3-yl}phenyl)acetonitrile | 423/2.10 | 3.49 (t, 2H, J = 7.6 Hz), 3.79 (s, 3H), 4.73 (t, 2H, J = 7.6 Hz), 7.31-7.37 (m, 3H), 7.48-7.51 (m, 4H), 7.65-7.69 (m, 1H), 7.99 (d, 1H, J = 8.4 Hz), 8.05 (d, 1H, J = 8.4 Hz), 8.22 (s, 1H) |

| EX. | Name | LC-MS: m/e (M + H)+/ R_t [min] | ¹H NMR (CDCl₃) δ: |
|---|---|---|---|
| 16 | 3-(4-hydroxy-phenyl)-5-[2-(quinolin-2-yl)ethyl]thieno[2,3-d]pyridazin-4(5H)-one | 400/2.00 | 2.17 (s, 1H), 3.53 (t, 2H, J = 7.6 Hz), 4.77 (t, 2H, J = 7.6 Hz), 7.80 (d, 2H, J = 8.8 Hz), 7.33~7.42 (m, 4H), 7.51 (t, 1H, J = 7.2 Hz), 7.69 (t, 1H, J = 7.2 Hz), 7.79 (d, 1H, J = 7.6 Hz), 8.08 (d, 2H, J = 8.4 Hz), 8.22 (s, 1H) |
| 17 | 3-(2-chlorophenyl)-5-[2-(quinolin-2-yl)ethyl]thieno[2,3-d]pyridazin-4(5H)-one | 418/2.22 | 3.47 (t, 2H, J = 7.6 Hz), 4.71 (t, 2H, J = 7.6 Hz), 7.28-7.36 (m, 4H), 7.46-7.50 (m, 3H), 7.64-7.68 (m, 1H), 7.76 (d, 1H, J = 8.0 Hz), 8.00-8.04 (m, 2H), 8.21 (s, 1H). |
| 18 | 3-(2-methylphenyl)-5-[2-(quinolin-2-yl)ethyl]thieno[2,3-d]pyridazin-4(5H)-one | 398/2.29 | 2.09 (s, 3H), 3.48 (t, 2H, J = 7.6 Hz), 4.69 (t, 2H, J = 7.6 Hz), 7.17-7.33 (m, 5H), 7.37 (s, 1H), 7.49 (t, 1H, J = 7.2 Hz), 7.67 (t, 1H, J = 7.2 Hz), 7.76 (d, 1H, J = 8.0 Hz), 7.99-8.05 (m, 2H), 8.22 (s, 1H) |
| 19 | 3-(2-ethylphenyl)-5-[2-(quinolin-2-yl)ethyl]thieno[2,3-d]pyridazin-4(5H)-one | 412/2.36 | 1.02 (t, 3H, J = 7.6 Hz), 2.36~2.49 (m, 2H), 3.47 (t, 2H, J = 7.6 Hz), 4.65~4.71 (m, 2H), 7.15 (d, 1H, J = 7.2 Hz), 7.02~7.38 (m, 6H), 7.49 (m, 1H, J = 7.6 Hz), 7.77 (d, 1H, J = 8 Hz), 7.99~8.04 (m, 2H), 8.22 (s, 1H) |
| 20 | 3-(2-fluorophenyl)-5-[2-(quinolin-2-yl)ethyl]thieno[2,3-d]pyridazin-4(5H)-one | 402/2.16 | 3.49 (t, 2H, J = 7.6 Hz), 4.73 (t, 2H, J = 7.6 Hz), 7.14-7.21 (m, 2H), 7.26-7.31 (m, 1H), 7.38 (t, 2H, J = 7.6 Hz), 7.48 (t, 1H, J = 7.6 Hz), 7.54 (s, 1H), 7.67 (t, 1H, J = 7.6 Hz), 7.76 (d, 1H, J = 8 Hz), 8.02 (t, 2H, J = 7.6 Hz), 8.20 (s, 1H) |
| 21 | 3-(2-methoxyphenyl)-5-[2-(quinolin-2-yl)ethyl]thieno[2,3-d]pyridazin-4(5H)-one | 414/2.22 | 3.47 (t, 2H, J = 7.2 Hz), 3.74(s, 3H), 4.69 (t, 2H, J = 7.6 Hz), 6.97~7.02 (m, 2H), 7.28 (t, 2H, J = 8.4 Hz), 7.38 (t, 1H, J = 8 Hz), 7.48 (t, 2H, J = 7.6 Hz), 7.67 (t, 1H, J = 7.6 Hz), 7.76 (d, 1H, J = 8 Hz), 8.03 (d, 2H, J = 8.4 Hz), 8.17 (s, 1H) |
| 22 | 3-(2-ethoxyphenyl)-5-[2-(quinolin-2-yl)ethyl]thieno[2,3-d]pyridazin-4(5H)-one | 428/2.31 | 1.18 (t, 3H, J = 6.8 Hz), 3.47 (t, 2H, J = 7.6 Hz), 4.01~4.06 (m, 2H), 4.69 (t, 2H, J = 7.6 Hz), 6.96~7.01 (m, 2H), 7.27~7.36 (m, 3H), 7.48 (t, 2H, J = 8.8 Hz), 7.67 (t, 1H, J = 7.2 Hz), 7.76 (d, 1H, J = 8.4 Hz), 8.03 (d, 2H, J = 8 Hz), 818 (s, 1H) |
| 23 | 3-(2-hydroxyphenyl)-5-[2-(quinolin-2-yl)ethyl]thieno[2,3-d]pyridazin-4(5H)-one | 400/2.04 | 3.52 (t, 2H, J = 7.6 Hz), 4.83 (t, 2H, J = 7.6 Hz), 7.05 (t, 1H, J = 8 Hz), 7.17 (d, 1H, J = 7.6 Hz), 7.27~7.38 (m, 3H), 7.48~7.55 (m, 2H), 7.68 (t, 1H, J = 7.6 Hz), 7.78 (d, 1H, J = 7.2 Hz), 8.01~8.08 (m, 2H), 8.32 (s, 1H), 8.71 (s, 1H) |
| 24 | 5-[2-(quinolin-2-yl)ethyl]-3-[2-(trifluoromethyl)phenyl]thieno[2,3-d]pyridazin-4(5H)-one | 452/2.30 | 3.47 (t, 2H, J = 7.6 Hz), 4.67 (t, 2H, J = 7.6 Hz), 7.25-7.29 (m, 2H), 7.47-7.57 (m, 4H), 7.66-7.58 (m, 3H), 8.02 - 8.04 (m, 2H), 8.22 (s, 1H) |
| 25 | 3-[3-(methoxymethyl)phenyl]-5-[2-(quinolin-2-yl)ethyl]thieno[2,3-d]pyridazin-4(5H)-one | 428/2.16 | 3.42 (s, 1H), 3.49 (t, 2H, J = 7.6 Hz), 4.52 (s, 2H), 3.79 (s, 3H), 4.74(t, 2H, J = 7.6 Hz), 7.31 (d, 1H, J = 8.4 Hz), 7.35-7.51 (m, 6H), 7.65-7.69 (m, 1H), 7.77 (d, 1H, J = 8.0 Hz), 7.99-8.05 (m, 2H), 8.20 (s, 1H) |
| 26 | 3-(3-methoxyphenyl)-5-[2-(quinolin-2-yl)ethyl]thieno[2,3-d]pyridazin-4(5H)-one | 414/2.19 | 3.50 (t, 2H, J = 7.6 Hz), 3.83 (s, 3H), 4.74 (t, 2H, J = 7.6 Hz), 6.92-6.95 (m, 1H), 7.07-7.12 (m, 2H), 7.31-7.35 (m, 2H), 7.47-7.51 (m, 2H), 7.66-7.70 (m, 1H), 7.77 (d, 1H, J = 8.4 Hz), 8.01-8.06 (m, 2H), 8.20 (s, 1H) |
| 27 | 3-(3-ethoxyphenyl)-5-[2-(quinolin-2-yl)ethyl]thieno[2,3-d]pyridazin-4(5H)-one | 428/2.27 | 1.43 (t, 3H, J = 6.8 Hz), 3.50 (t, 2H, J = 7.2 Hz), 4.06 (q, 2H, J = 6.8 Hz), 4.74 (t, 2H, J = 7.2 Hz), 6.91-6.94 (m, 2H), 7.07-7.09 (m, 2H), 7.29-7.33 (m, 2H), 7.47-7.51 (m, 2H), 7.65-7.78 (m, 2H), 8.01-8.06 (m, 2H), 8.20 (s, 1H) |
| 28 | 3-[3-(dimethylamino)phenyl]-5-[2-(quinolin-2-yl)ethyl]thieno[2,3-d] | 427/2.26 | 2.97 (s, 6H), 3.49 (t, 2H, J = 7.2 Hz), 4.73 (t, 2H, J = 7.6 Hz), 6.77 (dd, 1H, J = 2.4 Hz, J = 8.4 Hz), 6.85-6.88 (m, 2H), 7.26-7.32 (m, 2H), 7.47-7.51 (m, 2H), 7.65-7.77 (m, 2H), 8.03 (t, 2H, J = 7.6 Hz), 8.19 (s, 1H) |

| EX. | Name | LC-MS: m/e (M + H)⁺/ R_t [min] | ¹H NMR (CDCl₃) δ: |
|---|---|---|---|
| | d]pyridazin-4(5H)-one | | |
| 29 | 3-[4-Oxo-5-(2-quinolin-2-yl-ethyl)-4,5-dihydrothieno[2,3-d]pyridazin-3-yl}-benzonitrile | 409/2.11 | 3.49 (t, 2H, J = 7.6 Hz), 4.74 (t, 2H, J = 7.6 Hz), 7.35 (d, 1H, J = 8.4 Hz), 7.47~7.52 (m, 3H), 7.65~7.73 (m, 4H), 7.79 (d, 1H, J = 8 Hz), 7.97 (d, 1H, J = 8.4 Hz), 8.08 (d, 1H, J = 8.4 Hz), 8.24 (s, 1H) |
| 30 | 3-(3-fluorophenyl)-5-[2-(quinolin-2-yl)ethyl]thieno[2,3-d]pyridazin-4(5H)-one | 402/2.21 | 3.49 (t, 2H, J = 7.6 Hz), 4.47 (t, 2H, J = 7.6 Hz), 7.06-7.11 (m, 1H), 7.20-7.24 (m, 1H), 7.27-7.39 (m, 3H), 7.47-7.51 (m, 2H), 7.65-7.69 (m, 1H), 7.77 (d, 1H, J = 8.0 Hz), 8.00 (d, 1H, J = 8.4 Hz), 8.06 (d, 1H, J = 8.4 Hz), 8.21 (s, 1H) |
| 31 | 3-(3-hydroxyphenyl)-5-[2-(quinolin-2-yl)ethyl]thieno[2,3-d]pyridazin-4(5H)-one | 400/2.00 | 3.51 (t, 2H, J = 7.6 Hz), 3.76 (s, 1H), 4.72 (t, 2H, J = 7.6 Hz), 6.85 (d, 1H, J = 1.6 Hz, J = 8.0 Hz), 6.99-7.02 (m, 2H), 7.23 (t, 1H, J = 8.0 Hz), 7.34 (d, 1H, J = 8.8 Hz), 7.48-7.53 (m, 2H), 7.66-7.70 (m, 1H), 7.78 (d, 1H, J = 8.0 Hz), 8.03-8.08 (m, 2H), 8.21 (s, 1H) |
| 32 | N,N-dimethyl-3-{4-oxo-5-[2-(quinolin-2-yl)ethyl]-4,5-dihydrothieno[2,3-d]pyridazin-3-yl}benzamide | 455/1.97 | 3.09 (d, 6H, J = 17.6 Hz), 3.50 (t, 2H, J = 7.6 Hz), 4.74 (t, 2H, J = 7.6 Hz), 7.31 (d, 1H, J = 8.4 Hz), 7.43~7.51 (m, 6H), 7.65~7.69 (m, 1H), 7.78 (d, 1H, J = 8.4 Hz), 8.00 (d, 1H, J = 8.4 Hz), 8.06 (d, 1H, J = 8.4 Hz), 8.21 (s, 1H) |
| 33 | 3-(3-methylphenyl)-5-[2-(quinolin-2-yl)ethyl]thieno[2,3-d]pyridazin-4(5H)-one | 398/2.08 | 2.40 (s, 3H), 3.49 (t, 2H, J = 7.6 Hz), 4.74 (t, 2H, J = 7.6 Hz), 7.19-7.21 (m, 1H), 7.30-7.33 (m, 4H), 7.45 (s, 1H), 7.49 (t, 1H, J = 7.6 Hz), 7.65-7.69 (m, 1H), 7.77 (d, 1H, J = 7.6 Hz), 8.01 (d, 1H, J = 8.4 Hz), 8.04 (d, 1H, J = 8.4 Hz), 8.19 (s, 1H) |
| 34 | 5-[2-(quinolin-2-yl)ethyl]-3-(thiophen-2-yl)thieno[2,3-d]pyridazin-4(5H)-one | 390/1.53 | 3.92 (t, 2H, J = 6.4 Hz), 4.81 (t, 2H, J = 6.4 Hz), 7.02-7.04 (m, 1H), 7.32 (d, 1H, J = 3.6 Hz), 7.38 (d, 1H, J = 3.6 Hz), 7.62 (s, 1H), 7.71 (d, 1H, J = 8.4 Hz), 7.82 (t, 1H, J = 7.6 Hz), 8.01-8.05 (m, 2H), 8.17 (s, 1H), 8.52 (d, 1H, J = 8.4 Hz), 8.64 (d, 1H, J = 8.4 Hz) |
| 35 | 3-(1-methyl-1H-indol-5-yl)-5-(2-quinolin-2-yl-ethyl)-5H-thieno[2,3-d]pyridazin-4-one | 437/2.23 | 3.49 (t, 2H, J = 7.8 Hz), 3.82 (s, 3H), 4.73 (t, 2H, J = 8 Hz), 6.51 (d, 1H, J = 2.8 Hz), 7.07 (d, 1H, J = 2.8 Hz), 7.26-7.48 (m, 5H), 7.65~7.77 (m, 3H), 8.01~8.04 (m, 2H), 8.20 (s, 1H) |
| 36 | 3-(1H-indol-6-yl)-5-[2-(quinolin-2-yl)ethyl]thieno[2,3-d]pyridazin-4(5H)-one | 423/2.14 | 3.49 (t, 2H, J = 7.6 Hz), 4.74 (t, 2H, J = 7.6 Hz), 6.57 (s, 1H), 7.25-7.32 (m, 2H), 7.48-7.52 (m, 2H), 7.59 (s, 1H), 7.65-7.70 (m, 2H), 7.78 (d, 1H, J = 8.0 Hz), 8.04 (t, 2H, J = 8.4 Hz), 8.22 (s, 1H), 8.28 (s, 1H) |
| 37 | 3-(pyrimidin-5-yl)-5-[2-(quinolin-2-yl)ethyl]thieno[2,3-d]pyridazin-4(5H)-one | 386/1.73, | 3.50 (t, 2H, J = 7.6 Hz), 4.76 (t, 2H, J = 7.6 Hz), 7.34 (d, 1H, J = 8.4 Hz), 7.49 (t, 1H, J = 8.0 Hz), 7.61 (s, 1H), 7.66 (t, 1H, J = 8.0 Hz), 7.78 (d, 2H, J = 8.4 Hz), 7.96 (d, 1H, J = 8.4 Hz), 8.07 (d, 1H, J = 8.4 Hz), 8.26 (s, 1H), 8.76 (s, 2H), 9.22 (s, 1H) |
| 38 | 3-(2-methoxypyridin-3-yl)-5-[2-(quinolin-2-yl)ethyl]thieno[2,3-d]pyridazin-4(5H)-one | 415/2.06 | 3.48 (t, 2H, J = 7.6 Hz), 3.90 (s, 3H), 4.71 (t, 2H, J = 7.6 Hz), 6.93-6.96 (m, 1H), 7.30 (d, 1H, J = 8.4 Hz), 7.49 (t, 1H, J = 7.6 Hz), 7.56-7.59 (m, 2H), 7.67 (t, 1H, J = 7.6 Hz), 7.77 (d, 1H, J = 8.0 Hz), 8.00-8.05 (m, 2H), 8.19 (s, 1H), 8.21 (dd, 1H, J = 1.2, J = 5.2 Hz) |
| 39 | 3-(pyridin-3-yl)-5-[2-(quinolin-2-yl)ethyl]thieno[2,3-d]pyridazin-4(5H)-one | 385/1.91 | 3.49 (t, 2H, J = 7.6 Hz), 4.75 (t, 2H, J = 7.6 Hz), 7.32-7.36 (m, 2H), 7.49 (t, 1H, J = 8.0 Hz), 7.55 (s, 1H), 7.64-7.69 (m, 1H), 7.77 (d, 1H, J = 8.0 Hz), 7.88 (d, 1H, J = 8.0 Hz), 8.06 (d, 1H, J = 8.8 Hz), 8.23 (s, 1H), 8.62 (br, 1H), 8.73 (br, 1H). |
| 40 | 3-(4-methoxypyridin-3-yl)-5-[2-(quinolin-2-yl)ethyl]thieno[2,3-d]pyridazin-4(5H)-one | 415/1.90 | 3.47 (t, 2H, J = 7.6 Hz), 3.79 (s, 3H), 4.70 (t, 2H, J = 5.6 Hz), 6.91 (d, 1H, J = 5.6 Hz), 7.30 (d, 1H, J = 8 Hz), 7.47~7.51 (m, 2H), 7.68 (t, 1H, J = 7.2 Hz), 7.77 (d, 1H, J = 7.6 Hz), 8.00~8.06 (m, 2H), 8.20 (s, 1H), 8.37 (s, 1H), 8.54 (d, 1H, J = 5.6 Hz) |
| 41 | 3-(furan-3-yl)-5-[2-(quinolin-2- | 374/2.14 | 3.53 (t, 2H, J = 7.6 Hz), 4.77 (t, 2H, J = 7.6 Hz), 6.76 (d, 1H, J = 1.2 Hz), 7.35 (d, 1H, |

| EX. | Name | LC-MS: m/e (M + H)+/ R$_t$ [min] | $^1$H NMR (CDCl$_3$) δ: |
|---|---|---|---|
|  | yl)ethyl]thieno[2,3-d]pyridazin-4(5H)-one |  | J = 8.8 Hz), 7.46~7.52 (m, 3H), 7.68 (t, 1H, J = 7.6 Hz), 7.78 (d, 1H, J = 8 Hz), 8.02~8.08 (m, 2H), 8.15 (s, 1H), 8.23 (s, 1H) |
| 42 | 3-(quinolin-3-yl)-5-[2-(quinolin-2-yl)ethyl]thieno[2,3-d]pyridazin-4(5H)-one | 435/1.93 | 3.50 (t, 2H, J = 7.6 Hz), 4.76 (t, 2H, J = 7.6 Hz), 7.32 (d, 1H, J = 8.4 Hz), 7.49 (t, 1H, J = 7.6 Hz), 7.57 (t, 1H, J = 7.6 Hz), 7.65-7.69 (m, 4H), 7.85 (d, 1H, J = 8.4 Hz), 7.99 (d, 1H, J = 8.4 Hz), 8.05 (d, 1H, J = 8.4 Hz), 8.14 (d, 1H, J = 8.4 Hz), 8.31 (s, 1H), 9.06 (s, 1H) |
| 43 | 3-(isoquinolin-4-yl)-5-[2-(quinolin-2-yl)ethyl]-thieno[2,3-d]pyridazin-4(5H)-one | 435/1.89 | 3.42 (t, 2H, J = 7.6 Hz), 4.62-4.68 (m, 2H), 7.25 (d, 1H, J = 8.0 Hz), 7.47-7.68 (m, 7H), 7.76 (d, 1H, J = 8.4 Hz), 7.95-8.04 (m, 3H), 8.29 (s, 1H), 8.45 (s, 1H), 8.30 (s, 1H) |
| 44 | 3-(isoquinolin-5-yl)-5-[2-(quinolin-2-yl)ethyl]thieno[2,3-d]pyridazin-4(5H)-one | 435/1.87 | 3.43 (t, 2H, J = 7.6 Hz), 4.65 (t, 2H, J = 7.6 Hz), 7.25-7.30 (m, 2H), 7.47-7.51 (m, 1H), 7.56 (s, 1H), 7.63-7.68 (m, 3H), 7.76 (d, 1H, J = 8.0 Hz), 7.95-8.05 (m, 2H), 8.30 (s, 1H), 8.36 (d, 1H, J = 7.0 Hz), 8.30 (s, 1H) |
| 45 | 3-(1H-indol-4-yl)-5-(2-quinolin-2-yl-ethyl)-5H-thieno[2,3-d]pyridazin-4-one | 423/2.10 | 3.47 (t, 2H, J = 7.6 Hz), 4.71 (t, 2H, J = 7.6 Hz), 6.26 (s, 1H), 7.05 (s, 1H, J = 2.4 Hz), 7.15~7.33 (m, 4H), 7.46 (t, 1H, J = 7.2 Hz), 7.61~7.67 (m, 2H), 7.74 (d, 1H, J = 8.4 Hz), 8.00 (d, 2H, J = 8.4 Hz), 8.22 (s, 1H), 8.49 (s, 1H) |
| 46 | 3-(2,3-dihydrobenzofuran-5-yl)-5-(2-quinolin-2-yl-ethyl)-5H-thieno[2,3-d]pyridazin-4-one | 426/2.19 | 3.26 (t, 2H, J = 8.4 Hz), 3.50 (t, 2H, J = 7.6 Hz), 4.61 (t, 2H, J = 8.8 Hz), 4.74 (t, 2H, J = 7.6 Hz), 6.81 (d, 1H, J = 8.4 Hz), 7.23~7.40 (m, 4H), 7.49 (t, 1H, J = 7.6 Hz), 7.67 (t, 1H, J = 7.6 Hz), 7.77 (d, 1H, J = 8 Hz), 8.00~8.06 (m, 2H), 8.19 (s, 1H) |
| 47 | 3-(quinolin-5-yl)-5-[2-(quinolin-2-yl)ethyl]thieno[2,3-d]pyridazin-4(5H)-one | 435/1.88 | 3.43 (t, 2H, J = 7.6 Hz), 3.98 (s, 3H), 4.74 (t, 2H, J = 7.6 Hz), 7.21-7.27 (m, 2H), 7.47-7.51 (m, 2H), 7.55 (s, 1H), 7.64-7.77 (m, 3H), 7.83 (d, 1H, J = 8.4 Hz), 7.97 (d, 1H, J = 8.4 Hz), 8.01 (d, 1H, J = 8.4 Hz), 8.18 (d, 1H, J = 8.8 Hz), 8.29 (s, 1H), 8.90 (d, 1H, J = 2.8 Hz) |
| 48 | 3-(3,5-dimethyl-1,2-oxazol-4-yl)-5-[2-(quinolin-2-yl)ethyl]thieno[2,3-d]pyridazin-4(5H)-one | 403/2.01 | 2.07 (s, 3H), 2.25 (s, 3H), 3.49 (t, 2H, J = 7.6 Hz), 4.71~4.75 (m, 2H), 7.35 (t, 2H, J = 8.4 Hz), 7.49 (t, 1H, J = 8 Hz), 7.66 (t, 1H, J = 8.4 Hz), 7.77 (d, 1H, J = 8.4 Hz), 7.98 (d, 1H, J = 8 Hz), 8.06 (d, 1H, J = 8.4 Hz), 8.22 (s, 1H) |
| 49 | 3-(6-methoxypyridin-3-yl)-5-[2-(quinolin-2-yl)ethyl]thieno[2,3-d]pyridazin-4(5H)-one | 415/2.09 | 3.49 (t, 2H, J = 7.6 Hz), 4.65 (t, 2H, J = 7.6 Hz), 6.79 (d, 1H, J = 8.4 Hz), 7.33 (d, 1H, J = 8.8 Hz), 7.47-7.52 (m, 2H), 7.65-7.69 (m, 2H), 7.75-7.79 (m, 2H), 8.00 (d, 1H, J = 8.4 Hz), 8.06 (d, 1H, J = 8.4 Hz), 8.22 (s, 1H), 8.28 (d, 1H, J = 2.0 Hz) |
| 50 | 3-(2,3-dihydro-1,4-benzodioxin-6-yl)-5-[2-(quinolin-2-yl)ethyl]thieno[2,3-d]pyridazin-4(5H)-one | 442/2.17 | 3.50 (t, 2H, J = 7.6 Hz), 4.30 (s, 4H), 4.74 (t, 2H, J = 7.6 Hz), 6.90 (d, 1H, J = 8.8 Hz), 7.00~7.02 (m, 1H), 7.08 (d, 1H, J = 2 Hz), 7.32 (d, 1H, J = 8 Hz), 7.42 (s, 1H), 7.49 (t, 1H, J = 8 Hz), 7.67 (t, 1H, J = 6.8 Hz), 7.77 (d, 1H, J = 8 Hz), 8.01~8.06 (m, 2H), 8.18 (s, 1H) |
| 51 | 3-(2-methylpyridin-4-yl)-5-[2-(quinolin-2-yl)ethyl]thieno[2,3-d]pyridazin-4(5H)-one | 399/1.97 | 2.61 (s, 3H), 3.50 (t, 2H, J = 7.6 Hz), 4.75 (t, 2H, J = 7.6 Hz), 7.22-7.28 (m, 2H), 7.33 (d, 1H, J = 8.0 Hz), 7.47-7.51 (m, 1H), 7.56 (s, 1H), 7.65-7.69 (m, 1H), 7.78 (d, 1H, J = 7.6 Hz), 7.98 (d, 1H, J = 8.4 Hz), 8.06 (d, 1H, J = 8.4 Hz), 8.23 (s, 1H), 8.52 (d, 1H, J = 5.2 Hz). |
| 52 | 3-(5-methoxypyridin-3-yl)-5-[2-(quinolin-2-yl)ethyl]thieno[2,3-d]pyridazin-4(5H)-one | 415/1.96 | 3.50 (t, 2H, J = 7.6 Hz), 3.87 (s, 3H), 4.75 (t, 2H, J = 7.6 Hz), 7.45-7.51 (m, 2H), 7.57 (s, 1H), 7.67 (t, 1H, J = 7.6 Hz), 7.77 (d, 1H, J = 8.0 Hz), 7.99 (d, 1H, J = 8.4 Hz), 8.05 (d, 1H, J = 8.4 Hz), 8.23 (s, 1H), 8.33 (m, 2H) |
| 53 | 3-[6-(morpholin-4-yl)pyridin-3-yl]-5-[2-(quinolin-2-yl)ethyl]thieno[2,3-d]pyridazin-4(5H)- | 470/2.05 | 3.50 (t, 2H, J = 7.6 Hz), 3.58 (t, 4H, J = 4.8 Hz), 3.84 (t, 4H, J = 4.8 Hz), 4.75 (t, 2H, J = 7.6 Hz), 6.69 (d, 1H, J = 8.8 Hz), 7.32 (d, 1H, J = 8.4 Hz), 7.44 (s, 1H), 7.49 (t, 1H, J = 7.2 Hz), 7.68 (m, 1H, J = 8.4 Hz), |

-continued

| EX. | Name | LC-MS: m/e (M + H)+/ R$_t$ [min] | $^1$H NMR (CDCl$_3$) δ: |
|---|---|---|---|
|  | one |  | 7.76~7.79 (m, 2H), 8.00~8.07 (m, 2H), 8.20 (s, 1H), 8.33 (d, 1H, J = 2 Hz) |
| 54 | 3-(1,3-benzodioxol-5-yl)-5-[2-(quinolin-2-yl)ethyl]thieno[2,3-d]pyridazin-4(5H)-one | 428/2.16 | 3.50 (t, 2H, J = 7.6 Hz), 4.74(t, 2H, J = 7.6 Hz), 6.00 (s, 2H), 6.84 (d, 1H, J = 8 Hz), 6.95~7.01 (m, 2H), 7.33 (d, 1H, J = 8.4 Hz), 7.42 (s, 1H), 7.49 (t, 1H, J = 7.6 Hz), 7.67 (t, 1H, J = 7.2 Hz), 7.77 (d, 1H, J = 8.4 Hz), 8.00~8.06 (m, 2H), 8.19 (s, 1H) |
| 55 | 3-(quinolin-6-yl)-5-[2-(quinolin-2-yl)ethyl]thieno[2,3-d]pyridazin-4(5H)-one | 435/2.03 | 3.50 (t, 2H, J = 7.2 Hz), 3.95 (d, 2H, J = 7.6 Hz), 4.75 (t, 2H, J = 7.6 Hz), 7.21 (d, 1H, J = 8.4 Hz), 7.40-7.50 (m, 2H), 7.60 (s, 1H), 7.65-7.69 (m, 1H), 7.77-7.84 (m, 2H), 7.94 (d, 1H, J = 2.4 Hz), 7.99 (d, 1H, J = 8.4 Hz), 8.05 (d, 1H, J = 8.4 Hz), 8.12 (d, 1H, J = 8.4 Hz), 8.17 (d, 1H, J = 8.0 Hz), 8.25 (s, 1H), 8.93-8.94 (m, 1H) |
| 56 | 3-(1-methyl-1H-pyrazol-4-yl)-5-[2-(quinolin-2-yl)ethyl]thieno[2,3-d]pyridazin-4(5H)-one | 388/1.93 | 3.52 (t, 2H, J = 7.6 Hz), 3.95 (s, 3H), 4.77 (t, 2H, J = 7.6 Hz), 7.34 (d, 1H, J = 8.4 Hz), 7.48-7.55 (m, 2H), 7.66-7.71 (m, 1H), 7.77-7.80 (m, 2H), 8.02-8.08 (m, 2H), 8.16 (s, 1H), 8.23 (s, 1H) |
| 57 | 3-[1-(2-methylpropyl)-1H-pyrazol-4-yl]-5-[2-(quinolin-2-yl)ethyl]thieno[2,3-d]pyridazin-4(5H)-one | 430/2.17 | 0.95 (d, 6H, J = 6.8 Hz), 2.26 (m, 1H), 3.54 (t, 2H, J = 7.6 Hz), 3.95 (d, 2H, J = 7.2 Hz), 4.78 (t, 2H, J = 7.6 Hz), 7.34 (d, 1H, J = 8.4 Hz), 7.50-7.54 (m, 2H), 7.69 (t, 1H, J = 7.6 Hz), 7.78 (d, 1H, J = 8.4 Hz), 7.82 (s, 1H), 8.02-8.08 (m, 2H), 8.14 (s, 1H), 8.28 (s, 1H) |
| 58 | tert-butyl 2-{4-oxo-5-[2-(quinolin-2-yl)ethyl]-4,5-dihydrothieno[2,3-d]pyridazin-3-yl}-1H-pyrrole-1-carboxylate | 473/2.11 | 1.35 (s, 9H), 3.46 (t, 2H, J = 7.6 Hz), 4.68 (t, 2H, J = 7.6 Hz), 6.23~6.28 (m, 2H), 7.29 (d, 1H, J = 8.4 Hz), 7.45~7.51 (m, 3H), 7.69 (t, 1H, J = 8 Hz), 7.77 (d, 1H, J = 7.6 Hz), 8.05 (d, 2H, J = 8 Hz), 8.15 (s, 1H) |
| 59 | 3-(2-methoxypyrimidin-5-yl)-5-[2-(quinolin-2-yl)ethyl]thieno[2,3-d]pyridazin-4(5H)-one | 416/1.95 | 3.50 (t, 2H, J = 7.6 Hz), 4.07 (s, 3H), 4.75 (t, 2H, J = 7.6 Hz), 7.35 (d, 1H, J = 8.4 Hz), 7.54 (s, 1H), 7.67 (t, 2H, J = 9.2 Hz), 7.79 (d, 1H, J = 7.6 Hz), 7.98 (d, 1H, J = 8.4 Hz), 8.07 (d, 1H, J = 8.4 Hz), 8.24 (s, 1H), 8.67 (s, 2H) |
| 60 | 5-[2-(quinolin-2-yl)ethyl]-3-(2,3,4-trifluorophenyl)thieno[2,3-d]pyridazin-4(5H)-one | 438/1.60 | 3.88 (t, 2H, J = 6.0 Hz), 4.76 (t, 2H, J = 6.0 Hz), 6.88-7.02 (m, 2H), 7.55 (s, 1H), 7.68 (d, 1H, J = 7.6 Hz), 7.82 (t, 1H, J = 7.6 Hz), 7.98-8.06 (m, 2H), 8.24 (s, 1H), 8.48 (d, 1H, J = 8.4 Hz), 8.63 (d, 1H, J = 8.4 Hz) |
| 61 | 3-(4-fluoro-3-methylphenyl)-5-[2-(quinolin-2-yl)ethyl]thieno[2,3-d]pyridazin-4(5H)-one | 416/2.28 | 2.24 (d, 3H, J = 1.6 Hz), 3.42 (t, 2H, J = 7.6 Hz), 4.66 (t, 2H, J = 7.6 Hz), 6.95 (t, 1H, J = 8.8 Hz), 7.19~7.24 (m, 3H), 7.35 (s, 1H), 7.44 (t, 1H, J = 6.8 Hz), 7.58~7.62 (m, 1H), 7.70 (d, 1H, J = 8.4 Hz), 7.93~7.99 (m, 2H), 8.13 (s, 1H) |
| 62 | 3-(4-fluoro-2-methylphenyl)-5-[2-(quinolin-2-yl)ethyl]thieno[2,3-d]pyridazin-4(5H)-one | 416/1.61 | 3.87 (t, 2H, J = 6.0 Hz), 4.73 (t, 2H, J = 6.0 Hz), 6.78-7.03 (m, 3H), 7.38 (s, 1H), 7.68 (d, 1H, J = 8.4 Hz), 7.82 (t, 1H, J = 7.6 Hz), 7.98-8.04 (m, 2H), 8.25 (s, 1H), 8.48 (d, 1H, J = 8.4 Hz), 8.60 (d, 1H, J = 8.4 Hz) |
| 63 | 3-(3-chloro-4-fluorophenyl)-5-[2-(quinolin-2-yl)ethyl]thieno[2,3-d]pyridazin-4(5H)-one | 436/2.09 | 3.50 (t, 2H, J = 7.6 Hz), 4.74 (t, 2H, J = 7.6 Hz), 7.15 (t, 1H, J = 8.8 Hz), 7.33-7.38 (m, 2H), 7.47-7.53 (m, 3H), 7.68 (t, 2H, J = 7.6 Hz), 7.79 (d, 1H, J = 7.6 Hz), 7.99-8.08 (m, 2H), 8.22 (s, 1H) |
| 64 | 3-(2-chloro-4-fluorophenyl)-5-[2-(quinolin-2-yl)ethyl]thieno[2,3-d]pyridazin-4(5H)-one | 436/2.24 | 3.47 (t, 2H, J = 7.6 Hz), 4.71 (t, 2H, J = 7.6 Hz), 6.99-7.04 (m, 1H), 7.31-7.44 (m, 2H), 7.47-7.51 (m, 2H), 7.64-7.69 (m, 1H), 7.76 (d, 1H, J = 8.0 Hz), 7.98 (d, 1H, J = 8.8 Hz), 8.03 (d, 1H, J = 8.8 Hz), 8.22 (s, 1H) |
| 65 | 3-(3,4-dimethylphenyl)-5- | 412/2.13, | 2.30 (s, 6H), 3.49 (t, 2H, J = 7.6 Hz), 4.73 (t, 2H, J = 7.6 Hz), 7.18 (d, 1H, J = 7.6 Hz), 7.24- |

| EX. | Name | LC-MS: m/e (M + H)+/ R$_t$ [min] | $^1$H NMR (CDCl$_3$) δ: |
|---|---|---|---|
| | [2-(quinolin-2-yl)ethyl]thieno[2,3-d]pyridazin-4(5H)-one | | 7.27 (m, 2H), 7.31 (d, 1H, J = 8.4 Hz), 7.43 (s, 1H), 7.46-7.50 (m, 1H), 7.65-7.69 (m, 1H), 7.77 (d, 1H, J = 8.4 Hz), 8.03 (t, 2H, J = 8.8 Hz), 8.18 (s, 1H). |
| 66 | 3-(2,4-dimethylphenyl)-5-[2-(quinolin-2-yl)ethyl]thieno[2,3-d]pyridazin-4(5H)-one | 412/2.12 | 2.05 (s, 3H), 2.36 (s, 3H), 3.47 (t, 2H, J = 7.6 Hz), 4.69 (t, 2H, J = 7.6 Hz), 7.02~7.08 (m, 4H), 7.29 (d, 1H, J = 8.8 Hz), 7.35 (s, 1H), 7.48 (t, 1H, J = 7.2 Hz), 7.66 (t, 1H, J = 7.2 Hz), 7.76 (d, 1H, J = 8 Hz), 8.01 (d, 1H, J = 8.8 Hz), 8.21 (s, 1H) |
| 67 | 3-(2,4-difluorophenyl)-5-[2-(quinolin-2-yl)ethyl]thieno[2,3-d]pyridazin-4(5H)-one | 420/2.19 | 3.48 (t, 2H, J = 7.6 Hz), 4.73 (t, 2H, J = 7.6 Hz), 6.89-6.94 (m, 2H), 7.29-7.36 (m, 2H), 7.47-7.53 (m, 2H), 7.67-7.69 (m, 1H) 7.76 (d, 1H, J = 8.0 Hz), 8.00 (d, 1H, J = 8.4 Hz), 8.04 (d, 1H, J = 8.4 Hz), 8.21 (s, 1H) |
| 68 | 3-(2,4-dimethoxyphenyl)-5-[2-(quinolin-2-yl)ethyl]thieno[2,3-d]pyridazin-4(5H)-one | 444/2.17 | 3.47 (t, 2H, J = 7.6 Hz), 3.72 (s, 3H), 3.84 (s, 3H), 4.69 (t, 2H, J = 7.6 Hz), 6.52-6.55 (m, 2H), 7.19 (s, 1H, J = 8.0 Hz), 7.30 (d, 1H, J = 8.0 Hz), 7.44 (s, 1H) 7.46-7.50 (m, 1H), 7.65-7.77 (m, 2H), 8.03 (d, 2H, J = 8.4 Hz), 8.16 (s, 1H) |
| 69 | 3-(2,5-dimethoxyphenyl)-5-[2-(quinolin-2-yl)ethyl]thieno[2,3-d]pyridazin-4(5H)-one | 444/2.16 | 3.46~3.50 (m, 2H), 3.69 (s, 3H), 3.79 (s, 3H), 4.69 (t, 2H, J = 7.6 Hz), 6.87 (d, 1H, J = 2 Hz), 6.91 (s, 2H), 7.30 (d, 1H, J = 8.4 Hz), 7.49 (t, 2H, J = 6.8 Hz), 7.68 (t, 1H, J = 8.4 Hz), 7.76 (d, 1H, J = 8.4 Hz), 8.02~8.05 (m, 2H), 8.17 (s, 1H) |
| 70 | 3-(2,3-difluorophenyl)-5-[2-(quinolin-2-yl)ethyl]thieno[2,3-d]pyridazin-4(5H)-one | 420/2.19 | 3.50 (t, 2H, J = 7.6 Hz), 4.73 (t, 2H, J = 7.6 Hz), 7.10-7.13 (m, 2H), 7.18-7.23 (m, 1H), 7.31 (d, 1H, J = 8.4 Hz), 7.49 (t, 1H, J = 7.6 Hz), 7.57 (s, 1H), 7.68 (t, 1H, J = 7.6 Hz), 7.77 (d, 1H, J = 7.6 Hz), 8.01-8.06 (m, 2H), 8.22 (s, 1H) |
| 71 | 3-(3,4-dimethoxyphenyl)-5-[2-(quinolin-2-yl)ethyl]thieno[2,3-d]pyridazin-4(5H)-one | 444/1.95, | 3.50 (t, 2H, J = 7.6 Hz), 3.88 (s, 3H), 3.92 (s, 3H), 4.75 (t, 2H, J = 7.6 Hz), 6.92 (d, 1H, J = 8.4 Hz), 7.09~7.11 (m, 2H), 7.32 (d, 1H, J = 8.4 Hz), 7.46~7.51 (m, 2H), 7.68 (t, 1H, J = 7.6 Hz), 7.77 (d, 1H, J = 7.6 Hz), 8.04 (t, 2H, J = 8.8 Hz), 8.20 (s, 1H) |
| 72 | 3-(3,4-difluorophenyl)-5-[2-(quinolin-2-yl)ethyl]thieno[2,3-d]pyridazin-4(5H)-one | 420/2.22 | 3.49 (t, 2H, J = 7.6 Hz), 4.74 (t, 2H, J = 7.6 Hz), 7.15-7.21 (m, 2H), 7.28-7.35 (m, 2H), 7.47 (s, 1H), 7.50 (d, 1H, J = 7.2 Hz), 7.65-7.69 (m, 1H), 7.78 (d, 1H, J = 8.0 Hz), 7.98 (d, 1H, J = 8.4 Hz), 8.06 (d, 1H, J = 8.0 Hz), 8.22 (s, 1H) |
| 73 | 3-(5-fluoro-2-methoxyphenyl)-5-[2-(quinolin-2-yl)ethyl]thieno[2,3-d]pyridazin-4(5H)-one | 432/2.19 | 3.48 (t, 2H, J = 7.6 Hz), 3.71 (s, 1H), 4.71 (t, 2H, J = 7.6 Hz), 6.87-7.08 (m, 3H), 7.30 (d, 1H, J = 8.8 Hz), 7.47-7.51 (m, 2H), 7.68 (t, 1H, J = 7.6 Hz), 7.77 (d, 1H, J = 8.4 Hz), 8.03 (t, 2H, J = 8.0 Hz), 8.18 (s, 1H). |
| 74 | 3-(4-fluoro-2-methoxyphenyl)-5-[2-(quinolin-2-yl)ethyl]thieno[2,3-d]pyridazin-4(5H)-one | 432/2.01, | 3.47 (t, 2H, J = 7.6 Hz), 3.72 (s, 3H), 4.70 (t, 2H, J = 7.6 Hz), 6.70-6.72 (m, 2H), 7.18-7.22 (m, 1H), 7.44 (s, 1H), 7.49 (t, 1H, J = 7.6 Hz), 7.67 (d, 1H, J = 7.6 Hz), 7.77 (d, 1H, J = 8.4 Hz), 7.99 (d, 1H, J = 8.4 Hz), 8.02 (t, 2H, J = 8.8 Hz), 8.17 (s, 1H) |
| 75 | 3-(3,5-dimethoxyphenyl)-5-[2-(quinolin-2-yl)ethyl]thieno[2,3-d]pyridazin-4(5H)-one | 444/2.20 | 3.50 (t, 2H, J = 7.6 Hz), 4.74 (t, 2H, J = 7.6 Hz), 6.50 (t, 1H, J = 2.4 Hz), 6.68 (d, 2H, J = 2.4 Hz), 7.31 (d, 1H, J = 7.6 Hz), 7.46-7.50 (m, 2H), 7.65-7.69 (m, 1H), 7.76 (d, 1H, J = 8.4 Hz), 8.00-8.05 (m, 2H), 8.19 (s, 1H) |
| 76 | 3-(2,5-difluorophenyl)-5-[2-(quinolin-2-yl)ethyl]thieno[2,3-d]pyridazin-4(5H)-one | 420/2.19 | 3.49 (t, 2H, J = 6.0 Hz), 4.73 (t, 2H, J = 6.0 Hz), 7.06-7.11 (m, 3H), 7.31 (d, 1H, J = 8.4 Hz), 7.48 (t, 1H, J = 8.4 Hz), 7.56 (s, 1H), 7.64-7.69 (m, 1H), 7.76 (d, 1H, J = 8.0 Hz), 8.00 (d, 1H, J = 8.4 Hz), 8.04 (d, 1H, J = 8.4 Hz), 8.21 (s, 1H) |
| 77 | 3-(2,3-dimethoxyphenyl)-5-[2-(quinolin-2-yl)ethyl]thieno[2,3-d]pyridazin-4(5H)-one | 444/2.15 | 3.48 (t, 2H, J = 7.6 Hz), 3.59 (s, 3H), 3.89 (s, 3H), 4.71 (t, 2H, J = 7.6 Hz), 6.86 (dd, 1H, J = 1.2 Hz, J = 7.6 Hz), 6.97 (d, 1H, J = 8.0 Hz), 7.05-7.09 (m, 1H), 7.30 (d, 1H, J = 8.0 Hz), 7.47-7.51 (m, 2H), 7.67 (t, 1H, J = 7.6 |

-continued

| EX. | Name | LC-MS: m/e (M + H)+/ R$_t$ [min] | $^1$H NMR (CDCl$_3$) δ: |
|---|---|---|---|
| | one | | Hz), 7.76 (d, 1H, J = 8.0 Hz), 8.00-8.04 (m, 2H), 8.20 (s, 1H) |
| 78 | 3-(3-fluoro-4-methoxyphenyl)-5-[2-(quinolin-2-yl)ethyl]thieno[2,3-d]pyridazin-4(5H)-one | 432/2.19 | 3.50 (t, 2H, J = 7.6 Hz), 3.93 (s, 3H), 4.74(t, 2H, J = 7.6 Hz), 6.99 (t, 1H, J = 8.4 Hz), 7.23-7.27 (m, 2H), 7.33 (d, 1H, J = 8.4 Hz), 7.44 (s, 1H), 7.49 (t, 1H, J = 7.6 Hz), 7.65-7.69 (m, 1H), 7.78 (d, 1H, J = 8.0 Hz), 8.00 (d, 1H, J = 8.0 Hz), 8.05 (d, 1H, J = 8.4 Hz), 8.19 (s, 1H) |
| 79 | 3-(2-fluoro-3-methoxyphenyl)-5-[2-(quinolin-2-yl)ethyl]thieno[2,3-d]pyridazin-4(5H)-one | 432/2.17 | 3.48 (t, 2H, J = 7.6 Hz), 3.92 (s, 3H), 4.72 (t, 2H, J = 7.6 Hz), 6.93-7.13 (m, 3H), 7.29 (d, 1H, J = 8.0 Hz), 7.46-7.50 (m, 1H), 7.55 (s, 1H), 7.65-7.69 (m, 1H), 7.77 (d, 1H, J = 8.0 Hz), 8.01-8.04 (m, 2H), 8.19 (s, 1H) |
| 80 | 3-(3,5-difluorophenyl)-5-[2-(quinolin-2-yl)ethyl]thieno[2,3-d]pyridazin-4(5H)-one | 420/2.24 | 3.50 (t, 2H, J = 7.6 Hz), 4.75 (t, 2H, J = 7.6 Hz), 6.81-6.85 (m, 1H), 7.01-7.03 (m, 2H), 7.34 (d, 1H, J = 8.4 Hz), 7.47-7.51 (m, 2H), 7.66 (t, 1H, J = 8.4 Hz), 7.77 (d, 1H, J = 8.4 Hz), 7.98 (d, 1H, J = 8.4 Hz), 8.06 (d, 1H, J = 8.4 Hz), 8.21 (s, 1H) |
| 81 | 3-(3-fluoro-5-methoxyphenyl)-5-[2-(quinolin-2-yl)ethyl]thieno[2,3-d]pyridazin-4(5H)-one | 432/2.23 | 3.51 (t, 2H, J = 7.6 Hz), 3.81 (s, 1H), 4.75 (t, 2H, J = 7.6 Hz), 6.63-6.67 (m, 1H), 6.79-6.82 (m, 1H), 6.87 (s, 1H), 7.33 (d, 1H, J = 8.4 Hz), 7.47-7.51 (m, 2H), 7.67 (t, 1H, J = 7.6 Hz), 7.78 (d, 1H, J = 8.0 Hz), 8.00-8.07 (m, 2H), 8.20 (s, 1H). |
| 82 | 3-(2-methoxy-5-methylphenyl)-5-[2-(quinolin-2-yl)ethyl]thieno[2,3-d]pyridazin-4(5H)-one | 428/1.61 | 2.21 (s, 3H), 3.59 (s, 3H), 3.78 (t, 2H, J = 6.0 Hz), 4.66 (t, 2H, J = 6.0 Hz), 6.77 (d, 1H, J = 8.4 Hz), 6.94 (s, 1H), 7.07 (d, 1H, J = 8.4 Hz), 7.37 (s, 1H), 7.50 (d, 1H, J = 8.4 Hz), 7.69 (t, 1H, J = 7.6 Hz), 7.86-7.92 (m, 2H), 8.05 (s, 1H), 8.45 (m, 2H) |
| 83 | 3-(2,5-dichlorophenyl)-5-[2-(quinolin-2-yl)ethyl]thieno[2,3-d]pyridazin-4(5H)-one | 452/2.09 | 3.48 (t, 2H, J = 7.6 Hz), 4.72 (t, 2H, J = 7.6 Hz), 7.29~7.33 (m, 3H), 7.39 (d, 1H, J = 8 Hz), 7.48 (d, 2H, J = 6.4 Hz), 7.66 (t, 1H, J = 7.2 Hz), 7.76 (d, 1H, J = 8 Hz), 7.98~8.04 (m, 2H), 8.22 (s, 1H) |
| 84 | 3-(naphthalen-2-yl)-5-[2-(quinolin-2-yl)ethyl]thieno[2,3-d]pyridazin-4(5H)-one | 434/2.11 | 3.55 (t, 2H, J = 7.6 Hz), 4.75 (t, 2H, J = 7.6 Hz), 7.35 (d, 1H, J = 8.4 Hz), 7.48~7.63 (m, 5H), 7.71 (t, 1H, J = 7.2 Hz), 7.79~7.87 (m, 4H), 7.94 (s, 1H), 8.09 (t, 2H, J = 8.4 Hz), 8.23 (s, 1H) |
| 85 | 3-phenyl-5-[2-(quinolin-2-yl)ethyl]thieno[2,3-d]pyridazin-4(5H)-one | 384/2.19 | 3.50 (t, 2H, J = 7.6 Hz), 4.74 (t, 2H, J = 7.6 Hz), 7.32 (d, 1H, J = 8.4 Hz), 7.39~7.53 (m, 7 H), 7.67 (t, 1H, J = 7.6 Hz), 7.77 (d, 1H, J = 7.6 Hz), 8.04 (t, 2H, J = 8.8 Hz), 8.20 (s, 1H) |
| 86 | 3-(1-benzofuran-2-yl)-5-[2-(quinolin-2-yl)ethyl]thieno[2,3-d]pyridazin-4(5H)-one | 423/1.70 | 3.75 (t, 2H, J = 6.8 Hz), 4.79 (t, 2H, J = 6.8 Hz), 7.14-7.18 (m, 1H), 7.24 (t, 1H, J = 7.2 Hz), 7.07 (d, 1H, J = 8.4 Hz), 7.40-7.61 (m, 4H), 7.77-7.85 (m, 2H), 8.00 (s, 1H), 8.10 (s, 2H), 8.30-8.34 (m, 2H) |
| 87 | 3-(1H-indazol-5-yl)-5-[2-(quinolin-2-yl)ethyl]thieno[2,3-d]pyridazin-4(5H)-one | 424/2.00 | 3.50 (t, 2H, J = 7.6 Hz), 4.75 (t, 2H, J = 7.6 Hz), 7.32 (d, 1H, J = 8.4 Hz), 6.63-6.67 (m, 1H), 6.79-6.82 (m, 1H), 6.87 (s, 1H), 7.33 (d, 1H, J = 8.4 Hz), 7.47-7.51 (m, 2H), 7.67 (t, 1H, J = 7.6 Hz), 7.78 (d, 1H, J = 8.0 Hz), 8.00-8.07 (m, 2H), 8.20 (s, 1H). |
| 88 | 3-(1-methyl-1H-pyrazol-5-yl)-5-[2-(quinolin-2-yl)ethyl]thieno[2,3-d]pyridazin-4(5H)-one | 388/1.89 | 3.49 (t, 2H, J = 7.6 Hz), 3.56 (s, 3H), 4.73 (t, 2H, J = 7.6 Hz), 6.31 (d, 1H, J = 2.0 Hz), 7.34 (d, 1H, J = 8.0 Hz), 7.47-7.52 (m, 2H), 7.56 (s, 1H), 7.64-7.69 (m, 1H), 7.77 (d, 1H, J = 8.0 Hz), 7.96 (d, 1H, J = 8.8 Hz), 8.06 (d, 1H, J = 8.4 Hz), 8.25 (s, 1H) |
| 89 | 3-(4,5-difluoro-2-methoxyphenyl)-5-[2-(quinolin-2-yl)ethyl]thieno[2,3-d]pyridazin-4(5H)-one | 450/2.22 | 3.47 (t, 2H, J = 7.6 Hz), 3.60 (s, 3H), 4.70 (t, 2H, J = 7.6 Hz), 6.75~6.80 (m, 1H), 7.07 (t, 1H, J = 7.6 Hz), 7.30 (d, 1H, J = 8.4 Hz), 7.45~7.50 (m, 2H), 7.67 (t, 1H, J = 7.2 Hz), 7.77 (d, 1H, j = 8 Hz), 7.99~8.05 (m, 2H), 8.18 (s, 1H) |
| 90 | 3-(2-fluoro-4-methylphenyl)-5-[2-(quinolin-2- | 416/1.60 | 2.26 (s, 3H), 3.77 (t, 2H, J = 6.0 Hz), 4.68 (t, 2H, J = 6.0 Hz), 6.73 (d, 1H, J = 8.4 Hz), 6.83 (d, 1H, J = 8.0 Hz), 7.05 (t, 1H, J = 8.0 Hz), |

-continued

| EX. | Name | LC-MS: m/e (M + H)+/ R$_t$ [min] | $^1$H NMR (CDCl$_3$) δ: |
|---|---|---|---|
| | yl)ethyl]thieno[2,3-d]pyridazin-4(5H)-one | | 7.44 (s, 1H), 7.60 (d, 1H, J = 8.4 Hz), 7.75 (t, 1 H, J = 8.0 Hz), 7.90-7.99 (m, 2H), 8.14 (s, 1H), 8.28 (d, 1H, J = 8.4 Hz), 8.59 (d, 1H, J = 8.4 Hz) |
| 91 | 3-(2-fluoro-5-methoxyphenyl)-5-[2-(quinolin-2-yl)ethyl]thieno[2,3-d]pyridazin-4(5H)-one | 432/2.18 | 3.49 (t, 2H, J = 7.6 Hz), 3.80 (s, 3H), 4.73 (t, 2H, J = 7.6 Hz), 6.88-6.93 (m, 2H), 7.08 (t, 1H, J = 8.8 Hz), 7.30 (d, 1H, J = 8.4 Hz), 7.46-7.51 (m, 1H), 7.65-7.69 (m, 1H), 7.55 (s, 1H), 7.65-7.69 (m, 1H), 7.76 (d, 1H, J = 8.4 Hz), 8.03 (t, 2H, J = 8.0 Hz), 8.20 (s, 1H). |
| 92 | 3-methyl-4-{4-oxo-5-[2-(quinolin-2-yl)ethyl]-4,5-dihydrothieno[2,3-d]pyridazin-3-yl}benzonitrile | 423/1.54 | 1.99 (s, 3H), 3.84 (t, 2H, J = 6.0 Hz), 4.73 (t, 2H, J = 6.0 Hz), 7.15 (d, 1H, J = 8.0 Hz), 7.39-7.46 (m, 3H), 7.77 (d, 1H, J = 8.4 Hz), 7.87 (t, 1H, J = 8.0 Hz), 8.02-8.09 (m, 2H), 8.32 (s, 1H), 8.36 (d, 1H, J = 8.4 Hz), 8.69 (d, 1H, J = 8.4 Hz) |

Example 93: 5-[2-(6-Fluoroquinolin-2-yl)ethyl]-3-(pyridin-4-yl)thieno[2,3-d]pyridazin-4(5H)-one

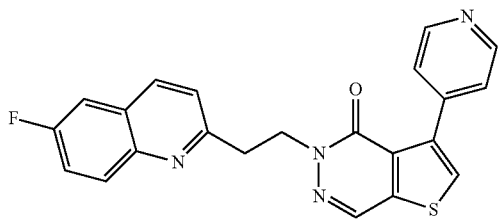 [SMILES: O=c1c2c(-c3ccncc3)csc2cnn1CCc1ccc2cc(F)ccc2n1]

93.1 3-Bromo-5-(2-(6-fluoroquinolin-2-yl)ethyl)thieno[2,3-d]pyridazin-4(5H)-one 2-(6-Fluoroquinolin-2-yl)ethanol (182 mg, 0.952 mmol) from Example a2) and 3-bromo-5H-thieno[2,3-d]pyridazin-4(5H)-one (200 mg, 0.865 mmol) from Example 3.3 were dissolved in THF (10 mL) and stirred for about 10 min. Then Ph$_3$P (342 mg, 1.305 mmol) and DEAD (226 mg, 1.298 mmol) were each added sequentially rapidly to the solution. The reaction mixture was stirred under nitrogen atmosphere overnight. The reaction solution was concentrated and purified by TLC (PE/EA=1/1). The crude product was recrystallized from methanol (130 mg, yield: 37.1%). LC-MS: m/e (M+H)+; R$_t$: 1.90 min.

93.2 5-[2-(6-Fluoroquinolin-2-yl)ethyl]-3-(pyridin-4-yl)thieno[2,3-d]pyridazin-4(5H)-one 3-Bromo-5-(2-(6-fluoroquinolin-2-yl)ethyl)thieno[2,3-d]pyridazin-4(5H)-one (66 mg, 0.163 mmol) was dissolved in dioxane (2.1 mL) and H$_2$O (0.7 mL), pyridin-4-yl boronic acid (20.07 mg, 0.163 mmol), K$_2$CO$_3$ (45.1 mg, 0.327 mmol) and Pd(dppf)Cl$_2$ (7.23 mg, 9.80 μmol) were each added sequentially to the suspension. The suspension was heated in a microwave tube at about 110° C. for 1 h. The crude product was purified by TLC (EA) to give the title compound (45 mg, yield: 68.5%).

LC-MS: m/e (M+H)+: 403.7, R$_t$: 1.81 min; $^1$H NMR (CDCl$_3$, 400 MHz) δ: 8.65 (d, J=6.0 Hz, 2H), 8.24 (s, 1H), 8.02-7.96 (m, 2H), 7.61 (s, 1H), 7.46-7.42 (m, 3H), 7.41-7.38 (m, 1H), 7.34 (d, J=8.4 Hz, 1H), 4.75 (t, J=7.4 Hz, 2H), 3.48 (t, J=7.4 Hz, 2H).

Example 94: 5-[2,2-Difluoro-2-(quinolin-2-yl)ethyl]-3-(pyridin-4-yl)thieno[2,3-d]pyridazin-4(5H)-one

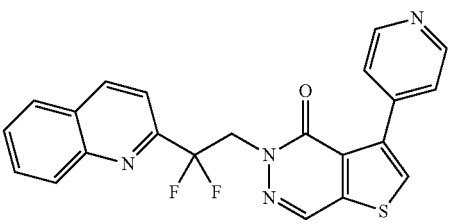 [SMILES: O=c1c2c(-c3ccncc3)csc2cnn1CC(F)(F)c1ccc2ccccc2n1]

94.1 3-Bromo-5-(2,2-difluoro-2-(quinolin-2-yl)ethyl)thieno[2,3-d]pyridazin-4(5H)-one A mixture of 3-bromothieno[2,3-d]pyridazin-4(5H)-one (10 mg, 0.043 mmol) from Example 3.3, trifluoromethanesulfonic acid 2,2-difluoro-2-quinolin-2-yl ethyl ester (14.77 mg, 0.043 mmol) from Example b1 and Cs$_2$CO$_3$ (28.2 mg, 0.087 mmol) in DMF (0.5 mL) was stirred at room temperature for 5 h. The solution was purified by Pre-TLC (PE/EA=1/2) to give a dark yellow oil (4 mg, yield 22%).
LC-MS (ESI+): m/e 422 (M+H)+, R$_t$: 1.96 min.

94.2 5-[2,2-Difluoro-2-(quinolin-2-yl)ethyl]-3-(pyridin-4-yl)thieno[2,3-d]pyridazin-4(5H)-one A mixture of 3-bromo-5-(2,2-difluoro-2-(quinolin-2-yl)ethyl)thieno[2,3-d]pyridazin-4(5H)-one (0.118 mmol), pyridin-4-yl boronic acid (0.118 mmol), Na$_2$CO$_3$ (31.4 mg, 0.296 mmol) and PdCl$_2$(dppf)-CH$_2$Cl$_2$ adduct (9.67 mg, 0.012 mmol) in dioxane (1.5 mL) and water (0.5 mL) was stirred at 100° C. for 2 h. The solvent was evaporated and the residue was purified by Pre-TLC (PE/EA=1/1) to give a crude yellow solid. The solid was dissolved in DCM (1.5 mL) and filtered. The white solid obtained was the title compound (40 mg, yield 80%).

LC-MS (ESI+): m/e 421 (M+H)+, R$_t$: 2.00 min; $^1$H NMR (CDCl$_3$, 400 MHz) δ: 8.70 (s, 1H), 8.61 (d, J=8.4 Hz, 1H), 8.50 (dd, J=4.4 Hz, 1.2 Hz, 1H), 8.22 (s, 1H), 8.13 (d, J=8.4 Hz, 1H), 8.03 (d, J=8.4 Hz, 1H), 7.88-7.84 (m, 1H), 7.80 (d, J=8.4 Hz, 1H), 7.76-7.73 (m, 1H), 7.30 (dd, J=4.4 Hz, 2.0 Hz, 2H), 5.15 (t, J=14 Hz, 2H).

Example 95: 3-(Pyridin-4-yl)-5-[2-(thieno[3,2-b]pyridin-5-yl)ethyl]thieno[2,3-d]pyridazin-4(5H)-one

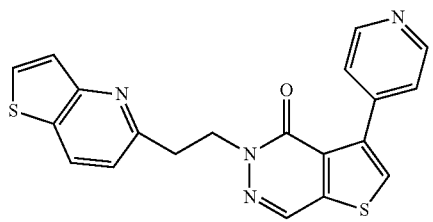 [SMILES: O=c1c2c(-c3ccncc3)csc2cnn1CCc1ccc2sccc2n1]

95.1 3-Bromo-5-[2-(thieno[3,2-b]pyridin-5-yl)ethyl]thieno[2,3-d]pyridazin-4(5H)-one To a mixture of 3-bromothieno[2,3-d]pyridazin-4(5H)-one (100 mg, 0.433 mmol) from Example 3.3 and triphenylphosphine (227 mg, 0.866 mmol) in THF (2 mL) was added (E)-diethyl diazene-1,2-dicarboxylate (151 mg, 0.866 mmol) dropwise at 0° C. After the addition, the mixture was stirred for 1 h at 0° C. Then 2-(thieno[3,2-b]pyridin-5-yl)ethanol from Example a3 (78 mg, 0.433 mmol) in THF (1 mL) was added dropwise. The mixture was stirred at room temperature overnight. The solution was filtered to obtain the title compound (80 mg, yield 47.1%).

LC-MS (ESI+): m/e 392 (M+H)$^+$, R$_t$: 1.60 min; $^1$H NMR (CDCl$_3$, 400 MHz) δ: 8.67 (d, J=4.4 Hz, 2H), 8.24 (s, 1H), 8.09 (d, J=6.4 Hz, 1H), 7.72 (d, J=4.4 Hz, 1H), 7.60 (s, 1H), 7.49 (d, J=4.4 Hz, 1H), 7.45 (d, J=4.8 Hz, 2H), 7.17 (d, J=6.4 Hz, 1H), 4.7 (t, J=6.4 Hz, 2H), 3.44 (t, J=6.0 Hz, 2H).

95.2 3-(Pyridin-4-yl)-5-[2-(thieno[3,2-b]pyridin-5-yl)ethyl]thieno[2,3-d]pyridazin-4(5H)-one A mixture of pyridin-4-ylboronic acid (37.6 mg, 0.306 mmol), the compound from Example 95.1 (80 mg, 0.204 mmol), Na$_2$CO$_3$ (54.0 mg, 0.510 mmol) and PdCl$_2$(dppf)-CH$_2$Cl$_2$ adduct (16.65 mg, 0.020 mmol) in dioxane (3 mL) and water (1 mL) was stirred at 100° C. in a microwave for 10 min. The solvent was evaporated and the residue was washed with methanol, filtered, the filtrate was concentrated and purified by HPLC to afford the title compound (59 mg, yield 74.1%) as a white solid.

LC-MS (ESI+): m/e 391 (M+H)$^+$, R$_t$: 1.86 min.

Example 96: 5-[2-(Imidazo[1,2-a]pyridin-2-yl)ethyl]-3-(pyridin-4-yl)thieno[2,3-d]pyridazin-4(5H)-one

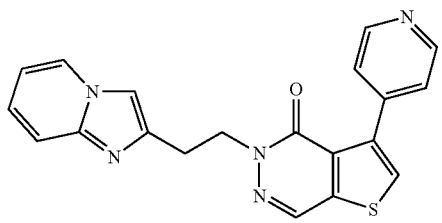 [SMILES: O=c1c2c(-c3ccncc3)csc2cnn1CCc1cn2ccccc2n1]

96.1 2-(2-Chloroethyl)imidazo[1,2-a]pyridine

A mixture of 2-(imidazo[1,2-a]pyridin-2-yl)ethanol (400 mg, 2.466 mmol) from Example a4) and SOCl$_2$ (2 mL, 27.4 mmol) in DCM (10 mL) was stirred at room temperature for 2 days. The mixture was concentrated in vacuo. The residue was diluted with EtOAc (3×100 mL) and washed with saturated NaHCO$_3$ solution (6 mL×4) and brine (6 mL). The organic layer was dried over Na$_2$SO$_4$, filtered and concentrated in vacuo. The residue was purified by Pre-TLC (PE/EA=1/1, v/v) to give the title compound as an oil (300 mg, yield 70%).

LC-MS (ESI+): m/e 181 (M+H)$^+$, R$_t$: 1.68 min.

96.2 3-Bromo-5-[2-(imidazo[1,2-a]pyridin-2-yl)ethyl]-5H-thieno[2,3-d]pyridazin-4(5H)-one A mixture of 2-(2-chloroethyl)imidazo[1,2-a]pyridine (90 mg, 0.498 mmol), 3-bromothieno[2,3-d]pyridazin-4(5H)-one from Example 3.4 (115 mg, 0.498 mmol) and Cs$_2$CO$_3$ (325 mg, 0.996 mmol) in DMF (3 mL) was stirred at 60° C. for 16 h. The solvent was evaporated. The residue was purified by Pre-TLC (PE/EA=1/2, v/v) to give the title compound as an oil (140 mg, yield 80%).

LC-MS (ESI+): m/e 374 (M+H)$^+$, R$_t$: 1.79 min.

96.3 5-[2-(Imidazo[1,2-a]pyridin-2-yl)ethyl]-3-(pyridin-4-yl)thieno[2,3-d]pyridazin-4(5H)-one A mixture of pyridin-4-ylboronic acid (29.5 mg, 0.240 mmol), the compound from Example 96.2 (60 mg, 0.160 mmol), Na$_2$CO$_3$ (42.4 mg, 0.400 mmol) and PdCl$_2$(dppf)-CH$_2$Cl$_2$ adduct (13.06 mg, 0.016 mmol) in dioxane (3 mL) and water (1 mL) was stirred at 100° C. in a microwave for 10 min. The solvent was evaporated and the residue was purified by Pre-TLC (PE/EA=1/4) and purified by HPLC to afford the title product as a white solid (45 mg, yield 75%).

LC-MS (ESI+): m/e 374 (M+H)$^+$, R$_t$: 1.70 min; $^1$H NMR (DMSO-d$_6$, 400 MHz): 8.68 (s, 1H), 8.60 (d, J=6.0 Hz, 2H), 8.46 (d, J=6.4 Hz, 1H), 8.21 (s, 1H), 7.74 (s, 1H), 7.75 (d, J=6.0 Hz, 2H), 7.46 (d, J=9.2 Hz, 1H), 7.19-7.15 (m, 1H), 6.84-6.80 (m, 1H), 4.47 (t, J=7.6 Hz, 2H), 3.13 (t, J=7.6 Hz, 2H).

Example 97: 5-[2-(7-Fluoroimidazo[1,2-a]pyridin-2-yl)ethyl]-3-(pyridin-4-yl)thieno[2,3-d]pyridazin-4(5H)-one

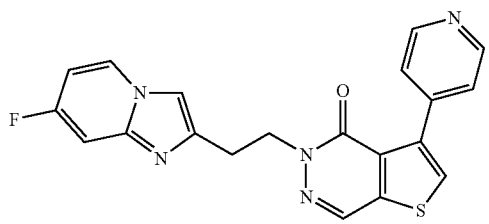 [SMILES: O=c1c2c(-c3ccncc3)csc2cnn1CCc1cn2ccc(F)cc2n1]

97.1 3-Bromo-5-(2-(7-fluoroimidazo[1,2-a]pyridin-2-yl)ethyl)thieno[2,3-d]pyridazin-4(5H)-one A mixture of 3-bromothieno[2,3-d]pyridazin-4(5H)-one from Example 3.4 (231 mg, 1 mmol), 2-(7-fluoroimidazo[1,2-a]pyridin-2-yl)ethanol from Example a5 (180 mg, 1.00 mmol) and Ph₃P (525 mg, 2.00 mmol) was dissolved in THF (6 mL). Then DEAD (0.317 mL, 2.00 mmol) in THF (1 mL) was added. The resulting mixture was stirred at room temperature under nitrogen overnight. The mixture was concentrated and purified on the ISCO Combiflash system using a 40 g C-18 column using the following gradient: A: Water (0.1% NH₄HCO₃); B: Methanol; 30% B to 80% B over 20 min (160 mg, yield: 17.7%).

LC-MS: m/e 393 (M+H)⁺; $R_t$:1.74 min; ¹H NMR (DMSO-d₆) δ: 3.12 (t, 2H), 4.44 (t, 2H), 6.88-6.92 (m, 1H), 7.32 (dd, J=10, 2, 1H), 7.74 (s, 1H), 8.17 (s, 1H), 8.52-8.56 (m, 1H), 8.62 (s, 1H).

97.2 5-[2-(7-Fluoroimidazo[1,2-a]pyridin-2-yl)ethyl]-3-(pyridin-4-yl)thieno[2,3-d]pyridazin-4(5H)-one A mixture of 3-bromo-5-(2-(7-fluoroimidazo[1,2-a]pyridin-2-yl)ethyl)thieno[2,3-d]pyridazin-4(5H)-one (80 mg, 0.203 mmol), pyridin-4-ylboronic acid (37.5 mg, 0.305 mmol), PdCl₂(dppf)-CH₂Cl₂ adduct (16.61 mg, 0.020 mmol) and Cs₂CO₃ (133 mg, 0.407 mmol) in 1,4-dioxane (3 mL) and water (1.5 mL) was heated under microwave at about 110° C. for about 15 min. The mixture was concentrated and was chromatographed on the ISCO Combiflash system using a 40 g Silicycle SiliaSep Silica gel column C-18 column using the following gradient: A: Water (0.1% NH₄HCO₃); B: Methanol; 30% B to 80% B over 20 min (15 mg, 18.8%).

LC-MS: m/e 392 (M+H); $R_t$: 1.74 min; ¹H NMR (CDCl₃) δ: 3.30 (t, 2H), 4.64 (t, 2H), 6.61-6.65 (m, 1H), 7.15 (dd, J=9.6 Hz, 2.4 Hz, 1H), 7.38 (s, 1H), 7.50 (d, J=6 Hz, 2H), 7.61 (s, 1H), 7.96-7.99 (m, 1H), 8.26 (s, 1H), 8.68 (d, J=6 Hz, 2H).

II.2 Preparation of Compounds of the Formula I in which A is A¹, X¹ is N, R¹ is Y¹-Cyc¹ and X³ is —C(R⁹)=C(R⁸)—

Example 98: 8-(Pyridin-4-yl)-2-[2-(quinolin-2-yl)ethyl]phthalazin-1(2H)-one

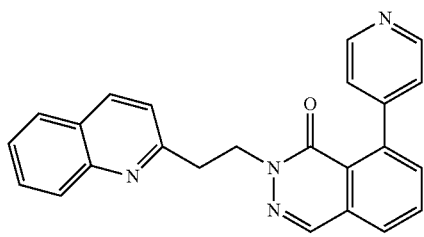 [SMILES: O=c1c2c(-c3ccncc3)cccc2cnn1CCc1ccc2ccccc2n1]

98.1 N-tert-Butyl-2-chlorobenzamide

The mixture of 2-chlorobenzoic acid (20 g, 128 mmol), HOBT (34.6 g, 256 mmol), EDCI (48.8 g, 256 mmol), 2-methylpropan-2-amine (9.3 g, 128 mmol) and TEA (25.9 g, 256 mmol) in THF (600 mL) was stirred at room temperature overnight. After solvent evaporation, the mixture was diluted with ethyl acetate (600 mL) and washed with water (3×300 mL). The organic layer was dried over Na₂SO₄, filtered and concentrated. The residue was purified by column chromatography on silica gel, eluting with EtOAc/PE (1:5) to give the title product as a white solid (23.9 g, yield: 88.5%).

LC-MS: m/e=212 (M+H)⁺; $R_t$=0.85 min.

98.2 2-tert-Butyl-7-chloro-3-hydroxy-2,3-dihydroisoindol-1-one

N-tert-Butyl-2-chlorobenzamide (5.4 g, 25.6 mmol) was dissolved in THF (280 mL) and the solution was added with TMEDA (12.4 mL, 81.9 mmol) and then added with sec-butyllithium-hexane solution (1.0 mol/L, 82.7 mL, 81.9 mmol) dropwise at −78° C. for 40 minutes under argon atmosphere, followed by stirring at the same temperature for 2.5 hours. Then, the mixture was added with DMF (4.36 mL, 56.3 mmol) and warmed from −78° C. to room temperature over 2 hours. The reaction mixture was added with water (200 mL), and extracted with ethyl acetate (100 mL*3). The organic layer was washed with saturated brine and dried over anhydrous sodium sulfate. The solvent was evaporated under reduced pressure and the residue was purified by crystallization using diisopropyl ether to obtain product 3 (5.0 g, Yield: 81%).

LC-MS: m/e=240 (M+H)⁺; $R_t$=1.74 min; ¹H NMR (400 MHz, DMSO-d6): δ 7.58-7.54 (m, 1H), 7.49-7.45 (m, 2H), 6.35 (d, J=8.4 Hz, 1H), 5.98 (d, J=8.4 Hz, 1H), 1.52 (s, 9H).

98.3 8-Chloro-2H-phthalazin-1-one

The compound from Example 98.2 (5 g, 21 mmol) was suspended in 20 mL acetic acid under nitrogen. The resulting thick slurry was heated to 90° C. At approximately 80° C., a homogeneous solution was obtained. Hydrazine monohydrate (64%, 3.2 mL, 63 mmol) was added dropwise (exotherm), keeping the internal temperature between 90 and 93° C. over approximately 4 h. The resulting suspension was continued to stir at 90° C. as the conversion of starting material was monitored by LC (<1%). Water (40 mL) preheated to 80° C. was added, maintaining the mixture at 80-90° C. followed by ramping down to 20° C. over approximately 3 h time. At this point, the resulting suspension was transferred onto a filter. The filter cake was rinsed with water (10 mL*3). The wet product was air-dried overnight to afford the title product (2.6 g, Yield: 69%).

LC-MS: m/e=181 (M+H)⁺; $R_t$=1.51 min; ¹H NMR (400 MHz, DMSO-d6) δ: 12.61 (s, 1H), 8.32 (s, 1H), 7.88-7.83 (m, 3H).

98.4 8-Chloro-2-(2-quinolin-2-yl-ethyl)-2H-phthalazin-1-one

To a solution of triphenylphosphine (9.00 g, 34.3 mmol) in THF (100 mL), DEAD (5.44 mL, 34.3 mmol) was added at 0° C. After stirring for 15 min, 2-(quinolin-2-yl)ethanol from Example a1 (2.97 g, 17.17 mmol) was added. After another 15 min, 8-chlorophthalazin-1(2H)-one (3.1 g, 17.17 mmol) was added. The mixture was stirred overnight at room temperature; LC-MS indicated complete conversion to the product. 1 N HCl was added (pH=4). The mixture was extracted with EtOAc (3×50 mL), the EtOAc layers were discarded. The aqueous layer was neutralized by aq.NaHCO₃ and extracted with ethyl acetate (3×500 mL). The combined organic layers were washed with brine, dried over Na₂SO₄, filtered, and concentrated under reduced pressure. The crude product was suspended in EtOAc. The solid was filtered through a Büchner funnel. The purity of the title product was 95%.

LC-MS: m/e=336 (M+H)+; $R_t$=1.54 min; 1H NMR (400 MHz, DMSO-$d_6$) δ: =8.35 (s, 1H), 8.29-8.26 (d, J=8.8 Hz, 1H), 7.94-7.90 (m, 2H), 7.88-7.86 (m, 3H), 7.73-7.69 (m, 1H), 7.57-7.55 (m, 1H), 7.48-7.46 (m, 1H), 4.58-4.55 (t, J=5.4 Hz, 2H), 3.42-3.38 (t, J=5.4 Hz, 2H).

98.5 8-(Pyridin-4-yl)-2-[2-(quinolin-2-yl)ethyl]phthalazin-1(2H)-one

A reaction tube was charged with pyridin-4-ylboronic acid (0.223 mmol), $K_2CO_3$ (61.7 mg, 0.447 mmol) under a dry nitrogen atmosphere. A solution of 8-chloro-2-(2-quinolin-2-yl-ethyl)-2H-phthalazin-1-one (50 mg, 0.186 mmol) in 1,4-dioxane (5 mL) along with $PdCl_2$(dppf) (5.45 mg, 7.45 μmol) was added. After addition of water (1 mL), the resulting mixture was heated at 100° C. overnight. After removal of the solvent under reduced pressure, the title compound was obtained as a crude product. It was purified by Prep-HPLC.

LC-MS m/e=379.1 (M+H)+; $R_t$=1.80 min; 1H NMR (400 MHz, $CDCl_3$) δ ppm 8.58 (s, 2H), 8.18 (s, 1H), 8.04 (d, J=8.0 Hz, 1H), 7.94 (d, J=8.0 Hz, 1H), 7.74-7.78 (m, 3H), 7.66 (d, J=1.6 Hz, 1H), 7.46-7.52 (m, 2H), 7.30 (d, J=8.4 Hz, 1H), 7.11 (d, J=5.2 Hz, 2H), 4.65 (t, J=7.4 Hz, 2H), 3.45 (t, J=7.4 Hz, 2H).

Examples 99 to 164 were prepared analogously to the method for Example 98.

| EX. | Name | LC-MS: m/e (M + H)+/ $R_t$ [min] |
|---|---|---|
| 99 | 2-[2-(Quinolin-2-yl)ethyl]-8-[4-(trifluoromethyl)phenyl]phthalazin-1(2H)-one | 446/2.34 |
| 100 | 8-(4-Methylphenyl)-2-[2-(quinolin-2-yl)ethyl]phthalazin-1(2H)-one | 392/2.30 |
| 101 | 8-[4-(Propan-2-yl)phenyl]-2-[2-(quinolin-2-yl)ethyl]phthalazin-1(2H)-one | 420/2.45 |
| 102 | 8-(4-Ethylphenyl)-2-[2-(quinolin-2-yl)ethyl]phthalazin-1(2H)-one | 406/2.15 |
| 103 | 4-{4-Oxo-3-[2-(quinolin-2-yl)ethyl]-3,4-dihydrophthalazin-5-yl}benzonitrile | 403/1.96 |
| 104 | 8-(4-Methoxyphenyl)-2-[2-(quinolin-2-yl)ethyl]phthalazin-1(2H)-one | 408/2.19 |
| 105 | 8-(4-Fluorophenyl)-2-[2-(quinolin-2-yl)ethyl]phthalazin-1(2H)-one | 396/2.22 |
| 106 | (4-{4-Oxo-3-[2-(quinolin-2-yl)ethyl]-3,4-dihydrophthalazin-5-yl}phenyl)acetonitrile | 417/2.11 |
| 107 | 8-(4-Hydroxyphenyl)-2-[2-(quinolin-2-yl)ethyl]phthalazin-1(2H)-one | 394/1.99 |
| 108 | 8-(2-chlorophenyl)-2-[2-(quinolin-2-yl)ethyl]phthalazin-1(2H)-one | 412/2.06 |
| 109 | 8-(2-Methylphenyl)-2-[2-(quinolin-2-yl)ethyl]phthalazin-1(2H)-one | 392/2.08 |
| 110 | 8-(2-Ethylphenyl)-2-[2-(quinolin-2-yl)ethyl]phthalazin-1(2H)-one | 406/2.35 |
| 111 | 8-(2-Fluorophenyl)-2-[2-(quinolin-2-yl)ethyl]phthalazin-1(2H)-one | 396/2.20 |
| 112 | 8-(2-Methoxyphenyl)-2-[2-(quinolin-2-yl)ethyl]phthalazin-1(2H)-one | 408/2.20 |
| 113 | 8-(3-Methoxyphenyl)-2-[2-(quinolin-2-yl)ethyl]phthalazin-1(2H)-one | 408/2.02 |
| 114 | 3-{4-Oxo-3-[2-(quinolin-2-yl)ethyl]-3,4-dihydrophthalazin-5-yl}benzonitrile | 403/1.96 |
| 115 | 8-(3-Fluorophenyl)-2-[2-(quinolin-2-yl)ethyl]phthalazin-1(2H)-one | 396/2.04 |
| 116 | 8-(3-Hydroxyphenyl)-2-[2-(quinolin-2-yl)ethyl]phthalazin-1(2H)-one | 394/1.87 |
| 117 | N,N-Dimethyl-3-{4-oxo-3-[2-(quinolin-2-yl)ethyl]-3,4-dihydrophthalazin-5-yl}benzamide | 449/1.98 |
| 118 | 8-(3-Methylphenyl)-2-[2-(quinolin-2-yl)ethyl]phthalazin-1(2H)-one | 392/2.10 |
| 119 | 2-[2-(Quinolin-2-yl)ethyl]-8-(thiophen-2-yl)phthalazin-1(2H)-one | 384/2.19 |
| 120 | 8-(1-Methyl-1H-indol-5-yl)-2-[2-(quinolin-2-yl)ethyl]phthalazin-1(2H)-one | 431/2.26 |
| 121 | 8-(3,5-Dimethyl-1H-pyrazol-4-yl)-2-[2-(quinolin-2-yl)ethyl]phthalazin-1(2H)-one | 396/1.90 |
| 122 | 8-(1H-Indol-5-yl)-2-[2-(quinolin-2-yl)ethyl]phthalazin-1(2H)-one | 417/1.97 |
| 123 | 8-(1H-Indol-6-yl)-2-[2-(quinolin-2-yl)ethyl]phthalazin-1(2H)-one | 417/1.98 |
| 124 | 8-(Pyrimidin-5-yl)-2-[2-(quinolin-2-yl)ethyl]phthalazin-1(2H)-one | 380/1.82 |
| 125 | 8-(2-Methoxypyridin-3-yl)-2-[2-(quinolin-2-yl)ethyl]phthalazin-1(2H)-one | 409/2.07 |
| 126 | 8-(Pyridin-3-yl)-2-[2-(quinolin-2-yl)ethyl]phthalazin-1(2H)-one | 379/1.81 |
| 127 | 8-(Furan-3-yl)-2-[2-(quinolin-2-yl)ethyl]phthalazin-1(2H)-one | 368/1.95 |
| 128 | 8-(Quinolin-3-yl)-2-[2-(quinolin-2-yl)ethyl]phthalazin-1(2H)-one | 439 |
| 129 | 8-(1H-Indol-4-yl)-2-[2-(quinolin-2-yl)ethyl]phthalazin-1(2H)-one | 417/2.12 |
| 130 | 8-(2,3-Dihydro-1-benzofuran-5-yl)-2-[2-(quinolin-2-yl)ethyl]phthalazin-1(2H)-one | 420/2.19 |
| 131 | 8-(3,4-Dihydro-2H-1,5-benzodioxepin-7-yl)-2-[2-(quinolin-2-yl)ethyl]phthalazin-1(2H)-one | 450/2.19 |
| 132 | 8-(1-Benzofuran-5-yl)-2-[2-(quinolin-2-yl)ethyl]phthalazin-1(2H)-one | 418/2.25 |
| 133 | 8-(6-Methoxypyridin-3-yl)-2-[2-(quinolin-2-yl)ethyl]phthalazin-1(2H)-one | 409/2.10 |
| 134 | 8-(2,3-Dihydro-1,4-benzodioxin-6-yl)-2-[2-(quinolin-2-yl)ethyl]phthalazin-1(2H)-one | 436/1.99 |
| 135 | 8-(2-Methylpyridin-4-yl)-2-[2-(quinolin-2-yl)ethyl]phthalazin-1(2H)-one | 393/1.95 |
| 136 | 8-(5-Methoxypyridin-3-yl)-2-[2-(quinolin-2-yl)ethyl]phthalazin-1(2H)-one | 409/1.97 |
| 137 | 8-(5-Fluoropyridin-3-yl)-2-[2-(quinolin-2-yl)ethyl]phthalazin-1(2H)-one | 397/2.00 |
| 138 | 8-(1,3-Benzodioxol-5-yl)-2-[2-(quinolin-2-yl)ethyl]phthalazin-1(2H)-one | 422/2.00 |
| 139 | 8-(1-Methyl-1H-pyrazol-4-yl)-2-[2-(quinolin-2-yl)ethyl]phthalazin-1(2H)-one | 382/1.90 |
| 140 | 8-[1-(2-Methylpropyl)-1H-pyrazol-4-yl]-2-[2-(quinolin-2-yl)ethyl]phthalazin-1(2H)-one | 424/2.14 |
| 141 | tert-Butyl 2-{4-oxo-3-[2-(quinolin-2-yl)ethyl]-3,4-dihydrophthalazin-5-yl}-1H-pyrrole-1-carboxylate | 467/2.34 |
| 142 | 8-(3-Chloro-4-fluorophenyl)-2-[2-(quinolin-2-yl)ethyl]phthalazin-1(2H)-one | 430/2.32 |
| 143 | 8-(2-Chloro-4-fluorophenyl)-2-[2-(quinolin-2-yl)ethyl]phthalazin-1(2H)-one | 430/2.28 |
| 144 | 8-(3,4-dimethylphenyl)-2-[2-(quinolin-2-yl)ethyl]phthalazin-1(2H)-one | 406/2.37 |
| 145 | 8-(2,4-Dimethoxyphenyl)-2-[2-(quinolin-2-yl)ethyl]phthalazin-1(2H)-one | 438/2.20 |
| 146 | 8-(2,5-Dimethoxyphenyl)-2-[2-(quinolin-2-yl)ethyl]phthalazin-1(2H)-one | 438/2.18 |
| 147 | 8-(2,3-Difluorophenyl)-2-[2-(quinolin-2-yl)ethyl]phthalazin-1(2H)-one | 414/2.23 |
| 148 | 8-(3,4-Dimethoxyphenyl)-2-[2-(quinolin-2-yl)ethyl]phthalazin-1(2H)-one | 438/2.11 |
| 149 | 8-(3,4-difluorophenyl)-2-[2-(quinolin-2-yl)ethyl]phthalazin-1(2H)-one | 414/2.25 |
| 150 | 8-(5-Fluoro-2-methoxyphenyl)-2-[2-(quinolin-2-yl)ethyl]phthalazin-1(2H)-one | 426/2.21 |
| 151 | 8-(4-Fluoro-2-methoxyphenyl)-2-[2-(quinolin-2-yl)ethyl]phthalazin-1(2H)-one | 426/2.22 |
| 152 | 8-(3,5-Fimethoxyphenyl)-2-[2-(quinolin-2-yl)ethyl]phthalazin-1(2H)-one | 438/2.21 |
| 153 | 8-(2,5-Difluorophenyl)-2-[2-(quinolin-2-yl)ethyl]phthalazin-1(2H)-one | 414/2.23 |

| EX. | Name | LC-MS: m/e (M + H)+/ R_t [min] |
|---|---|---|
| 154 | 8-(3-Fluoro-4-methoxyphenyl)-2-[2-(quinolin-2-yl)ethyl]phthalazin-1(2H)-one | 426/2.20 |
| 155 | 8-(2-Fluoro-3-methoxyphenyl)-2-[2-(quinolin-2-yl)ethyl]phthalazin-1(2H)-one | 426/2.19 |
| 156 | 8-(3,5-Difluorophenyl)-2-[2-(quinolin-2-yl)ethyl]phthalazin-1(2H)-one | 414/2.06 |
| 157 | 8-(3-Fluoro-5-methoxyphenyl)-2-[2-(quinolin-2-yl)ethyl]phthalazin-1(2H)-one | 426/2.25 |
| 158 | 8-(Naphthalen-2-yl)-2-[2-(quinolin-2-yl)ethyl]phthalazin-1(2H)-one | 428/2.35 |
| 159 | 8-Phenyl-2-[2-(quinolin-2-yl)ethyl]phthalazin-1(2H)-one | 378/2.21 |
| 160 | 8-(1-Benzofuran-2-yl)-2-[2-(quinolin-2-yl)ethyl]phthalazin-1(2H)-one | 418/2.29 |
| 161 | 8-(1-Methyl-1H-pyrazol-5-yl)-2-[2-(quinolin-2-yl)ethyl]phthalazin-1(2H)-one hydrochloride | 382/1.90 |
| 162 | 8-(4,5-Difluoro-2-methoxyphenyl)-2-[2-(quinolin-2-yl)ethyl]phthalazin-1(2H)-one | 434 |
| 163 | 8-(2-Fluoro-4-methylphenyl)-2-[2-(quinolin-2-yl)ethyl]phthalazin-1(2H)-one | 410/2.28 |
| 164 | 8-(2-Fluoro-5-methoxyphenyl)-2-[2-(quinolin-2-yl)ethyl]phthalazin-1(2H)-one | 442 |

Example 165: 2-[2-(Imidazo[1,2-a]pyridin-2-yl)ethyl]-8-(pyridin-3-yl)phthalazin-1(2H)-one

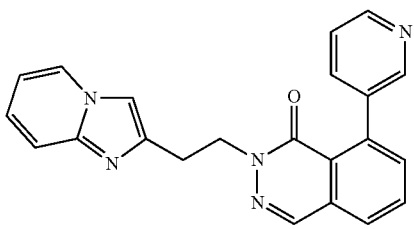 [SMILES: O=c1c2c(-c3cccnc3)cccc2cnn1CCc1cn2ccccc2n1]

165.1 8-Chloro-2-(2-imidazo[1,2-a]pyridin-2-yl)ethyl]phthalazin-1(2H)-one

To a solution of triphenylphosphine (5.81 g, 22.15 mmol) in THF (150 mL), DIAD (7.54 mL, 38.8 mmol) was added at 0° C. After stirring for 15 min, 2-(imidazo[1,2-a]pyridin-2-yl)ethanol from Example a4 (2.00 g, 11.07 mmol) was added. After another 15 min, 8-chlorophthalazin-1(2H)-one from Example 98.3 (1.80 g, 11.07 mmol) was added. The mixture was stirred overnight at room temperature. LC-MS indicated complete conversion to the product. 1 N HCl was added (pH=4). The mixture was extracted with EtOAc, the EtOAc layers were discarded. The aqueous layer was neutralized by aq.NaHCO3 and extracted with ethyl acetate. The combined organic layers were washed with brine, dried over Na2SO4, filtered, and concentrated under reduced pressure. The crude title product was recrystallized from ethyl acetate to give 3.1 g (yield: 86%) of a bright beige solid.

165.2 2-[2-(Imidazo[1,2-a]pyridin-2-yl)ethyl]-8-(pyridin-3-yl)phthalazin-1(2H)-one A reaction tube was charged with 8-chloro-2-(2-imidazo[1,2-a]pyridin-2-yl)ethyl]phthalazin-1(2H)-one (80 mg, 0.246 mmol) and a mixture of 1.5 mL of ethanol and 1.5 mL of toluene under argon. To this suspension, pyridin-3-ylboronic acid (30.3 mg, 0.246 mmol) and Na2CO3 (39.2 mg, 0.369 mmol) were added. Then, tetrakis-(triphenylphoshine)palladium (28.5 mg, 0.025 mmol) was added. The reaction mixture was heated in a Biotage microwave at about 130° C. for about 30 min. The reaction was monitored by TLC (DCM/methanol=9:1). After completion of the reaction, EA was added followed by the addition of 1 N HCl. The mixture was extracted twice with EtOAc. The aqueous layer was basified with 2N NaOH and extracted three times with ethyl acetate. The combined organic layers were washed with brine, dried over MgSO4, filtered, and concentrated under reduced pressure. The crude product was triturated from ethyl acetate to give the title compound as a white solid (12 mg, 13.26%).

LC-MS: m/e=368.1 (M+H)+

The compound of Examples 166-172 were prepared in analogy to the method described in Example 165.2.

| EX. | Name | LC-MS: m/e (M + H)+ |
|---|---|---|
| 166 | 2-[2-(Imidazo[1,2-a]pyridin-2-yl)ethyl]-8-(pyridin-4-yl)phthalazin-1(2H)-one | 368.1 |
| 167 | 2-[2-(Imidazo[1,2-a]pyridin-2-yl)ethyl]-8-(3-methoxypyridin-4-yl)phthalazin-1(2H)-one | 398.1 |
| 168 | 2-[2-(Imidazo[1,2-a]pyridin-2-yl)ethyl]-8-(pyrimidin-5-yl)phthalazin-1(2H)-one | 368.8 |
| 169 | 2-[2-(Imidazo[1,2-a]pyridin-2-yl)ethyl]-8-(1-methyl-1H-pyrazol-3-yl)phthalazin-1(2H)-one | 371.1 |
| 170 | 8-(Furan-3-yl)-2-[2-(Imidazo[1,2-a]pyridin-2-yl)ethyl]phthalazin-1(2H)-one | 357.1 |
| 171 | 2-[2-(Imidazo[1,2-a]pyridin-2-yl)ethyl]-8-(2-oxo-2,3-dihydro-1H-indol-6-yl)phthalazin-1(2H)-one | 422.1 |
| 172 | 8-(3,4-Dihydro-2H-chromen-6-yl)-2-[2-(imidazo[1,2-a]pyridin-2-yl)ethyl]phthalazin-1(2H)-one | 423.2 |

Example 173: 8-(1,1-Dioxidothiomorpholin-4-yl)-2-[2-(quinolin-2-yl)ethyl]-phthalazin-1 (2H)-one

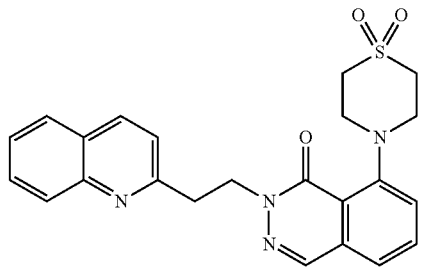 [SMILES: O=c1c2c(N3CCS(=O)(=O)CC3)cccc2cnn1CCc1ccc2ccccc2n1]

A microwave reaction vial was charged with the 8-chloro-2-(2-(quinolin-2-yl)ethyl)phthalazin-1(2H)-one from Example 98.4 (100 mg, 0.30 mmol), Cs2CO3 (194 mg, 0.59 mmol), Pd2(dba)3 (5.45 mg, 5.96 µmol) and BINAP (11.13 mg, 0.018 mmol). The solids were purged with argon for 1 h. A separate flask was charged with toluene (993 µl) and thiomorpholin 1,1-dioxide (48.3 mg, 0.36 mmol), degas with argon for 1 h and then transferred to the microwave reaction vial under inert conditions. The resulting reaction mixture was heated on microwave at 100° C. for 20 h. The reaction mixture was poured into water and extracted with DCM. The solids were removed. The organic layer was washed with water, dried over MgSO4, filtered and concentrated in vacuo. The residue was purified on a silica column (eluent: DCM/methanol) and then recrystallized from EA to afford the title product (87 mg, 67.2%).

LC-MS: m/e=435.1 (M+H)$^+$

Example 174: 2-[2-(Imidazo[1,2-a]pyridin-2-yl)ethyl]-8-(morpholin-4-yl)phthalazin-1(2H)-on

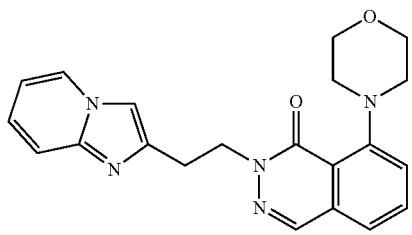 [SMILES: O=c1c2c(N3CCOCC3)cccc2cnn1CCc1cn2ccccc2n1]

A microwave reaction vial was charged with the 8-chloro-2-(2-imidazo[1,2-a]pyridin-2-yl)ethyl]phthalazin-1(2H)-one from Example 165.1 (100 mg, 0.31 mmol), Cs$_2$CO$_3$ (201 mg, 0.62 mmol), Pd$_2$(dba)$_3$ (5.64 mg, 6.16 μmol) and BINAP (11.50 mg, 0.018 mmol). The solids were purged with argon for 1 h. A separate flask was charged with toluene (993 μl) and morpholine (32.2 mg, 0.37 mmol), degas with argon for 1 h and then transferred to the microwave reaction vial under inert conditions. The resulting reaction mixture was heated on microwave at 100° C. for 20 h. The reaction mixture was poured into water and extracted with DCM. The solids were removed. The organic layer was washed with water, dried over MgSO$_4$, filtered and concentrated in vacuo. The residue was purified on a silica column (eluent: DCM/methanol) and then recrystallized from EA to afford the title product (11 mg, 9.52%).

LC-MS: m/e=376.1 (M+H)$^+$

The compound of Examples 175 to 191 were prepared in analogy to the method described in Example 174.

| EX. | Name | LC-MS: m/e (M + H)$^+$ |
|---|---|---|
| 175 | 8-(1,1-Dioxidothiomorpholin-4-yl)-2-[2-(imidazo[1,2-a]pyridin-2-yl)ethyl]phthalazin-1(2H)-one | 424.1 |
| 176 | 2-[2-(Imidazo[1,2-a]pyridin-2-yl)ethyl]-8-(tetrahydro-1H-furo[3,4-c]pyrrol-5(3H)-yl)phthalazin-1(2H)-one hydrochloride | 402.2 |
| 177 | 8-(5,5-Difluorohexahydrocyclopenta[c]pyrrol-2(1H)-yl)-2-[2-(imidazo[1,2-a]pyridin-2-yl)ethyl]phthalazin-1(2H)-one hydrochloride | 436.2 |
| 178 | 2-[2-(Imidazo[1,2-a]pyridin-2-yl)ethyl]-8-(piperazin-1-yl)phthalazin-1(2H)-one hydrochloride | 375.2 |
| 179 | 8-(4,4-Difluoropiperidin-1-yl)-2-[2-(imidazo[1,2-a]pyridin-2-yl)ethyl]phthalazin-1(2H)-one | 410.2 |
| 180 | 8-[4-(Chloromethyl)-4-(hydroxymethyl)piperidin-1-yl]-2-[2-(imidazo[1,2-a]pyridin-2-yl)ethyl]phthalazin-1(2H)-one hydrochloride | 451.9 |
| 181 | 2-[2-(Imidazo[1,2-a]pyridin-2-yl)ethyl]-8-(piperidin-1-yl)phthalazin-1(2H)-one hydrochloride | 374.2 |
| 182 | 8-(2,3-Dihydro-4H-1,4-benzoxazin-4-yl)-2-[2-(imidazo[1,2-a]pyridin-2-yl)ethyl]phthalazin-1(2H)-one hydrochloride | 424.1 |
| 183 | 2-[2-(Imidazo[1,2-a]pyridin-2-yl)ethyl]-8-[4-(trifluoromethyl)piperidin-1-yl]phthalazin-1(2H)-one hydrochloride | 442.2 |
| 184 | 2-[2-(Imidazo[1,2-a]pyridin-2-yl)ethyl]-8-(4-methylpiperazin-1-yl)phthalazin-1(2H)-one hydrochloride | 389.2 |
| 185 | 8-(1,3-Dihydro-2H-isoindol-2-yl)-2-[2-(imidazo[1,2-a]pyridin-2-yl)ethyl]phthalazin-1(2H)-one | 408.2 |
| 186 | 8-(7-Benzyl-2,7-diazaspiro[4.4]non-2-yl)-2-[2-(imidazo[1,2-a]pyridin-2-yl)ethyl]phthalazin-1(2H)-one hydrochloride | 505.3 |
| 187 | 8-({[(3aR,4S,6aS)-2-benzyloctahydrocyclopenta[c]pyrrol-4-yl]methyl}amino)-2-[2-(imidazo[1,2-a]pyridin-2-yl)ethyl]phthalazin-1(2H)-one hydrochloride | 519.3 |
| 188 | tert-butyl (3R)-3-({3-[2-(imidazo[1,2-a]pyridin-2-yl)ethyl]-4-oxo-3,4-dihydrophthalazin-5-yl}amino)pyrrolidine-1-carboxylate | 475.2 |
| 189 | 8-(2,6-Dimethylmorpholin-4-yl)-2-[2-(imidazo[1,2-a]pyridin-2-yl)ethyl]phthalazin-1(2H)-one hydrochloride | 404.2 |
| 190 | 2-[2-(Imidazo[1,2-a]pyridin-2-yl)ethyl]-8-(1,4-oxazepan-4-yl)phthalazin-1(2H)-one hydrochloride | 390.2 |
| 191 | tert-Butyl 4-{3-[2-(imidazo[1,2-a]pyridin-2-yl)ethyl]-4-oxo-3,4-dihydrophthalazin-5-yl}-3,6-dihydropyridine-1(2H)-carboxylate | 472.2 |

II.3 Preparation of Compounds of the Formula I in which A is A$^1$, X$^1$ is N and X$^3$ is —C(R$^9$)═C(R$^8$)— with R$^9$ being Y$^3$-Cyc$^3$ Example 192: 5-(Pyridin-4-yl)-2-[2-(quinolin-2-yl)ethyl]phthalazin-1(2H)-one hydrochloride

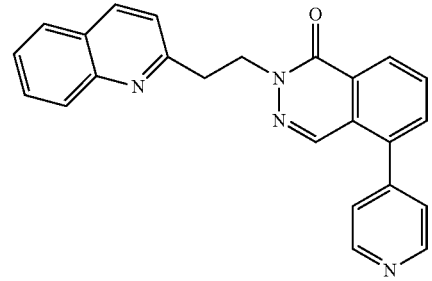 [SMILES: O=c1c2cccc(-c3ccncc3)c2cnn1CCc1ccc2ccccc2n1]

192.1 4-Bromo-3-hydroxy-3H-isobenzofuran-1-one

To a stirred solution of n-butyllithium 1.6 M in hexanes (17.5 mL, 28.1 mmol) was added at −20° C. under argon 2,2,6,6-tetramethylpiperidine (4.7 mL, 28.1 mmol) in anhydrous THF (40 mL). After cooling (−50° C.), 3-bromobenzoic acid (2.54 g, 12.8 mmol) in anhydrous THF (10 mL) was added dropwise and the mixture was stirred for 1 h. The mixture was then treated with an excess of DMF (3.7 g, 50.4 mmol). The resulting solution was allowed to warm up to ambient temperature, after which water was added. The aqueous layer was washed with diethyl ether, and then acidified with 4M HCl. The mixture was diluted with diethyl ether and the organic layer was separated and dried with MgSO$_4$. The residue was purified by crystallization using with EtOAc/PE to give the crude title product (1.18 g, yield: 41%).

LC-MS: m/e=229 (M+H)$^+$; R$_t$=1.47 min.

192.2 5-Bromo-2H-phthalazin-1-one

The compound from Example 192.1 (1 g, 4.4 mmol) was suspended in 5 mL acetic acid under nitrogen. The resulting thick slurry was heated to 90° C. At approximately 80° C., a homogeneous solution was obtained. Hydrazine monohydrate (64%, 0.66 mL, 13.2 mmol) was added dropwise (exotherm), keeping the internal temperature between 90 and 93° C. over approximately 4 h. The resulting suspension was continued to stir at 90° C. as the conversion of starting material was monitored by LC (<1%). Water (10 mL) preheated to 80° C. was added, maintaining the mixture at 80-90° C. followed by cooling down to 20° C. over approximately 2 h time. At this point, the resulting suspension was transferred onto a filter. The filter cake was rinsed with water (10 mL*3). The wet product was air-dried overnight to afford the title product (570 mg, Yield: 58%).

LC-MS: m/e=227 (M+H)$^+$; R$_t$=1.65 min, $^1$H NMR (400 MHz, DMSO-d6): δ 12.94 (s, 1H), 8.41 (s, 1H), 8.25-8.19 (m, 2H), 7.77-7.73 (m, 1H).

192.3 5-Bromo-2-[2-(quinolin-2-yl)ethyl]phthalazin-1(2H)-one

To a mixture of PPh$_3$ (699 mg, 2.67 mmol) in THF (50 mL) and DIAD (198 mg, 0.98 mmol), 5-bromo-2H-phthalazin-1-one (300 mg, 1.33 mmol) and then 2-quinolin-2-yl-ethanol from example a1 (254 mg, 1.46 mmol) were added dropwise at 15° C. under nitrogen. The mixture was stirred at room temperature overnight. Water was added and the mixture was extracted with EtOAc. The organic phase was washed with HCl (1 N). The aqueous phase was basified and extracted with DCM. The organic phase was washed with a NaHCO$_3$-solution, dried over Na$_2$SO$_4$, filtered and concentrated. The crude product was recrystallized from EA and dried to give the title compound as bright beige solid (300 mg, 59.2% yield).

192.4 5-(Pyridin-4-yl)-2-[2-(quinolin-2-yl)ethyl]phthalazin-1(2H)-one hydrochloride A reaction tube was charged with a solution of 5-bromo-2-[2-(quinolin-2-yl)ethyl]phthalazin-1(2H)-one (70 mg, 0.184 mmol) in 1.5 mL of ethanol and 1.5 mL of toluene under argon. To this suspension, pyridin-4-ylboronic acid (22.63 mg, 0.184 mmol) and a 2M solution of Na$_2$CO$_3$ (39.2 mg, 0.369 mmol) were added. Then, tetrakis-(triphenylphoshine)palladium (21.27 mg, 0.018 mmol) was added. The reaction mixture was heated in a Biotage microwave at about 130° C. for about 30 min. The reaction was monitored by TLC (DCM/methanol=9:1). After completion of the reaction, EA was added followed by the addition of 1 N HCl. The mixture was extracted twice with EtOAc. The organic layer was basified with NaHCO$_3$ and extracted with brine. The organic layers were dried over MgSO$_4$, filtered, and concentrated under reduced pressure. The crude product was dissolved in isopropanol. Isopropanol containing HCl was added. The precipitate was sucked off and recrystallized from hot isopropanol to give a bright gray solid (55 mg, 72.0%).

LC-MS: m/e=379.1 (M+H)$^+$

Example 193: 5-(Pyrimidin-5-yl)-2-[2-(quinolin-2-yl)ethyl]phthalazin-1(2H)-one hydrochloride The title compound was prepared in analogy to the method described in Example 192. LC-MS: m/e=380.1 (M+H)$^+$

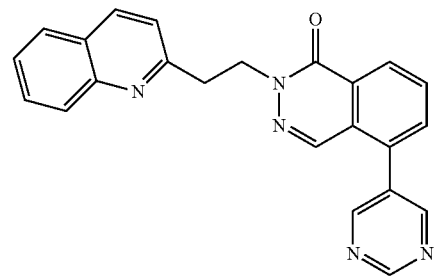 [SMILES: O=c1c2cccc(-c3cncnc3)c2cnn1CCc1ccc2ccccc2n1]

Example 194: 5-(1-Methyl-H-pyrazol-5-yl)-2-[2-(quinolin-2-yl)ethyl]phthalazin-1(2H)-one

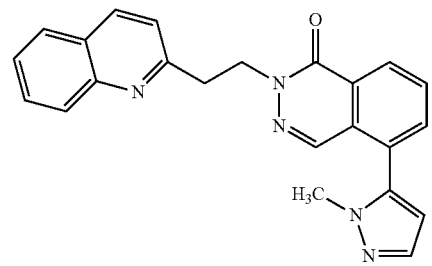 [SMILES: Cn1nccc1-c1cccc2c(=O)n(CCc3ccc4ccccc4n3)ncc12]

The title compound was prepared in analogy to the method described in Example 192. LC-MS: m/e=382.2 (M+H)$^+$

Example 195: 5-(1,1-Dioxidothiomorpholin-4-yl)-2-[2-(quinolin-2-yl)ethyl]phthalazin-1(2H)-one

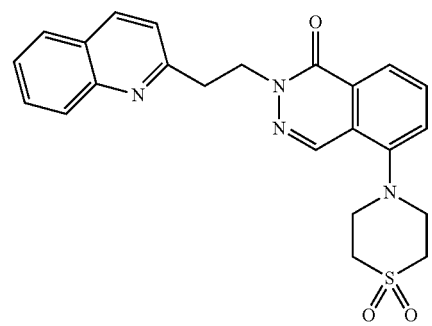 [SMILES: O=c1c2cccc(N3CCS(=O)(=O)CC3)c2cnn1CCc1ccc2ccccc2n1]

The title compound was prepared in analogy to the method described in Example 173 but using 5-bromo-2-[2-(quinolin-2-yl)ethyl]phthalazin-1(2H)-one instead of 8-chloro-2-(2-(quinolin-2-yl)ethyl)phthalazin-1(2H)-one. LC-MS: m/e=435.1 (M+H)$^+$.

Example 196: 2-[2-(Imidazo[1,2-a]pyridin-2-yl)ethyl]-5-(pyridin-3-yl)phthalazin-1(2H)-one

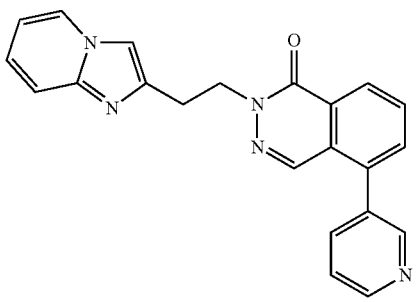 [SMILES: O=c1c2cccc(-c3cccnc3)c2cnn1CCc1cn2ccccc2n1]

196.1 5-Bromo-2-[2-(imidazo[1,2-a]pyridin-2-yl)ethyl]phthalazin-1(2H)-one

The title compound was prepared in analogy to the method described in Example 192.3 but using 2-(imidazo[1,2-a]pyridin-2-yl)ethanol from Example a4. Yield: 84%.

196.2 2-[2-(Imidazo[1,2-a]pyridin-2-yl)ethyl]-5-(pyridin-3-yl)phthalazin-1 (2H)-one The title compound was prepared in analogy to the method described in Example 192.4 but using 5-bromo-2-[2-(imidazo[1,2-a]pyridin-2-yl)ethyl]phthalazin-1(2H)-one. LC-MS: m/e=368.1 (M+H)$^+$

Example 197: 2-[2-(Imidazo[1,2-a]pyridin-2-yl)ethyl]-5-(pyrimidin-5-yl)phthalazin1(2H)-on

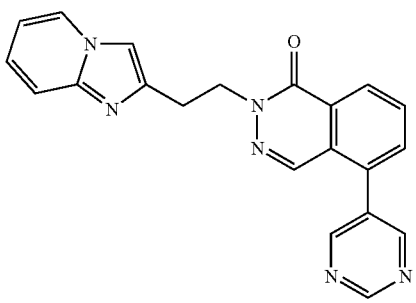 [SMILES: O=c1c2cccc(-c3cncnc3)c2cnn1CCc1cn2ccccc2n1]

The title compound was prepared in analogy to the method described in Example 196 but using 5-(4,4,5,5-tetramethyl-1,3,2-dioxoborolan-2-yl)pyrimidine. Yield: 73.9%. LC-MS: m/e=368.8 (M+H)$^+$

Example 198: 2-[2-(Imidazo[1,2-a]pyridin-2-yl)ethyl]-5-(morpholin-4-yl)phthalazin-1(2H)-one hydrochloride

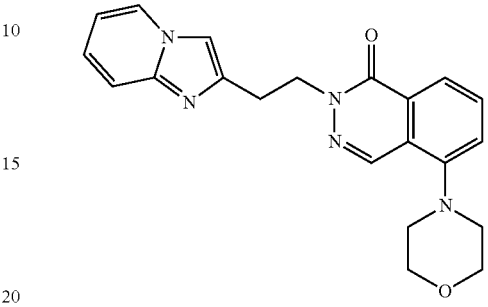

The title compound was prepared in analogy to the method described in Example 174 but using 5-bromo-2-[2-(imidazo[1,2-a]pyridin-2-yl)ethyl]phthalazin-1(2H)-one from Example 196.1 instead of 8-chloro-2-(2-imidazo[1,2-a]pyridin-2-yl)ethyl]phthalazin-1(2H)-one. Yield: 2.1%. LC-MS: m/e=376.2 (M+H)$^+$

Example 199: 2-[2-(Imidazo[1,2-a]pyridin-2-yl)ethyl]-5-(tetrahydro-1H-furo[3,4-c]pyrrol-5(3H)-yl)phthalazin-1(2H)-one hydrochloride

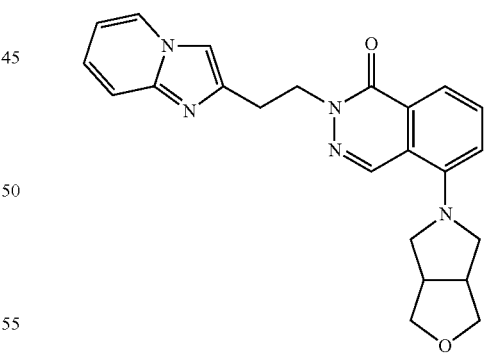

The title compound was prepared in analogy to the method described in Example 176 but using 5-bromo-2-[2-(imidazo[1,2-a]pyridin-2-yl)ethyl]phthalazin-1(2H)-one from Example 196.1 instead of 8-chloro-2-(2-imidazo[1,2-a]pyridin-2-yl)ethyl]phthalazin-1(2H)-one. Yield: 11.8%. LC-MS: m/e=402.2 (M+H)$^+$ II.4 Preparation of Compounds of the Formula I in which A is A¹, X¹ is N, X² is C—R⁷ with R⁷ being Y²-Cyc² and X³ is —C(R⁹)=C(R⁸)—

Example 200: 2-[2-(Imidazo[1,2-a]pyridin-2-yl) ethyl]-4-(pyrimidin-5-yl)phthalazin-1(2H)-one

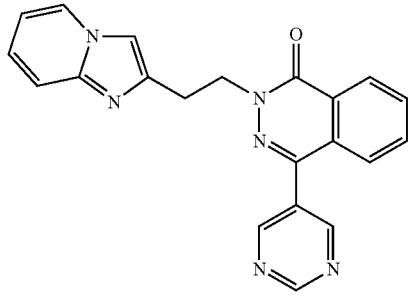 [SMILES: O=c1c2ccccc2c(-c2cncnc2)nn1CCc1cn2ccccc2n1]

200.1 4-Bromo-2-[2-(imidazo[1,2-a]pyridin-2-yl) ethyl]-phthalazin-1 (2H)-one

To a solution of triphenylphosphine (1165 mg, 4.44 mmol) in THF (60 mL), DIAD (1.5 mL, 7.78 mmol) was added at 0° C. under nitrogen. After stirring for 30 min, 4-bromophthalazin-1(2H)-1-one (0.5 g, 2.22 mmol) was added. After further stirring, 2-(2-imidazo[1,2-a]pyridin-2-ethanol from Example a4 (396 mg, 2.44 mmol) was added. The mixture was stirred for 12 h at room temperature. LC-MS indicated complete conversion to the product. EA and water were added. The organic phase was washed with 1 N HCl. The EtOAc layers were discarded. The aqueous layer was neutralized by aq.NaHCO₃ and extracted with ethyl acetate. The combined organic layers were washed with brine, dried over MgSO₄, filtered, and concentrated under reduced pressure. The crude title product was recrystallized from diisopropyl ether/EA (1:1) to give 710 mg (yield: 87%) of a white solid.

200.2 2-[2-(Imidazo[1,2-a]pyridin-2-yl)ethyl]-4-(pyrimidin-5-yl)phthalazin-1 (2H)-one The title compound was prepared in analogy to the method described in Example 168 but using 4-bromo-2-[2-(imidazo[1,2-a]pyridin-2-yl)ethyl]-phthalazin-1 (2H)-one. Yield: 35.1%. LC-MS: m/e=369.1 (M+H)⁺

Example 201: 2-[2-(Imidazo[1,2-a]pyridin-2-yl) ethyl]-4-(morpholin-4-yl)phthalazin-1(2H)-one The title compound was prepared in analogy to the method described in Example 198 but using 4-bromo-2-[2-(imidazo[1,2-a]pyridin-2-yl)ethyl]-phthalazin-1 (2H)-one. Yield: 48.2%. LC-MS: m/e=376.2 (M+H)⁺

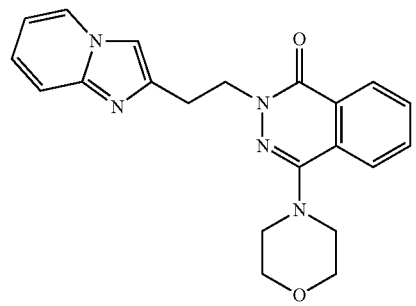 [SMILES: O=c1c2ccccc2c(N2CCOCC2)nn1CCc1cn2ccccc2n1]

II.5 Preparation of Compounds of the Formula I in which A is A¹, X¹ is CH, R¹ is Y¹-Cyc¹ and X³ is S Example 202: 3-(3-Methoxypyridin-4-yl)-5-[2-(quinolin-2-yl)ethyl]thieno[3,2-c]pyridin-4(5H)-one

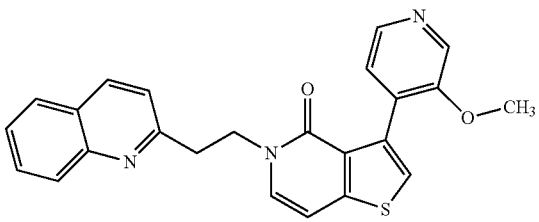 [SMILES: COc1cnccc1-c1csc2ccn(CCc3ccc4ccccc4n3)c(=O)c12]

202.1 (E)-3-(4-Bromothiophen-2-yl)acrylic acid

Piperidine (1.036 mL, 10.47 mmol) was added to a mixture of 4-bromothiophene-2-carbaldehyde (20 g, 105 mmol) and malonic acid (13.07 g, 126 mmol) at 80° C. under nitrogen atmosphere. The reaction mixture was stirred for 2 h at 100° C. The reaction mixture was cooled to room temperature and extracted with EA/water. The organic phase was washed with 2N NaOH. The aqueous phase was acidified and a precipitate was formed. The solid was stirred in a mixture of DCM and diisopropyl ether (1:1). The solid was sucked off and dried under reduced pressure to give a bright beige solid (12.3 g, 50.4%).

202.2 (E)-3-(4-Bromothiophen-2-yl)acryloyl azide

To a solution of (E)-3-(4-bromothiophen-2-yl)acrylic acid (9.30 g, 39.9 mmol) in acetone (100 mL), triethylamine (4.24 g, 41.9 mmol) was added under nitrogen atmosphere. At 0° C., isobutyl chloroformate (5.72 g, 41.9 mmol) was slowly added and then, the mixture was stirred for 1 h. 4.67 g (71.8 mmol) of sodium azide dissolved in 10 mL of water was slowly added at 0° C., the mixture was stirred at 0° C. for a further hour and then warmed up to room temperature overnight. The reaction mixture was extracted with EA/water. The organic phase was washed aq. NaHCO₃ solution and then with brine. The organic phase was dried over MgSO₄, concentrated to dryness and the residue was purified by trituration with diisopropyl ether to afford a bright beige solid (9.00 g, 34.9 mmol). Yield: 87%.

202.3 3-Bromothieno[3,2-c]pyridin-4(5H)-one 100 mL of diphenyl ether were warmed to 210° C. and then a solution of (E)-3-(4-bromothiophen-2-yl)acryloyl azide (9.95 g, 38.6 mmol) in 50 mL of diphenyl ether was added under nitrogen. The reaction mixture was held at this temperature for 15 min. After cooling to room temperature, the reaction mixture was diluted with 100 mL of cyclohexane. The precipitate was sucked off and dried in vacuo to give 6.6 g (yield: 74.4%) of the title compound as brown solid.

202.4 3-Bromo-5-[2-(quinolin-2-yl)ethyl]thieno[3,2-c]pyridin-4(5H)-one

The title compound was prepared in analogy to the method described in Example 192.3 but using 3-bromothieno[3,2-c]pyridin-4(5H)-one. Yield: 26.6%. As a byproduct, 3-bromo-4-(2-quinolin-2-yl)ethoxy)thieno[3,2-c]pyridine was obtained (yield: 23.3%). Using a Companion® chromatography system (normal phase, eluent cyclohexane/ethyl acetate), the title compound was obtained as a bright beige solid.

202.5 3-(3-Methoxypyridin-4-yl)-5-[2-(quinolin-2-yl)ethyl]thieno[3,2-c]pyridin-4(5H)-one A reaction tube was charged with a solution of 3-bromo-5-[2-(quinolin-2-yl)ethyl]thieno[3,2-c]pyridin-4(5H)-on (100 mg, 0.260 mmol) in 1.5 mL of ethanol and 1.5 mL of toluene under argon. To this suspension, 3-methoxypyridin-4-ylboronic acid (39.7 mg, 0.260 mmol) and a 2M solution of $Na_2CO_3$ (41.3 mg, 0.389 mmol) were added. Then, tetrakis(triphenylphoshine)palladium (30.0 mg, 0.026 mmol) was added. The reaction mixture was heated in a Biotage microwave at about 130° C. for about 30 min. The reaction was monitored by TLC (DCM/methanol=9:1). After completion of the reaction, EA was added followed by the addition of 1 N HCl. The mixture was extracted twice with EtOAc. The organic layer was basified with $NaHCO_3$ and extracted with brine. The organic layers were dried over $MgSO_4$, filtered, and concentrated under reduced pressure. The crude product was dissolved in isopropanol. Isopropanol containing HCl was added. The precipitate was sucked off and recrystallized from hot ethyl acetate to give a white solid (32 mg, 29.8%).
LC-MS: m/e=414.1 (M+H)$^+$

Example 203: 3-(3-Hydroxypyridin-4-yl)-5-[2-(quinolin-2-yl)ethyl]thieno[3,2-c]pyridin-4(5H)-one hydrochloride

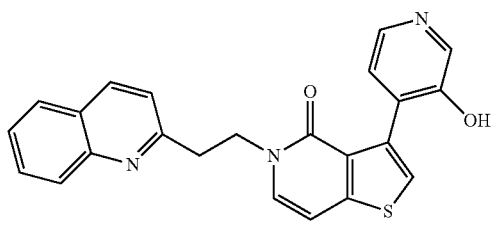 [SMILES: O=c1c2c(-c3ccncc3O)csc2ccn1CCc1ccc2ccccc2n1]

To 3-(3-methoxypyridin-4-yl)-5-[2-(quinolin-2-yl)ethyl]thieno[3,2-c]pyridin-4(5H)-one (50.0 mg, 0.121 mmol) in DCM (20 mL) was added 1M BBr$_3$ in DCM (0.363 mmol, 91 mg). The reaction mixture was stirred for 2 h under nitrogen. The reaction mixture was poured onto water and basified with 1N NaOH, extracted with DCM and dried. The organic phase was concentrated to dryness and the residue was purified by column chromatography (normal phase) on silica using DCM/methanol to give the title compound (13 mg, 0.030 mmol).
LC-MS: m/e=400.1 (M+H)$^+$ The compounds of Example 204 to 210 were prepared in analogy to the method described above.

| EX. | Name | LC-MS: m/e (M + H)$^+$ |
|---|---|---|
| 204 | 3-(1-Methyl-1H-pyrazol-5-yl)-5-[2-(quinolin-2-yl)ethyl]thieno[3,2-c]pyridin-4(5)H-one hydrochloride | 387.1 |
| 205 | 3-(Pyridin-4-yl)-5-[2-(quinolin-2-yl)ethyl]thieno[3,2-c]pyridin-4(5H)-one hydrochloride | 384.1 |
| 206 | 3-(Pyrimidin-5-yl)-5-(2-quinolin-2-yl)ethyl)thieno[3,2-c]pyridin-4(5H)-one | 385.1 |
| 207 | 3-(2-Oxoindolin-6-yl)-5-[2-(quinolin-2-yl)ethyl]thieno[3,2-c]pyridin-4(5H)-one | 438.1 |
| 208 | 3-(3-Hydroxyphenyl)-5-[2-(quinolin-2-yl)ethyl]thieno[3,2-c]pyridin-4(5H)-one hydrochloride | 399.1 |
| 209 | 5-[2-(5-Ethylpyridin-2-yl)ethyl]-3-(pyridin-4-yl)thieno[3,2-c]pyridin-4(5H)-one hydrochloride | 362.1 |
| 210 | 5-[2-(Imidazo[1,2-a]pyridin-2-yl)ethyl]-3-(pyridin-4-yl)thieno[3,2-c]pyridin-4(5H)-one hydrochloride | 373.1 |

Example 211: 3-(Morpholin-4-yl)-5-[2-(quinolin-2-yl)ethyl]thieno[3,2-c]pyridin-4(5H)-one hydrochloride

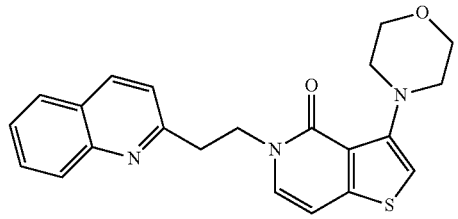 [SMILES: O=c1c2c(N3CCOCC3)csc2ccn1CCc1ccc2ccccc2n1]

211.1 3-Morpholinothieno[3,2-c]pyridin-4(5H)-one

3-Bromothieno[3,2-c]pyridin-4(5H)-one from Example 202.3 (411 mg, 1.786 mmol) and morpholine 81501 mg, 17.23 mmol) were stirred in a microwave for 3 h at 220° C. The mixture was poured onto water and extracted with DCM. The organic phase was concentrated and the residue was recrystallized from EA to give 180 mg (yield: 42.6%) of the title compound.

211.2 3-(Morpholin-4-yl)-5-[2-(quinolin-2-yl)ethyl]thieno[3,2-c]pyridin-4(5H)-one hydrochloride The title compound was prepared in analogy to the method described in Example 1.6 but using THF as solvent. Yield: 20.5%. LC-MS: m/e=392.1 (M+H)$^+$

Example 212: tert-Butyl-4-(4-oxo-5-(2-quinolin-2-yl)ethyl)-4,5-dihydrothieno[3,2-c]pyridin-3-yl)-5,6-dihydropyridine-1(2H) carboxylate The title compound was prepared in analogy to the method described in Example 202.5.

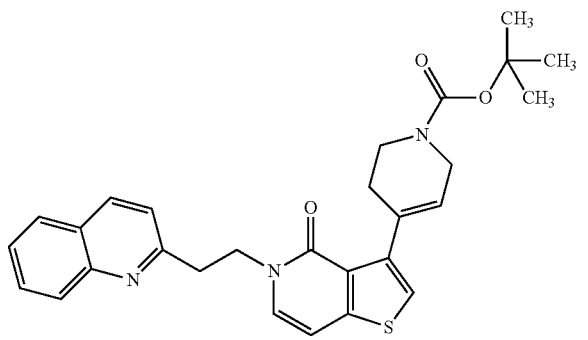 [SMILES: CC(C)(C)OC(=O)N1CC=C(c2csc3ccn(CCc4ccc5ccccc5n4)c(=O)c23)CC1]

Example 213: 5-(2-(Quinolin-2-yl)ethyl)-3-(1,2,3,6-tetrahydropyridin-4-yl)thieno[3,2-c]pyridin-4(5H)-one hydrochloride

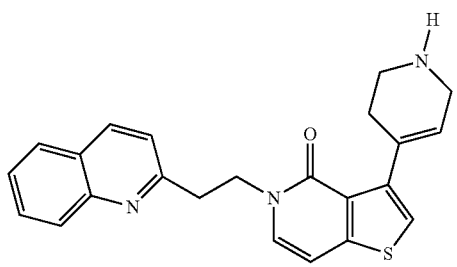 [SMILES: O=c1c2c(C3=CCNCC3)csc2ccn1CCc1ccc2ccccc2n1]

Tert-butyl-4-(4-oxo-5-(2-quinolin-2-yl)ethyl)-4,5-dihydrothieno[3,2-c]pyridin-3-yl)-5,6-dihydropyridine-1(2H) carboxylate from Example 212 (120 mg, 0.246 mmol) in 1 mL of HCl containing isopropanol was stirred under nitrogen for 12 h at room temperature. The reaction mixture was extracted with DCM, the aqueous phase was basified with 1N NaOH and extracted with DCM. The organic phase was dried, concentrated and the residue was recrystallized from HCl-isopropanol to give the title compound as hydrochloride salt as yellow solid (90 mg, 86%).
LC-MS: m/e=388.1 (M+H)$^+$ Example 214: tert-Butyl-4-(4-oxo-5-(2-quinolin-2-yl)ethyl)-4,5-dihydrothieno[3,2-c]pyridin-3-yl)-piperidine-1 carboxylate

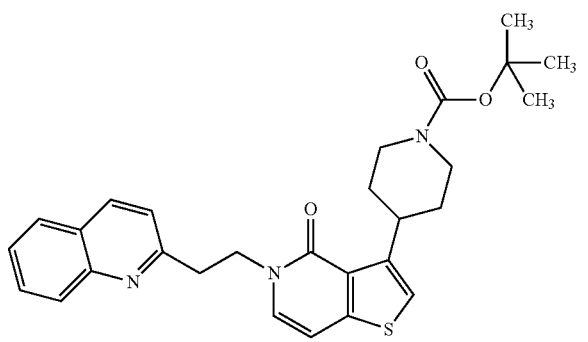 [SMILES: CC(C)(C)OC(=O)N1CCC(c2csc3ccn(CCc4ccc5ccccc5n4)c(=O)c23)CC1]

The title compound was prepared in analogy to the method described in Example 202.5

Example 215: 3-(Piperidin-4-yl)-5-[2-(quinolin-2-yl)ethyl]thieno[3,2-c]pyridin-4(5H)-one trifluoroacetate

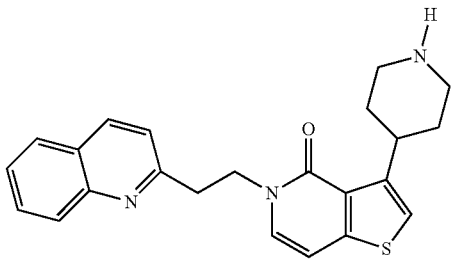 [SMILES: O=c1c2c(C3CCNCC3)csc2ccn1CCc1ccc2ccccc2n1]

Route a)
Under nitrogen, 5-(2-(quinolin-2-yl)ethyl)-3-(1,2,3,6-tetrahydropyridin-4-yl)thieno[3,2-c]pyridin-4(5H)-one hydrochloride from Example 213 (80 mg, 0.189 mmol) in methanol (15 mL) was hydrogenated at room temperature for 12 h. The title compound was obtained as 2,2,2-trifluoroacetate salt a bright beige solid (4.1 mg, 4.32%).
LC-MS: m/e=390.2 (M+H)$^+$
Route b)
The title compound was prepared in analogy to the method described in Example 213 starting from tert-butyl-4-(4-oxo-5-(2-quinolin-2-yl)ethyl)-4,5-dihydrothieno[3,2-c]pyridin-3-yl)-piperidine-1 carboxylate from Example 214.
LC-MS: m/e=390.2 (M+H)$^+$ II.6 Preparation of Compounds of the Formula I in which A is A$^1$, X$^1$ is CH, R$^7$ is Y$^2$-Cyc$^2$ and X$^3$ is S Example 216: 3-Methyl-7-(pyridin-4-yl)-5-(2-(quinolin-2-yl)ethyl)thieno[3,2-c]pyridin-4(5H)-one

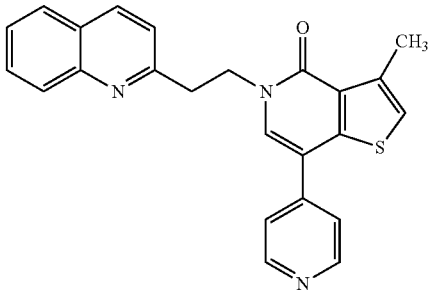 [SMILES: Cc1csc2c(-c3ccncc3)cn(CCc3ccc4ccccc4n3)c(=O)c12]

216.1 7-Iodo-3-methyl-5-(2-quinolin-2-yl)ethyl) thieno[3,2-c]pyridin-4(5)H-one

To a mixture of triphenylphosphine (901 mg, 3.44 mmol) and DIAD (1.2 mL, 6.01 mmol) in THF (10 mL), 7-iodo-3-methyl-thieno[3,2-c]pyridin-4(5)H-one (500 mg, 1.72 mmol) was added followed by the addition of 2-(quinolin-2-yl)ethanol from example a1 (327 mg, 1.89 mmol) at 15° C. under nitrogen. The mixture was stirred overnight at room temperature. The mixture was extracted with EtOAc/H$_2$O, the EtOAc layers were washed with 1N HCl and then discharged. The aqueous layer was neutralized by aq.NaHCO$_3$ and extracted with ethyl acetate. The combined organic layers were washed with brine, dried over MgSO$_4$, filtered, and concentrated under reduced pressure. The crude title product was recrystallized from ethyl acetate to give the title compound as bright beige solid (yield: 14.35%). LC-MS: m/e=447.0 (M+H)$^+$; R$_t$: 2.11 min.

216.2 3-Methyl-7-(pyridin-4-yl)-5-(2-(quinolin-2-yl)ethyl)thieno[3,2-c]pyridin-4(5H)-one The title compound was prepared in analogy to the method described in Example 165.2 but using 7-iodo-3-methyl-5-(2-quinolin-2-yl)ethyl)thieno[3,2-c]pyridin-4(5)H-one (0.22 mmol) and pyridin-4-ylboronic acid (0.22 mmol). The title compound was obtained as white solid (yield: 22.9%).
LC-MS: m/e=398.1 (M+H)$^+$ II.7 Preparation of Compounds of the Formula I in which A is A$^1$, X$^1$ is N, R$^1$ is Y$^1$-Cyc$^1$ Example 217: 3-(Pyridin-4-yl)-5-[2-(5,6,7,8-tetrahydroquinolin-2-yl)ethyl]thieno[2,3-d]pyridazin-4(5H)-one hydrochloride

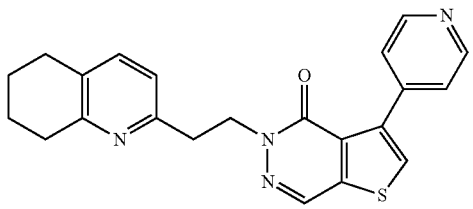 [SMILES: O=c1c2c(-c3ccncc3)csc2cnn1CCc1ccc2c(n1)CCCC2]

The title compound was prepared in analogy to the method described in Example 1.6 but starting from 3-(pyridin-4-yl)thieno[2,3-d]pyridazin-4(5H)one (obtainable by Suzuki coupling of 3-bromo-5H-thieno[2,3-d]pyridazin-4-one from Example 3.3 and pyridin-4-yl boronic acid as described above) and 2-(5,6,7,8-tetrahydroquinolin-2-yl)ethanol from example a6). The title compound was obtained as white solid.
LC-MS: m/e=389.1 (M+H)$^+$ Example 218: (R)-tert-butyl 3-(3-(2-(imidazo[1,2-a]pyridin-2-yl)ethyl)-4-oxo-3,4-dihydrophthalazin-5-ylamino)pyrrolidine-1-carboxylate

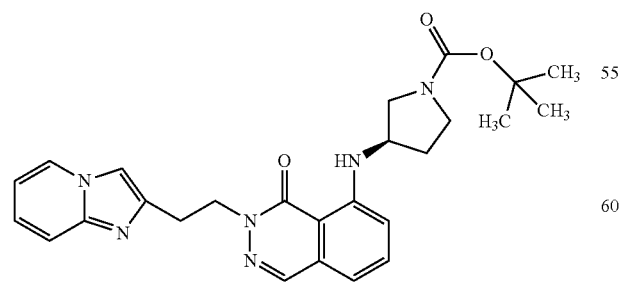

A reaction tube was charged with 8-chloro-2-(2-(imidazo[1,2-a]pyridin-2-yl)ethyl)phthalazin-1(2H)-one (155 mg, 0.48 mmol), BINAP (17.83 mg, 0.029 mmol), tris(dibenzylideneacetone)dipalladium(0) (8.74 mg, 9.55 μmol) and cesium carbonate (311 mg, 0.955 mmol) in 1591 μl of toluene. The mixture was stirred for 1 h under argon. To this mixture, (R)-tert-butyl 3-aminopyrrolidine-1-carboxylate (89 mg, 0.477 mmol) was added. The reaction mixture was heated in a microwave at 105° C. for 20 h. After completion of the reaction, the reaction mixture was extracted with water and DCM. The organic layers were washed with water, dried over MgSO$_4$, filtered, and concentrated under reduced pressure. The crude product was purified by column chromatography using a normal phase Companion® system (4 g gold, gradient elution: DCM to 10% methanol). Yield: 24.73%. LC-MS: m/e=475.2 (M+H)$^+$.

Example 219: 2-[2-(Imidazo[1,2-a]pyridin-2-yl)ethyl]-8-[(3R)-pyrrolidin-3-ylamino]phthalazin-1(2H)-one dihydrochloride

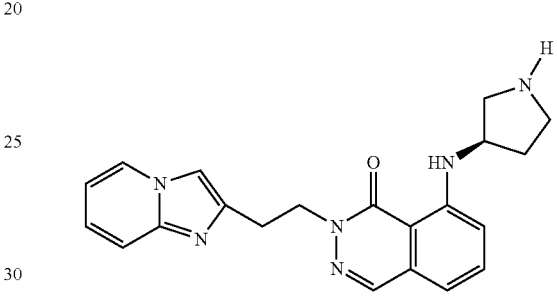

A solution of (R)-tert-butyl 3-(3-(2-(imidazo[1,2-a]pyridin-2-yl)ethyl)-4-oxo-3,4-dihydrophthalazin-5-ylamino)pyrrolidine-1-carboxylate from Example 218 (52 mg, 0.110 mmol) in 20 mL of DCM was mixed with 1 mL of HCl containing isopropanol and the reaction mixture was stirred under nitrogen for 12 h at room temperature. The reaction mixture was mixed with diisopropyl ether and the supernatant was discharged. Then, the residue was dissolved in isopropanol and diisopropyl ether was added. The supernatant was discharged. The precipitate was dried to give 24 mg of a yellow salt as solid foam. LC-MS: m/e=357.2 (M+H)$^+$ II.8 Preparation of Compounds of the Formula I in which A is A$^1$, X$^1$ is N, X$^3$ is —C(R$^9$)=C(R$^8$)— with R$^9$ being Y$^3$-Cyc$^3$ Example 220: 5-(3-hydroxyphenyl)-2-[2-(quinolin-2-yl)ethyl]phthalazin-1(2H)-one

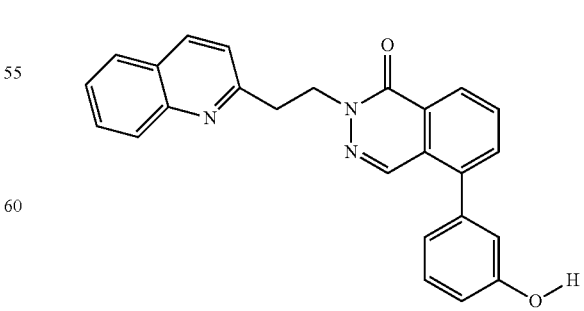

The title compound was prepared in analogy to the method described in Example 192.

II.9 Preparation of Compounds of the Formula I in which A is A³, X¹ is CH and R¹ is Y¹-Cyc¹

Example 221: (E)-8-(Pyridin-4-yl)-2-(2-(quinolin-2-yl)vinyl)isoquinolin-1(2H)-one

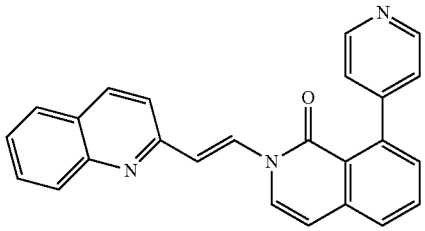 [SMILES: O=c1c2c(-c3ccncc3)cccc2ccn1/C=C/c1ccc2ccccc2n1]

221.1 8-(Pyridin-4-yl)isoquinolin-1(2H)-one

A reaction tube was charged with 8-bromoisoquinolin-1(2H)-one (1 g, 4.46 mmol) and a mixture of 3 mL of ethanol and 3 mL of toluene under argon. To this, an aqueous sodium bicarbonate solution (2 M, 710 mg, 3.35 mL, 6.69 mmol) was added and then pyridin-4-ylboronic acid (549 mg, 4.46 mmol). Then, tetrakis(triphenylphoshine)palladium (516 mg, 4.46 mmol) was added. The reaction mixture was heated in a Biotage microwave at 130° C. for 30 min. The reaction was monitored by TLC (DCM/methanol=9:1). After completion of the reaction, the reaction mixture was mixed with water and dichloromethane. The solid was sucked off. The organic phase was washed with an aqueous NaHCO₃ solution, brine, dried (MgSO₄) and evaporated. The residue was taken up with EA and the precipitate was sucked off. The crude product was purified by chromatography (Campanion normal phase, gradient elution, using 3-10% DCM in methanol) to yield 465 mg (46.9%) of the title compound.

221.2 (E)-8-(pyridin-4-yl)-2-(2-(quinolin-2-yl)vinyl)isoquinolin-1(2H)-one 8-(Pyridin-4-yl)isoquinolin-1 (2H)-one (40 mg, 0.180 mmol) and (E)-2-(2-bromovinyl)quinoline (50.6 mg, 0.216 mmol) were dissolved in 2 mL of DMF under argon. The reaction mixture was stirred for 10 h at 115° C. Then, water and EA were added. The organic phase was washed with water and brine, dried (MgSO₄) and concentrated. The crude product was purified by chromatography (CombiFlash, normal phase, gradient elution, using 3-5% DCM in methanol) to yield the title compound as yellow solid (27 mg, 40.0%). LCMS: 376.1; $R_t$=1.497.

II.10 Preparation of Compounds of the Formula I in which A is A⁴, X¹ is CH and R¹ is Y¹-Cyc¹

Example 222: anti (rac) 8-(Pyridin-4-yl)-2-(2-(quinolin-2-yl)cyclopropyl)isoquinolin-1(2H)-one

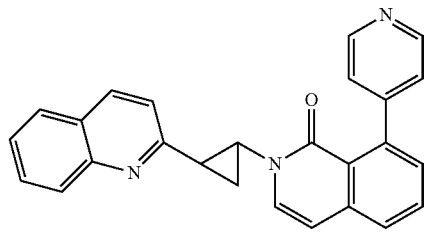 [SMILES: O=c1c2c(-c3ccncc3)cccc2ccn1C1CC1c1ccc2ccccc2n1]

8-(Pyridin-4-yl)isoquinolin-1(2H)-one (200 mg, 0.900 mmol) and syn-2-(2-bromocyclopropyl)quinoline (223 mg, 0.900 mmol) from Example c1) were dissolved in 10 mL of DMF under argon. The reaction mixture was stirred for 1 h at 115° C. Then, an aqueous solution of sodium chloride and DCM were added. The phases were separated. The organic phase was washed with brine, dried (MgSO₄) and evaporated. The crude product was taken up in a small amount of EA. The precipitate formed was sucked off and dried to yield anti (rac) 8-(pyridin-4-yl)-2-(2-(quinolin-2-yl)cyclopropyl)isoquinolin-1(2H)-one as bright beige solids (248 mg, 70.8%). LCMS: 390.2.

Separation of anti (rac) 8-(pyridin-4-yl)-2-(2-(quinolin-2-yl)cyclopropyl)isoquinolin-1(2H)-one 230 mg (0.591 mmol) of anti (rac) 8-(pyridin-4-yl)-2-(2-(quinolin-2-yl)cyclopropyl)isoquinolin-1(2H)-one dissolved in 60 µl of trifluoroacetic acid were separated by chromatography (chiral chromatography, Chiralpack AD-H, n-heptane/EtOH) to give 76 mg (33.0%) of compound 222a with positive rotation and 62 mg (27%) of compound 222b with negative rotation.

Compound 222a: (+) 8-(pyridin-4-yl)-2-(2-(quinolin-2-yl)cyclopropyl)isoquinolin-1(2H)-one

[α]=+87.8° (methanol, 1 mg/mL); yellow solid.

Compound 222b: (−) 8-(pyridin-4-yl)-2-(2-(quinolin-2-yl)cyclopropyl)isoquinolin-1(2H)-one

[α]=−98.3° (methanol, 1 mg/mL); bright yellow solid.

II.11 Preparation of Compounds of the Formula I in which A is A¹, X¹ is CH and R¹ is Y¹-Cyc¹

Example 223: 8-(Pyridin-4-yl)-2-(2-quinolin-2-yl-ethyl)isoquinolin-1(2H)-one

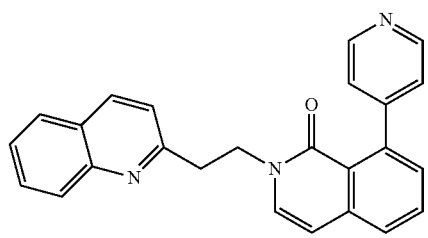 [SMILES: O=c1c2c(-c3ccncc3)cccc2ccn1CCc1ccc2ccccc2n1]

A flask was charged with 8-(pyridin-4-yl)isoquinolin-1 (2H)-one (0.113 mmol, 50 mg) in NH₃/ethanol (2 mol/L) (15 mL, 30.0 mmol). Then, Raney-Nickel in water (5 drops) was added. At room temperature, the hydrogen flow was turned on. The hydrogenation reaction was stopped after 4 days. Under nitrogen, the reaction mixture was filtered over Celite and evaporated to yield 52 mg (80% yield) of the crude title product as soli, yellow oil. The crude product was purified by Combi-flash chromatography (gradient elution using methanol/DCM up to a concentration of 10%). LC-MS: 378.2.

II.12 Preparation of Compounds of the Formula I in which A is $A^4$, $X^1$ is CH and $R^1$ is $Y^1$-$Cyc^1$ Example 224: anti (rac) 3-(Pyridin-4-yl)-5-(2-(quinolin-2-yl)cyclopropyl)thieno[3,2-c]pyridin-4(5H)-one

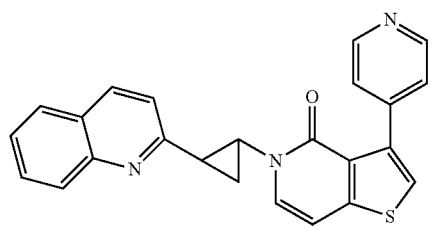 [SMILES: O=c1c2c(-c3ccncc3)csc2ccn1C1CC1c1ccc2ccccc2n1]

224.1
3-(Pyridin-4-yl)thieno[3,2-c]pyridin-4(5H)-one

3-Bromothieno[3,2-c]pyridin-4(5H)-one (1000 mg, 4.35 mmol) from Example 202.3 was suspended in 2 mL of toluene and 2 mL of ethanol under argon. Then, an aqueous solution of sodiumcarbonate (691 mg, 6.52 mmol, 2 M) was added. To the suspension, pyridin-4-boronic acid (534 mg, 4.35 mmol) and then tetrakis(triphenyl phosphine)palladium (0) (502 mg, 0.435 mmol) were added. The reaction mixture was heated in a Biotage microwave at 130° C. for 30 min. Water and EA were added. The precipitate formed was collected to give 480 mg of the title compound. The filtrate was acidified with 2 M HCl and extracted with EA (twice). The aqueous phase was basified and extracted three times with EA. The organic phases were combined, washed with HCl, dried (MgSO₄) and evaporated to give further 43 mg of the title compound. Total yield: 523 mg (52.4%). LC-MS: 229.1 [M+H]+; $R_f$: 0.427.

224.2 anti (rac) 3-(Pyridin-4-yl)-5-(2-(quinolin-2-yl)cyclopropyl)thieno[3,2-c]pyridin-4(5H)-one The title compound was prepared in analogy to the method described in Example 222. Yield: 57.7%, LC-MS: 396.1.

II.13 Preparation of Compounds of the Formula I in which A is $A^3$, $X^1$ is N and $R^1$ is $Y^1$-$Cyc^1$ Example 225: (E)-8-Pyridin-4-yl-2-((2-quinolin-2-yl-vinyl)-2H-phthalazin-1-one

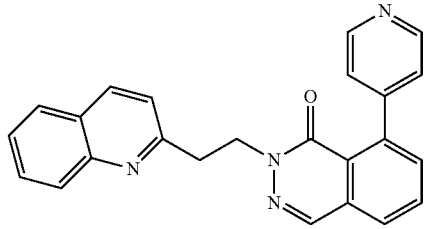 [SMILES: O=c1c2c(-c3ccncc3)cccc2cnn1CCc1ccc2ccccc2n1]

The title compound was prepared according to the general procedure given above but starting from 8-pyridin-4-yl-2H-phthalazin-1-one. Yield: 5%. LC-MS: 377.1

II.14 Preparation of Compounds of the Formula I in which A is $A^4$, $X^1$ is N and $R^1$ is $Y^1$-$Cyc^1$ Example 226: anti (rac) 8-Pyridin-4-yl-2-(2-quinolin-2-yl-cyclopropyl)-2H-phthalazin-1-one 2,2,2-trifluoroacetate

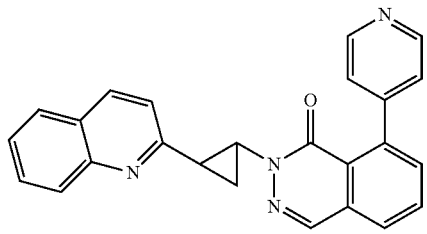 [SMILES: O=c1c2c(-c3ccncc3)cccc2cnn1C1CC1c1ccc2ccccc2n1]

Under argon, a flask was charged with (E)-8-(pyridin-4-yl)-2-(2-(quinolin-2-yl)vinyl)phthalazin-1(2H)-on (85 mg, 0.226 mmol) in dichloroethane, extra dry, (2,823 mL) at 0° C. Then, diethylzinc (1 mol/L in hexane) (1,129 mL, 1,129 mmol) was added within 5 min at −3 to 0° C. The reaction mixture was stirred for 10 min at 0° C. Diiodomethane (0.182 mL, 2,258 mmol) was added at 0° C. within 2 min. The reaction mixture was warmed to room temperature and stirred overnight at room temperature. Then, a further portion of diethyl zinc (1 mol/L in hexane) (1,129 mL, 1,129 mmol) was added at 0° C. followed by a further portion of diidomethane (0.182 mL, 2,259 mmol), and the reaction mixture was warmed to room temperature. The reaction mixture was stirred for further 3 days at room temperature. The reaction mixture was poured onto an ice-cold aqueous solution of NaHCO₃ (5%). The reaction mixture was extracted with DCM (3 times). The organic phase was washed with brine, water, dried over sodium sulfate and evaporated. Purification by prep. HPLC yielded 7.1 mg (6.23% yield) of the title compound. LC-MS: 391.1.

II.15 Preparation of Compounds of the Formula I in which A is $A^1$, $X^1$ is CH, $R^7$ is $Y^2$-$Cyc^2$ and $X^3$ is O Example 227: 7-(Pyridin-4-yl)-5-[2-(quinolin-2-yl)ethyl]furo[3,2-c]pyridin-4(5H)-one

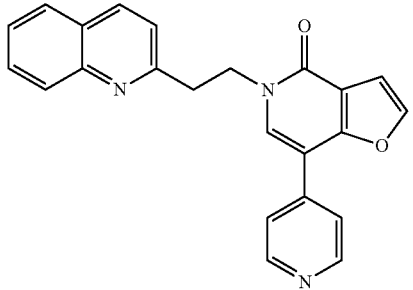 [SMILES: O=c1c2ccoc2c(-c2ccncc2)cn1CCc1ccc2ccccc2n1]

227.1 7-Bromo-5-(2-(quinolin-2-yl)ethyl)furo[3,2-c]pyridin-4(5H)-one

DIAD (4.91 mmol, 992 mg) was added dropwise to $PPh_3$ (753 mg, 2.80 mmol) in 20 mL of THF. The mixture was stirred for 30 min. Then 7-bromofuro[3,2-c]pyridine-4(5H)-one (300 mg, 1.402 mmol) was added followed by the addition of 2-(quinolin-2-yl)ethanol (243 mg, 1.402 mmol). The reaction mixture was stirred overnight at room temperature. The reaction mixture was extracted with water/ethyl acetate. The organic phase was extracted with 1N HCl. The acidic aqueous phase was basified with 1N NaOH and extracted with DCM. The organic phase was extracted with water, dried over $MgSO_4$, filtered, concentrated and purified by chromatography to give the title compound as white solid (119 mg, 23%).

227.2 7-(Pyridin-4-yl)-5-[2-(quinolin-2-yl)ethyl]furo[3,2-c]pyridin-4(5H)-one

The title compound was prepared in analogy to the method described in Example 165.2 but using 7-bromo-5-(2-(quinolin-2-yl)ethyl)furo[3,2-c]pyridin-4(5H)-one (61.7 mg, 0.167 mmol) and pyridin-4-ylboronic acid (22.82 mg, 0.167 mmol). The title compound was obtained as yellowish solid (yield: 22 mg, 35.8.9%).
LC-MS: m/e=368.1 $(M+H)^+$ II.16 Preparation of Compounds of the Formula I in which A is $A^1$, $X^1$ is CH, $R^1$ is $Y^1$-$Cyc^1$ and $X^3$ is O Example 228: 3-(Pyridin-4-yl)-5-(2-(quinolin-2-yl)ethyl)furo[3,2-c]pyridin-4(5H)-one hydrochloride

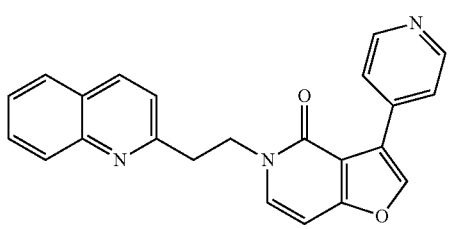 [SMILES: O=c1c2c(-c3ccncc3)coc2ccn1CCc1ccc2ccccc2n1]

228.1 (E)-3-(4-Bromofuran-2-yl)acryloyl chloride

To a solution of (E)-3-(4-bromofuran-2-yl)acrylic acid (3.8 g, 17.51 mmol) in 35 mL of trichloromethane was added a solution of 2.6 mL of thionyl chloride in 200 μL of DMF. The reaction mixture was refluxed for 1 h and after cooling to room temperature concentrated to give 4 g (97% yield) of the title compound as light brown oil.

228.2 (E)-3-(4-Bromofuran-2-yl)acryloyl azide

A solution of (E)-3-(4-bromofuran-2-yl)acryloyl chloride (4.0 g, 16.99 mmol) in 10 mL of 1,4-dioxane was added to a solution of sodium azide (2.21 g, 34.0 mmol) in 10 mL of water and 10 mL of 1,4-dioxane. The reaction mixture was stirred for 2.5 h at room temperature. The reaction mixture was mixed with ethyl acetate and water. Phases were separated and the aqueous phase was extracted with ethyl acetate (twice). The combined organic phases were washed with brine, dried, filtrated and concentrated to give 4 g of the title compound (yield: 97%).

228.3 3-Bromofuro[3,2-c]pyridin-4(5H)-one

A solution of (E)-3-(4-bromofuran-2-yl)acryloyl azide (4 g, 16.53 mmol) in 20 mL of diphenyl ether was slowly added to 80 mL of diphenyl ether at 230° C. The mixture was stirred for further 15 min. The reaction mixture was allowed to cool down to room temperature. 100 mL of cyclohexane were added and the reaction mixture was stirred overnight. A precipitate was formed, filtered off and suspended in 50 mL of cyclohexane. The mixture was stirred for 1 h at room temperature. The precipitate was filtered off to give 2.76 g (78%) of the title compound as brownish solid.
LC-MS: m/e 215.9 $(M+H)^+$ 228.4 3-(Pyridin-4-yl)furo[3,2-c]pyridin-4(5H)-one A reaction tube was charged with 3-bromofuro[3,2-c]pyridin-4(5H)-one (1000 mg, 4.67 mmol) and a mixture of 1 mL of ethanol and 1 mL of toluene under argon. To this mixture, pyridin-4-ylboronic acid (574 mg, 4.67 mmol) and a 2 M solution of $Na_2CO_3$ (743 mg, 7.01 mmol) were added followed by the addition of tetrakis-(triphenylphoshine)palladium (540 mg, 0.467 mmol). The reaction mixture was heated in a Cem microwave at about 130° C. for about 30 min. After completion of the reaction, EA was added followed by the addition of 2 N HCl. The mixture was extracted twice with EtOAc. The aqueous layer was extracted three times with ethyl acetate. The combined organic layers were washed with brine, dried over $MgSO_4$, filtered, and concentrated under reduced pressure. The crude product was purified by chromatography to give the title compound as dark yellow solid (430 mg, 43.4%).

228.5 3-(Pyridin-4-yl)-5-(2-(quinolin-2-yl)ethyl)furo[3,2-c]pyridin-4(5H)-one

To a solution of triphenylphosphine (247 mg, 0.942 mmol) in THF (10 mL), DIAD (0.321 mL, 1.65 mmol) was added. The mixture was cooled to 15° C. 3-(Pyridin-4-yl)furo[3,2-c]pyridin-4(5H)-one (100 mg, 0.471 mmol) and 2-(quinolin-2-yl)ethanol from example from example a1 were added. After stirring overnight at room temperature, EA and 2M HCl were added. The phases were separated and extracted with EA. The organic phase was washed with water. The acidic aqueous phase was basified with 2M NaOH and extracted with ethyl acetate. The combined organic layers were washed with brine, dried over MgSO$_4$, filtered, and concentrated under reduced pressure. The residue was purified by chromatography to give 69 mg of the title compound (36.3%) as hydrochloride salt as dark yellow solid.

LC-MS: m/e 368.1 (M+H)$^+$

The compounds of examples 229 to 231 were prepared in analogy to the method described in example 228.

Example 229: 5-(2-(1H-Benzo[d]imidazol-2-yl)ethyl)-3-(pyridin-4-yl)furo[3,2-c]pyridin-4(5H)-one hydrochloride

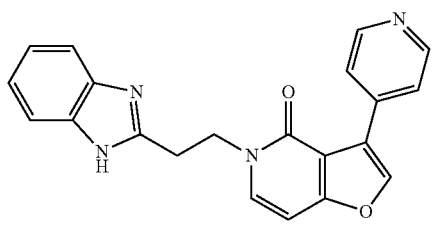 [SMILES: O=c1c2c(-c3ccncc3)coc2ccn1CCc1nc2ccccc2[nH]1]

The title compound was obtained as grey solid (Yield: 3.46%).
LC-MS: m/e 357.1 (M+H)$^+$ Example 230: 5-(2-(Imidazo[1,2-a]pyridin-2-yl)ethyl)-3-(pyridin-4-yl)furo[3,2-c]pyridin-4(5H)-one hydrochloride

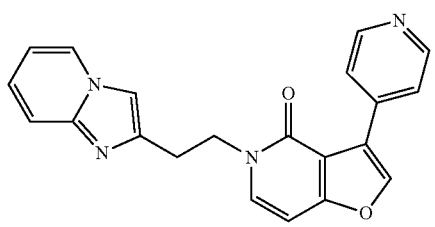 [SMILES: O=c1c2c(-c3ccncc3)coc2ccn1CCc1cn2ccccc2n1]

The title compound was obtained as grey solid (Yield: 30.3%)
LC-MS: m/e 357.1 (M+H)$^+$ Example 231: 3-(Pyrimidin-5-yl)-5-(2-(quinolin-2-yl)ethyl)furo[3,2-c]pyridin-4(5H)-one

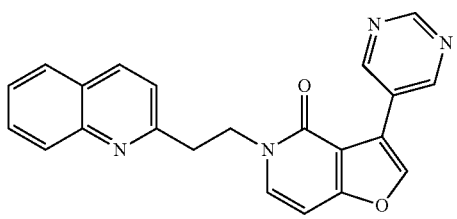 [SMILES: O=c1c2c(-c3cncnc3)coc2ccn1CCc1ccc2ccccc2n1]

The title compound was obtained as bright yellow solid (Yield: 28.1.3%)
LC-MS: m/e 369.1 (M+H)$^+$ II.17 Preparation of Compounds of the Formula I in which A is A$^4$, X$^1$ is CH, R$^1$ is Y$^1$-Cyc$^1$ and X$^3$ is O Example 232: anti 3-(Pyridazin-4-yl)-5-(2-(quinolin-2-yl)cyclopropyl)furo[3,2-c]pyridin-4(5H)-one

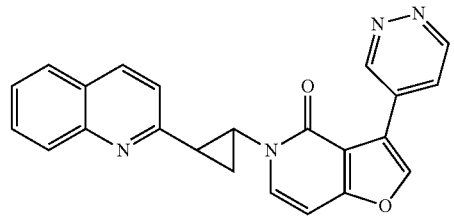 [SMILES: O=c1c2c(-c3ccnnc3)coc2ccn1C1CC1c1ccc2ccccc2n1]

232.1 anti 3-Bromo-5-(2-(quinolin-2-yl)cyclopropyl)furo[3,2-c]pyridin-4(5H)-one

A microwave reaction tube was charged with 3-bromo-furo[3,2-c]pyridin-4(5H)-one (300 mg, 1.402 mmol) from Example 228.3, syn 2-(2-bromocyclopropyl)quinoline (348 mg, 1.402 mmol) from example c1), cesium carbonate (913 mg, 2.80 mmol) and 5 mL of DMF. The reaction mixture was stirred for 1.5 h at 110° C. EA and water were added. The phases were separated. The aqueous phase was washed with EA (twice). The organic phases were washed with brine, dried over MgSO$_4$, filtered, and concentrated under reduced pressure. The crude product was purified by chromatography to give 450 mg (84%) of the title compound as light brown yellow solid 232.2 anti 3-(pyridazin-4-yl)-5-(2-(quinolin-2-yl)cyclopropyl)furo[3,2-c]pyridin-4(5H)-one The compound from Example 232.1 was suspended in 1 mL of toluene and 1 mL of methanol under argon. Then, an aqueous solution of sodium carbonate (41.7 mg, 0.39 mmol, 2 M) was added. To the suspension, 4-(4,4,5,5-tetramethyl-1,3,2-dioxaborolan-2-yl)pyridazine (54 mg, 0.26 mmol) and then tetrakis(triphenylphosphine)palladium(0) (30.3 mg, 0.026 mmol) were added. The reaction mixture was heated in a Biotage microwave at 130° C. for 30 min. Water and EA were added. The aqueous phase was extracted twice with EA. The organic phases were combined, washed with HCl, dried (MgSO$_4$) and evaporated. The residue was purified by chromatography to give 15.5 mg (yield: 15.53%) of the title compound as light brownish solid.
LC-MS: m/e 380.8 (M+H)$^+$ Example 233: anti 3-(pyridin-4-yl)-5-(2-(quinolin-2-yl)cyclopropyl)furo[3,2-c]pyridin-4(5H)-one

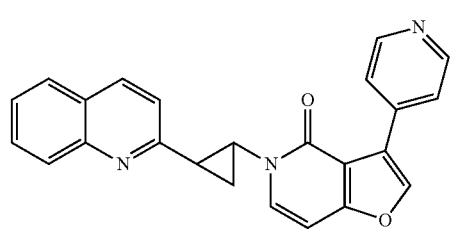 [SMILES: O=c1c2c(-c3ccncc3)coc2ccn1C1CC1c1ccc2ccccc2n1]

The title compound was prepared according to the method described for example 232.2. The title compound was obtained as yellow solid. LC-MS: m/e 379.9 (M+H)+

II.18 Preparation of Compounds of the Formula I in which A is $A^5$, $X^1$ is N, $R^1$ is $Y^1$-$Cyc^1$ and $X^3$ is N=C($R^8$)

Example 234: 4-(Pyridin-4-yl)-6-(2-(quinolin-2-yl)allyl)pyrido[2,3-d]pyridazin-5(6H)-one

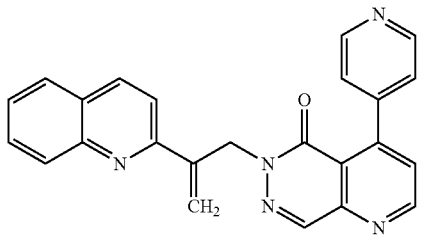 [SMILES: C=C(Cn1ncc2nccc(-c3ccncc3)c2c1=O)c1ccc2ccccc2n1]

234.1 (E)-Ethyl 2-((2-acetylhydrazono)methyl)-4-chloronicotinate

To 2.1 g (9.83 mmol) of ethyl 4-chloro-2-formylnicotinate in 60 mL of ethanol was added 0.874 g (11.80 mmol) of acetohydrazide at room temperature. Then, the reaction mixture was heated under reflux for 2 h. The reaction mixture was extracted with water/DCM. The organic phase was washed with brine, dried, filtrated and concentrated to give 1.95 g (73.6%) of the title compound as white solid.

234.2 4-Chloropyrido[3,2-d]pyridazin-5(6H)-one (E)-ethyl 2-((2-acetylhydrazono)methyl)-4-chloronicotinate (2850 mg, 10.57 mmol) in 15 mL of dioxane was mixed with aq. NaOH (42.3 mg, 1.06 mmol, 2 M). The reaction mixture was stirred in a microwave for 60 min at 145° C. After cooling to room temperature, the solid was filtered off. The solid was dissolved in methanol and the residue was filtered off. The filtrate was concentrated and triturated with EA to give 1.4 g (73.0%) of the title compound as orange brown solid.

234.3 4-(Pyridin-4-yl)pyrido[3,2-d]pyridazin-5(6H)-one

A reaction tube was charged with a solution of 4-chloropyrido[3,2-d]pyridazin-5(6H)-one (0.354 mmol) in 1 mL of ethanol and 1 mL of toluene under argon. To this suspension, a 2M solution of Na₂CO₃ (0.531 mmol) and pyridin-4-ylboronic acid (0.354 mmol) were added. Then, tetrakis(triphenylphoshine)palladium (0.035 mmol) was added. The reaction mixture was heated in a CEM microwave at about 130° C. for about 20 min. The reaction was monitored by TLC (DCM/methanol=9:1). After completion of the reaction, EA was added followed by the addition of water. The organic layer was basified with NaHCO₃. The organic layers were dried over MgSO₄, filtered, and concentrated under reduced pressure. The crude product was purified by column chromatography (25.2%).

234.4 4-(Pyridin-4-yl)-6-(2-(quinolin-2-yl)allyl)pyrido[2,3-d]pyridazin-5(6H)-one A reaction tube was charged with 307 mg (1.369 mmol) of 4-(pyridin-4-yl)pyrido[2,3-d]pyridazin-5(6H)-one, syn-2-(2-bromocyclopropyl)quinoline from example c1 and cesium carbonate (892 mg, 2.74 mmol). The reaction mixture was heated for 6 h at 110° C. under argon. After cooling to room temperature, EA was added followed by the addition of water. The organic layer was basified with NaHCO₃. The organic layers were dried over MgSO₄, filtered, and concentrated under reduced pressure. The crude product was purified by column chromatography to give 106 mg of the title compound (yield: 19.78%).

II.19 Preparation of Compounds of the Formula I in which A is $A^4$

Example 235: anti 8-(Oxetan-3-ylamino)-2-(2-(quinolin-2-yl)cyclopropyl)isoquinolin-1(2H)-one

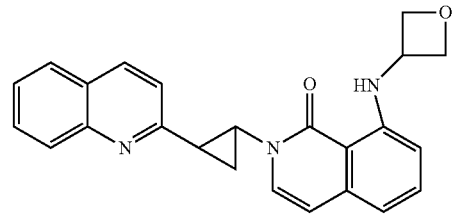 [SMILES: O=c1c2c(NC3COC3)cccc2ccn1C1CC1c1ccc2ccccc2n1]

235.1 anti 8-bromo-2-(2-(quinolin-2-yl)cyclopropyl)isoquinolin-1(2H)-one 8-bromoisoquinolin-1(2H)-one (300 mg, 1.339 mmol) and syn-2-(2-bromocyclopropyl)quinoline (332 mg, 1.339 mmol) from Example c1 were dissolved in 4 mL of DMF under argon. Cesium carbonate (873 mg, 2.68 mmol) was added. The reaction mixture was stirred for 1 h at 115° C. Then, an aqueous solution of sodium chloride and DCM were added. The phases were separated. The organic phase was washed with brine, dried (MgSO₄) and evaporated. The crude product was taken up in a small amount of EA. The precipitate formed was sucked off and dried to yield anti 8-bromo-2-(2-(quinolin-2-yl)cyclopropyl)isoquinolin-1(2H)-one as bright beige solid (330 mg, 63.0%). LC-MS: 391.0 (M+); $R_t$: 1.6 min.

Separation of anti 8-bromo-2-(2-(quinolin-2-yl)cyclopropyl)isoquinolin-1(2H)-one 33 g of anti 8-bromo-2-(2-(quinolin-2-yl)cyclopropyl)isoquinolin-1(2H)-one were suspended in isopropyl acetate/heptane 1:4 (5 mL/g). The racemate was separated by chiral chromatography to give 16.1 g of anti (+) 8-bromo-2-(2-(quinolin-2-yl)cyclopropyl)isoquinolin-1(2H)-one (compound 235.1a) $R_t$=4.885 min and 20.25 g of anti (−) 8-bromo-2-(2-(quinolin-2-yl)cyclopropyl)isoquinolin-1(2H)-one (compound 235.1b), $R_t$=9.253 min.

235.2 anti 8-(oxetan-3-ylamino)-2-(2-(quinolin-2-yl)cyclopropyl)isoquinolin-1(2H)-one A microwave reaction vial was charged with the anti 8-bromo-2-(2-(quinolin-2-yl)cyclopropyl)isoquinolin-1

(2H)-one from Example 235.1 (70 mg, 0.18 mmol), Cs$_2$CO$_3$ (175 mg, 0.54 mmol), Pd$_2$(dba)$_3$ (3.28 mg, 3.58 μmol) and BINAP (6.68 mg, 10.73 μmol). The solids were purged with argon for 1 h. A separate flask was charged with toluene (2 mL) and oxetan-3-amine (19.6 mg, 0.18 mmol), degas with argon for 1 h and then transferred to the microwave reaction vial under inert conditions. The resulting reaction mixture was heated on microwave at 105° C. for 48 h. The reaction mixture was poured into water and extracted with DCM. The solids were removed. The organic layer was washed with water, dried over MgSO$_4$, filtered and concentrated in vacuo. The residue was purified on a silica column (eluent: DCM/methanol) and then triturated with EA to afford the title product (35 mg, 51.0%).

LC-MS: m/e=384.2 (M+H)$^+$.

Separation of anti 8-(oxetan-3-ylamino)-2-(2-(quinolin-2-yl)cyclopropyl)isoquinolin-1(2H)-one 484 mg (0.591 mmol) of anti 8-(oxetan-3-ylamino)-2-(2-(quinolin-2-yl)cyclopropyl)isoquinolin-1(2H)-one dissolved in 20 mL of ethanol-DCM (1:1 mixture) and 1 mL of the solution were chromatographed on a Whelk-O (R,R) 2×25 cm (10 mkm particles) column in EtOH (containing 0.1% n-propylamine) at 40 mL/min and 254 nm detection. Peaks obtained were concentrated to give first-eluting compound 235a (220 mg, chiral purity 98.6%) and second-eluting compound 235b (230 mg, chiral purity 97.3%), recovery ~93%.

Compound 235a: (+) anti 8-(oxetan-3-ylamino)-2-(2-(quinolin-2-yl)cyclopropyl)isoquinolin-1(2H)-one Compound 235b: (−) anti 8-(oxetan-3-ylamino)-2-(2-(quinolin-2-yl)cyclopropyl)isoquinolin-1(2H)-one.

Example 236: anti (−) 8-(pyridazin-4-yl)-2-(2-(quinolin-2-yl)cyclopropyl)isoquinolin-1(2H)-one The title compound was prepared according to the method described in example 232.2 starting from anti (−) 8-bromo-2-(2-(quinolin-2-yl)cyclopropyl)isoquinolin-1(2H)-one (compound 235.1b). LC-MS: m/e=391.2 (M+H)$^+$.

Example 237: anti (−) 8-(6-fluoropyridin-3-yl)-2-(2-(quinolin-2-yl)cyclopropyl)isoquinolin-1(2H)-one The title compound was prepared according to the method described in example 232 starting from anti (−) 8-bromo-2-(2-(quinolin-2-yl)cyclopropyl)isoquinolin-1(2H)-one (compound 235.1 b) and 2-fluoro-5-(4,4,5,5-tetramethyl-1,3,2-dioxaborolan-2-yl)pyridine. LC-MS: m/e=408.2 (M+H)$^+$

[α]=−107° (methanol)

Example 238: anti (−) 8-(2-fluoropyridin-4-yl)-2-(2-(quinolin-2-yl)cyclopropyl)isoquinolin-1(2H)-one The title compound was prepared according to the method described in example 232 starting from anti (−) 8-bromo-2-(2-(quinolin-2-yl)cyclopropyl)isoquinolin-1(2H)-one (compound 235.1b) and 2-fluoropyridin-4-ylboronic acid.

LC-MS: m/e=408.2 (M+H)$^+$

Example 239: anti 8-(pyridin-3-yl)-2-(2-(quinolin-2-yl)cyclopropyl)isoquinolin-1(2H)-one hydrochloride

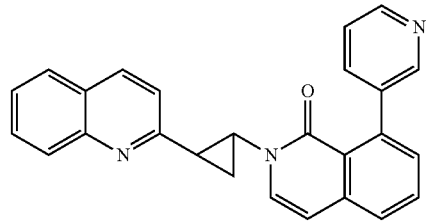 [SMILES: O=c1c2c(-c3cccnc3)cccc2ccn1C1CC1c1ccc2ccccc2n1]

The title compound was prepared according to the method described in example 232 starting from anti 8-bromo-2-(2-(quinolin-2-yl)cyclopropyl)isoquinolin-1(2H)-one and pyridin-3-ylboronic acid. LC-MS: m/e=390.1 (M+H)$^+$ Separation of anti 8-(pyridin-3-yl)-2-(2-(quinolin-2-yl)cyclopropyl)isoquinolin-1(2H)-one 320 mg of anti 8-(pyridin-3-yl)-2-(2-(quinolin-2-yl)cyclopropyl)isoquinolin-1(2H)-one were subjected to a chromatography on a Chiralpak IC column, eluent: 500 parts of n-heptane, 450 parts of DCM, 50 parts of methanol and 1 part of triethylamine to give 105 mg of compound 239a (R$_t$: 4.74 min), 98.8% ee and 120 mg of compound 239b (R$_t$: 4.68 min), 97.6% ee.

Compound 239a: (+) anti 8-(pyridin-3-yl)-2-(2-(quinolin-2-yl)cyclopropyl)isoquinolin-1(2H)-one

[α]=+108.5° (methanol)

Compound 239b: (−) anti 8-(pyridin-3-yl)-2-(2-(quinolin-2-yl)cyclopropyl)isoquinolin-1(2H)-one

[α]=−94.8° (methanol)

Example 240: anti 8-(pyrimidin-5-yl)-2-(2-(quinolin-2-yl)cyclopropyl)isoquinolin-1(2H)-one

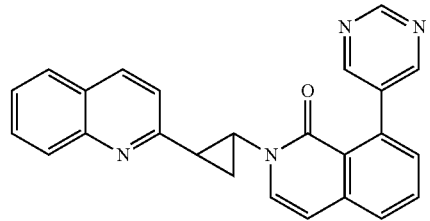 [SMILES: O=c1c2c(-c3cncnc3)cccc2ccn1C1CC1c1ccc2ccccc2n1]

The title compound was prepared according to the method described in example 232 starting from anti 8-bromo-2-(2-(quinolin-2-yl)cyclopropyl)isoquinolin-1(2H)-one and pyrimidin-5-ylboronic acid.

LC-MS: m/e=391.1 (M+H)$^+$

Separation of anti 8-(pyrimidin-5-yl)-2-(2-(quinolin-2-yl)cyclopropyl)isoquinolin-1(2H)-one 330 mg of anti 8-(pyrimidin-5-yl)-2-(2-(quinolin-2-yl)cyclopropyl)isoquinolin-1(2H)-one were subjected to a chromatography on a Chiralpak IC column, eluent: 500 parts of n-heptane, 450 parts of DCM, 50 parts of methanol and 1 part of triethylamine to give 112 mg of compound 240a (R$_f$: 9.80), 95.6% ee and 98 mg of compound 240b (R$_f$: 5.52), 81.2% ee.

Compound 240a: anti (+) 8-(pyrimidin-5-yl)-2-(2-(quinolin-2-yl)cyclopropyl)isoquinolin-1(2H)-one

[α]=+118.3° (methanol)

Compound 240b: anti (−) 8-(pyrimidin-5-yl)-2-(2-(quinolin-2-yl)cyclopropyl)isoquinolin-1(2H)-one

[α]=−120.4° (methanol)

Example 241: anti 8-(1-methyl-1H-pyrazol-4-yl)-2-(2-(quinolin-2-yl)cyclopropyl)isoquinolin-1(2H)-one

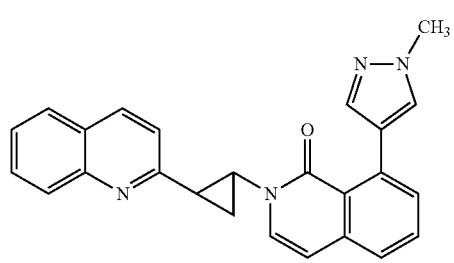 [SMILES: Cn1cc(-c2cccc3ccn(C4CC4c4ccc5ccccc5n4)c(=O)c23)cn1]

The title compound was prepared according to the method described in example 232 starting from anti 8-bromo-2-(2-(quinolin-2-yl)cyclopropyl)isoquinolin-1(2H)-one and 1-methyl-4-(4,4,5,5-tetramethyl-1,3,2-dioxaborolan-2-yl)-1H-pyrazole.

LC-MS: m/e=393.1 (M+H)$^+$

Example 242: anti 8-(3-fluoropyridin-4-yl)-2-(2-(quinolin-2-yl)cyclopropyl)isoquinolin-1(2H)-one

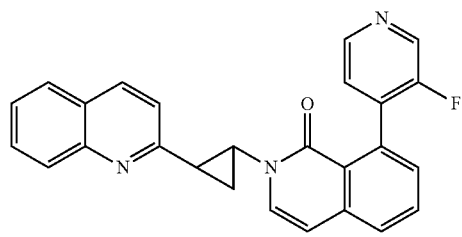 [SMILES: O=c1c2c(-c3ccncc3F)cccc2ccn1C1CC1c1ccc2ccccc2n1]

The title compound was prepared according to the method described in example 232 starting from anti 8-bromo-2-(2-(quinolin-2-yl)cyclopropyl)isoquinolin-1(2H)-one and 3-fluoro-4-(4,4,5,5-tetramethyl-1,3,2-dioxaborolan-2-yl)pyridine.

LC-MS: m/e=408.1 (M+H)$^+$

Example 243: anti 8-(2-fluoropyridin-4-yl)-2-(2-(quinolin-2-yl)cyclopropyl)isoquinolin-1(2H)-one

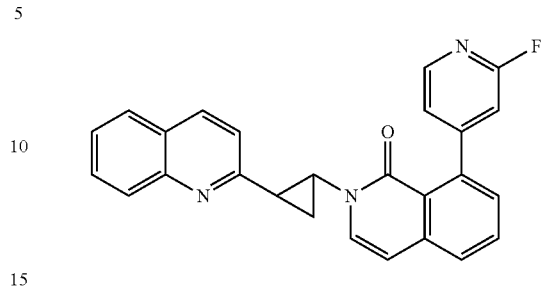

The title compound was prepared according to the method described in example 232 starting from anti 8-bromo-2-(2-(quinolin-2-yl)cyclopropyl)isoquinolin-1(2H)-one and 2-fluoropyridin-4-ylboronic acid. LC-MS: m/e=408.1 (M+H)$^+$ Example 244: anti 8-((3 S)-3-hydroxypiperidin-1-yl)-2-(2-(quinolin-2-yl)cyclopropyl)isoquinolin-1(2H)-one (2E)-but-2-enedioate

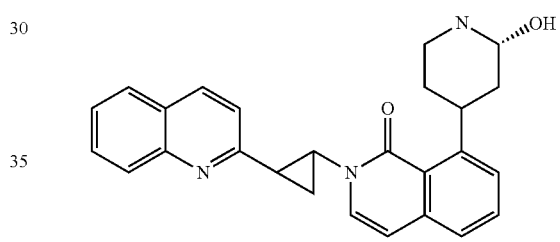

The title compound was prepared according to the method described in example 173 starting from anti 8-bromo-2-(2-(quinolin-2-yl)cyclopropyl)isoquinolin-1(2H)-one and (S)-piperidin-3-ol. The title compound was converted into the fumarate salt. LC-MS: m/e=412.2

Examples 245 to 253 were prepared in analogy to the method described in example 244.

Example 245: anti 8-(3-methoxypiperidin-1-yl)-2-(2-(quinolin-2-yl)cyclopropyl)isoquinolin-1(2H)-one (2E)-but-2-enedioate

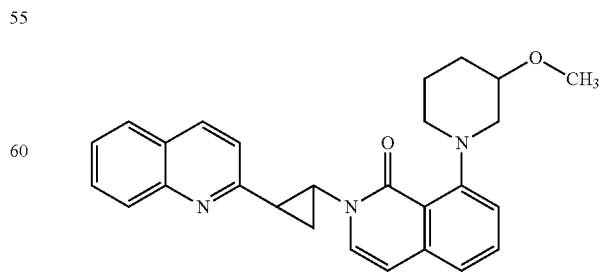

LC-MS: m/e=426.2

Example 246: anti 8-morpholino-2-(2-(quinolin-2-yl)cyclopropyl)isoquinolin-1(2H)-one

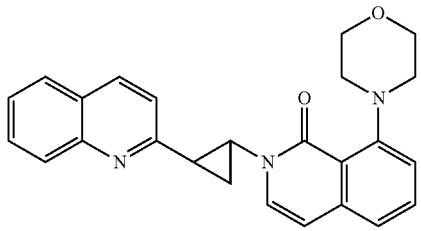 [SMILES: O=c1c2c(N3CCOCC3)cccc2ccn1C1CC1c1ccc2ccccc2n1]

LC-MS: m/e=398.2 (M+H)+

Separation of anti 8-morpholino-2-(2-(quinolin-2-yl)cyclopropyl)isoquinolin-1(2H)-one 246 mg of anti 8-morpholino-2-(2-(quinolin-2-yl)cyclopropyl)isoquinolin-1(2H)-one were subjected to a chromatography on a Chiralpak IC column, eluent: 500 parts of n-heptane, 450 parts of DCM, 50 parts of methanol and 1 part of triethylamine to give 95 mg of compound 246 a ($R_t$: 8.1), 90.2% ee and 74 mg of compound 246b ($R_t$: 9.4), 90.2% ee.

Compound 246a: anti (+) 8-morpholino-2-(2-(quinolin-2-yl)cyclopropyl)isoquinolin-1(2H)-one

[α]=+141.4° (methanol)

Compound 246b: anti (−) 8-morpholino-2-(2-(quinolin-2-yl)cyclopropyl)isoquinolin-1(2H)-one

[α]=−142.0° (methanol)

Examples 247: anti 1-(1-oxo-2-(2-(quinolin-2-yl)cyclopropyl)-1,2-dihydroisoquinolin-8-yl)piperidine-4-carbonitrile

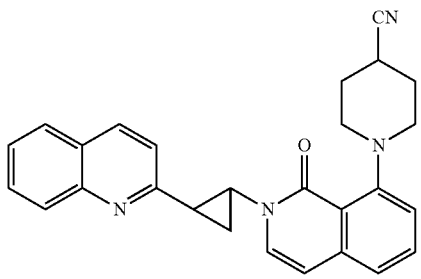 [SMILES: N#CC1CCN(c2cccc3ccn(C4CC4c4ccc5ccccc5n4)c(=O)c23)CC1]

LC-MS: m/e=421.2 (M+H)+

Example 248: anti 8-((3R,4R)-4-fluoro-3-hydroxypiperidin-1-yl)-2-(2-(quinolin-2-yl)cyclopropyl)isoquinolin-1(2H)-one

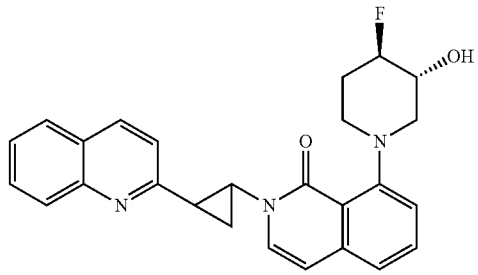 [SMILES: O=c1c2c(N3CC[C@@H](F)[C@H](O)C3)cccc2ccn1C1CC1c1ccc2ccccc2n1]

LC-MS: m/e=430.2 (M+H)+

Example 249: anti 8-((3S)-3-hydroxypyrrolidin-1-yl)-2-(2-(quinolin-2-yl)cyclopropyl)isoquinolin-1(2H)-one di[(2E)-but-2-enedioate]

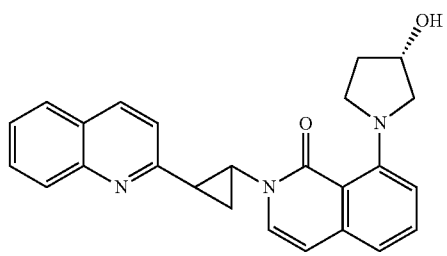 [SMILES: O=c1c2c(N3CC[C@H](O)C3)cccc2ccn1C1CC1c1ccc2ccccc2n1]

LC-MS: m/e=398.2 (M+H)+

Example 250: anti 8-((3R)-3-hydroxypyrrolidin-1-yl)-2-(2-(quinolin-2-yl)cyclopropyl)isoquinolin-1(2H)-one (2E)-but-2-enedioate

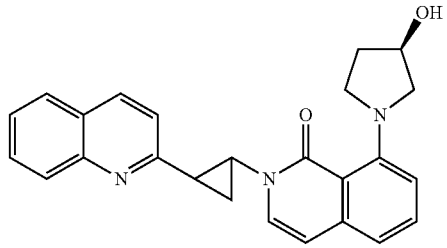 [SMILES: O=c1c2c(N3CC[C@@H](O)C3)cccc2ccn1C1CC1c1ccc2ccccc2n1]

LC-MS: m/e=398.2 (M+H)+

Example 251: anti 8-(methyl(oxetan-3-yl)amino)-2-(2-(quinolin-2-yl)cyclopropyl)isoquinolin-1(2H)-one

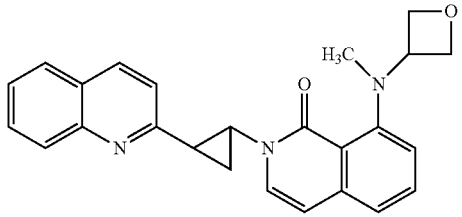 [SMILES: CN(c1cccc2ccn(C3CC3c3ccc4ccccc4n3)c(=O)c12)C1COC1]

LC-MS: m/e=398.1 (M+H)+

Example 252: anti 8-(4-methoxypiperidin-1-yl)-2-(2-(quinolin-2-yl)cyclopropyl)isoquinolin-1(2H)-one (2E)-but-2-enedioate

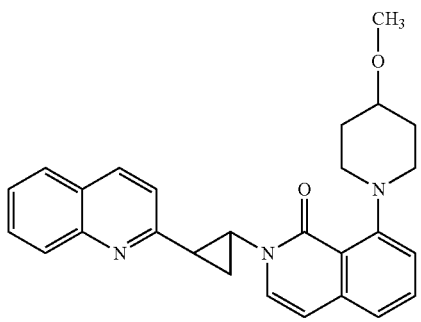 [SMILES: COC1CCN(c2cccc3ccn(C4CC4c4ccc5ccccc5n4)c(=O)c23)CC1]

LC-MS: m/e=426.2 (M+H)+

Example 253: anti 8-(4-hydroxypiperidin-1-yl)-2-(2-(quinolin-2-yl)cyclopropyl)isoquinolin-1(2H)-one (2E)-but-2-enedioate

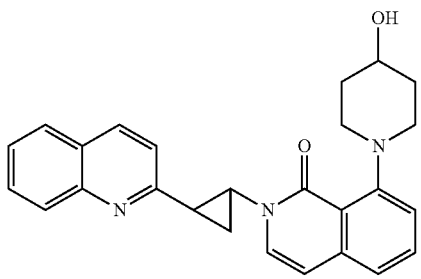 [SMILES: O=c1c2c(N3CCC(O)CC3)cccc2ccn1C1CC1c1ccc2ccccc2n1]

LC-MS: m/e=412.2 (M+H)+

Example 254: anti 8-(1-acetylpiperidin-4-ylamino)-2-(2-quinolin-2-cyclopropyl)isoquinolin-1(2H)-one

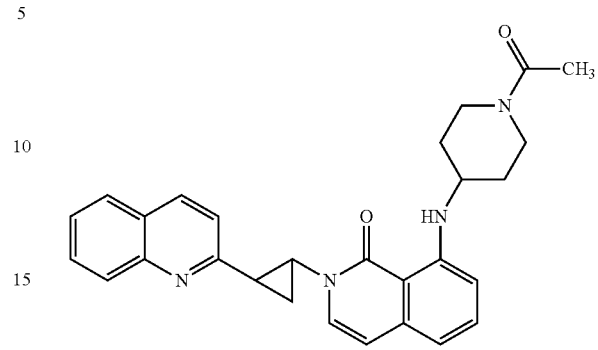

The title compound was prepared in analogy to the method described in example 235.

Example 255: anti 8-(piperidin-4-ylamino)-2-(2-(quinolin-2-yl)cyclopropyl)isoquinolin-1(2H)-one hydrochloride

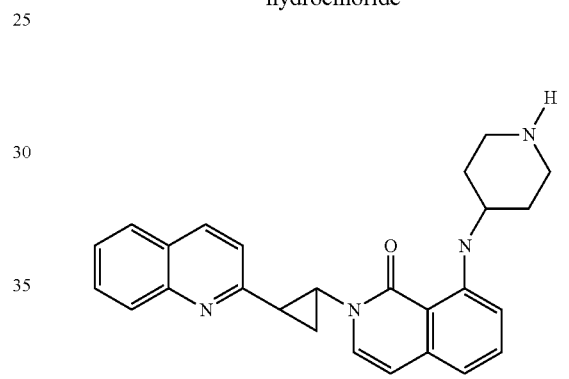

The title compound was prepared in analogy to the method described in example 213 but heating for 3 h under reflux and the solvent used was ethanol.
LC-MS: m/e=411.2 (M+H)+.

Example 256: syn 8-(pyridin-4-yl)-2-(2-(quinolin-2-yl)cyclopropyl)isoquinolin-1(2H)-one hydrochloride 256.1 8-(pyridin-4-yl)-2-(2-(quinolin-2-yl)cyclopropyl)isoquinolin-1(2H)-one The title compound was prepared as described in example 222.
LC-MS: 390.1 (M+H)+

256.2 Separation of 8-(pyridin-4-yl)-2-(2-(quinolin-2-yl)cyclopropyl)isoquinolin-1(2H)-one 2.8 g of 8-(pyridin-4-yl)-2-(2-(quinolin-2-yl)cyclopropyl)isoquinolin-1(2H)-one were dissolved in 50 mL of EA and separated by column chromatography, normal phase, eluent: DCM/methanol to give compound 222 and compound 256.
Compound 222: anti 8-(pyridin-4-yl)-2-(2-(quinolin-2-yl)cyclopropyl)isoquinolin-1(2H)-one, yield: 80%; LC-MS: 390.1 (M+H)+, $R_t$: 1.128 min
Compound 256: syn 8-(pyridin-4-yl)-2-(2-(quinolin-2-yl)cyclopropyl)isoquinolin-1(2H)-one, yield: 4.3%; LC-MS: 390.1 (M+H)+, $R_t$: 1.127 min.

Examples 257 to 275 were prepared in analogy to the methods described above.

| Ex. | Name | LC-MS: m/e (M + H)+/ [α] |
|---|---|---|
| 257 | anti 2-(2-(quinolin-2-yl)cyclopropyl)-8-(tetrahydro-2H-pyran-4-yl)isoquinolin-1(2H)-one | 397.1 |
| 258 | anti (−) 2-(2-(quinolin-2-yl)cyclopropyl)-8-(2-oxa-6-azaspiro[3.4]octan-6-yl)isoquinolin-1(2H)-one | 424.2/ [α] = −194° |
| 259 | anti (−) 8-(dihydro-1H-furo[3,4-c]pyrrol-5(3H,6H,6aH)-yl)-2-(2-(quinolin-2-yl)cyclopropyl)isoquinolin-1(2H)-one | 424.2/ [α] = −193° |
| 260 | anti (−) 8-(4,4-difluoropiperidin-1-yl)-2-(2-(quinolin-2-yl)cyclopropyl)isoquinolin-1(2H)-one | 432.2/ [α] = −162° |
| 261 | anti 8-morpholino-2-(2-(quinolin-2-yl)cyclopropyl)isoquinolin-1(2H)-one, dimethanesulfonate | 398.1 |
| 262 | anti 8-(3-(difluoromethyl)pyrrolidin-1-yl)-2-(2-(quinolin-2-yl)cyclopropyl)isoquinolin-1(2H)-one, trifluoroacetate | 432.2 |
| 263 | anti 8-((1R,5S)-3-oxa-8-azabicyclo[3.2.1]octan-8-yl)-2-(2-(quinolin-2-yl)cyclopropyl)isoquinolin-1(2H)-one | 424.2 |
| 264 | anti 8-(4-methylpiperazin-1-yl)-2-(2-(quinolin-2-yl)cyclopropyl)isoquinolin-1(2H)-one, | 411.2 |
| 265 | anti 8-(3-(fluoromethyl)pyrrolidin-1-yl)-2-(2-(quinolin-2-yl)cyclopropyl)isoquinolin-1(2H)-one, trifluoroacetate | 414.2 |
| 266 | 8-((1R,5S)-8-oxa-3-azabicyclo[3.2.1]octan-3-yl)-2-(2-(quinolin-2-yl)cyclopropyl)isoquinolin-1(2H)-one, | 424.2 |
| 267 | anti 8-(4-fluorophenyl)-2-(2-(quinolin-2-yl)cyclopropyl)isoquinolin-1(2H)-one, | 407.2 |
| 268 | anti 8-(furan-3-yl)-2-(2-(quinolin-2-yl)cyclopropyl)isoquinolin-1(2H)-one | 379.1 |
| 269 | anti 8-(4,5-dihydrofuran-3-yl)-2-(2-(quinolin-2-yl)cyclopropyl)isoquinolin-1(2H)-one | 381.2 |
| 270 | anti (−) 8-(4-methoxyphenyl)-2-(2-(quinolin-2-yl)cyclopropyl)isoquinolin-1(2H)-one | 419.2/ [α] = −68° |
| 271 | anti 2-(2-(6-fluoroquinolin-2-yl)cyclopropyl)-8-morpholinoisoquinolin-1(2H)-one | 416.2 |
| 272 | anti 2-((2-(6-fluoroquinolin-2-yl)cyclopropyl)-8-(pyridin-3-yl)isoquinolin-1(2H)-one | 408.1 |
| 273 | anti 2-(2-(6-fluoroquinolin-2-yl)cyclopropyl)-8-(pyrimidin-5-yl)isoquinolin-1(2H)-one | 409.1 |
| 274 | anti 2-((2-(6-fluoroquinolin-2-yl)cyclopropyl)-8-(pyridin-4-yl)isoquinolin-1(2H)-one | 408.1 |
| 275 | anti 4-fluoro-8-(pyridin-4-yl)-2-(2-(quinolin-2-yl)cyclopropyl)isoquinolin-1(2H)-one | 408.1 |

Example 276: anti (−)-4-chloro-8-(pyrimidin-5-yl)-2-(2-(quinolin-2-yl)cyclopropyl)isoquinolin-1(2H)-one

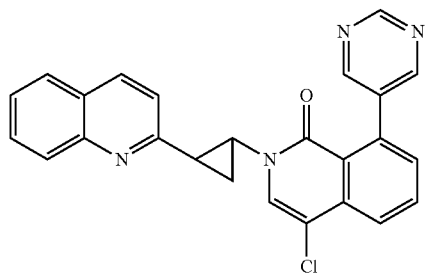 [SMILES: O=c1c2c(-c3cncnc3)cccc2c(Cl)cn1C1CC1c1ccc2ccccc2n1]

Anti (−)-8-(pyrimidin-5-yl)-2-(2-(quinolin-2-yl)cyclopropyl)isoquinolin-1(2H)-one hydrochloride from example 240b was mixed with sodium hydrogencarbonate solution and DCM. The phases were separated and the organic phase dried. Purification by column chromatography (DCM/methanol) gave the title compound (7.89% yield) as white solid. LC-MS: m/e=425.1

Example 276a: anti (−)-4-chloro-8-(pyrimidin-5-yl)-2-(2-(quinolin-2-yl)cyclopropyl)isoquinolin-1(2H)-one hydrochloride

[α]=+217.7° (methanol)

Example 277: anti 4-(pyridin-4-yl)-6-(2-(quinolin-2-yl)cyclopropyl)pyrido[2,3-d]pyridazin-5 (6H)-one

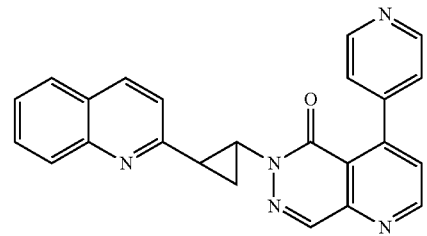 [SMILES: O=c1c2c(-c3ccncc3)ccnc2cnn1C1CC1c1ccc2ccccc2n1]

4-(pyridin-4-yl)pyrido[2,3-d]pyridazin-5(6H)-one (19 mg, 0.085 mmol) was suspended in 1 mL of DMF under argon. Then, cesium carbonate (55.2 mg, 0.169 mmol)) and syn 2-(2-bromocyclopropyl)quinoline (22.08 mg, 0,089 mmol) from example c1 were added. The reaction mixture was heated at 110° C. for 3 h min. Water and EA were added. The aqueous phase was extracted twice with EA. The organic phases were combined, washed with HCl, dried (MgSO$_4$) and evaporated. The residue was purified by chromatography to give 12 mg (yield: 36.2%) of the title compound as bright beige solid. LC-MS: m/e 392.1 (M+H)+

Examples 278 to 300 were prepared in analogy to the methods described above.

| Ex. | Name | LC-MS: m/e (M + H)+/ R$_t$ [min/[α] |
|---|---|---|
| 278 | anti 2-(2-(6-fluoroquinolin-2-yl)cyclopropyl)-8-(pyridin-4-yl)phthalazin-1(2H)-one | 409.1 |
| 279 | anti 7-fluoro-3-(pyridin-4-yl)-5-(2-(quinolin-2-yl)cyclopropyl)thieno[3,2-c]pyridin-4(5H)-one | 414.1 |
| 280 | anti 3-(2-fluoropyridin-4-yl)-5-(2-(6-fluoroquinolin-2-yl)cyclopropyl)thieno[3,2-c]pyridin-4(5H)-one | 432.1 |
| 281 | anti 5-(2-(6-fluoroquinolin-2-yl)cyclopropyl)-3-(pyridin-4-yl)thieno[3,2-c]pyridin-4(5H)-one | 414 |
| 282 | anti 3-(pyrimidin-5-yl)-5-(2-(quinolin-2-yl)cyclopropyl)thieno[3,2-c]pyridin-4(5H)-one | 397.1 |
| 282a | anti 3-(pyrimidin-5-yl)-5-(2-(quinolin-2-yl)cyclopropyl)thieno[3,2-c]pyridin-4(5H)-one, hydrochloride, enantiomer 1 | 397.1 |
| 282b | anti 3-(pyrimidin-5-yl)-5-(2-(quinolin-2-yl)cyclopropyl)thieno[3,2-c]pyridin-4(5H)-one, hydrochloride, enantiomer 2 | 397.1 |
| 283 | anti 3-(6-fluoropyridin-3-yl)-5-(2-(quinolin-2-yl)cyclopropyl)thieno[3,2-c]pyridin-4(5H)-one hydrochloride | 414.1 |
| 284 | anti 3-(2-methylpyrimidin-5-yl)-5-(2-(quinolin-2-yl)cyclopropyl)thieno[3,2-c]pyridin-4(5H)-one | 411.1 |
| 285 | anti 3-(pyridazin-4-yl)-5-(2-(quinolin-2-yl)cyclopropyl)thieno[3,2-c]pyridin-4(5H)-one | 397.1 |
| 286 | anti 3-(2-fluoropyridin-4-yl)-5-[(2-(quinolin-2-yl)cyclopropyl]thieno[3,2-c]pyridin-4(5H)-one | 414.1 |
| 287 | anti 3-(morpholin-4-yl)-5[2-(quinolin-2-yl)cyclopropyl]thieno[3,2-c]pyridin-4(5H)-one | 404.1 |

-continued

| Ex. | Name | LC-MS: m/e (M + H)+/ $R_t$ [min/[α] |
|---|---|---|
| 288 | anti 3-(pyridin-3-yl)-5-[2-(thieno[3,2-b]pyridin-5-yl)cyclopropyl]thieno[3,2-c]pyridin-4(5H)-one | 401.5 |
| 289 | anti 3-(pyridin-3-yl)-5-[2-(quinolin-2-yl)cyclopropyl]thieno[3,2-c]pyridin-4(5H)-one | 396.1 |
| 290 | anti 3-(pyrimidin-5-yl)-5-[2-(quinolin-2-yl)cyclopropyl]thieno[2,3-d]pyridazin-4(5H)-one, hydrochloride | 398.1 |
| 291 | anti 3-(pyridin-4-yl)-5-[2-(thieno[3,2-b]pyridin-5-yl)cyclopropyl]thieno[2,3-d]pyridazin-4(5H)-one | |
| 292 | anti 3-(pyridin-4-yl)-5-[2-(thieno[3,2-b]pyridin-5-yl)cyclopropyl]thieno[3,2-c]pyridin-4(5H)-one | 402.0 |
| 293 | anti 3-(pyridin-4-yl)-5-[2-(quinolin-2-yl)cyclopropyl]thieno[3,2-c]pyridin-4(5H)-one | 396.1 |
| 293a | anti (+) 3-(pyridin-4-yl)-5-[2-(quinolin-2-yl)cyclopropyl]thieno[3,2-c]pyridin-4(5H)-one | 396.1 |
| 293b | anti (−) 3-(pyridin-4-yl)-5-[2-(quinolin-2-yl)cyclopropyl]thieno[3,2-c]pyridin-4(5H)-one | 396.1/[α] = (methanol) −301.7° |
| 294 | anti 3-(pyridin-4-yl)-5-[2-(quinolin-2-yl)cyclopropyl]thieno[2,3-d]pyridazin-4(5H)-one hydrochloride | 397.1/ $R_t$ = 1.084 |
| 295 | syn 3-(pyridin-4-yl)-5-[2-(quinolin-2-yl)cyclopropyl]thieno[2,3-d]pyridazin-4(5H)-one | 397.4/ $R_t$ = 0.998 |
| 296 | anti 5-(pyrimidin-5-yl)-2-[2-(quinolin-2-yl)cyclopropyl]isoquinolin-1(2H)-one | 391.1 |
| 297 | anti 5-(pyridin-4-yl)-2-[2-(quinolin-2-yl)cyclopropyl]isoquinolin-1(2H)-one | 390.1 |
| 298 | anti 5-(pyridin-3-yl)-2-[2-(quinolin-2-yl)cyclopropyl]isoquinolin-1(2H)-one | 390.2 |
| 299 | anti 5-(morpholin-4-yl)-2-[2-(quinolin-2-yl)cyclopropyl]isoquinolin-1(2H)-one | 398.2 |
| 300 | anti (−) 4-fluoro-8-(pyrimidin-5-yl)-2-(2-(quinolin-2-yl)cyclopropyl)isoquinolin-1(2H)-one | 396.1 |

II.20 Preparation of Compounds of the Formula I in which A is $A^1$, $Y^1$-$Cyc^1$ and $X^3$ is N=C($R^9$)

Example 301: 8-(pyridin-4-yl)-2-[2-(quinolin-2-yl)ethyl]pyrido[3,4-d]pyridazin-1(2H)-one

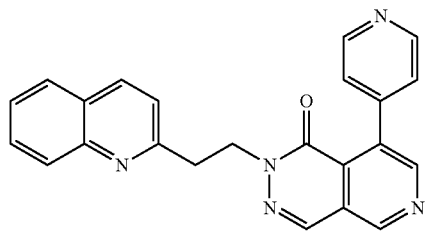 [SMILES: O=c1c2c(-c3ccncc3)cncc2cnn1CCc1ccc2ccccc2n1]

301.1 Ethyl 3-chloro-5-formylisonicotinate

To a solution of diethyl 5-chloropyridine-3,4-dicarboxylate (2.43 g, 9.43 mmol) in 100 mL of toluene was added diisobutylaluminiumhydride (2.68 g, 18.86 mL, 1 molar) in hexane at −70° C. The reaction mixture was stirred for 2 h at this temperature. The reaction mixture was poured into an 5% aqueous acetic acid solution followed by the addition of EA. The phases were separated and the organic phase was washed with aq. NaHCO$_3$ solution. The organic phase was dried and concentrated to give 2.02 g (100%) of the title compound as brown oil.

301.2 (E)-ethyl 3-((2-acetylhydrazono)methyl)-5-chloroisonicotinate

To ethyl 3-chloro-5-formylisonicotinate (2 g, 9.36 mmol) in 60 mL of ethanol was added acetohydrazide (0.832 g, 11.24 mmol) at room temperature. The reaction mixture was stirred for 2 h. Then, the reaction mixture was mixed with DCM and water. The organic phase was washed with brine, dried and concentrated. The crude title compound was purified by chromatography (eluent: DCM/methanol) to give 220 mg (8.7%) of the title compound as orange oil.

301.3 8-chloropyrido[4,3-d]pyridazin-1(2H)-one (E)-ethyl 3-((2-acetylhydrazono)methyl)-5-chloroisonicotinate (220 mg, 0.816 mmol) and aq. NaOH solution (3.26 mg, 0.082 mmol, 2 molar) in 5 mL of dioxane were stirred in a microwave at 165° C. for 60 min. Then the reaction mixture was basified by addition of aq. NaHCO$_3$ and extracted with DCM. The organic phase was washed with brine, dried and concentrated. The crude title compound was purified by chromatography (eluent: DCM/methanol) to give 25 mg (16.88%) of the title compound as beige solid.

301.4 8-chloro-2-(2-(quinolin-2-yl)ethyl)pyrido[4,3-d]pyridazin-1(2H)-one

To 69.3 mg (0.264 mmol) in THF was added diisopropylazodicarboxylate (94 mg, 0.463 mmol) in THF under ice-cooling and under nitrogen. Then, the resulting solution was stirred for 30 min at room temperature to give a suspension. 8-Chloropyrido[4,3-d]pyridazin-1(2H)-one (24 mg, 0.132 mmol) in THF and then 2-(quinolin-2-yl)ethanol (22.89 mg, 0.132 mmol) in THF were added and the reaction mixture was stirred overnight at room temperature. The total amount of THF was 60 mL. Then, the reaction mixture was mixed with DCM and water. The organic phase was washed with 1N HCl and the organic phase was discharged. The aqueous phase was basified by 1N NaOH and extracted with DCM. The organic phase was dried and concentrated to give 34 mg (76%) of the title compound as bright beige solid. LC-MS: m/e 337.1 (M+H)+.

301.5 8-(pyridin-4-yl)-2-[2-(quinolin-2-yl)ethyl]pyrido[3,4-d]pyridazin-1(2H)-one 8-chloro-2-(2-(quinolin-2-yl)ethyl)pyrido[4,3-d]pyridazin-1(2H)-one (34 mg, 0.101 mmol) was suspended in 2 mL of toluene and 2 mL of methanol under argon. Then, an aqueous solution of sodium carbonate (16.5 mg, 0.15 mmol, 2 M) was added. To the suspension, pyridin-4-boronic acid (13.79 mg, 0.101 mmol) and then tetrakis(triphenylphosphine)palladium(0) (11.67 mg, 10.10 μmol) were added. The reaction mixture was heated in a CEM microwave at 130° C. for 30 min. Water and EA were added. The organic phase was extracted with water, dried (MgSO$_4$) and evaporated. The residue was purified by chromatography (eluent: DCM/methanol) and then recrystallized from EA/diisopropyl ether (1:1) to give 2.6 mg (yield: 6.79%) of the title compound as off-white solid. LC-MS: m/e 380.1 (M+H)+

II.21 Preparation of Compounds of the Formula I in which A is $A^1$

The compounds of example 302 to 409 were prepared in analogy to the methods described above.

| Ex. | Name | LC-MS: m/e (M + H)+/ R_t[min] |
|---|---|---|
| 302 | 5-[2-(imidazo[1,2-a]pyridin-2-yl)ethyl]-7-(1-methyl-1H-imidazol-4-yl)-3-(pyridin-4-yl)thieno[2,3-d]pyridazin-4(5H)-one | 454.0/1.69 |
| 303 | 5-[2-(imidazo[1,2-a]pyridin-2-yl)ethyl]-7-(1-methyl-1H-pyrazol-4-yl)-3-(pyridin-4-yl)thieno[2,3-d]pyridazin-4(5H)-one | |
| 304 | 5-[2-(imidazo[1,2-a]pyridin-2-yl)ethyl]-7-(pyridin-3-yl)-3-(pyridin-4-yl)thieno[2,3-d]pyridazin-4(5H)-one | 451.2/1.74 |
| 305 | 5-[2-(6-chloroquinolin-2-yl)ethyl]-3-(pyridin-4-yl)thieno[3,2-c]pyridin-4(5H)-one | 418.1 |
| 306 | 5-[2-(3-methylquinolin-2-yl)ethyl]-3-(pyridin-4-yl)thieno[3,2-c]pyridin-4(5H)-one | 398.1 |
| 307 | 5-[2-(8-fluoroquinolin-2-yl)ethyl]-3-(pyridin-4-yl)thieno[3,2-c]pyridin-4(5H)-one | 402.1 |
| 308 | 5-[2-(6-fluoroquinolin-2-yl)ethyl]-3-(pyridin-3-yl)thieno[3,2-c]pyridin-4(5H)-one hydrochloride | 402.1 |
| 309 | 5-[2-(6-fluoroquinolin-2-yl)ethyl]-3-(pyridin-4-yl)thieno[3,2-c]pyridin-4(5H)-one | 402.1 |
| 310 | 5-[2-(imidazo[1,2-a]pyridin-2-yl)ethyl]-3-(pyridin-3-yl)thieno[3,2-c]pyridin-4(5H)-one | 373.3 |
| 311 | 3-(pyridin-4-yl)-5-[2-(quinoxalin-2-yl)ethyl]thieno[2,3-d]pyridazin-4(5H)-one hydrochloride | 386.1 |
| 312 | 5-[2-(1,5-naphthyridin-2-yl)ethyl]-3-(pyridin-4-yl)thieno[2,3-d]pyridazin-4(5H)-one | 386.1 |
| 313 | 5-[2-(1H-indazol-1-yl)ethyl]-3-(pyridin-4-yl)thieno[2,3-d]pyridazin-4(5H)-one | 374.1 |
| 314 | 3-(1-methyl-1H-pyrazol-3-yl)-5-[2-(quinolin-2-yl)ethyl]thieno[2,3-d]pyridazin-4(5H)-one hydrochloride | 388.1 |
| 315 | 3-(1H-pyrazol-3-yl)-5-[2-(quinolin-2-yl)ethyl]thieno[2,3-d]pyridazin-4(5H)-one | 374.1 |
| 316 | 5-[2-(1H-benzimidazol-1-yl)ethyl]-3-(pyridin-4-yl)thieno[2,3-d]pyridazin-4(5H)-one | 374.1 |
| 317 | 5-[2-(1H-benzimidazol-2-yl)ethyl]-3-(pyridin-4-yl)thieno[2,3-d]pyridazin-4(5H)-one hydrochloride | 374.1 |
| 318 | 5-[2-(6-chloroquinolin-2-yl)ethyl]-3-(pyridin-4-yl)thieno[2,3-d]pyridazin-4(5H)-one hydrochloride | 419.1 |
| 319 | 3-(pyridin-3-ylethynyl)-5-[2-(quinolin-2-yl)ethyl]thieno[2,3-d]pyridazin-4(5H)-one hydrochloride | 409.1 |
| 320 | 3-(pyridin-4-ylethynyl)-5-[2-(quinolin-2-yl)ethyl]thieno[2,3-d]pyridazin-4(5H)-one hydrochloride | 409.1 |
| 321 | 5-[2-(3,5-dimethylpyridin-2-yl)ethyl]-3-(pyridin-4-yl)thieno[2,3-d]pyridazin-4(5H)-one | 363.1 |
| 322 | 5-[2-(7-fluoroquinolin-2-yl)ethyl]-3-(pyridin-4-yl)thieno[2,3-d]pyridazin-4(5H)-one | 403.1 |
| 323 | 5-[2-(pyrazin-2-yl)ethyl]-3-(pyridin-4-yl)thieno[2,3-d]pyridazin-4(5H)-one | 336.1 |
| 324 | 2-[2-(1,6-naphthyridin-2-yl)ethyl]-8-(pyridin-4-yl)isoquinolin-1(2H)-one | 379.1 |
| 325 | 2-[2-(8-fluoroquinolin-2-yl)ethyl]-8-(pyridin-4-yl)isoquinolin-1(2H)-one | 396.1 |
| 326 | 8-(pyridin-4-yl)-2-[1-(quinolin-2-yl)propan-2-yl]isoquinolin-1(2H)-one | 392.1 |
| 327 | 2-[2-(3-methylquinolin-2-yl)ethyl]-8-(pyridin-4-yl)isoquinolin-1(2H)-one | 392.2 |
| 328 | 2-[2-(imidazo[1,2-a]pyridin-2-yl)ethyl]-8-(1H-pyrazol-3-yl)phthalazin-1(2H)-one | 357.1 |
| 329 | 8-(morpholin-4-yl)-2-[2-(quinolin-2-yl)ethyl]phthalazin-1(2H)-one hydrochloride | 387.1 |
| 330 | 2-[2-(imidazo[1,2-a]pyridin-2-yl)ethyl]-8-(1-oxa-4,9-diazaspiro[5.6]dodec-9-yl)phthalazin-1(2H)-one dihydrochloride | 459.2 |
| 331 | 2-[2-(imidazo[1,2-a]pyridin-2-yl)ethyl]-8-(2-oxa-7-azaspiro[3.5]non-7-yl)phthalazin-1(2H)-one (2E)-but-2-enedioate | |
| 332 | 8-[(3R)-3-hydroxypiperidin-1-yl]-2-[2-(imidazo[1,2-a]pyridin-2-yl)ethyl]phthalazin-1(2H)-one (2E)-but-2-enedioate (salt) | 390.2 |
| 333 | 8-[(3S)-3-hydroxypiperidin-1-yl]-2-[2-(imidazo[1,2-a]pyridin-2-yl)ethyl]phthalazin-1(2H)-one (2E)-but-2-enedioate (salt) | 390.2 |
| 334 | 2-[2-(imidazo[1,2-a]pyridin-2-yl)ethyl]-8-(2-oxa-6-azaspiro[3.3]hept-6-yl)phthalazin-1(2H)-one | 388.1 |
| 335 | 2-[2-(imidazo[1,2-a]pyridin-2-yl)ethyl]-8-(1,2-oxazolidin-2-yl)phthalazin-1(2H)-one | 362.1 |
| 336 | 8-(hexahydrocyclopenta[b][1,4]oxazin-4(4aH)-yl)-2-[2-(imidazo[1,2-a]pyridin-2-yl)ethyl]phthalazin-1(2H)-one | 416.2 |
| 337 | 2-[2-(imidazo[1,2-a]pyridin-2-yl)ethyl]-8-(tetrahydrofuran-3-yl)phthalazin-1(2H)-one | 361.2 |
| 338 | 2-[2-(imidazo[1,2-a]pyridin-2-yl)ethyl]-8-(3-oxa-8-azabicyclo[3.2.1]oct-8-yl)phthalazin-1(2H)-one | 402.2 |
| 339 | 2-[2-(imidazo[1,2-a]pyridin-2-yl)ethyl]-8-(2-oxa-6-azaspiro[3.4]oct-6-yl)phthalazin-1(2H)-one | 402.2 |
| 340 | 2-[2-(imidazo[1,2-a]pyridin-2-yl)ethyl]-8-(2,2,6,6-tetrafluoromorpholin-4-yl)phthalazin-1(2H)-one | 448.1 |
| 341 | 8-(4-hydroxypiperidin-1-yl)-2-[2-(imidazo[1,2-a]pyridin-2-yl)ethyl]phthalazin-1(2H)-one | 390.1 |
| 342 | 2-[2-(imidazo[1,2-a]pyridin-2-yl)ethyl]-8-(2-methylpyrimidin-5-yl)phthalazin-1(2H)-one | 383.2 |
| 343 | 8-(2-cyclopropylpyrimidin-5-yl)-2-[2-(imidazo[1,2-a]pyridin-2-yl)ethyl]phthalazin-1(2H)-one | 409.1 |
| 344 | 2-[2-(imidazo[1,2-a]pyridin-2-yl)ethyl]-8-(pyridazin-4-yl)phthalazin-1(2H)-one | 369.1 |
| 345 | 8-(5-fluoropyridin-3-yl)-2-[2-(imidazo[1,2-a]pyridin-2-yl)ethyl]phthalazin-1(2H)-one hydrochloride | 386.2 |
| 346 | 8-[2-(3-fluorophenyl)morpholin-4-yl]-2-[2-(imidazo[1,2-a]pyridin-2-yl)ethyl]phthalazin-1(2H)-one hydrochloride | 470.2 |
| 347 | 2-[2-(imidazo[1,2-a]pyridin-2-yl)ethyl]-8-(2-methoxypyrimidin-5-yl)phthalazin-1(2H)-one | 399.1 |
| 348 | 2-[2-(imidazo[1,2-a]pyridin-2-yl)ethyl]-8-[2-(trifluoromethyl)pyridin-4-yl]phthalazin-1(2H)-one | 436.1 |
| 349 | 2-[2-(imidazo[1,2-a]pyridin-2-yl)ethyl]-8-(8-oxa-3-azabicyclo[3.2.1]oct-3-yl)phthalazin-1(2H)-one | 402.2 |
| 350 | 2-[2-(imidazo[1,2-a]pyridin-2-yl)ethyl]-8-[2-(trifluoromethyl)morpholin-4-yl]phthalazin-1(2H)-one hydrochloride | 444.2 |
| 351 | 8-(2,2-dimethylmorpholin-4-yl)-2-[2-(imidazo[1,2-a]pyridin-2-yl)ethyl]phthalazin-1(2H)-one hydrochloride | 404.2 |
| 352 | 8-[2-(4-chlorophenyl)morpholin-4-yl]-2-[2-(imidazo[1,2-a]pyridin-2-yl)ethyl]phthalazin-1(2H)-one hydrochloride | 486.2 |
| 353 | 8-[2-(3,4-difluorophenyl)morpholin-4-yl]-2-[2-(imidazo[1,2-a]pyridin-2-yl)ethyl]phthalazin-1(2H)-one | 488.2 |
| 354 | 2-[2-(imidazo[1,2-a]pyridin-2-yl)ethyl]-8-(piperidin-4-yl)phthalazin-1(2H)-one hydrochloride | 374.2 |
| 355 | 2-[2-(imidazo[1,2-a]pyridin-2-yl)ethyl]-8-(tetrahydro-2H-pyran-4-yl)phthalazin-1(2H)-one | 375.2 |
| 356 | 8-(2,6-diazabicyclo[3.2.1]oct-6-yl)-2-[2-(imidazo[1,2-a]pyridin-2-yl)ethyl]phthalazin-1(2H)-one dihydrochloride | 401.2 |
| 357 | 8-[(1S,5S)-3,6-diazabicyclo[3.2.0]hept-3-yl]-2-[2-(imidazo[1,2-a]pyridin-2-yl)ethyl]phthalazin-1(2H)-one hydrochloride | 387.2 |
| 358 | 8-(furan-2-yl)-2-[2-(imidazo[1,2-a]pyridin-2-yl)ethyl]phthalazin-1(2H)-one hydrochloride | 357.1 |
| 359 | 2-[2-(imidazo[1,2-a]pyridin-2-yl)ethyl]-8-(1-methyl-1H-pyrazol-4-yl)phthalazin-1(2H)-one hydrochloride | 371.2 |
| 360 | 8-(hexahydropyrrolo[3,4-c]pyrrol-2(1H)-yl)-2-[2-(imidazo[1,2-a]pyridin-2-yl)ethyl]phthalazin-1(2H)-one dihydrochloride | 401.2 |
| 361 | 8-(2,7-diazaspiro[4.4]non-2-yl)-2-[2-(imidazo[1,2-a]pyridin-2-yl)ethyl]phthalazin-1(2H)-one dihydrochloride | 415.2 |
| 362 | 8-[(1S,4S)-2,5-diazabicyclo[2.2.1]hept-2-yl]-2-[2-(imidazo[1,2-a]pyridin-2-yl)ethyl]phthalazin-1(2H)-one trifluoroacetate | 387.2 |
| 363 | 8-(2,7-diazaspiro[3.5]non-7-yl)-2-[2-(imidazo[1,2-a]pyridin-2-yl)ethyl]phthalazin-1(2H)-one hydrochloride | 415.2 |

| Ex. | Name | LC-MS: m/e (M + H)+/ R$_t$[min] |
|---|---|---|
| 364 | 8-(2,6-diazaspiro[3.5]non-6-yl)-2-[2-(imidazo[1,2-a]pyridin-2-yl)ethyl]phthalazin-1(2H)-one hydrochloride | 415.2 |
| 365 | 8-(piperidin-4-yl)-2-[2-(5,6,7,8-tetrahydroimidazo[1,2-a]pyridin-2-yl)ethyl]phthalazin-1(2H)-one hydrochloride | 378.2 |
| 366 | 8-[2-(aminomethyl)-4-chloropyrrolidin-1-yl]-2-[2-(imidazo[1,2-a]pyridin-2-yl)ethyl]phthalazin-1(2H)-one trifluoroacetate | 423.2 |
| 367 | 2-[2-(imidazo[1,2-a]pyridin-2-yl)ethyl]-4,8-di(pyridin-4-yl)phthalazin-1(2H)-one | 445.2 |
| 368 | 2-[2-(imidazo[1,2-a]pyridin-2-yl)ethyl]-8-[(3aR,4S,7R,7aS)-octahydro-1H-4,7-epiminoisoindol-8-yl]phthalazin-1(2H)-one dihydrochloride | 427.2 |
| 369 | 8-[5-(4-chlorophenyl)-2,5-diazabicyclo[2.2.1]hept-2-yl]-2-[2-(imidazo[1,2-a]pyridin-2-yl)ethyl]phthalazin-1(2H)-one | 497.2 |
| 370 | 4-bromo-2-[2-(imidazo[1,2-a]pyridin-2-yl)ethyl]-8-(pyridin-4-yl)phthalazin-1(2H)-one | 448 |
| 371 | 2-[2-(imidazo[1,2-a]pyridin-2-yl)ethyl]-8-[(3aS,8aS)-octahydropyrrolo[3,4-c]azepin-2(1H)-yl]phthalazin-1(2H)-one dihydrochloride | 429.2 |
| 372 | 2-[2-(imidazo[1,2-a]pyridin-2-yl)ethyl]-8-[(3aS,8aR)-octahydropyrrolo[3,4-c]azepin-2(1H)-yl]phthalazin-1(2H)-one dihydrochloride | 429.2 |
| 373 | tert-butyl (3aR,4S,7R,7aS)-8-{3-[2-(imidazo[1,2-a]pyridin-2-yl)ethyl]-4-oxo-3,4-dihydrophthalazin-5-yl}octahydro-2H-4,7-epiminoisoindole-2-carboxylate | 527.3 |
| 374 | 8-(hexahydro-5H-furo[2,3-c]pyrrol-5-yl)-2-[2-(imidazo[1,2-a]pyridin-2-yl)ethyl]phthalazin-1(2H)-one hydrochloride | 402.2 |
| 375 | 2-[2-(imidazo[1,2-a]pyridin-2-yl)ethyl]-8-(1,2,3,6-tetrahydropyridin-4-yl)phthalazin-1(2H)-one hydrochloride | 372.2 |
| 376 | 2-[2-(imidazo[1,2-a]pyridin-2-yl)ethyl]-8-[(3S)-tetrahydrofuran-3-ylamino]phthalazin-1(2H)-one | |
| 377 | 2-[2-(imidazo[1,2-a]pyridin-2-yl)ethyl]-8-[(3R)-tetrahydrofuran-3-ylamino]phthalazin-1(2H)-one | |
| 378 | 8-{[5-(hydroxymethyl)-1,4-dioxan-2-yl]methoxy}-2-[2-(imidazo[1,2-a]pyridin-2-yl)ethyl]phthalazin-1(2H)-one | 437.1 |
| 379 | 2-[2-(imidazo[1,2-a]pyridin-2-yl)ethyl]-8-(oxetan-3-yloxy)phthalazin-1(2H)-one | 363.1 |
| 380 | 2-[2-(imidazo[1,2-a]pyridin-2-yl)ethyl]-8-(pyridin-4-ylmethoxy)phthalazin-1(2H)-one | 398.1 |
| 381 | 2-[2-(imidazo[1,2-a]pyridin-2-yl)ethyl]-8-(morpholin-4-ylmethyl)phthalazin-1(2H)-one | 390.2 |
| 382 | 2-[2-(imidazo[1,2-a]pyridin-2-yl)ethyl]-8-(pyridin-3-yloxy)phthalazin-1(2H)-one | 384.1 |
| 383 | 2-[2-(imidazo[1,2-a]pyridin-2-yl)ethyl]-8-[(oxetan-3-ylmethyl)amino]phthalazin-1(2H)-one | 376.2 |
| 384 | 2-[2-(imidazo[1,2-a]pyridin-2-yl)ethyl]-8-(tetrahydro-2H-pyran-4-ylamino)phthalazin-1(2H)-one | 390.2 |
| 385 | 2-[2-(imidazo[1,2-a]pyridin-2-yl)ethyl]-8-[(1-methylazetidin-3-yl)amino]phthalazin-1(2H)-one | 375.2 |
| 386 | 2-[2-(imidazo[1,2-a]pyridin-2-yl)ethyl]-8-(1,3-oxazol-2-ylamino)phthalazin-1(2H)-one | 372.3 |
| 387 | 2-[2-(imidazo[1,2-a]pyridin-2-yl)ethyl]-8-[methyl(oxetan-3-yl)amino]phthalazin-1(2H)-one | 376.2 |
| 388 | 2-[2-(imidazo[1,2-a]pyridin-2-yl)ethyl]-8-(piperidin-4-ylamino)phthalazin-1(2H)-one dihydrochloride | 389.2 |
| 389 | 8-[(1-acetylpiperidin-3-yl)amino]-2-[2-(imidazo[1,2-a]pyridin-2-yl)ethyl]phthalazin-1(2H)-one hydrochloride | 431.2 |
| 390 | 8-[(1-acetylpiperidin-4-yl)amino]-2-[2-(imidazo[1,2-a]pyridin-2-yl)ethyl]phthalazin-1(2H)-one hydrochloride | 431.2 |
| 391 | 2-[2-(imidazo[1,2-a]pyridin-2-yl)ethyl]-8-(tetrahydrofuran-3-ylamino)phthalazin-1(2H)-one | 376.2 |
| 392 | 2-[2-(imidazo[1,2-a]pyridin-2-yl)ethyl]-8-(tetrahydro-2H-pyran-3-ylamino)phthalazin-1(2H)-one hydrochloride | 390.2 |
| 393 | 2-[2-(imidazo[1,2-a]pyridin-2-yl)ethyl]-8-(piperidin-3-ylamino)phthalazin-1(2H)-one dihydrochloride | 389.2 |
| 394 | 2-[2-(imidazo[1,2-a]pyridin-2-yl)ethyl]-8-{methyl[(3-methyloxetan-3-1(2H)-one | 404.2 |
| 395 | 2-[2-(imidazo[1,2-a]pyridin-2-yl)ethyl]-8-(oxetan-3-ylamino)phthalazin-1(2H)-one | 362.2 |
| 396 | 8-{[(3aS,4S,6aS)-octahydrocyclopenta[c]pyrrol-4-ylmethyl]amino}-2-[2-(5,6,7,8-tetrahydroimidazo[1,2-a]pyridin-2-yl)ethyl]phthalazin-1(2H)-one hydrochloride | 433.3 |
| 397 | 5-(morpholin-4-yl)-2-[2-(quinolin-2-yl)ethyl]phthalazin-1(2H)-one hydrochloride | 387.2 |
| 398 | 2-[2-(1H-benzimidazol-2-yl)ethyl]-5-(pyridin-4-yl)phthalazin-1(2H)-one | 368.1 |
| 399 | 4-(pyridin-3-yl)-2-[2-(quinolin-2-yl)ethyl]phthalazin-1(2H)-one | 379.1 |
| 400 | 5-(1,4-dihydropyrimidin-5-yl)-2-[2-(5,6,7,8-tetrahydroimidazo[1,2-a]pyridin-2-yl)ethyl]phthalazin-1(2H)-one dihydrochloride | 375.2 |
| 401 | 2-[2-(imidazo[1,2-a]pyridin-2-yl)ethyl]-5-(pyridin-4-yl)phthalazin-1(2H)-one | 368.1 |
| 402 | 5-(pyridin-3-yl)-2-[2-(quinolin-2-yl)ethyl]phthalazin-1(2H)-one | 379.2 |
| 403 | 2-[2-(imidazo[1,2-a]pyridin-2-yl)ethyl]-8-{[(3-methyloxetan-3-yl)methyl]amino}phthalazin-1(2H)-one | 390.2 |
| 404 | 4-(pyridin-4-yl)-6-[2-(quinolin-2-yl)ethyl]pyrido[2,3-d]pyridazin-5(6H)-one | 380.1 |
| 405 | 4-(morpholin-4-yl)-6-[2-(quinolin-2-yl)ethyl]pyrido[2,3-d]pyridazin-5(6H)-one | 388.2 |
| 406 | 4-(oxetan-3-ylamino)-6-[2-(quinolin-2-yl)ethyl]pyrido[2,3-d]pyridazin-5(6H)-one | 374.1 |
| 407 | 2-[2-(6-methoxypyridin-2-yl)ethyl]-8-(pyridin-4-yl)isoquinolin-1(2H)-one | 358.1 |
| 408 | 2-[2-(1,3-benzothiazol-2-yl)ethyl]-8-(pyridin-4-yl)isoquinolin-1(2H)-one | 384.1 |
| 409 | 2-[2-(5-methylpyridin-2-yl)ethyl]-8-(pyridin-4-yl)isoquinolin-1(2H)-one | 342.1 |

II.22 Preparation of Compounds of the Formula I in which A is A$^3$

The compounds of example 410 to 415 were prepared in analogy to the methods described above.

| Ex. | Name | LC-MS: m/e (M + H)+ |
|---|---|---|
| 410 | 5-[(E)-2-(6-methoxyquinolin-2-yl)ethenyl]-3-(pyridin-4-yl)thieno[3,2-c]pyridin-4(5H)-one | 412.8 |
| 411 | 8-(pyridin-4-yl)-2-[(E)-2-(quinazolin-2-yl)ethenyl]isoquinolin-1(2H)-one | 377.1 |
| 412 | 5-[(E)-2-(6-chloroquinolin-2-yl)ethenyl]-3-(pyridin-4-yl)thieno[3,2-c]pyridin-4(5H)-one | 416.1 |
| 413 | 5-[(E)-2-(3-methylquinolin-2-yl)ethenyl]-3-(pyridin-4-yl)thieno[3,2-c]pyridin-4(5H)-one | 396.1 |
| 414 | 8-(pyridin-4-yl)-2-[(E)-2-(quinolin-2-yl)ethenyl]isoquinolin-1(2H)-one | 376.1 |
| 415 | 5-[(E)-2-(1,3-benzothiazol-2-yl)ethenyl]-3-(pyridin-4-yl)thieno[3,2-c]pyridin-4(5H)-one | 388 |
| 416 | 3-(pyridin-4-yl)-5-[(E)-2-(quinolin-2-yl)ethenyl]thieno[3,2-c]pyridin-4(5H)-one | 382.1 |

Biological Tests
a) Measurement of PDE Activity

The recombinant PDE proteins are used in in vitro enzymatic reaction for measurement of PDE activity. These recombinant proteins, including PDE10A (human, rat and mouse PDE10) and isoforms of PDEs 1, 3, 4, and 5, were purchased from commercial vendor BPS Bioscience. The enzymatic activity of PDEs was determined by cAMP measurement kit from CisBio (IBA) using HTRF technology.

The PDE enzymatic reaction was carried out in assay buffer (20 mM Tris-HCl pH7.5, 10 mM $MgCl_2$, 0.1% bovine serum albumin) containing enzyme and substrate. The PDE enzymes concentration ranged from 10 pM-250 pM, depending on each enzyme's specific activity. The substrate cyclic nucleotide (cAMP or cGMP) concentration used in the assay was 20 nM for PDE10, and 100 nM for other PDEs. The inhibitory effect of compound was determined by incubating various concentration of inhibitor in the enzymatic assay. Typically, compound was serial diluted in DMSO then further diluted in assay buffer. Next, the compound at varying concentration was mixed with PDE enzyme. The reaction was initiated by addition of cyclic nucleotide substrate, and incubated for 60 minutes at 29 C. The reaction was stopped by addition of lysis buffer from assay kit. The cAMP-d2 and anti-cAMP cryptate in the lysis buffer detected the level of cAMP left from the PDE hydrolysis reaction. The PDE activity is reversely correlated with the amount of cAMP left in the reaction and can be converted to the percent activity of an uninhibited control (100%). Thus, $IC_{50}$ value of inhibitor can be obtained by plotting inhibitor concentration against PDE activity at that concentration. The results are shown in Table 1.

TABLE 1

| Ex. | $IC_{50}$[1] |
|---|---|
| 1 | +++ |
| 2 | +++ |
| 3 | +++ |
| 5 | +++ |
| 7 | + |
| 8 | +++ |
| 10 | +++ |
| 11 | ++ |
| 12 | +++ |
| 15 | + |
| 16 | +++ |
| 17 | ++ |
| 18 | + |
| 20 | +++ |
| 23 | +++ |
| 26 | + |
| 29 | +++ |
| 30 | ++ |
| 31 | ++ |
| 32 | + |
| 34 | ++ |
| 36 | +++ |
| 37 | +++ |
| 38 | + |
| 39 | +++ |
| 41 | +++ |
| 44 | + |
| 45 | ++ |
| 46 | +++ |
| 47 | ++ |
| 48 | +++ |
| 49 | ++ |
| 50 | + |
| 51 | +++ |
| 52 | ++ |
| 54 | ++ |
| 55 | +++ |
| 56 | +++ |
| 57 | + |
| 59 | +++ |
| 60 | + |
| 62 | + |
| 64 | + |
| 67 | ++ |

TABLE 1-continued

| Ex. | $IC_{50}$[1] |
|---|---|
| 70 | ++ |
| 71 | + |
| 72 | ++ |
| 76 | ++ |
| 78 | + |
| 79 | + |
| 80 | ++ |
| 85 | ++ |
| 87 | +++ |
| 88 | +++ |
| 90 | + |
| 91 | ++ |
| 93 | +++ |
| 94 | +++ |
| 95 | +++ |
| 96 | +++ |
| 97 | +++ |
| 98 | +++ |
| 100 | + |
| 103 | +++ |
| 104 | ++ |
| 105 | ++ |
| 106 | +++ |
| 107 | +++ |
| 108 | + |
| 109 | + |
| 111 | +++ |
| 113 | ++ |
| 114 | ++ |
| 115 | +++ |
| 116 | +++ |
| 117 | ++ |
| 119 | + |
| 121 | ++ |
| 122 | + |
| 123 | + |
| 124 | +++ |
| 125 | + |
| 126 | +++ |
| 127 | +++ |
| 130 | + |
| 133 | +++ |
| 135 | +++ |
| 136 | +++ |
| 137 | +++ |
| 138 | + |
| 139 | +++ |
| 140 | + |
| 143 | + |
| 147 | +++ |
| 148 | ++ |
| 149 | + |
| 152 | + |
| 153 | ++ |
| 154 | + |
| 156 | ++ |
| 157 | + |
| 159 | +++ |
| 161 | +++ |
| 163 | + |
| 164 | ++ |
| 165 | + |
| 166 | +++ |
| 167 | + |
| 168 | +++ |
| 169 | + |
| 170 | +++ |
| 171 | +++ |
| 173 | +++ |
| 174 | +++ |
| 175 | ++ |
| 176 | +++ |
| 179 | ++ |
| 181 | + |
| 190 | ++ |
| 191 | + |
| 192 | +++ |
| 193 | +++ |

TABLE 1-continued

| Ex. | IC$_{50}$[1] |
|---|---|
| 194 | +++ |
| 195 | ++ |
| 196 | +++ |
| 197 | +++ |
| 198 | +++ |
| 199 | +++ |
| 200 | +++ |
| 201 | + |
| 203 | + |
| 204 | +++ |
| 205 | +++ |
| 206 | +++ |
| 207 | +++ |
| 208 | +++ |
| 209 | + |
| 210 | +++ |
| 211 | + |
| 213 | + |
| 215 | ++ |
| 216 | +++ |
| 219 | +++ |
| 220 | +++ |
| 221 | +++ |
| 222 | +++ |
| 222a | +++ |
| 222b | +++ |
| 223 | +++ |
| 224 | +++ |
| 225 | +++ |
| 226 | +++ |
| 228 | +++ |
| 229 | +++ |
| 230 | ++ |
| 231 | +++ |
| 232 | +++ |
| 233 | +++ |
| 234 | +++ |
| 235 | +++ |
| 235a | +++ |
| 235b | +++ |
| 236 | +++ |
| 237 | +++ |
| 238 | +++ |
| 239 | +++ |
| 239a | ++ |
| 239b | +++ |
| 240 | +++ |
| 240a | +++ |
| 240b | +++ |
| 241 | +++ |
| 242 | +++ |
| 243 | +++ |
| 244 | +++ |
| 246 | +++ |
| 246a | +++ |
| 246b | +++ |
| 247 | +++ |
| 249 | + |
| 250 | ++ |
| 252 | +++ |
| 253 | +++ |
| 256 | +++ |
| 257 | +++ |
| 258 | +++ |
| 259 | +++ |
| 260 | +++ |
| 262 | ++ |
| 263 | +++ |
| 266 | +++ |
| 267 | +++ |
| 268 | +++ |
| 269 | +++ |
| 270 | +++ |
| 271 | +++ |
| 272 | +++ |
| 273 | +++ |
| 274 | +++ |
| 275 | +++ |
| 276 | +++ |
| 277 | +++ |
| 278 | +++ |
| 279 | +++ |
| 280 | +++ |
| 281 | +++ |
| 282 | +++ |
| 282a | +++ |
| 282b | +++ |
| 283 | +++ |
| 284 | +++ |
| 285 | +++ |
| 286 | +++ |
| 287 | +++ |
| 288 | +++ |
| 289 | +++ |
| 290 | +++ |
| 291 | +++ |
| 292 | +++ |
| 293 | +++ |
| 293a | +++ |
| 293b | +++ |
| 295 | +++ |
| 296 | ++ |
| 297 | +++ |
| 298 | ++ |
| 299 | +++ |
| 300 | +++ |
| 301 | +++ |
| 302 | +++ |
| 303 | +++ |
| 304 | +++ |
| 306 | +++ |
| 307 | + |
| 308 | +++ |
| 309 | +++ |
| 310 | +++ |
| 311 | ++ |
| 312 | +++ |
| 315 | +++ |
| 317 | +++ |
| 318 | + |
| 319 | +++ |
| 320 | + |
| 321 | ++ |
| 322 | + |
| 327 | +++ |
| 328 | + |
| 329 | +++ |
| 330 | + |
| 332 | + |
| 333 | +++ |
| 334 | ++ |
| 337 | +++ |
| 338 | +++ |
| 339 | +++ |
| 341 | +++ |
| 342 | ++ |
| 343 | + |
| 344 | ++ |
| 345 | ++ |
| 347 | ++ |
| 348 | ++ |
| 349 | +++ |
| 354 | +++ |
| 355 | +++ |
| 358 | ++ |
| 359 | +++ |
| 365 | +++ |
| 366 | +++ |
| 367 | +++ |
| 370 | +++ |
| 374 | + |
| 375 | +++ |
| 376 | +++ |
| 377 | +++ |
| 378 | + |
| 380 | ++ |

TABLE 1-continued

| Ex. | IC$_{50}$[1] |
|---|---|
| 382 | +++ |
| 383 | +++ |
| 384 | ++ |
| 385 | + |
| 387 | +++ |
| 388 | +++ |
| 389 | ++ |
| 390 | + |
| 391 | +++ |
| 392 | +++ |
| 393 | +++ |
| 394 | + |
| 395 | +++ |
| 397 | +++ |
| 398 | ++ |
| 399 | +++ |
| 401 | +++ |
| 402 | +++ |
| 403 | +++ |
| 404 | +++ |
| 405 | +++ |
| 406 | +++ |
| 410 | +++ |
| 411 | ++ |
| 412 | +++ |
| 413 | +++ |
| 414 | +++ |
| 415 | +++ |
| 416 | +++ |

[1]+++: IC$_{50}$ <100 nM  ++: 100 nM ≤ IC$_{50}$ ≤ 200 nM  +: 200 nM < IC$_{50}$ < 500 nM

We claim:

1. A compound of formula (I)

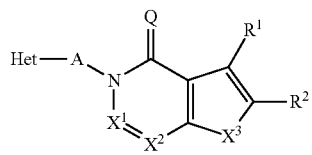

wherein
Q is O or S;
when $X^1$ is CH, $X^3$ is O or S;
when $X^1$ is N, $X^3$ is S or —$X^5$=C($R^9$)—, where $X^5$ is bound to the carbon atom which carries $R^2$;
$X^2$ is C—$R^7$;
$X^5$ is N;
Het is selected from the group consisting of
  i. 5- or 6-membered monocyclic hetaryl having 1 or 2 nitrogen atoms and optionally a further heteroatom selected from O, S and N as ring members, which is unsubstituted or may carry 1, 2, 3 or 4 identical or different substituents $R^x$,
  ii. 8- to 10-membered bicyclic hetaryl having 1 or 2 nitrogen atoms and optionally a further heteroatom selected from O, S and N as ring members, benzothienyl or benzofuryl, where bicyclic hetaryl, benzothienyl and benzofuryl are, independently of each other, unsubstituted or may carry 1, 2, 3 or 4 identical or different substituents $R^x$, and
  iii. phenyl, which carries a monocyclic hetaryl radical having 1 or 2 nitrogen atoms and optionally a further heteroatom selected from O, S and N as ring members, which in addition to monocyclic hetaryl, may carry 1, 2 or 3 identical or different substituents $R^x$, where
$R^x$ is selected from the group consisting of hydrogen, halogen, $C_1$-$C_4$-alkyl, $C_1$-$C_4$-alkoxy, $C_1$-$C_4$-fluoroalkyl, $C_1$-$C_4$-fluoroalkoxy, $C_3$-$C_6$-cycloalkyl, $C_1$-$C_4$-alkoxy-$C_1$-$C_4$-alkoxy, $C_1$-$C_4$-alkoxy-$C_1$-$C_4$-alkyl, OH, hydroxy-$C_1$-$C_4$-alkyl, O—$C_3$-$C_6$-cycloalkyl, benzyloxy, C(O)O—($C_1$-$C_4$-alkyl), O—($C_1$-$C_4$-alkyl)-CO$_2$H, N($R^{x1}$)($R^{x2}$), C(O)N($R^{x1}$)($R^{x2}$), $C_1$-$C_4$-alkyl-N($R^{x1}$)($R^{x2}$), —N$R^{x3}$—C(O)—N($R^{x1}$)($R^{x2}$), N$R^{x3}$—C(O)O—($C_1$-$C_4$-alkyl), —N($R^{x3}$)—SO$_2$—$R^{x4}$, phenyl, CN, —SF$_5$, —OSF$_5$, —SO$_2$$R^{x4}$, —S$R^{x4}$ and trimethylsilyl, where $R^{x1}$, $R^{x2}$, $R^{x3}$, and $R^{x4}$, independently of each other are selected from the group consisting of hydrogen, $C_1$-$C_4$-alkyl, $C_1$-$C_4$-fluoroalkyl and $C_3$-$C_6$-cycloalkyl or $R^{x1}$ and $R^{x2}$ form together with the N atom to which they are attached a 3- to 7-membered, nitrogen heterocycle which may have 1, 2 or 3 further different or identical heteroatoms or heteroatom containing groups selected from the group of O, N, S, SO and SO$_2$ as ring members and which may carry 1, 2, 3, 4, 5 or 6 substituents selected from $C_1$-$C_4$-alkyl; or two radicals $R^x$ which are bound at adjacent carbon atoms may form a fused 5- or 6-membered saturated carbocyclic radical or a fused 5- or 6-membered heterocyclic radical having 1, 2 or 3 heteroatoms as ring members, which are selected from O, S and N;

$R^1$ is selected from the group consisting of hydrogen, halogen, OH, $C_1$-$C_4$-alkyl, trimethylsilyl, $C_1$-$C_4$-alkylsulfanyl, $C_1$-$C_4$-alkoxy-$C_1$-$C_4$-alkyl, $C_1$-$C_4$-alkoxy, $C_1$-$C_4$-alkoxy-$C_1$-$C_4$-alkoxy, $C_1$-$C_4$-alkylsulfanyl-$C_1$-$C_4$-alkoxy, $C_2$-$C_4$-alkenyloxy, $C_1$-$C_4$-fluoroalkyl, $C_1$-$C_4$-fluoroalkoxy, cyclopropyl, optionally substituted by 1, 2 or 3 methyl groups, fluorinated cyclopropyl, CN, N$R^{x1}$$R^{x2}$, N$R^{x1}$$R^{x2}$—$C_1$-$C_4$-alkoxy and the moiety $Y^1$-Cyc$^1$;

$R^2$ is selected from the group consisting of hydrogen, halogen, OH, $C_1$-$C_4$-alkyl, trimethylsilyl, $C_1$-$C_4$-alkoxy-$C_1$-$C_4$-alkyl, $C_1$-$C_4$-alkoxy, $C_1$-$C_4$-alkoxy-$C_1$-$C_4$-alkoxy, $C_2$-$C_4$-alkenyloxy, $C_1$-$C_4$-fluoroalkyl, $C_1$-$C_4$-fluoroalkoxy, cyclopropyl, optionally substituted by 1, 2 or 3 methyl groups, fluorinated cyclopropyl, CN and N$R^{x1}$$R^{x2}$;

A is selected from the group consisting of ($A^1$), ($A^2$), ($A^3$), ($A^4$) and ($A^5$):

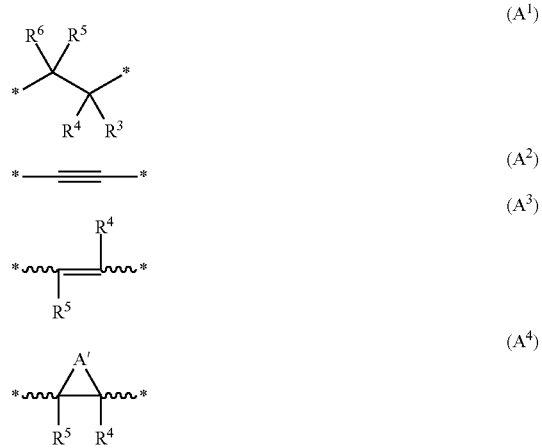

-continued

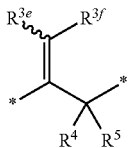
(A⁵)

where * indicates the points of attachment to Het and to the nitrogen atom, respectively, $R^3$, $R^4$, $R^5$, and $R^6$ independently of each other are selected from the group consisting of hydrogen, halogen, $C_1$-$C_4$-alkyl, trimethylsilyl, $C_1$-$C_4$-fluoroalkyl, $C_1$-$C_4$-fluoroalkoxy, and $C_3$-$C_6$-cycloalkyl, or the radicals together with the carbon atoms to which they are bound form a saturated 3- to 6-membered carbocycle or a saturated 3- to 6-membered heterocycle having 1 or 2 non-adjacent heteroatoms as ring members, where the carbocycle and the heterocycle are unsubstituted or may carry 1, 2, 3 or 4 substituents selected from fluoro and methyl or either the radicals $R^3$ and $R^4$ or the radicals $R^5$ and $R^6$ together with the carbon atom to which they are bound form a saturated 3- to 6-membered carbocycle or a saturated 3- to 6-membered heterocycle having 1 or 2 non-adjacent heteroatoms as ring members, where the carbocycle and the heterocycle are unsubstituted or may carry 1, 2, 3 or 4 substituents selected from fluoro and methyl;

A' is selected from the group consisting of O, $NR^{3a}$, $CR^{3b}R^{3c}$ and linear $C_2$-$C_3$-alkanediyl, where one of the $CH_2$-moieties of $C_2$-$C_3$-alkanediyl may be replaced by oxygen or $NR^{3a}$, and where 1, 2, 3, or 4 of the hydrogen atoms of $C_2$-$C_3$-alkanediyl may be replaced by a radical $R^{3d}$, where $R^{3a}$ is hydrogen or $C_1$-$C_4$-alkyl, $R^{3b}$ and $R^{3c}$ independently of each other are selected from the group consisting of hydrogen, halogen, and $C_1$-$C_4$-alkyl or $R^{3b}$ and $R^{3c}$ together form $C_2$-$C_3$-alkanediyl;

$R^{3d}$ is selected from the group consisting of halogen and $C_1$-$C_4$-alkyl;

$R^{3e}$ and $R^{3f}$ independently of each other are selected from the group consisting of hydrogen and $C_1$-$C_4$-alkyl;

$R^7$ is selected from the group consisting of hydrogen, halogen, OH, $C_1$-$C_4$-alkyl, trimethylsilyl, $C_1$-$C_4$-alkylsulfanyl, $C_1$-$C_4$-alkoxy-$C_1$-$C_4$-alkyl, $C_1$-$C_4$-alkoxy, $C_1$-$C_4$-alkoxy-$C_1$-$C_4$-alkoxy, $C_1$-$C_4$-alkylsulfanyl-$C_1$-$C_4$-alkoxy, $C_2$-$C_4$-alkenyloxy, $C_1$-$C_4$-fluoroalkyl, $C_1$-$C_4$-fluoroalkoxy, cyclopropyl, optionally substituted by 1, 2 or 3 methyl groups, fluorinated cyclopropyl, CN, $NR^{x1}R^{x2}$; $NR^{x1}R^{x2}$—$C_1$-$C_4$-alkoxy and $Y^2$-$Cyc^2$;

$R^8$ is selected from the group consisting of hydrogen, halogen, OH, $C_1$-$C_4$-alkyl, trimethylsilyl, $C_1$-$C_4$-alkoxy-$C_1$-$C_4$-alkyl, $C_1$-$C_4$-alkoxy, $C_1$-$C_4$-alkoxy-$C_1$-$C_4$-alkoxy, $C_2$-$C_4$-alkenyloxy, $C_1$-$C_4$-fluoroalkyl, $C_1$-$C_4$-fluoroalkoxy, cyclopropyl, optionally substituted by 1, 2 or 3 methyl groups, fluorinated cyclopropyl, CN and $NR^{x1}R^{x2}$;

$R^9$ is selected from the group consisting of hydrogen, halogen, OH, $C_1$-$C_4$-alkyl, trimethylsilyl, $C_1$-$C_4$-alkylsulfanyl, $C_1$-$C_4$ alkoxy $C_1$-$C_4$ alkyl $C_1$-$C_4$-alkoxy, $C_1$-$C_4$-alkoxy-$C_1$-$C_4$-alkoxy, $C_1$-$C_4$-alkylsulfanyl-$C_1$-$C_4$-alkoxy, $C_2$-$C_4$-alkenyloxy, $C_1$-$C_4$-fluoroalkyl, $C_1$-$C_4$-fluoroalkoxy, cyclopropyl, optionally substituted by 1, 2 or 3 methyl groups, fluorinated cyclopropyl, CN, $NR^{x1}R^{x2}$, $NR^{x1}R^{x2}$—$C_1$-$C_4$-alkoxy and $Y^3$-$Cyc^3$;

$Y^1$, $Y^2$ and $Y^3$ independently of each other are selected from the group consisting of a chemical bond, $CH_2$, O, O—$CH_2$, $NR^y$, $NR^y$—$CH_2$, $NR^y$—$S(O)_2$, S, S(O), $S(O)_2$, 1,2-ethandiyl, 1,2-ethendiyl and 1,2-ethyndiyl, where $R^y$ is selected from the group consisting of hydrogen, $C_1$-$C_4$-alkyl, $C_1$-$C_4$-alkylcarbonyl, $C_1$-$C_4$-alkylsulfonyl, $C_1$-$C_4$-fluoroalkylsulfonyl;

$Cyc^1$, $Cyc^2$ and $Cyc^3$ independently of each other are selected from the group consisting of phenyl, naphthyl, 4- to 8-membered saturated or partially unsaturated heteromonocyclic radicals, saturated or partially unsaturated 7- to 10 membered heterobicyclic radicals, 5- or 6-membered monocyclic hetaryl, and 8- to 10 membered bicyclic hetaryl, where the saturated or partially unsaturated heteromonocyclic and heterobicyclic radicals have 1, 2, 3 or 4 heteroatoms or heteroatom containing groups as ring members, which are selected from the group consisting of O, S, SO, $SO_2$ and N, and where the 5- or 6-membered monocyclic hetaryl and the 8- to 10-membered bicyclic hetaryl have 1, 2, 3 or 4 heteroatoms as ring members, which are selected from the group consisting of O, S and N, where phenyl, naphthyl, the saturated or partially unsaturated heteromonocyclic and heterobicyclic radicals and the monocyclic and bicyclic heteroaromatic radicals are unsubstituted or carry 1, 2, 3, 4 or 5 radicals $R^{C1}$ or one radical $Y^1$—$R^{C2}$ and 0, 1, 2, 3 or 4 radicals $R^{C1}$;

where $R^{C1}$ is selected from the group consisting of hydrogen, halogen, OH, CN, $NO_2$, $C_1$-$C_4$-alkyl, $C_1$-$C_4$-alkoxy, $C_1$-$C_4$-alkylsulfanyl, hydroxy-$C_1$-$C_4$-alkyl, $C_1$-$C_4$-alkoxy-$C_1$-$C_4$-alkyl, $C_1$-$C_4$-alkoxy-$C_1$-$C_4$-alkoxy, cyano-$C_1$-$C_4$-alkyl, $C_1$-$C_4$-fluoroalkyl, $C_1$-$C_4$-fluoroalkoxy, $C_1$-$C_4$-alkylsulfonyl, $C(O)R^a$, Z—C(O)$OR^b$, Z—C(O)$NR^cR^d$, $S(O)_2NR^cR^d$ and Z—$NR^eR^f$, where $R^a$ is selected from the group consisting of $C_1$-$C_4$-alkyl and $C_1$-$C_4$-fluoroalkyl, $R^b$ is selected from the group consisting of hydrogen, $C_1$-$C_4$-alkyl, $C_2$-$C_4$-alkenyl and $C_1$-$C_4$-fluoroalkyl, $R^c$ and $R^d$ is selected from the group consisting of hydrogen, $C_1$-$C_4$-alkyl, $C_1$-$C_4$-fluoroalkyl, $C_1$-$C_4$-alkoxy and $C_1$-$C_4$-fluoroalkoxy, $R^e$ and $R^f$ is selected from the group consisting of hydrogen, $C_1$-$C_4$-alkyl, $C_1$-$C_4$-fluoroalkyl, $C_1$-$C_4$-alkoxy and $C_1$-$C_4$-fluoroalkoxy, Z is selected from the group consisting of a covalent bond and $C_1$-$C_4$-alkanediyl, or two radicals $R^{C1}$ which are bound at adjacent carbon atoms may form a fused 5- or 6-membered carbocyclic radical or a fused 5- or 6-membered heterocyclic radical having 1, 2 or 3 heteroatoms as ring members, which are selected from the group consisting of O, S and N;

or two radicals $R^{C1}$ which are bound at the same carbon atom may form a spiro 5- or 6-membered carbocyclic radical or a spiro 5- or 6-membered heterocyclic radical having 1 or 2 heteroatoms as ring members, which are selected from the group consisting of O, S and N, or two radicals $R^{C1}$ which are bound at the same carbon atom may form an oxygen atom, where the fused and the spiro radicals are unsubstituted or carry 1, 2, 3 or 4 radicals $R^{C3}$;

Y' is a chemical bond, $CH_2$, O, O—$CH_2$, $S(O)_2$, $NR^{y'}$, $NR^{y'}$—$CH_2$ or $NR^{y'}$—$S(O)_2$, where $R^{y'}$ is selected from the group consisting of hydrogen, $C_1$-$C_4$-alkyl, $C_1$-$C_4$-alkylcarbonyl, $C_1$-$C_4$-alkylsulfonyl, and $C_1$-$C_4$-fluoroalkylsulfonyl;

$R^{C2}$ is a carbocyclic or heterocyclic radical selected from the group consisting of phenyl, 3- to 7-membered saturated or partially unsaturated monocarbocyclic radicals, 3- to 7-membered saturated or partially unsaturated heteromonocyclic radicals, having 1, 2 or 3 heteroatoms as ring members, which are selected from the group consisting of O, S and N, and 5- or 6-membered heteroaromatic radicals, having 1, 2 or 3 heteroatoms as ring members, which are selected from the group consisting of O, S and N, where the carbocyclic and the heterocyclic radical is unsubstituted or carries 1, 2, 3, 4 or 5 radicals $R^{C3}$;

$R^{C3}$ is selected from the group consisting of hydrogen, halogen, OH, CN, $C_1$-$C_4$-alkyl, $C_1$-$C_4$-alkoxy, hydroxy-$C_1$-$C_4$-alkyl, $C_1$-$C_4$-alkoxy-$C_1$-$C_4$-alkyl, cyano-$C_1$-$C_4$-alkyl, $C_1$-$C_4$-fluoroalkyl, $C_1$-$C_4$-fluoroalkoxy, $C_2$-$C_6$-alkenyl, $C(O)R^a$, benzyl, Z—$C(O)OR^b$, Z—$C(O)NR^cR^d$, $S(O)_2NR^cR^d$ and Z—$NR^eR^f$, where, Z, $R^a$, $R^b$, $R^c$, $R^d$, $R^e$ and $R^f$ are as defined above or two radicals $R^{C3}$ which are bound at the same atom may form an oxygen atom;

provided that for $X^3$ being O or S, at least one of the radicals $R^1$ and $R^7$ is $Y^1$-$Cyc^1$ or $Y^2$-$Cyc^2$, respectively;

further provided that for $X^3$ being $X^5$=$C(R^9)$, one or two of the radicals $R^1$, $R^7$ and $R^9$ are $Y^1$-$Cyc^1$, $Y^2$-$Cyc^2$ or $Y^3$-$Cyc^3$, respectively;

or an N-oxide, tautomer or pharmaceutically acceptable salt thereof.

2. The compound of claim 1, wherein
when $X^1$ is CH, $X^3$ is O or S;
when $X^1$ is N, $X^3$ is S;
Het is selected from the group consisting of
  i. 5- or 6-membered monocyclic hetaryl having 1 or 2 nitrogen atoms and optionally a further heteroatom selected from the group consisting of O, S and N as ring members, which is unsubstituted or may carry 1, 2, 3 or 4 identical or different substituents $R^x$,
  ii. 8- to 10-membered bicyclic hetaryl having 1 or 2 nitrogen atoms and optionally a further heteroatom selected from the group consisting of O, S and N as ring members, benzothienyl or benzofuryl, where bicyclic hetaryl, benzothienyl and benzofuryl are, independently of each other, unsubstituted or may carry 1, 2, 3 or 4 identical or different substituents $R^x$, and
  iii. phenyl, which carries a monocyclic hetaryl radical having 1 or 2 nitrogen atoms and optionally a further heteroatom selected from the group consisting of O, S and N as ring members, which in addition to monocyclic hetaryl, may carry 1, 2 or 3 identical or different substituents $R^x$,
where
$R^x$ is selected from the group consisting of hydrogen, halogen, $C_1$-$C_4$-alkyl, $C_1$-$C_4$-alkoxy, $C_1$-$C_4$-fluoroalkyl, $C_1$-$C_4$-fluoroalkoxy, $C_3$-$C_6$-cycloalkyl, $C_1$-$C_4$-alkoxy-$C_1$-$C_4$-alkoxy, $C_1$-$C_4$-alkoxy-$C_1$-$C_4$-alkyl, OH, hydroxy-$C_1$-$C_4$-alkyl, O—$C_3$-$C_6$-cycloalkyl, benzyloxy, $C(O)O$—($C_1$-$C_4$-alkyl), O—($C_1$-$C_4$-alkyl)-$CO_2H$, $N(R^{x1})(R^{x2})$, $C(O)N(R^{x1})(R^{x2})$, $C_1$-$C_4$-alkyl-$N(R^{x1})(R^{x2})$, —$NR^{x3}$—$C(O)$—$N(R^{x1})(R^{x2})$, $NR^{x3}$—$C(O)O$—($C_1$-$C_4$-alkyl), —$N(R^{x3})$—$SO_2$—$R^{x4}$, phenyl, CN, —$SF_5$, —$OSF_5$, —$SO_2R^{x4}$, —$SR^{x4}$ and trimethylsilyl, where $R^{x1}$, $R^{x2}$, $R^{x3}$, and $R^{x4}$, independently of each other are selected from the group consisting of hydrogen, $C_1$-$C_4$-alkyl, $C_1$-$C_4$-fluoroalkyl and $C_3$-$C_6$-cycloalkyl or $R^{x1}$ and $R^{x2}$ form together with the N atom to which they are attached a 3- to 7-membered, nitrogen heterocycle which may have 1, 2 or 3 further different or identical heteroatoms or heteroatom containing groups selected from the group consisting of O, N, S, SO and $SO_2$ as ring members and which may carry 1, 2, 3, 4, 5 or 6 substituents selected from $C_1$-$C_4$-alkyl;

A is selected from the group consisting of ($A^1$), ($A^2$), ($A^3$) and ($A^4$):

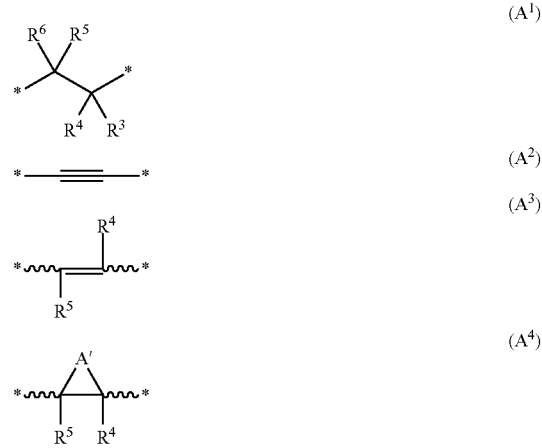

where * indicates the points of attachment to Het and to the nitrogen atom, respectively, $R^3$, $R^4$, $R^5$ and $R^6$ independently of each other are selected from the group consisting of hydrogen, halogen, $C_1$-$C_4$-alkyl, trimethylsilyl, $C_1$-$C_4$-fluoroalkyl, $C_1$-$C_4$-fluoroalkoxy, and $C_3$-$C_6$-cycloalkyl, or the radicals together with the carbon atoms to which they are bound form a saturated 3- to 6-membered carbocycle or a saturated 3- to 6-membered heterocycle having 1 or 2 non-adjacent heteroatoms as ring members, where the carbocycle and the heterocycle are unsubstituted or may carry 1, 2, 3 or 4 substituents selected from the group consisting of fluoro and methyl or either the radicals $R^3$ and $R^4$ or the radicals $R^5$ and $R^6$ together with the carbon atom to which they are bound form a saturated 3- to 6-membered carbocycle or a saturated 3- to 6-membered heterocycle having 1 or 2 non-adjacent heteroatoms as ring members, where the carbocycle and the heterocycle are unsubstituted or may carry 1, 2, 3 or 4 substituents selected from the group consisting of fluoro and methyl;

A' is selected from the group consisting of O, $NR^{3a}$, $CR^{3b}R^{3c}$ and linear $C_2$-$C_3$-alkanediyl, where one of the $CH_2$-moieties of $C_2$-$C_3$-alkanediyl may be replaced by oxygen or $NR^{3a}$, and where 1, 2, 3, or 4 of the hydrogen atoms of $C_2$-$C_3$-alkanediyl may be replaced by a radical $R^{3d}$, where $R^{3a}$ is hydrogen or $C_1$-$C_4$-alkyl, $R^{3b}$ and $R^{3c}$ independently of each other are selected from the group consisting of hydrogen, halogen and $C_1$-$C_4$-alkyl or $R^{3b}$ and $R^{3c}$ together form $C_2$-$C_3$-alkanediyl, $R^{3d}$ is selected from the group consisting of halogen and $C_1$-$C_4$-alkyl;

$R^8$ is selected from the group consisting of hydrogen, halogen, OH, $C_1$-$C_4$-alkyl, trimethylsilyl, $C_1$-$C_4$-alkoxy-$C_1$-$C_4$-alkyl, $C_1$-$C_4$-alkoxy, $C_1$-$C_4$-alkoxy-$C_1$-$C_4$-alkoxy, $C_2$-$C_4$-alkenyloxy, $C_1$-$C_4$-fluoroalkyl, $C_1$-$C_4$-fluoroalkoxy, cyclopropyl, optionally substituted by 1, 2 or 3 methyl groups, fluorinated cyclopropyl, CN and $NR^{x1}R^{x2}$; and $R^9$ is selected from the group consisting of hydrogen, halogen, OH, $C_1$-$C_4$-alkyl, trimethylsilyl, $C_1$-$C_4$-alkylsulfanyl, $C_1$-$C_4$ alkoxy $C_1$-$C_4$ alkyl $C_1$-$C_4$-alkoxy, $C_1$-$C_4$-alkoxy-$C_1$-$C_4$-alkoxy, $C_1$-$C_4$-alkylsulfanyl-$C_1$-$C_4$-alkoxy, $C_2$-$C_4$-alkenyloxy, $C_1$-$C_4$-fluoroalkyl, $C_1$-$C_4$-fluoroalkoxy, cyclopropyl, optionally substituted by 1, 2 or 3 methyl groups, fluorinated cyclopropyl, CN, $NR^{x1}R^{x2}$, $NR^{x1}R^{x2}$—$C_1$-$C_4$-alkoxy and $Y^3$-$Cyc^3$.

3. The compound of claim 1, where A is ($A^1$), ($A^2$), ($A^3$), or ($A^4$).

4. The compound of claim 1, where A is ($A^1$).

5. The compound of claim 4, where $R^3$ and $R^4$ are, independently of each other, selected from the group consisting of hydrogen and fluoro.

6. The compound of claim 4, where $R^5$ and $R^6$ are, independently of each other, selected from the group consisting of hydrogen, fluoro and methyl.

7. The compound of claim 1, where A is ($A^2$).

8. The compound of claim 1, where A is ($A^3$).

9. The compound of claim 8, where $R^4$ and $R^5$ are, independently of each other, selected from the group consisting of hydrogen and fluoro.

10. The compound of claim 1, where A is ($A^4$).

11. The compound of claim 10, where A' is $CR^{3b}R^{3c}$, where $R^{3b}$ and $R^{3c}$ are, independently of each other, selected from the group consisting of hydrogen, fluoro and methyl or together form $CH_2CH_2$.

12. The compound of claim 11, where $R^{3b}$ and $R^{3c}$ are each hydrogen.

13. The compound of claim 1, where A is ($A^5$).

14. The compound of claim 13, where $R^{3e}$, $R^{3f}$, $R^4$ and $R^5$ are each hydrogen.

15. The compound of claim 1, where Het is selected from the group consisting of C-bound 6-membered monocyclic hetaryl, which has 1 or 2 nitrogen atoms as ring members, benzofuryl and C-bound, 8- to 10-membered bicyclic hetaryl, which has 1 or 2 nitrogen atoms as ring members and optionally a further heteroatom selected from the group consisting of O, S and N as ring member;
where monocyclic hetaryl, benzofuryl and bicyclic hetaryl may be unsubstituted or may carry 1, 2, 3 or 4 substituents $R^x$.

16. The compound of claim 15, where Het has at least one nitrogen as a ring member, which is located in the position adjacent to the carbon atom which is bound to A.

17. The compound of claim 16, where Het is selected from the group consisting of 2-pyridyl, 2-pyrimidinyl, 4-pyrimidinyl, 2-pyrazinyl, 3-pyridazinyl, 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyrid-2-yl, thieno[3,2-b]pyrid-5-yl, imidazo[2,1-b]thiazol-6-yl and 1,2,4-triazolo[1,5-a]pyrid-2-yl, where the aforementioned radicals may carry 1, 2 or 3 radicals selected from fluoro, chloro, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

18. The compound of claim 1, where Q is O.

19. The compound of claim 1, where $R^1$ is $Y^1$-$Cyc^1$.

20. The compound of claim 1, where $R^2$ is selected from the group consisting of hydrogen, fluoro, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups, and fluorinated cyclopropyl.

21. The compound of claim 20, where $R^2$ is hydrogen.

22. The compound of claim 1, where $R^7$ is hydrogen or $Y^2$-$Cyc^2$.

23. The compound of claim 1, where $X^1$ is N and $X^3$ is S.

24. The compound of claim 1, wherein
$X^1$ is N;
$X^3$ is S; and
$R^1$ is $Y^1$-$Cyc^1$;
or an N-oxide, tautomer or pharmaceutically acceptable salt thereof.

25. The compound of claim 1, where $X^1$ is CH and $X^3$ is S.

26. The compound of claim 1, where $X^1$ is CH and $X^3$ is O.

27. The compound of claim 1, wherein
$X^1$ is CH; and
$X^3$ is O or S;
or an N-oxide, tautomer or pharmaceutically acceptable salt thereof.

28. The compound of claim 1, where $X^3$ is —$X^5$=C($R^9$)—.

29. The compound of claim 1, where $Y^1$, $Y^2$ and $Y^3$, independently of each other, are selected from the group consisting of a chemical bond, O and NH.

30. The compound of claim 1, where $Y^1$, $Y^2$ and $Y^3$ are each a chemical bond.

31. The compound of claim 1, where $Cyc^1$ is selected from the group consisting of saturated 4-, 5-, 6-, 7- or 8-membered heteromonocycles and saturated 7-, 8-, 9- or 10-membered heterobicycles, where the heteromonocycles and the heterobicycles have one nitrogen or oxygen atom as a ring member and may have one further heteroatom or heteroatom group as a ring member, which is selected from the group consisting of O, S, S(=O), S(=O)$_2$ and N, where the saturated heteromonocycle and the saturated heterobicycle are unsubstituted or carry 1, 2, 3, 4 or 5 radicals $R^{C1}$ or one radical $Y'$—$R^{C2}$ and 0, 1, 2, 3 or 4 radicals $R^{C1}$.

32. The compound of claim 1, where $Cyc^1$ is selected from the group consisting of phenyl, 5- or 6 membered monocyclic hetaryl, and 9- or 10 membered bicyclic hetaryl, where hetaryl has one heteroatom, selected from O, S and N as a ring member and optionally one or two further nitrogen atoms as ring members, where phenyl and the hetaryl radical are unsubstituted or either carry, independently of each other, 1, 2, 3, 4 or 5 radicals $R^{C1}$.

33. The compound of claim 32, where $Y^1$ is a chemical bond and $Cyc^1$ is selected from the group consisting of phenyl, 5- or 6-membered monocyclic hetaryl selected from the group consisting of pyridyl, pyrimidinyl, furyl, thienyl, pyrrolyl, imidazolyl, pyrazolyl, oxazolyl and thiazolyl, 9- or 10-membered bicyclic hetaryl selected from the group consisting of indolyl, quinolinyl, isoquinolinyl, quinazolinyl, benzimidazolyl, benzotriazolyl, benzopyrazolyl and benzofuryl, where phenyl and hetaryl are unsubstituted or carry 1, 2 or 3 radicals $R^{C1}$ which are selected from the group consisting of fluoro, chloro, CN, methyl, difluoromethyl, trifluoromethyl, methoxy and $NH_2$, or, if $Cyc^1$ is phenyl, two radicals $R^{C1}$ which are bound to adjacent carbon atoms, together with the phenyl ring to which they are bound, form a bicyclic heterocyclic radical, which is selected from 2,3-dihydrobenzofuran-5-yl, 2,3-dihydrobenzofuran-6-yl, 1,3-dihydroindol-2-on-5-yl, 1,3-dihydroindol-2-on-6-yl, benzo-1,3-dioxolan-5-yl, benzo-1,3-dioxolan-6-yl, benzo-1,4-dioxan-5-yl, benzo-1,4-dioxan-6-yl, benzo-1,5-dioxepan-6-yl and benzo-1,4-dioxepan-7-yl.

34. The compound of claim 1, where $Y^1$-$Cyc^1$ is selected from the group consisting of 1-piperidinyl, 4,4-difluoro-1-piperidinyl, 4-piperidinyl, 1-methyl-4-piperidinyl, 1-piperazinyl, 4-methyl-1-piperazinyl, morpholin-4-yl, azepan-1-yl, 1,4-oxazepan-4-yl, hexahydrofuro[3,4-c]pyrrol-5-yl, 2,5-diazabicyclo[2.2.1]heptan-2-yl, 3,8-diazabicyclo[3.2.1]octan-8-yl, thiomorpholin-4-yl, 1-oxothiomorpholin-4-yl, N-(oxetan-3-yl)amino, 1,1-dioxothiomorpholin-4-yl and oxetan-3-ylamino.

35. The compound of claim 1, where $Cyc^2$ and $Cyc^3$, independently of each other, are selected from the group consisting of phenyl, saturated 4-, 5-, 6-, 7- or 8-membered heteromonocycles and saturated 7-, 8-, 9- or 10-membered heterobicycles, where the heteromonocycles and the heterobicycles have one nitrogen or oxygen atom as a ring member and may have one further heteroatom or heteroatom group as a ring member, which is selected from the group consisting of O, S, S(=O), S(=O)$_2$ and N, where the saturated heteromonocycle and the saturated heterobicycle are unsubstituted or carry 1, 2, 3, 4 or 5 radicals $R^{C1}$ or one radical $Y'$—$R^{C2}$ and 0, 1, 2, 3 or 4 radicals $R^{C1}$.

36. The compound of claim 35, where $Y^2$-$Cyc^2$ and $Y^3$-$Cyc^3$, independently of each other, are selected from the group consisting of phenyl, 5- or 6-membered monocyclic hetaryl selected from the group consisting of pyridyl, pyrimidinyl, furyl, thienyl, pyrrolyl, imidazolyl, pyrazolyl, oxazolyl and thiazolyl, 9- or 10-membered bicyclic hetaryl selected from the group consisting of indolyl, quinolinyl, isoquinolinyl, quinazolinyl, benzimidazolyl, benzotriazolyl, benzopyrazolyl and benzofuryl, where phenyl and hetaryl are unsubstituted or carry 1, 2 or 3 radicals $R^{C1}$ which are selected from the group consisting of fluoro, chloro, CN, methyl, difluoromethyl, trifluoromethyl, methoxy and NH$_2$, or, if $Cyc^2$ or $Cyc^3$ are phenyl, two radicals $R^{C1}$ which are bound to adjacent carbon atoms, together with the phenyl ring to which they are bound, form a bicyclic heterocyclic radical, which is selected from 2,3-dihydrobenzofuran-5-yl, 2,3-dihydrobenzofuran-6-yl, 1,3-dihydroindol-2-on-5-yl, 1,3-dihydroindol-2-on-6-yl, benzo-1,3-dioxolan-5-yl, benzo-1,3-dioxolan-6-yl, benzo-1,4-dioxan-5-yl, benzo-1,4-dioxan-6-yl, benzo-1,5-dioxepan-6-yl and benzo-1,4-dioxepan-7-yl.

37. The compound of claim 1, which is of the formula (I-1.A) or formula (I-2.A)

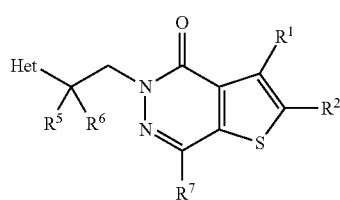
(I-1.A)

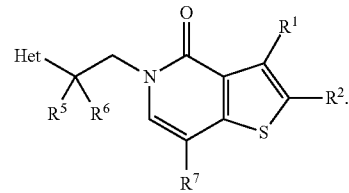
(I-2.A)

38. The compound of claim 37, where $R^1$ is $Y^1$-$Cyc^1$ and $R^7$ is selected from the group consisting of hydrogen, fluoro, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups, fluorinated cyclopropyl and $Y^2$-$Cyc^2$.

39. The compound of claim 37, where $R^1$ is selected from the group consisting of hydrogen, fluoro, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups and fluorinated cyclopropyl and $R^7$ is $Y^2$-$Cyc^2$.

40. The compound of claim 37, where $R^5$ and $R^6$ are each hydrogen.

41. The compound of claim 1, which is of the formula (I-1.B) or formula (I-2.B)

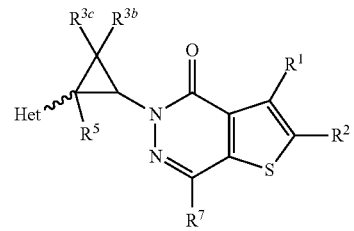
(I-1.B)

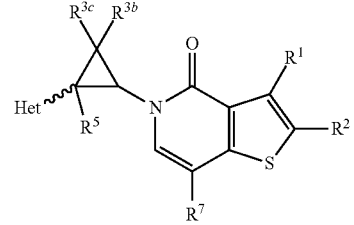
(I-2.B)

where $R^5$ is hydrogen.

42. The compound of claim 1, which is of the formula (I-1.C) or formula (I-2.C)

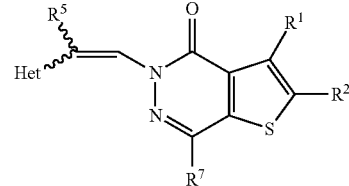
(I-1.C)

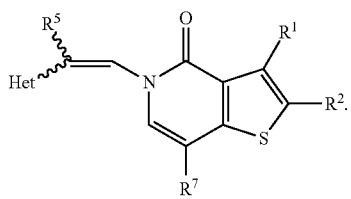
(I-2.C)

43. The compound of claim 1, which is of the formula (I-8.A), formula (I-8.B), or formula (I-8.C),

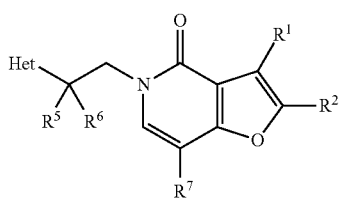
(I-8.A)

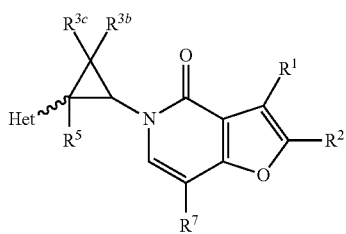
(I-8.B)

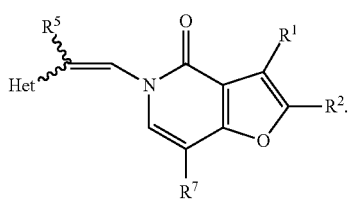
(I-8.C)

44. The compound of claim 43, where $R^1$ is $Y^1$-$Cyc^1$ and $R^7$ is selected from the group consisting of hydrogen, fluoro, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups, fluorinated cyclopropyl and $Y^2$-$Cyc^2$.

45. The compound of claim 1, which is of formula (I-9.A), formula (I-9.B), or formula (I-9.C)

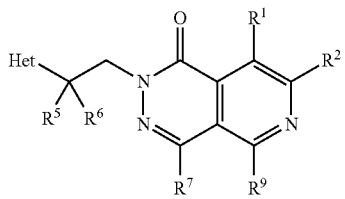
(I-9.A)

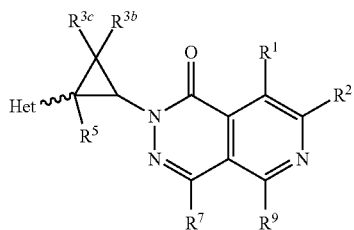
(I-9.B)

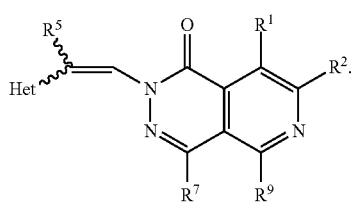
(I-9.C)

46. The compound of claim 45, where $R^1$ is $Y^1$-$Cyc^1$ and $R^7$ and $R^9$ are, independently of each other, selected from the group consisting of hydrogen, fluoro, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups, and fluorinated cyclopropyl, or $R^7$ is $Y^2$-$Cyc^2$ and $R^9$ is $Y^3$-$Cyc^3$.

47. The compound of claim 1, which is of the formula (I-1.D), formula (I-2.D), formula (I-8.D), or formula (I-9.D)

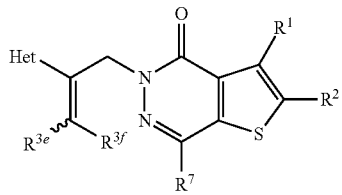
(I-1.D)

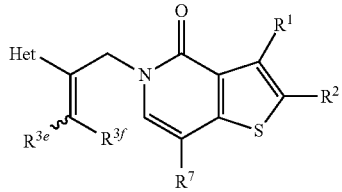
(I-2.D)

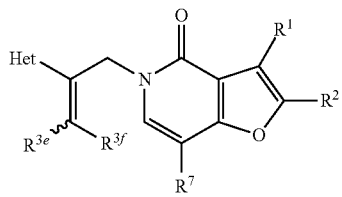
(I-8.D)

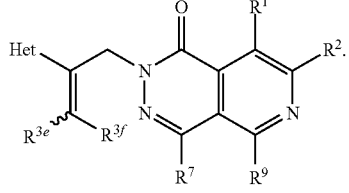
(I-9.D)

48. The compound of claim 47, where $R^1$ is $Y^1$-$Cyc^1$ and $R^7$ is selected from the group consisting of hydrogen, fluoro, $C_1$-$C_4$-alkyl, $C_1$-$C_2$-fluoroalkyl, $C_1$-$C_4$-alkoxy, $C_1$-$C_2$-fluororoalkoxy, cyclopropyl, optionally substituted by 1, 2 or 3 methyl groups, fluorinated cyclopropyl and Y²-Cyc².

49. The compound of claim 1, which is selected from the group consisting of 3,7-di(pyridin-4-yl)-5-[2-(quinolin-2-yl)ethyl]thieno[2,3-d]pyridazin-4(5H)-one;

7-(pyridin-4-yl)-5-[2-(quinolin-2-yl)ethyl]thieno[2,3-d]pyridazin-4(5H)-one;

3-(pyridin-4-yl)-5-[2-(quinolin-2-yl)ethyl]thieno[2,3-d]pyridazin-4(5H)-one;

3-(pyridin-4-yl)-5-[2-(pyridin-2-yl)ethyl]thieno[2,3-d]pyridazin-4(5H)-one;

3,7-di(pyridin-4-yl)-5-[2-(pyridin-2-yl)ethyl]thieno[2,3-d]pyridazin-4(5H)-one;

5-[2-(quinolin-2-yl)ethyl]-3-[4-(trifluoromethyl)phenyl]thieno[2,3-d]pyridazin-4(5H)-one;

3-(4-methylphenyl)-5-[2-(quinolin-2-yl)ethyl]thieno[2,3-d]pyridazin-4(5H)-one;

3-[4-(propan-2-yl)phenyl]-5-[2-(quinolin-2-yl)ethyl]thieno[2,3-d]pyridazin-4(5H)-one;

3-(4-ethylphenyl)-5-[2-(quinolin-2-yl)ethyl]thieno[2,3-d]pyridazin-4(5H)-one;

4-{4-oxo-5-[2-(quinolin-2-yl)ethyl]-4,5-dihydrothieno[2,3-d]pyridazin-3-yl}benzonitrile;

3-(4-methoxyphenyl)-5-[2-(quinolin-2-yl)ethyl]thieno[2,3-d]pyridazin-4(5H)-one;

3-(4-fluorophenyl)-5-[2-(quinolin-2-yl)ethyl]thieno[2,3-d]pyridazin-4(5H)-one;

3-(4-ethoxyphenyl)-5-[2-(quinolin-2-yl)ethyl]thieno[2,3-d]pyridazin-4(5H)-one;

3-[4-(dimethylamino)phenyl]-5-[2-(quinolin-2-yl)ethyl]thieno[2,3-d]pyridazin-4(5H)-one;

(4-{4-oxo-5-[2-(quinolin-2-yl)ethyl]-4,5-dihydrothieno[2,3-d]pyridazin-3-yl}phenyl)acetonitrile;

3-(4-hydroxyphenyl)-5-[2-(quinolin-2-yl)ethyl]thieno[2,3-d]pyridazin-4(5H)-one;

3-(2-chlorophenyl)-5-[2-(quinolin-2-yl)ethyl]thieno[2,3-d]pyridazin-4(5H)-one;

3-(2-methylphenyl)-5-[2-(quinolin-2-yl)ethyl]thieno[2,3-d]pyridazin-4(5H)-one;

3-(2-ethylphenyl)-5-[2-(quinolin-2-yl)ethyl]thieno[2,3-d]pyridazin-4-(5H)-one;

3-(2-fluorophenyl)-5-[2-(quinolin-2-yl)ethyl]thieno[2,3-d]pyridazin-4(5H)-one;

3-(2-methoxyphenyl)-5-[2-(quinolin-2-yl)ethyl]thieno[2,3-d]pyridazin-4(5H)-one;

3-(2-ethoxyphenyl)-5-[2-(quinolin-2-yl)ethyl]thieno[2,3-d]pyridazin-4(5H)-one;

3-(2-hydroxyphenyl)-5-[2-(quinolin-2-yl)ethyl]thieno[2,3-d]pyridazin-4(5H)-one;

5-[2-(quinolin-2-yl)ethyl]-3-[2-(trifluoromethyl)phenyl]thieno[2,3-d]pyridazin-4(5H)-one;

3-[3-(methoxymethyl)phenyl]-5-[2-(quinolin-2-yl)ethyl]thieno[2,3-d]pyridazin-4(5H)-one;

3-(3-methoxyphenyl)-5-[2-(quinolin-2-yl)ethyl]thieno[2,3-d]pyridazin-4(5H)-one;

3-(3-ethoxyphenyl)-5-[2-(quinolin-2-yl)ethyl]thieno[2,3-d]pyridazin-4(5H)-one;

3-[3-(dimethylamino)phenyl]-5-[2-(quinolin-2-yl)ethyl]thieno[2,3-d]pyridazin-4(5H)-one;

3-{[4-oxo-5-(2-quinolin-2-yl)ethyl]-4,5-dihydrothieno[2,3-d]pyridazin-3-yl}benzonitrile;

3-(3-fluorophenyl)-5-[2-(quinolin-2-yl)ethyl]thieno[2,3-d]pyridazin-4(5H)-one;

3-(3-hydroxyphenyl)-5-[2-(quinolin-2-yl)ethyl]thieno[2,3-d]pyridazin-4(5H)-one;

N,N-dimethyl-3-{4-oxo-5-[2-(quinolin-2-yl)ethyl]-4,5-dihydrothieno[2,3-d]-pyridazin-3-yl}benzamide;

3-(3-methylphenyl)-5-[2-(quinolin-2-yl)ethyl]thieno[2,3-d]pyridazin-4(5H)-one;

5-[2-(quinolin-2-yl)ethyl]-3-(thiophen-2-yl)thieno[2,3-d]pyridazin-4-(5H)-one;

3-(1-methyl-1H-indol-5-yl)-5-[2-(quinolin-2-yl)ethyl]-5-thieno[2,3-d]pyridazin-4-one;

3-(1H-indol-6-yl)-5-[2-(quinolin-2-yl)ethyl]thieno[2,3-d]pyridazin-4(5H)-one;

3-(pyrimidin-5-yl)-5-[2-(quinolin-2-yl)ethyl]thieno[2,3-d]pyridazin-4-(5H)-one;

3-(2-methoxypyridin-3-yl)-5-[2-(quinolin-2-yl)ethyl]thieno[2,3-d]pyridazin-4(5H)-one;

3-(pyridin-3-yl)-5-[2-(quinolin-2-yl)ethyl]thieno[2,3-d]pyridazin-4(5H)-one;

3-(4-methoxypyridin-3-yl)-5-[2-(quinolin-2-yl)ethyl]thieno[2,3-d]pyridazin-4(5H)-one;

3-(furan-3-yl)-5-[2-(quinolin-2-yl)ethyl]thieno[2,3-d]pyridazin-4(5H)-one;

3-(quinolin-3-yl)-5-[2-(quinolin-2-yl)ethyl]thieno[2,3-d]pyridazin-4(5H)-one;

3-(isoquinolin-4-yl)-5-[2-(quinolin-2-yl)ethyl]thieno[2,3-d]pyridazin-4(5H)-one;

3-(isoquinolin-5-yl)-5-[2-(quinolin-2-yl)ethyl]thieno[2,3-d]pyridazin-4(5H)-one;

3-(1H-indol-4-yl)-5-(2-quinolin-2-yl-ethyl)-5H-thieno[2,3-d]pyridazin-4-one;

3-(2,3-dihydrobenzofuran-5-yl)-5-(2-quinolin-2-yl-ethyl)-5H-thieno[2,3-d]pyridazin-4-one;

3-(quinolin-5-yl)-5-[2-(quinolin-2-yl)ethyl]thieno[2,3-d]pyridazin-4(5H)-one;

3-(3,5-dimethyl-1,2-oxazol-4-yl)-5-[2-(quinolin-2-yl)ethyl]thieno[2,3-d]pyridazin-4(5H)-one;

3-(6-methoxypyridin-3-yl)-5-[2-(quinolin-2-yl)ethyl]thieno[2,3-d]pyridazin-4(5H)-one;

3-(2,3-dihydro-1,4-benzodioxin-6-yl)-5-[2-(quinolin-2-yl)ethyl]thieno[2,3-d]pyridazin-4(5H)-one;

3-(2-methylpyridin-4-yl)-5-[2-(quinolin-2-yl)ethyl]thieno[2,3-d]pyridazin-4(5H)-one;

3-(5-methoxypyridin-3-yl)-5-[2-(quinolin-2-yl)ethyl]thieno[2,3-d]pyridazin-4(5H)-one;

3-[6-(morpholin-4-yl)pyridin-3-yl]-5-[2-(quinolin-2-yl)ethyl]thieno[2,3-d]pyridazin-4(5H)-one;

3-(1,3-benzodioxol-5-yl)-5-[2-(quinolin-2-yl)ethyl]thieno[2,3-d]pyridazin-4(5H)-one;

3-(quinolin-6-yl)-5-[2-(quinolin-2-yl)ethyl]thieno[2,3-d]pyridazin-4(5H)-one;

3-(1-methyl-1H-pyrazol-4-yl)-5-[2-(quinolin-2-yl)ethyl]thieno[2,3-d]pyridazin-4(5H)-one;

3-(1-(2-methylpropyl)-1H-pyrazol-4-yl)-5-[2-(quinolin-2-yl)ethyl]thieno[2,3-d]pyridazin-4(5H)-one;

tert-butyl 2-{4-oxo-5-[2-(quinolin-2-yl)ethyl]-4,5-dihydrothieno[2,3-d]pyridazin-3-yl}-1H-pyrrole-1-carboxylate;

3-(2-methoxypyridin-5-yl)-5-[2-(quinolin-2-yl)ethyl]thieno[2,3-d]pyridazin-4(5H)-one;

5-[2-(quinolin-2-yl)ethyl]-3-(2,3,4-trifluorophenyl)thieno[2,3-d]pyridazin-4(5H)-one;

3-(4-fluoro-3-methylphenyl)-5-[2-(quinolin-2-yl)ethyl]thieno[2,3-d]pyridazin-4(5H)-one;

3-(4-fluoro-2-methylphenyl)-5-[2-(quinolin-2-yl)ethyl]thieno[2,3-d]pyridazin-4(5H)-one;

3-(3-chloro-4-fluorophenyl)-5-[2-(quinolin-2-yl)ethyl]thieno[2,3-d]pyridazin-4(5H)-one;

3-(2-chloro-4-fluorophenyl)-5-[2-(quinolin-2-yl)ethyl]thieno[2,3-d]pyridazin-4(5H)-one;

3-(3,4-dimethylphenyl)-5-[2-(quinolin-2-yl)ethyl]thieno[2,3-d]pyridazin-4-(5H)-one;
3-(2,4-dimethylphenyl)-5-[2-(quinolin-2-yl)ethyl]thieno[2,3-d]pyridazin-4(5H)-one;
3-(2,4-difluorophenyl)-5-[2-(quinolin-2-yl)ethyl]thieno[2,3-d]pyridazin-4-(5H)-one;
3-(2,4-dimethoxyphenyl)-5-[2-(quinolin-2-yl)ethyl]thieno[2,3-d]pyridazin-4(5H)-one;
3-(2,5-dimethoxyphenyl)-5-[2-(quinolin-2-yl)ethyl]thieno[2,3-d]pyridazin-4(5H)-one;
3-(2,3-difluorophenyl)-5-[2-(quinolin-2-yl)ethyl]thieno[2,3-d]pyridazin-4(5H)-one;
3-(3,4-dimethoxyphenyl)-5-[2-(quinolin-2-yl)ethyl]thieno[2,3-d]pyridazin-4(5H)-one;
3-(3,4-difluorophenyl)-5-[2-(quinolin-2-yl)ethyl]thieno[2,3-d]pyridazin-4(5H)-one;
3-(5-fluoro-2-methoxyphenyl)-5-[2-(quinolin-2-yl)ethyl]thieno[2,3-d]pyridazin-4(5H)-one;
3-(4-fluoro-2-methoxyphenyl)-5-[2-(quinolin-2-yl)ethyl]thieno[2,3-d]pyridazin-4(5H)-one;
3-(3,5-dimethoxyphenyl)-5-[2-(quinolin-2-yl)ethyl]thieno[2,3-d]pyridazin-4(5H)-one;
3-(2,5-difluorophenyl)-5-[2-(quinolin-2-yl)ethyl]thieno[2,3-d]pyridazin-4(5H)-one;
3-(2,3-dimethoxyphenyl)-5-[2-(quinolin-2-yl)ethyl]thieno[2,3-d]pyridazin-4(5H)-one;
3-(3-fluoro-4-methoxyphenyl)-5-[2-(quinolin-2-yl)ethyl]thieno[2,3-d]pyridazin-4(5H)-one;
3-(2-fluoro-3-methoxyphenyl)-5-[2-(quinolin-2-yl)ethyl]thieno[2,3-d]pyridazin-4(5H)-one;
3-(3,5-difluorophenyl)-5-[2-(quinolin-2-yl)ethyl]thieno[2,3-d]pyridazin-4-(5H)-one;
3-(3-fluoro-5-methoxyphenyl)-5-[2-(quinolin-2-yl)ethyl]thieno[2,3-d]pyridazin-4(5H)-one;
3-(2-methoxy-5-methylphenyl)-5-[2-(quinolin-2-yl)ethyl]thieno[2,3-d]pyridazin-4(5H)-one;
3-(2,5-dichlorophenyl)-5-[2-(quinolin-2-yl)ethyl]thieno[2,3-d]pyridazin-4-(5H)-one;
3-(naphthalen-2-yl)-5-[2-(quinolin-2-yl)ethyl]thieno[2,3-d]pyridazin-4(5H)-one;
3-phenyl-5-[2-(quinolin-2-yl)ethyl]thieno[2,3-d]pyridazin-4(5H)-one;
3-(1-benzofuran-2-yl)-5-[2-(quinolin-2-yl)ethyl]thieno[2,3-d]pyridazin-4 (5H)-one;
3-(1H-indazol-5-yl)-5-[2-(quinolin-2-yl)ethyl]thieno[2,3-d]pyridazin-4(5H)-one;
3-(1-methyl-1H-pyrazol-5-yl)-5-[2-(quinolin-2-yl)ethyl]thieno[2,3-d]pyridazin-4(5H)-one;
3-(4,5-difluoro-2-methoxyphenyl)-5-[2-(quinolin-2-yl)ethyl]thieno[2,3-d]pyridazin-4(5H)-one;
3-(2-fluoro-4-methylphenyl)-5-[2-(quinolin-2-yl)ethyl]thieno[2,3-d]pyridazin-4(5H)-one;
3-(2-fluoro-5-methoxyphenyl)-5-[2-(quinolin-2-yl)ethyl]thieno[2,3-d]pyridazin-4(5H)-one;
3-methyl-4-{4-oxo-5-[2-(quinolin-2-yl)ethyl]-4,5-dihydrothieno[2,3-d]pyridazin-3-yl}benzonitrile;
5-[2-(6-fluoroquinolin-2-yl)ethyl]-3-(pyridin-4-yl)thieno[2,3-d]pyridazin-4(5H)-one;
5-[2,2-difluoro-2-(quinolin-2-yl)ethyl]-3-(pyridin-4-yl)thieno[2,3-d]pyridazin-4(5H)-one;
3-(pyridin-4-yl)-5-[2-(thieno[3,2-b]pyridin-5-yl)ethyl]thieno[2,3-d]pyridazin-4(5H)-one;
5-[2-(imidazo[1,2-a]pyridin-2-yl)ethyl]-3-(pyridin-4-yl)thieno[2,3-d]pyridazin-4(5H)-one;
5-[2-(7-fluoroimidazo[1,2-a]pyridin-2-yl)ethyl]-3-(pyridin-4-yl)thieno[2,3-d]pyridazin-4(5H)-one;
3-(3-methoxypyridin-4-yl)-5-[2-(quinolin-2-yl)ethyl]thieno[3,2-c]pyridin-4(5H)-one;
3-(3-hydroxypyridin-4-yl)-5-[2-(quinolin-2-yl)ethyl]thieno[3,2-c]pyridin-4(5H)-one;
3-(1-methyl-1H-pyrazol-5-yl)-5-[2-(quinolin-2-yl)ethyl]thieno[3,2-c]pyridin-4(5H)-one;
3-(pyridin-4-yl)-5-[2-(quinolin-2-yl)ethyl]thieno[3,2-c]pyridin-4(5H)-one;
3-(pyrimidin-5-yl)-5-(2-quinolin-2-yl)ethyl)thieno[3,2-c]pyridin-4(5H)-one;
3-(2-oxoindolin-6-yl)-5-[2-(quinolin-2-yl)ethyl]thieno[3,2-c]pyridin-4-(5H)-one;
3-(3-hydroxyphenyl)-5-[2-(quinolin-2-yl)ethyl]thieno[3,2-c]pyridin-4(5H)-one;
5-[2-(5-ethylpyridin-2-yl)ethyl]-3-(pyridin-4-yl)thieno[3,2-c]pyridin-4(5H)-one;
5-[2-(imidazo[1,2-a]pyridin-2-yl)ethyl]-3-(pyridin-4-yl)thieno[3,2-c]pyridin-4(5H)-one;
3-(morpholin-4-yl)-5-[2-(quinolin-2-yl)ethyl]thieno[3,2-c]pyridin-4(5H)-one;
tert-butyl-4-[4-oxo-(5-(2-quinolin-2-yl)ethyl)-4,5-dihydrothieno[3,2-c]pyridin-3-yl]-5,6-dihydropyridine-1(2H)-carboxylate;
5-(2-(quinolin-2-yl)ethyl)-3-(1,2,3,6-tetrahydropyridin-4-yl)thieno[3,2-c]pyridin-4(5H)-one;
tert-butyl-4-(4-oxo-5-(2-quinolin-2-yl)ethyl)-4,5-dihydrothieno[3,2-c]pyridin-3-yl)-piperidine-1 carboxylate;
3-(piperidin-4-yl)-5-[2-(quinolin-2-yl)ethyl]thieno[3,2-c]pyridin-4(5H)-one;
3-methyl-7-(pyridin-4-yl)-5-(2-(quinolin-2-yl)ethyl)thieno[3,2-c]pyridin-4(5H)-one;
3-(pyridin-4-yl)-5-[2-(5,6,7,8-tetrahydroquinolin-2-yl)ethyl]thieno[2,3-d]pyridazin-4(5H)-one;
anti-(rac)-3-(pyridin-4-yl)-5-(2-(quinolin-2-yl)cyclopropyl)thieno[3,2-c]pyridin-4(5H)-one;
anti-(+)-3-(pyridin-4-yl)-5-(2-(quinolin-2-yl)cyclopropyl)thieno[3,2-c]pyridin-4(5H)-one; and
anti-(−)-3-(pyridin-4-yl)-5-(2-(quinolin-2-yl)cyclopropyl)thieno[3,2-c]pyridin-4(5H)-one;

or an N-oxide, tautomer or pharmaceutically acceptable salt thereof.

50. The compound of claim 1, which is selected from the group consisting of 7-(pyridin-4-yl)-5-[2-(quinolin-2-yl)ethyl]furo[3,2-c]pyridin-4(5H)-one;
3-(pyridin-4-yl)-5-(2-(quinolin-2-yl)ethyl)furo[3,2-c]pyridin-4(5H)-one;
5-(2-(1H-benzo[d]imidazol-2-yl)ethyl)-3-(pyridin-4-yl)furo[3,2-c]pyridin-4(5H)-one;
5-(2-(imidazo[1,2-a]pyridin-2-yl)ethyl)-3-(pyridin-4-yl)furo[3,2-c]pyridin-4(5H)-one;
3-(pyrimidin-5-yl)-5-(2-(quinolin-2-yl)ethyl)furo[3,2-c]pyridin-4(5H)-one;
syn 3-(pyridin-4-yl)-5-(2-(quinolin-2-yl)cyclopropyl)thieno[3,2-c]pyridin-4(5H)-one;
anti 3-(pyridazin-4-yl)-5-(2-(quinolin-2-yl)cyclopropyl)furo[3,2-c]pyridin-4(5H)-one;
syn 3-(pyridazin-4-yl)-5-(2-(quinolin-2-yl)cyclopropyl)furo[3,2-c]pyridin-4(5H)-one;
anti 3-(pyridin-4-yl)-5-(2-(quinolin-2-yl)cyclopropyl)furo[3,2-c]pyridin-4(5H)-one;
syn 3-(pyridin-4-yl)-5-(2-(quinolin-2-yl)cyclopropyl)furo[3,2-c]pyridin-4(5H)-one;
anti 7-fluoro-3-(pyridin-4-yl)-5-(2-(quinolin-2-yl)cyclopropyl)thieno[3,2-c]pyridin-4(5H)-one;

syn 7-fluoro-3-(pyridin-4-yl)-5-(2-(quinolin-2-yl)cyclopropyl)thieno[3,2-c]pyridin-4(5H)-one;
anti-3-(2-fluoropyridin-4-yl)-5-(2-(6-fluoroquinolin-2-yl)cyclopropyl)thieno[3,2-c]pyridin-4(5H)-one;
syn-3-(2-fluoropyridin-4-yl)-5-(2-(6-fluoroquinolin-2-yl)cyclopropyl)thieno[3,2-c]pyridin-4(5H)-one;
anti 5-(2-(6-fluoroquinolin-2-yl)cyclopropyl)-3-(pyridin-4-yl)thieno[3,2-c]pyridin-4(5H)-one;
syn 5-(2-(6-fluoroquinolin-2-yl)cyclopropyl)-3-(pyridin-4-yl)thieno[3,2-c]pyridin-4(5H)-one;
anti 3-(pyrimidin-5-yl)-5-(2-(quinolin-2-yl)cyclopropyl)thieno[3,2-c]pyridin-4-(5H)-one;
syn 3-(pyrimidin-5-yl)-5-(2-(quinolin-2-yl)cyclopropyl)thieno[3,2-c]pyridin-4-(5H)-one;
anti 3-(pyrimidin-5-yl)-5-(2-(quinolin-2-yl)cyclopropyl)thieno[3,2-c]pyridin-4-(5H)-one;
syn 3-(pyrimidin-5-yl)-5-(2-(quinolin-2-yl)cyclopropyl)thieno[3,2-c]pyridin-4-(5H)-one;
anti 3-(pyrimidin-5-yl)-5-(2-(quinolin-2-yl)cyclopropyl)thieno[3,2-c]pyridin-4-(5H)-one;
syn 3-(pyrimidin-5-yl)-5-(2-(quinolin-2-yl)cyclopropyl)thieno[3,2-c]pyridin-4-(5H)-one;
anti 3-(6-fluoropyridin-3-yl)-5-(2-(quinolin-2-yl)cyclopropyl)thieno[3,2-c]pyridin-4(5H)-one;
syn 3-(6-fluoropyridin-3-yl)-5-(2-(quinolin-2-yl)cyclopropyl)thieno[3,2-c]pyridin-4(5H)-one;
anti 3-(2-methylpyrimidin-5-yl)-5-(2-(quinolin-2-yl)cyclopropyl)thieno[3,2-c]pyridin-4(5H)-one;
syn 3-(2-methylpyrimidin-5-yl)-5-(2-(quinolin-2-yl)cyclopropyl)thieno[3,2-c]pyridin-4(5H)-one;
anti 3-(pyridazin-4-yl)-5-(2-(quinolin-2-yl)cyclopropyl)thieno[3,2-c]pyridin-4-(5H)-one;
syn 3-(pyridazin-4-yl)-5-(2-(quinolin-2-yl)cyclopropyl)thieno[3,2-c]pyridin-4-(5H)-one;
anti 3-(2-fluoropyridin-4-yl)-5-(2-(quinolin-2-yl)cyclopropyl]thieno[3,2-c]pyridin-4(5H)-one;
syn 3-(2-fluoropyridin-4-yl)-5-(2-(quinolin-2-yl)cyclopropyl]thieno[3,2-c]pyridin-4(5H)-one;
anti-3-(morpholin-4-yl)-5-[2-(quinolin-2-yl)cyclopropyl]thieno[3,2-c]pyridin-4(5H)-one;
syn-3-(morpholin-4-yl)-5-[2-(quinolin-2-yl)cyclopropyl]thieno[3,2-c]pyridin-4(5H)-one;
anti-3-(pyridin-3-yl)-5-[2-(thieno[3,2-b]pyridin-5-yl)cyclopropyl]thieno[3,2-c]pyridin-4(5H)-one;
syn-3-(pyridin-3-yl)-5-[2-(thieno[3,2-b]pyridin-5-yl)cyclopropyl]thieno[3,2-c]pyridin-4(5H)-one;
anti 3-(pyridin-3-yl)-5-[2-(quinolin-2-yl)cyclopropyl]thieno[3,2-c]pyridin-4(5H)-one;
syn 3-(pyridin-3-yl)-5-[2-(quinolin-2-yl)cyclopropyl]thieno[3,2-c]pyridin-4(5H)-one;
anti 3-(pyrimidin-5-yl)-5-[2-(quinolin-2-yl)cyclopropyl]thieno[2,3-d]pyridazin-4(5H)-one;
syn 3-(pyrimidin-5-yl)-5-[2-(quinolin-2-yl)cyclopropyl]thieno[2,3-d]pyridazin-4(5H)-one;
anti-3-(pyridin-4-yl)-5-[2-(thieno[3,2-b]pyridin-5-yl)cyclopropyl)thieno[2,3-d]pyridazin-4(5H)-one;
syn-(pyridin-4-yl)-5-[2-(thieno[3,2-b]pyridin-5-yl)cyclopropyl]thieno[2,3-d]pyridazin-4(5H)-one;
anti-3-(pyridin-4-yl)-5-[2-(thieno[3,2-b]pyridin-5-yl)cyclopropyl]thieno[3,2-c]pyridin-4(5H)-one;
syn-3-(pyridin-4-yl)-5-[2-(thieno[3,2-b]pyridin-5-yl)cyclopropyl]thieno[3,2-c]pyridin-4(5H)-one;
anti 3-(pyridin-4-yl)-5-[2-(quinolin-2-yl)cyclopropyl]thieno[3,2-c]pyridin-4(5H)-one;
syn 3-(pyridin-4-yl)-5-[2-(quinolin-2-yl)cyclopropyl]thieno[3,2-c]pyridin-4(5H)-one;
anti 3-(pyridin-4-yl)-5-[2-(quinolin-2-yl)cyclopropyl]thieno[2,3-d]pyridazin-4-(5H)-one;
syn 3-(pyridin-4-yl)-5-[2-(quinolin-2-yl)cyclopropyl]thieno[2,3-d]pyridazin-4-(5H)-one;
8-(pyridin-4-yl)-2-[2-(quinolin-2-yl)ethyl]pyrido[3,4-d]pyridazin-1(2H)-one;
5-[2-(imidazo[1,2-a]pyridin-2-yl)ethyl]-7-(1-methyl-1H-imidazol-4-yl)-3-(pyridin-4-yl)thieno[2,3-d]pyridazin-4(5H)-one;
5-[2-(imidazo[1,2-a]pyridin-2-yl)ethyl]-7-(1-methyl-1H-pyrazol-4-yl)-3-(pyridin-4-yl)thieno[2,3-d]pyridazin-4(5H)-one;
5-[2-(imidazo[1,2-a]pyridin-2-yl)ethyl]-7-(pyridin-3-yl)-3-(pyridin-4-yl)-thieno[2,3-d]pyridazin-4(5H)-one;
5-[2-(6-chloroquinolin-2-yl)ethyl]-3-(pyridin-4-yl)thieno[3,2-c]pyridin-4-(5H)-one;
5-[2-(3-methylquinolin-2-yl)ethyl]-3-(pyridin-4-yl)thieno[3,2-c]pyridin-4(5H)-one;
5-[2-(8-fluoroquinolin-2-yl)ethyl]-3-(pyridin-4-yl)thieno[3,2-c]pyridin-4-(5H)-one;
5-[2-(6-fluoroquinolin-2-yl)ethyl]-3-(pyridin-3-yl)thieno[3,2-c]pyridin-4(5H)-one;
5-[2-(6-fluoroquinolin-2-yl)ethyl]-3-(pyridin-4-yl)thieno[3,2-c]pyridin-4-(5H)-one;
5-[2-(imidazo[1,2-a]pyridin-2-yl)ethyl]-3-(pyridin-3-yl)thieno[3,2-c]pyridin-4(5H)-one;
3-(pyridin-4-yl)-5-[2-(quinoxalin-2-yl)ethyl]thieno[2,3-d]pyridazin-4 (5H)-one;
5-[2-(1,5-naphthyridin-2-yl)ethyl]-3-(pyridin-4-yl)thieno[2,3-d]pyridazin-4(5H)-one;
5-[2-(1H-indazol-1-yl)ethyl]-3-(pyridin-4-yl)thieno[2,3-d]pyridazin-4(5H)-one;
3-(1-methyl-1H-pyrazol-3-yl)-5-[2-(quinolin-2-yl)ethyl]thieno[2,3-d]pyridazin-4(5H)-one;
3-(1H-pyrazol-3-yl)-5-[2-(quinolin-2-yl)ethyl]thieno[2,3-d]pyridazin-4(5H)-one;
5-[2-(1H-benzimidazol-1-yl)ethyl]-3-(pyridin-4-yl)thieno[2,3-d]pyridazin-4(5H)-one;
5-[2-(1H-benzimidazol-2-yl)ethyl]-3-(pyridin-4-yl)thieno[2,3-d]pyridazin-4(5H)-one;
5-[6-chloroquinolin-2-yl)ethyl]-3-(pyridin-4-yl)thieno[2,3-d]pyridazin-4(5H)-one;
3-(pyridin-3-ylethynyl)-5-[2-(quinolin-2-yl)ethyl]thieno[2,3-d]pyridazin-4(5H)-one;
3-(pyridin-4-ylethynyl)-5-[2-(quinolin-2-yl)ethyl]thieno[2,3-d]pyridazin-4(5H)-one;
5-[2-(3,5-dimethylpyridin-2-yl)ethyl]-3-(pyridin-4-yl)thieno[2,3-d]pyridazin-4(5H)-one;
5-[2-(7-fluoroquinolin-2-yl)ethyl]-3-(pyridin-4-yl)thieno[2,3-d]pyridazin-4(5H)-one;
5-[2-(pyrazin-2-yl)ethyl]-3-(pyridin-4-yl)thieno[2,3-d]pyridazin-4(5H)-one;
5-[(E)-2-(6-methoxyquinolin-2-yl)ethenyl]-3-(pyridin-4-yl)thieno[3,2-c]pyridin-4(5H)-one;
5-[(E)-2-(6-chloroquinolin-2-yl)ethenyl]-3-(pyridin-4-yl)thieno[3,2-c]pyridin-4(5H)-one;
5-[(E)-2-(3-methylquinolin-2-yl)ethenyl]-3-(pyridin-4-yl)thieno[3,2-c]pyridin-4(5H)-one;
5-[(E)-2-(1,3-benzothiazol-2-yl)ethenyl]-3-(pyridin-4-yl)thieno[3,2-c]pyridin-4(5H)-one; and
3-(pyridin-4-yl)-5-[(E)-2-(quinolin-2-yl)ethenyl]thieno[3,2-c]pyridin-4(5H)-one;

or an N-oxide, tautomer or pharmaceutically acceptable salt thereof.

51. The compound of claim 27, wherein the compound is anti-3-(pyridin-4-yl)-5-(2-(quinolin-2-yl)cyclopropyl)furo

[3,2-c]pyridin-4(5H)-one; or an N-oxide, tautomer or pharmaceutically acceptable salt thereof.

52. The compound of claim 27, wherein the compound is anti-3-(pyridazin-4-yl)-5-(2-(quinolin-2-yl)cyclopropyl)furo[3,2-c]pyridin-4(5H)-one; or an N-oxide, tautomer or pharmaceutically acceptable salt thereof.

53. The compound of claim 27, wherein the compound is anti-3-(pyridazin-4-yl)-5-(2-(quinolin-2-yl)cyclopropyl)thieno[3,2-c]pyridin-4(5H)-one; or an N-oxide, tautomer or pharmaceutically acceptable salt thereof.

54. A pharmaceutical composition which comprises the compound of claim 1 and at least one pharmaceutically acceptable excipient.

55. A method for inhibiting phosphodiesterase type 10A activity in a subject, comprising administering to a subject in need thereof a therapeutically effective amount of the compound of claim 1.

56. The method of claim 55, wherein the subject suffers from a disease or disorder selected from the group consisting of a central nervous system disorder, a neurological disorder and a psychiatric disorder.

57. The method of claim 56, wherein the central nervous system disorder is Huntington's disease.

58. The method of claim 56, wherein the neurological disorder is selected from the group consisting of cognitive dysfunction associated with schizophrenia and cognitive dysfunction associated with Alzheimer's disease.

59. The method of claim 56, wherein the neurological disorder is cognitive dysfunction associated with schizophrenia.

60. The method of claim 56, wherein the psychiatric disorder is selected from the group consisting of anxiety, diet-induced obesity, depression, schizophrenia and a bipolar disorder.

61. The method of claim 56, wherein the psychiatric disorder is schizophrenia.

* * * * *

UNITED STATES PATENT AND TRADEMARK OFFICE
CERTIFICATE OF CORRECTION

Page 1 of 1

PATENT NO. : 9,657,034 B2
APPLICATION NO. : 14/997997
DATED : May 23, 2017
INVENTOR(S) : Hervé Geneste et al.

It is certified that error appears in the above-identified patent and that said Letters Patent is hereby corrected as shown below:

On the Title Page

Item (73) Assignee name, "AbbVie Deuschland GmbH & Co. KG", should be changed to -AbbVie Deutschland GmbH & Co. KG-.

Signed and Sealed this
Third Day of October, 2017

Joseph Matal
*Performing the Functions and Duties of the*
*Under Secretary of Commerce for Intellectual Property and*
*Director of the United States Patent and Trademark Office*